US012134772B2

(12) United States Patent
Chen et al.

(10) Patent No.: US 12,134,772 B2
(45) Date of Patent: Nov. 5, 2024

(54) INCREASING GENE EXPRESSION

(71) Applicant: Klogenix LLC, Boston, MA (US)

(72) Inventors: Ci-Di Chen, Boston, MA (US); Ella Zeldich, Boston, MA (US); Carmela Abraham, Boston, MA (US)

(73) Assignee: Advantage Therapeutics, Inc., Miami, FL (US)

( * ) Notice: Subject to any disclaimer, the term of this patent is extended or adjusted under 35 U.S.C. 154(b) by 860 days.

(21) Appl. No.: 17/276,320

(22) PCT Filed: Sep. 6, 2019

(86) PCT No.: PCT/US2019/049918

§ 371 (c)(1),
(2) Date: Mar. 15, 2021

(87) PCT Pub. No.: WO2020/106351

PCT Pub. Date: May 28, 2020

(65) Prior Publication Data

US 2023/0101807 A1 Mar. 30, 2023

Related U.S. Application Data

(60) Provisional application No. 62/860,407, filed on Jun. 12, 2019, provisional application No. 62/827,471, filed on Apr. 1, 2019, provisional application No. 62/770,336, filed on Nov. 21, 2018.

(51) Int. Cl.

| | |
|---|---|
| ***C12N 15/67*** | (2006.01) |
| ***A61K 31/713*** | (2006.01) |
| ***C12N 9/24*** | (2006.01) |
| ***C12N 15/113*** | (2010.01) |

(52) U.S. Cl.

CPC ............ *C12N 15/67* (2013.01); *A61K 31/713* (2013.01); *C12N 9/2402* (2013.01); *C12N 15/113* (2013.01); *C12N 2310/113* (2013.01); *C12N 2310/14* (2013.01)

(58) Field of Classification Search

CPC .... C12N 15/67; C12N 9/2402; C12N 15/113; C12N 2310/113; C12N 2310/14; A61K 31/713

See application file for complete search history.

(56) References Cited

U.S. PATENT DOCUMENTS

| | | | | |
|---|---|---|---|---|
| 9,029,524 B2 * | 5/2015 | Han | C12N 15/113 536/24.5 | |
| 9,856,472 B2 * | 1/2018 | Pierce | C12N 15/111 | |

FOREIGN PATENT DOCUMENTS

| | | |
|---|---|---|
| CN | 102961739 | 3/2013 |
| WO | 2017201527 A2 | 11/2017 |

OTHER PUBLICATIONS

Marchese, D., de Groot, N.S., Lorenzo Gotor, N., Livi, C.M. and Tartaglia, G.G. (2016), Advances in the characterization of RNA-binding proteins. WIREs RNA, 7: 793-810 (Year: 2016).*

Lu et al., 2008, "Efficient siRNA selection using hybridization thermodynamics" Nucleic Acids Research, 36(3), p. 640-647 (Year: 2008).*

Gao et al., 2006, "Secondary structure effects on DNA hybridization kinetics: a solution versus surface comparison" Nucleic Acids Research, 34 (11), p. 3370-3377 (Year: 2006).*

Wang et al., 2022, "Developing predictive hybridization models for phosphorothioate oligonucleotides using high-resolution melting" PLOS One, 17(5), e0268575 (Year: 2022).*

Zeldich, Ella, et al. "The anti-aging protein Klotho enhances remyelination following cuprizone-induced demyelination." Journal of Molecular Neuroscience 57 (2015): 185-196. (Year: 2015).*

Chen, Ci-Di, et al. "Activation of the anti-aging and cognition-enhancing gene klotho by CRISPR-dCas9 transcriptional effector complex." Journal of Molecular Neuroscience 64 (2018): 175-184. (Year: 2015).*

Haniff, Hafeez S., Amanda Graves, and Matthew D. Disney. "Selective small molecule recognition of RNA base pairs." ACS combinatorial science 20.8 (2018): 482-491. (Year: 2018).*

Hentze, Matthias W et al. "A brave new world of RNA-binding proteins." Nature reviews. Molecular cell biology vol. 19,5 (2018): 327-341. doi:10.1038/nrm.2017.130 (Year: 2018).*

Warner, Katherine Deigan, Christine E. Hajdin, and Kevin M. Weeks. "Principles for targeting RNA with drug-like small molecules." Nature reviews Drug discovery 17.8 (2018): 547-558. (Year: 2018).*

Rossetto et al., "Kaposi's Sarcoma-Associated Herpesvirus Noncoding Polyadenylated Nuclear RNA Interacts with Virus- and Host Cell-Encoded Proteins and Suppresses Expression of Genes Involved in Immune Modulation", Journal of Virology, Dec. 2011, vol. 85, No. 24, pp. 13290-13297.

Wehling-Henricks et al., "Klotho gene silencing promotes pathology in the mdx mouse model of Duchenne muscular dystrophy", Human Molecular Genetics, May 2016, vol. 25, No. 12, pp. 2465-2482.

International Search Report for International Patent Application No. PCT/US2019/049918, mailed Dec. 2, 2019.

Written Opinion for International Patent Application No. PCT/US2019/049918, mailed Dec. 2, 2019.

Aigner, "Delivery Systems for the Direct Application of siRNAs to Induce RNA Interference (RNAi) In Vivo", Review Article, Feb. 2006, pp. 1-15, vol. 2006, Hindawi Publishing Corporation.

(Continued)

*Primary Examiner* — Neil P Hammell
*Assistant Examiner* — John Charles McKillop
(74) *Attorney, Agent, or Firm* — K&L Gates LLP

(57) ABSTRACT

The present disclosure relates to compositions and methods for modulating gene expression and in particular to compositions and methods for increasing expression of Klotho. In certain examples, the present disclosure provides a method of increasing expression of a Klotho gene in a cell the method comprising administering to the cell a binding molecule that binds to an RNA transcript transcribed from a chromosomal region within or near the Klotho gene, wherein the RNA transcript does not encode a Klotho protein.

18 Claims, 9 Drawing Sheets

Specification includes a Sequence Listing.

(56) References Cited

OTHER PUBLICATIONS

Bloch et al., "Klotho is a substrate for 60 -, β- and γ-secretase", Sep. 2009, pp. 3221-3224.
Chen et al., "Insulin stimulates the cleavage and release of the extracellular domain of Klotho by ADAM10 and ADAM17", Dec. 2007, pp. 19796-19801, vol. 104, No. 50.
Chen et al., "Activation of the anti-aging and cognition-enhancing gene Klotho by CRISPR-dCasp transcriptional effector complex", Feb. 2018, pp. 1-16.
Chien et al., "Novel cationic cardiolipin analogue-based liposome for efficient DNA and small interfering RNA delivery in vitro and in vivo", 2005, pp. 321-328.
Choi et al., "Transcriptional activation of the human Klotho gene by epidermal growth factor in HEK293 cells; role of Egr-1", 2010, pp. 121-127.
Connelly et al., "The Emerging Role of RNA as a Therapeutic Target for Small Molecules", 2016, pp. 1077-1090.
Core et al., "Nascent RNA Sequencing Reveals Widespread Pausing and Divergent Initiation at Human Promoters", Dec. 2008, pp. 1-9.
Dubal et al., "Life Extension Factor Klotho Enhances Cognition", May 2014, pp. 1065-1076.
Dubal et al., "Life Extension Factor Klotho Prevents Mortality and Enhances Cognition in hAPP Transgenic Mice", Feb. 2015, pp. 2358-2371.
Finkel et al., "Treatment of infantile-onset spinal muscular atrophy with nusinersen: a phase 2, open-label, dose-escalation study", Dec. 2016, pp. 3017-3026, vol. 388.
Furuno et al., "Role of Different Proteolytic Systems in the Degradation of Muscle Proteins during Denervation Atrophy", 1990, pp. 8550-8557, vol. 265, No. 15.
Gassmann et al., "Maintenance of an extrachromosomal plasmid vector in mouse embryonic stem cells", Feb. 1995, pp. 1292-1296, vol. 92.
Katayama et al., "Antisense Transcription in the Mammalian Transciptome", Sep. 2005, pp. 1564-1567, vol. 309.
Kim et al., "Local and systemic delivery of VEGF siRNA using polyelectrolyte complex micelles for effective treatment of cancer", 2008, pp. 107-116.
Liu, "Radiolabeled Multimeric Cyclic RGD Peptides as Integrin αvβ3 Targeted Radiotracers for Tumor Imaging", Apr. 2006, pp. 472-487, vol. 3. No. 5.
Masso et al., "Secreted and Transmembrane αKlotho Isoforms Have Different Spatio-Temporal Profiles in the Brain during Aging and Alzheimer's Diseas Progression", 2015, pp. 1-15.
Masuda et al., "Regulation of multiple ageing-like phenotypes by inducible klotho gene expression in klotho mutant mice", 2005, pp. 1274-1283.
Matsumura et al., "Identification of the Human Klotho Gene and Its Two Transcripts Encoding Membrane and Secreted Klotho Protein", 1998, pp. 626-630, vol. 242, No. 3.
Modarresi et al., "Knockdown of BACE1-AS Nonprotein-Coding Transcript Modulates Beta-Amyloid-Related Hippocampal Neurogenesis", 2011, pp. 1-11, vol. 2011.
Pal et al., "Systemic delivery of RafsiRNA using cationic cardiolipin liposomes silences Raf-1 expression and inhibits tumor growth in xenograft model of human prostate cancer", 2005, pp. 1087-1091.
Rusk, "AntagoNATs boost gene expression", May 2012, p. 437, vol. 9, No. 5.
Seila et al., "Divergent transcription from active promoters", Dec. 2008, pp. 1-9.
Shearwin et al., "Transcriptional interference—a crash course", Jun. 2005, pp. 1-13.
Sorensen et al., "Gene Silencing by Systemic Delivery of Synthetic siRNAs in Adult Mice", 2003, pp. 761-766.
Soutschek et al., "Therapeutic silencing of an endogenous gene by systemic administration of modified siRNAs", Nov. 2004, pp. 173-178, vol. 432.
Sun et al., "Evidence for a preferential targeting of 3'-UTRs by cis-encoded natural antisense transcripts", 2005, pp. 5533-5543, vol. 33, No. 17.
Tomalia et al., "Dendrimers as multi-purpose nanodevices for oncology drug delivery and diagnostic imaging", 2007, pp. 61-67, vol. 35, part 1.
Verma et al., "Small Interfering RNAs Directed against β-Catenin Inhibit the in Vitro and in Vivo Growth of Colon Cancer Cells", Apr. 2003, pp. 1291-1300, vol. 9.
Vo et al., "Klotho, the Key to Healthy Brain Aging?", 2018, pp. 183-194.
Zeldich et al., "The Anti-Aging Protein Klotho Enhances Remyelination Following Cuprizone-Induced Demyelination", 2015, pp. 185-196.
Zeng et al., "Organic small hairpin RNAs (OshR): a Do-It-Yourself platform for transgene-based gene silencing", Sep. 2013, pp. 1-19.
Zimmermann et al., "RNAi-mediated gene silencing in non-human primates", May 2006, pp. 111-114, vol. 441.

* cited by examiner

INCREASING GENE EXPRESSION

RELATED APPLICATIONS

This application claims the benefit of U.S. Provisional Application No. 62/770,336 filed Nov. 21, 2018; U.S. Provisional Application No. 62/827,471 filed Apr. 1, 2019; and U.S. Provisional Application No. 62/860,407 filed Jun. 12, 2019, all of which are incorporated herein in their entirety by reference.

STATEMENT REGARDING FEDERALLY FUNDED RESEARCH

This invention was made with Government support under contract No. 5R44 AG053084 awarded by the National Institutes of Health. The government has certain rights in the invention.

FIELD OF THE DISCLOSURE

The present disclosure relates to compositions and methods for modulating gene expression and in particular to compositions and methods for increasing expression of Klotho.

INCORPORATION BY REFERENCE OF SEQUENCE LISTING

This application contains a Sequence Listing in computer readable form (filename: 210095PCTUS Sequence Listing: 145,037 bytes—ASCII text file: created May 16, 2024), which is incorporated by reference in its entirety and forms part of the disclosure.

BACKGROUND OF THE DISCLOSURE

Any discussion of the prior art throughout the specification should in no way be considered as an admission that such prior art is widely known or forms part of the common general knowledge in the field.

The single copy gene Klotho plays important roles in ageing, cognition, anti-oxidative stress, neurological protection and development, and kidney health. Klotho is a Type I transmembrane protein which is mainly expressed in the brain, kidney and reproductive organs (Masuda et al., 2005. Mech. Ageing Dev. 126(21): 1274-1283). It is also shed by proteolytic cleavage resulting in a soluble form that is detectable in serum and cerebrospinal fluid (CSF) (Bloch et al., 2009. *FEBS Lett.* 583(19): 3221-3224; Chen et al., 2007. *Proc. Natl Acad. Sci. USA.* 104(50): 19796-19801; Matsumura et al., 1998. *Biochem. Biophys. Res. Commun.* 242(3): 626-630). A third form of Klotho, found mainly in the brain, results from differential mRNA splicing and is secreted from the cell into the blood and CSF (Masso et al., 2015. *PLoS One.* 10(11): e0143623). Both the transmembrane and soluble forms of Klotho have important functions in many homeostatic processes.

Klotho promotes oligodendrocyte maturation, and it protects neurons from oxidative stress by increasing expression of antioxidant factors. It also induces re-myelination in vivo in the cuprizone-induced demyelination model of multiple sclerosis (Zeldich et al., 2015. *J. Mol. Neurosci.* 57(2): 185-196). Studies have shown that Klotho overexpression reduces cognitive deficits in a mouse model of Alzheimer's disease, and that it enhances cognition in humans and mice (Dubal et al., 2014. Cell Rep. 7(4): 1065-1076; Dubal et al., 2015. *Off. J. Socr. Neuroscience.* 35(6): 2358-2371).

In this context, there is a need for compositions and methods for modulating Klotho activity.

SUMMARY OF THE DISCLOSURE

The present disclosure relates to compositions and methods for modulating gene expression and in particular to compositions and methods for increasing expression of Klotho. In work leading to the present disclosure, the inventors have identified RNA transcripts transcribed from chromosomal regions within or near the Klotho gene which suppress expression of the Klotho gene. By developing binding molecules in the form of nucleic acids which bind to the RNA transcripts, the inventors successfully increased expression of Klotho.

In one aspect, the present disclosure provides a method of increasing expression of a Klotho gene in a cell the method comprising administering to the cell a binding molecule that binds to an RNA transcript transcribed from a chromosomal region within or near the Klotho gene, wherein the RNA transcript does not encode a Klotho protein.

In some examples, the binding molecule is a nucleic acid comprising a sequence that is substantially complementary to the RNA transcript.

The chromosomal region may comprise a region of at least 200 nucleotides upstream of the Klotho gene translation start site. In some examples, the chromosomal region comprises the region between 302 nucleotides and 551 nucleotides upstream of the Klotho gene translation start site. In certain examples, the chromosomal region comprises the region between 106 nucleotides and 685 nucleotides upstream of the Klotho gene translation start site. In some examples, the chromosomal region comprises the sequence set forth in SEQ ID NO. 5 or a sequence having at least about 90% identity to SEQ ID NO. 5. In certain examples, the chromosomal region comprises the sequence set forth in SEQ ID NO. 8 or a sequence having at least about 90% identity to SEQ ID NO. 8.

The RNA transcript may comprise the sequence set forth in SEQ ID NO. 6 or a sequence having at least about 90% identity to SEQ ID NO. 6. In some examples, the RNA transcript comprises the sequence set forth in SEQ ID NO. 9 or a sequence having at least about 90% identity to SEQ ID NO. 9.

The nucleic acid may comprise at least 15 contiguous nucleotides which are substantially complementary to a nucleotide sequence set forth in SEQ ID NO. 3. In some examples, the nucleic acid comprises at least 15 contiguous nucleotides which are substantially complementary to a nucleotide sequence set forth in SEQ ID NO. 9. In certain examples, the nucleic acid comprises at least 15 contiguous nucleotides differing by no more than 3 nucleotides from a nucleotide sequence set forth in SEQ ID NO. 10. In some examples, the nucleic acid comprises at least 15 contiguous nucleotides which are at least about 90% identical to a nucleotide sequence set forth in SEQ ID NO. 10.

The nucleic acid may comprise a sequence that is at least about 90% identical to the sequence set forth in SEQ ID NO. 21, SEQ ID NO. 23, SEQ ID NO. 25, SEQ ID NO. 27 or SEQ ID NO. 29. In certain examples, the nucleic acid comprises a sequence that is at least about 90% identical to the sequence set forth in SEQ ID NO. 21, SEQ ID NO. 23 or SEQ ID NO. 27.

In certain examples, the RNA transcript is a sense RNA transcript.

In certain examples, the chromosomal region comprises the region between 183 nucleotides and 2,662 nucleotides upstream of the Klotho gene translation start site. In certain examples, the chromosomal region comprises the sequence set forth in SEQ ID NO. 53 or a sequence having at least about 90% identity to SEQ ID NO. 53.

In certain examples, the RNA transcript comprises the sequence set forth in SEQ ID NO. 51 or a sequence having at least about 90% identity to SEQ ID NO. 51.

In certain examples, the nucleic acid comprises at least 15 contiguous nucleotides which are substantially complementary to a nucleotide sequence set forth in SEQ ID NO. 51. In certain examples, the nucleic acid comprises at least 15 contiguous nucleotides differing by no more than 3 nucleotides from a nucleotide sequence set forth in SEQ ID NO. 52. In certain examples, the nucleic acid comprises at least 15 contiguous nucleotides which are at least about 90% identical to a nucleotide sequence set forth in SEQ ID NO. 52.

In certain examples, the chromosomal region comprises the region between 3,133 nucleotides upstream of the Klotho gene translation start site and 412 nucleotides downstream of the Klotho gene translation start site. In certain examples, the chromosomal region comprises the sequence set forth in SEQ ID NO. 50 or a sequence having at least about 90% identity to SEQ ID NO. 50.

In certain examples, the RNA transcript comprises the sequence set forth in SEQ ID NO. 48 or a sequence having at least about 90% identity to SEQ ID NO. 48.

In certain examples, the nucleic acid comprises at least 15 contiguous nucleotides which are substantially complementary to a nucleotide sequence set forth in SEQ ID NO. 48. In certain examples, the nucleic acid comprises at least 15 contiguous nucleotides differing by no more than 3 nucleotides from a nucleotide sequence set forth in SEQ ID NO. 49. In certain examples, the nucleic acid comprises at least 15 contiguous nucleotides which are at least about 90% identical to a nucleotide sequence set forth in SEQ ID NO. 49.

In certain examples, the nucleic acid comprises a sequence that is at least about 90% identical to the sequence set forth in SEQ ID NO. 54, SEQ ID NO. 55, SEQ ID NO. 56, SEQ ID NO. 57 or SEQ ID NO. 58. In certain examples, the nucleic acid comprises a sequence that is at least about 90% identical to the sequence set forth in SEQ ID NO. 56, SEQ ID NO. 57 or SEQ ID NO. 58.

In some examples, the chromosomal region comprises the region between 32 nucleotides upstream of the Klotho gene translation stop site and 457 nucleotides downstream of the Klotho gene translation stop site. The chromosomal region may comprise the region between 267 nucleotides upstream of the Klotho gene translation stop site and 517 nucleotides downstream of the Klotho gene translation stop site. In certain examples, the chromosomal region comprises the sequence set forth in SEQ ID NO. 14 or a sequence having at least about 90% identity to SEQ ID NO. 14. In some examples, the chromosomal region comprises the sequence set forth in SEQ ID NO. 17 or a sequence having at least about 90% identity to SEQ ID NO. 17.

The RNA transcript may comprise the sequence set forth in SEQ ID NO. 16 or a sequence having at least about 90% identity to SEQ ID NO. 16. In some examples, the RNA transcript comprises the sequence set forth in SEQ ID NO. 19 or a sequence having at least about 90% identity to SEQ ID NO. 19.

In certain examples, the nucleic acid comprises at least 15 contiguous nucleotides which are substantially complementary to a nucleotide sequence set forth in SEQ ID NO. 19. The nucleic acid may comprise at least 15 contiguous nucleotides differing by no more than 3 nucleotides from a nucleotide sequence set forth in SEQ ID NO. 18. In some examples, the nucleic acid comprises at least 15 contiguous nucleotides which are at least about 90% identical to a nucleotide sequence set forth in SEQ ID NO. 18.

In some examples, the nucleic acid comprises a sequence that is at least about 90% identical to the sequence set forth in SEQ ID NO. 31, SEQ ID NO. 33 or SEQ ID NO. 35. For example, the nucleic acid may comprise a sequence that is at least about 90% identical to the sequence set forth in SEQ ID NO. 35.

In some examples, the RNA transcript is an antisense RNA transcript.

In some examples, the nucleic acid is between 15 and 50 nucleotides in length. The nucleic acid may be a ribonucleic acid (RNA). In certain examples, the nucleic acid is a siRNA or a nucleic acid encoding a siRNA. The siRNA may be conjugated to N-acetylgalactosamine.

In some examples, the method comprises administering to the cell two nucleic acids wherein each nucleic acid is independently selected from the nucleic acids defined herein.

In some examples, the cell is a human cell.

In another aspect, the present disclosure provides a method of treating cancer in a subject the method comprising administering to the subject a therapeutically effective amount of a binding molecule that binds to an RNA transcript transcribed from a chromosomal region within or near the Klotho gene, wherein the RNA transcript does not encode a Klotho protein, and wherein administration of the binding molecule increases expression of the Klotho gene in the subject. The cancer may be selected from the group consisting of colon cancer, prostate cancer, lung cancer, cervical cancer, pancreatic cancer, ovarian cancer and breast cancer.

In another aspect, the present disclosure provides a method of treating a muscle disorder in a subject the method comprising administering to the subject a therapeutically effective amount of a binding molecule that binds to an RNA transcript transcribed from a chromosomal region within or near the Klotho gene, wherein the RNA transcript does not encode a Klotho protein, and wherein administration of the binding molecule increases expression of the Klotho gene in the subject. The muscle disorder may be selected from the group consisting of muscle atrophy and muscular dystrophy such as duchene muscular dystrophy.

In another aspect, the present disclosure provides a method of treating a kidney disorder in a subject the method comprising administering to the subject a therapeutically effective amount of a binding molecule that binds to an RNA transcript transcribed from a chromosomal region within or near the Klotho gene, wherein the RNA transcript does not encode a Klotho protein, and wherein administration of the binding molecule increases expression of the Klotho gene in the subject. The kidney disorder may be selected from the group consisting of renal dysfunction, acute kidney injury and kidney disease such as chronic kidney disease.

In another aspect, the present disclosure provides a method of enhancing cognition in a subject the method comprising administering to the subject a therapeutically effective amount of a binding molecule that binds to an RNA transcript transcribed from a chromosomal region within or near the Klotho gene, wherein the RNA transcript does not encode a Klotho protein, and wherein administration of the binding molecule increases expression of the Klotho gene in the subject.

In another aspect, the present disclosure provides a method of treating a neurological disorder in a subject the method comprising administering to the subject a therapeutically effective amount of a binding molecule that binds to an RNA transcript transcribed from a chromosomal region within or near the Klotho gene, wherein the RNA transcript does not encode a Klotho protein, and wherein administration of the binding molecule increases expression of the Klotho gene in the subject. The neurological disorder may be selected from the group consisting of memory loss, stress, biopolar disorder, epilepsy, dementia, Alzheimer's disease, Parkinson's disease, Huntington's disease, Creutzfeldt-Jakob disease, ataxia telangiectasia, craniocerebral trauma, amyotrophic lateral sclerosis, depression, schizophrenia, multiple sclerosis, myelin-related disease, oxidative stress and neurodegeneration.

In some examples, the binding molecule is a nucleic acid comprising a sequence that is substantially complementary to the RNA transcript.

The chromosomal region may comprise a region of at least 200 nucleotides upstream of the Klotho gene translation start site. In some examples, the chromosomal region comprises the region between 302 nucleotides and 551 nucleotides upstream of the Klotho gene translation start site. In certain examples, the chromosomal region comprises the region between 106 nucleotides and 685 nucleotides upstream of the Klotho gene translation start site. In some examples, the chromosomal region comprises the sequence set forth in SEQ ID NO. 5 or a sequence having at least about 90% identity to SEQ ID NO. 5. In certain examples, the chromosomal region comprises the sequence set forth in SEQ ID NO. 8 or a sequence having at least about 90% identity to SEQ ID NO. 8.

The RNA transcript may comprise the sequence set forth in SEQ ID NO. 6 or a sequence having at least about 90% identity to SEQ ID NO. 6. In some examples, the RNA transcript comprises the sequence set forth in SEQ ID NO. 9 or a sequence having at least about 90% identity to SEQ ID NO. 9.

The nucleic acid may comprise at least 15 contiguous nucleotides which are substantially complementary to a nucleotide sequence set forth in SEQ ID NO. 3. In some examples, the nucleic acid comprises at least 15 contiguous nucleotides which are substantially complementary to a nucleotide sequence set forth in SEQ ID NO. 9. In certain examples, the nucleic acid comprises at least 15 contiguous nucleotides differing by no more than 3 nucleotides from a nucleotide sequence set forth in SEQ ID NO. 10. In some examples, the nucleic acid comprises at least 15 contiguous nucleotides which are at least about 90% identical to a nucleotide sequence set forth in SEQ ID NO. 10.

The nucleic acid may comprise a sequence that is at least about 90% identical to the sequence set forth in SEQ ID NO. 21, SEQ ID NO. 23, SEQ ID NO. 25, SEQ ID NO. 27 or SEQ ID NO. 29. In certain examples, the nucleic acid comprises a sequence that is at least about 90% identical to the sequence set forth in SEQ ID NO. 21, SEQ ID NO. 23 or SEQ ID NO. 27.

In certain examples, the RNA transcript is a sense RNA transcript.

In certain examples, the chromosomal region comprises the region between 183 nucleotides and 2,662 nucleotides upstream of the Klotho gene translation start site. In certain examples, the chromosomal region comprises the sequence set forth in SEQ ID NO. 53 or a sequence having at least about 90% identity to SEQ ID NO. 53.

In certain examples, the RNA transcript comprises the sequence set forth in SEQ ID NO. 51 or a sequence having at least about 90% identity to SEQ ID NO. 51.

In certain examples, the nucleic acid comprises at least 15 contiguous nucleotides which are substantially complementary to a nucleotide sequence set forth in SEQ ID NO. 51. In certain examples, the nucleic acid comprises at least 15 contiguous nucleotides differing by no more than 3 nucleotides from a nucleotide sequence set forth in SEQ ID NO. 52. In certain examples, the nucleic acid comprises at least 15 contiguous nucleotides which are at least about 90% identical to a nucleotide sequence set forth in SEQ ID NO. 52.

In certain examples, the chromosomal region comprises the region between 3,133 nucleotides upstream of the Klotho gene translation start site and 412 nucleotides downstream of the Klotho gene translation start site. In certain examples, the chromosomal region comprises the sequence set forth in SEQ ID NO. 50 or a sequence having at least about 90% identity to SEQ ID NO. 50.

In certain examples, the RNA transcript comprises the sequence set forth in SEQ ID NO. 48 or a sequence having at least about 90% identity to SEQ ID NO. 48.

In certain examples, the nucleic acid comprises at least 15 contiguous nucleotides which are substantially complementary to a nucleotide sequence set forth in SEQ ID NO. 48. In certain examples, the nucleic acid comprises at least 15 contiguous nucleotides differing by no more than 3 nucleotides from a nucleotide sequence set forth in SEQ ID NO. 49. In certain examples, the nucleic acid comprises at least 15 contiguous nucleotides which are at least about 90% identical to a nucleotide sequence set forth in SEQ ID NO. 49.

In certain examples, the nucleic acid comprises a sequence that is at least about 90% identical to the sequence set forth in SEQ ID NO. 54, SEQ ID NO. 55, SEQ ID NO. 56, SEQ ID NO. 57 or SEQ ID NO. 58. In certain examples, the nucleic acid comprises a sequence that is at least about 90% identical to the sequence set forth in SEQ ID NO. 56, SEQ ID NO. 57 or SEQ ID NO. 58.

In some examples, the chromosomal region comprises the region between 32 nucleotides upstream of the Klotho gene translation stop site and 457 nucleotides downstream of the Klotho gene translation stop site. The chromosomal region may comprise the region between 267 nucleotides upstream of the Klotho gene translation stop site and 517 nucleotides downstream of the Klotho gene translation stop site. In certain examples, the chromosomal region comprises the sequence set forth in SEQ ID NO. 14 or a sequence having at least about 90% identity to SEQ ID NO. 14. In some examples, the chromosomal region comprises the sequence set forth in SEQ ID NO. 17 or a sequence having at least about 90% identity to SEQ ID NO. 17.

The RNA transcript may comprise the sequence set forth in SEQ ID NO. 16 or a sequence having at least about 90% identity to SEQ ID NO. 16. In some examples, the RNA transcript comprises the sequence set forth in SEQ ID NO. 19 or a sequence having at least about 90% identity to SEQ ID NO. 19.

In certain examples, the nucleic acid comprises at least 15 contiguous nucleotides which are substantially complementary to a nucleotide sequence set forth in SEQ ID NO. 19. The nucleic acid may comprise at least 15 contiguous nucleotides differing by no more than 3 nucleotides from a nucleotide sequence set forth in SEQ ID NO. 18. In some examples, the nucleic acid comprises at least 15 contiguous nucleotides which are at least about 90% identical to a nucleotide sequence set forth in SEQ ID NO. 18.

In some examples, the nucleic acid comprises a sequence that is at least about 90% identical to the sequence set forth in SEQ ID NO. 31, SEQ ID NO. 33 or SEQ ID NO. 35. For example, the nucleic acid may comprise a sequence that is at least about 90% identical to the sequence set forth in SEQ ID NO. 35.

In some examples, the RNA transcript is an antisense RNA transcript.

In some examples, the nucleic acid is between 15 and 50 nucleotides in length. The nucleic acid may be RNA. In certain examples, the nucleic acid is a siRNA or a nucleic acid encoding a siRNA. The siRNA may be conjugated to N-acetylgalactosamine.

In some examples, the method comprises administering to the subject two nucleic acids wherein each nucleic acid is independently selected from the nucleic acids defined herein.

In some examples, the subject is a human.

In another aspect, the present disclosure provides an isolated or recombinant nucleic acid molecule as defined herein.

In another aspect, the present disclosure provides a vector comprising a nucleic acid molecule as defined herein.

In another aspect, the present disclosure provides use of a binding molecule that binds to an RNA transcript transcribed from a chromosomal region within or near a Klotho gene in the manufacture of a medicament for increasing expression of the Klotho gene in a cell, wherein the RNA transcript does not encode a Klotho protein.

In another aspect, the present disclosure provides use of a binding molecule that binds to an RNA transcript transcribed from a chromosomal region within or near a Klotho gene in the manufacture of a medicament for the treatment of cancer in a subject, wherein the RNA transcript does not encode a Klotho protein, and wherein administration of the binding molecule increases expression of the Klotho gene in the subject.

In another aspect, the present disclosure provides use of a binding molecule that binds to an RNA transcript transcribed from a chromosomal region within or near a Klotho gene in the manufacture of a medicament for the treatment of a muscle disorder in a subject, wherein the RNA transcript does not encode a Klotho protein, and wherein administration of the binding molecule increases expression of the Klotho gene in the subject.

In another aspect, the present disclosure provides use of a binding molecule that binds to an RNA transcript transcribed from a chromosomal region within or near a Klotho gene in the manufacture of a medicament for the treatment of a kidney disorder in a subject, wherein the RNA transcript does not encode a Klotho protein, and wherein administration of the binding molecule increases expression of the Klotho gene in the subject.

In another aspect, the present disclosure provides use of a binding molecule that binds to an RNA transcript transcribed from a chromosomal region within or near a Klotho gene in the manufacture of a medicament for enhancing cognition in a subject, wherein the RNA transcript does not encode a Klotho protein, and wherein administration of the binding molecule increases expression of the Klotho gene in the subject.

In another aspect, the present disclosure provides use of a binding molecule that binds to an RNA transcript transcribed from a chromosomal region within or near a Klotho gene in the manufacture of a medicament for the treatment of a neurological disorder in a subject, wherein the RNA transcript does not encode a Klotho protein, and wherein administration of the binding molecule increases expression of the Klotho gene in the subject.

DETAILED DESCRIPTION

Definitions

Figure 1:
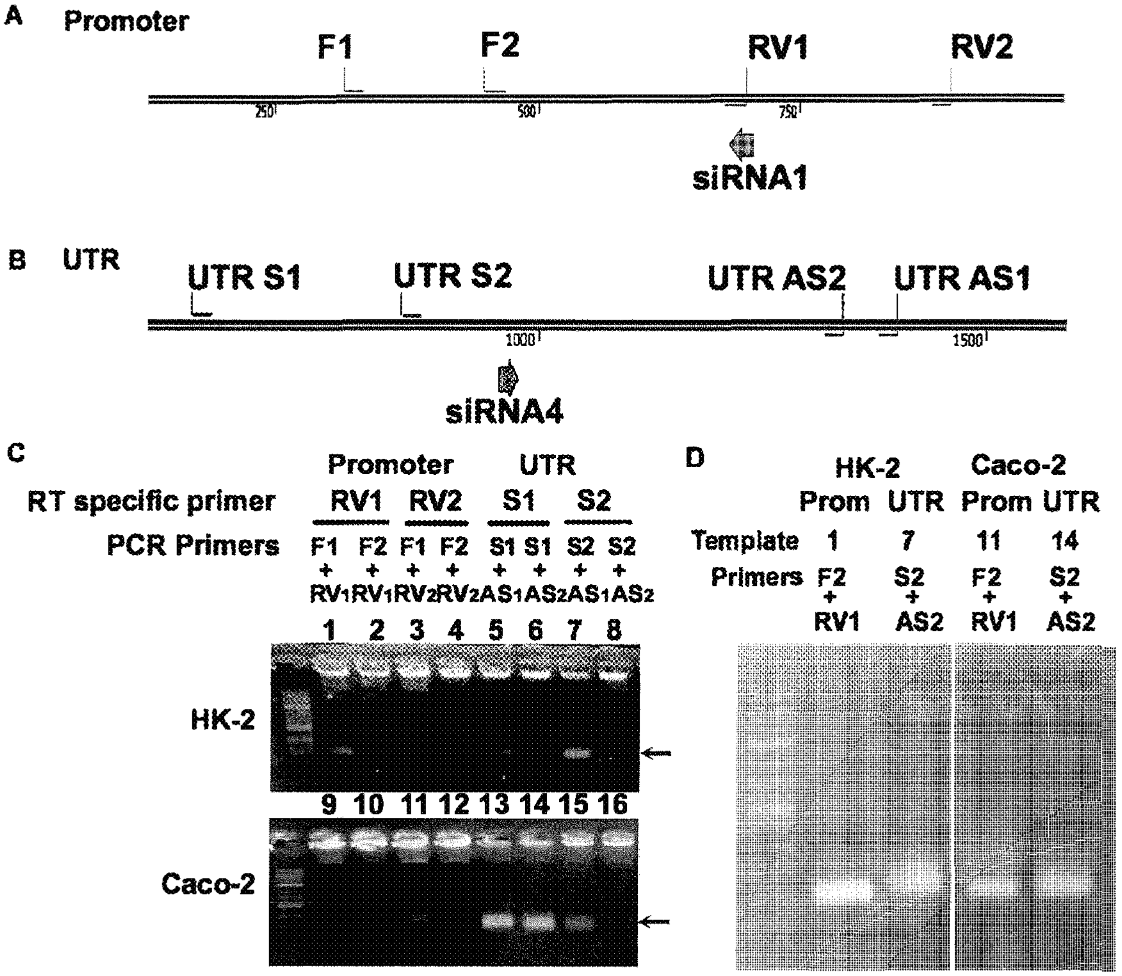
FIG. 1: A) Relative position of primers and siRNA upstream of the Klotho translation start site. B) Relative position of primers and siRNA in the Klotho 3' untranslated region (3'UTR). C) Gel electrophoresis of PCR products obtained using RV1 and RV2 for 1st strand cDNA synthesis (upstream region), or S1 and S1 for 1st strand cDNA synthesis (downstream region). D) Second PCR as confirmation using internal Klotho-specific primers.

In the context of this specification, the terms "a" and "an" are used herein to refer to one or to more than one (ie, to at least one) of the grammatical object of the article. By way of example, "an element" means one element or more than one element.

The term "about" is understood to refer to a range of +/−10%, preferably +/−5% or +/−1% or, more preferably, +/−0.1%.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and preferably together in the same formulation.

The terms "comprise", "comprises", "comprised" or "comprising", "including" or "having" and the like in the present specification and claims are used in an inclusive sense, ie, to specify the presence of the stated features but not preclude the presence of additional or further features.

The term "substantially complementary" when used to describe a first nucleotide sequence in relation to a second nucleotide sequence, refers to the ability of a nucleic acid (eg, oligonucleotide or siRNA) comprising the first nucleotide sequence to hybridize to, and form a duplex structure with, an oligonucleotide or polynucleotide comprising the second nucleotide sequence. It will be understood that the sequence of a nucleic acid need not be 100% complementary to that of its target. Conditions under which hybridisation occurs may be stringent, such as 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can also apply. Substantial complementarity allows the relevant function of the nucleic acid to proceed, eg, direct RNAi. The skilled person will be able to determine the set of conditions most appropriate for a test of complementarity of two sequences in accordance with the ultimate application of the hybridized nucleotides.

The term "identity" refers to a relationship between the sequences of two or more polypeptide molecules or two or more nucleic acid molecules, as determined by aligning and comparing the sequences. The percent identity between two sequences is a function of the number of identical positions shared by the sequences when the sequences are optimally aligned (ie, % homology=# of identical positions/total # of positions×100), with optimal alignment determined taking into account the number of gaps, and the length of each gap, which need to be introduced for optimal alignment of the two sequences. The comparison of sequences and determination of percent identity between two sequences can be accomplished using a mathematical algorithm.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4: 11-17 (1989)) which has been incorporated into the ALIGN program, using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The term "isolated" as used herein refers to material that is substantially or essentially free from components that normally accompany it in its native state. For example, an "isolated polynucleotide" as used herein refers to a polynucleotide which has been purified from the sequences which flank it in a naturally-occurring state, eg, a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell, ie, it is not associated with in vivo substances.

The term "operably connected" or "operably linked" as used herein refers to the functional relationship between two or more nucleic acid segments such as a gene and a regulatory element including but not limited to a promoter, which then regulates the expression of the gene.

The term "pharmaceutically acceptable" as used herein refers to substances that do not cause substantial adverse allergic or immunological reactions when administered to a subject. A "pharmaceutically acceptable carrier" includes, but is not limited to, solvents, coatings, dispersion agents, wetting agents, isotonic and absorption delaying agents and disintegrants.

The term "polynucleotide variant" refers to polynucleotides displaying substantial sequence identity with a reference polynucleotide sequence or polynucleotides that hybridize with a reference sequence under stringent conditions. The term also encompasses polynucleotides that are distinguished from a reference polynucleotide by the addition, deletion or substitution of at least one nucleotide. Accordingly, the term "polynucleotide variant" includes polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. The term "polynucleotide variant" also includes naturally occurring allelic variants. The terms "peptide variant" and "polypeptide variant" and the like refer to peptides and polypeptides that are distinguished from a reference peptide or polypeptide by the addition, deletion or substitution of at least one amino acid residue. In certain examples, a peptide or polypeptide variant is distinguished from a reference peptide or polypeptide by one or more substitutions, which may be conservative or non-conservative. In certain examples, the peptide or polypeptide variant comprises conservative substitutions and, in this regard, it is well understood in the art that some amino acids may be changed to others with broadly similar properties without changing the nature of the activity of the peptide or polypeptide. Peptide and polypeptide variants also encompass peptides and polypeptides in which one or more amino acids have been added or deleted, or replaced with different amino acid residues.

"Prevention" includes reduction of risk, incidence and/or severity of a condition or disorder. The terms "treatment" and "treat" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a pathologic condition or disorder; and treatment of patients at risk of contracting a disease or suspected to have contracted a disease, as well as patients who are ill or have been diagnosed as suffering from a disease or medical condition. The terms "treatment" and "treat" do not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment" and "treat" are also intended to include the potentiation or otherwise enhancement of one or more primary prophylactic or therapeutic measures. As non-limiting examples, a treatment can be performed by a patient, a caregiver, a doctor, a nurse, or another healthcare professional.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

The term "recombinant polypeptide" as used herein refers to a polypeptide made using recombinant techniques, ie, through the expression of a recombinant polynucleotide.

The terms "RNA interference agent" and "RNAi agent" refer to an agent that contains RNA and which mediates the targeted degradation of an RNA transcript via an RNA-induced silencing complex (RISC) pathway. The RNAi agent directs the sequence-specific degradation of target RNA (eg, a noncoding RNA transcript transcribed from a region within or near Klotho) through a process known as RNA interference (RNAi).

Without wishing to be bound by theory it is believed that long double stranded RNA introduced into cells is broken down into small interfering RNA (siRNA) by a Type III endonuclease known as Dicer (Sharp et al. 2001. Genes Dev. 15:485). Dicer, a ribonuclease III-like enzyme, processes the dsRNA into approximately 19 to 23 base pair siRNAs with two-base 3' overhangs (Bernstein, et al. 2001. Nature 409: 363), although that length and the extent of any 3' overhangs can vary. The siRNAs are then incorporated into a RISC where one or more helicases unwind the siRNA duplex, enabling one strand to guide target recognition (Nykanen, et al. 2001. Cell 107:309). Upon binding to the appropriate target RNA, the RISC can degrade the target and/or inhibit its translation to induce silencing (Elbashir, et al. 2001. Genes Dev. 15: 188).

Each siRNA typically comprises a guide strand and a complementary or substantially complementary passenger strand. The guide strand typically complexes with RNAi machinery and hybridises to a target nucleic acid such as an mRNA which is subsequently degraded.

A "therapeutically effective amount" is at least the minimum concentration or amount required to effect a measurable improvement of a particular disease or condition. A therapeutically effective amount herein may vary according to factors such as the disease state, age, sex and weight of the patient. A therapeutically effective amount is also one in which any toxic or detrimental effects are outweighed by the therapeutically beneficial effects.

Nucleic Acid Sequences

A human Klotho mRNA sequence is set forth below, with the translation start codon and translation stop codon in bold and underlined.

(SEQ ID NO. 1)

CGCGCAGCAUGCCCGCCAGCGCCCCGCCGCGCCGCC

CGCGGCCGCCGCCGCCGUCGCUGUCGCUGCUGCUG

GUGCUGCUGGGCCUGGGCGGCCGCCGCCUGCGUGC

GGAGCCGGGCGACGGCGCGCAGACCUGGGCCCGUU

UCUCGCGGCCUCCUGCCCCCGAGGCCGCGGGCCUC

UUCCAGGGCACCUUCCCCGACGGCUUCCUCUGGGC

CGUGGGCAGCGCCGCCUACCAGACCGAGGGCGGCU

GGCAGCAGCACGGCAAGGGUGCGUCCAUCUGGGAU

ACGUUCACCCACCACCCCCUGGCACCCCCGGGAGA

-continued

CUCCCGGAACGCCAGUCUGCCGUUGGGCGCCCCGU

CGCCGCUGCAGCCCGCCACCGGGGACGUAGCCAGC

GACAGCUACAACAACGUCUUCCGCGACACGGAGGC

GCUGCGCGAGCUCGGGGUCACUCACUACCGCUUCU

CCAUCUCGUGGGCGCGAGUGCUCCCCAAUGGCAGC

GCGGGCGUCCCCAACCGCGAGGGGCUGCGCUACUA

CCGGCGCCUGCUGGAGCGGCUGCGGGAGCUGGGCG

UGCAGCCCGUGGUCACCCUGUACCACUGGGACCUG

CCCCAGCGCCUGCAGGACGCCUACGGCGGCUGGGC

CAACCGCGCCCUGGCCGACCACUUCAGGGAUUACG

CGGAGCUCUGCUUCCGCCACUUCGGCGGUCAGGUC

AAGUACUGGAUCACCAUCGACAACCCCUACGUGGU

GGCCUGGCACGGCUACGCCACCGGGCGCCUGGCCC

CCGGCAUCCGGGGCAGCCCGCGGCUCGGGUACCUG

GUGGCGCACAACCUCCUCCUGGCUCAUGCCAAAGU

CUGGCAUCUCUACAAUACUUCUUUCCGUCCCACUC

AGGGAGGUCAGGUGUCCAUUGCCCUAAGCUCUCAC

UGGAUCAAUCCUCGAAGAAUGACCGACCACAGCAU

CAAAGAAUGUCAAAAAUCUCUGGACUUUGUACUAG

GUUGGUUUGCCAAACCCGUAUUUAUUGAUGGUGAC

UAUCCCGAGAGCAUGAAGAAUAACCUUUCAUCUAU

UCUGCCUGAUUUUACUGAAUCUGAGAAAAAGUUCA

UCAAAGGAACUGCUGACUUUUUUGCUCUUUGCUUU

GGACCCACCUUGAGUUUUCAACUUUUGGACCCUCA

CAUGAAGUUCCGCCAAUUGGAAUCUCCCAACCUGA

GGCAACUGCUUUCCUGGAUUGACCUUGAAUUUAAC

CAUCCUCAAAUAUUUAUUGUGGAAAAUGGCUGGUU

UGUCUCAGGGACCACCAAGAGAGAUGAUGCCAAAU

AUAUGUAUUACCUCAAAAAGUUCAUCAUGGAAACC

UUAAAAGCCAUCAAGCUGGAUGGGGUGGAUGUCAU

CGGGUAUACCGCAUGGUCCCUCAUGGAUGGUUUCG

AGUGGCACAGAGGUUACAGCAUCAGGCGUGGACUC

UUCUAUGUUGACUUUCUAAGCCAGGACAAGAUGUU

GUUGCCAAAGUCUUCAGCCUUGUUCUACCAAAAGC

UGAUAGAGAAAAAUGGCUUCCCUCCUUUACCUGAA

AAUCAGCCCCUAGAAGGGACAUUUCCCUGUGACUU

UGCUUGGGGAGUUGUUGACAACUACAUUCAAGUAG

AUACCACUCUGUCUCAGUUUACCGACCUGAAUGUU

UACCUGUGGGAUGUCCACCACAGUAAAAGGCUUAU

UAAAGUGGAUGGGGUUGUGACCAAGAAGAGGAAAU

CCUACUGUGUUGACUUUGCUGCCAUCCAGCCCCAG

-continued

AUCGCUUUACUCCAGGAAAUGCACGUUACACAUUU
UCGCUUCUCCCUGGACUGGGCCCUGAUUCUCCCUC
UGGGUAACCAGUCCCAGGUGAACCACACCAUCCUG
CAGUACUAUCGCUGCAUGGCCAGCGAGCUUGUCCG
UGUCAACAUCACCCCAGUGGUGGCCCUGUGGCAGC
CUAUGGCCCCGAACCAAGGACUGCCGCGCCUCCUG
GCCAGGCAGGGCGCCUGGGAGAACCCCUACACUGC
CCUGGCCUUUGCAGAGUAUGCCCGACUGUGCUUUC
AAGAGCUCGGCCAUCACGUCAAGCUUUGGAUAACG
AUGAAUGAGCCGUAUACAAGGAAUAUGACAUACAG
UGCUGGCCACAACCUUCUGAAGGCCCAUGCCCUGG
CUUGGCAUGUGUACAAUGAAAAGUUUAGGCAUGCU
CAGAAUGGGAAAAUAUCCAUAGCCUUGCAGGCUGA
UUGGAUAGAACCUGCCUGCCCUUUCUCCCAAAAGG
ACAAAGAGGUGGCCGAGAGAGUUUUGGAAUUUGAC
AUUGGCUGGCUGGCUGAGCCCAUUUUCGGCUCUGG
AGAUUAUCCAUGGGUGAUGAGGGACUGGCUGAACC
AAAGAAACAAUUUUCUUCUUCCUUAUUUCACUGAA
GAUGAAAAAAAGCUAAUCCAGGGUACCUUUGACUU
UUUGGCUUUAAGCCAUUAUACCACCAUCCUUGUAG
ACUCAGAAAAAGAAGAUCCAAUAAAAUACAAUGAU
UACCUAGAAGUGCAAGAAAUGACCGACAUCACGUG
GCUCAACUCCCCCAGUCAGGUGGCGGUAGUGCCCU
GGGGGUUGCGCAAAGUGCUGAACUGGCUGAAGUUC
AAGUACGGAGACCUCCCCAUGUACAUAAUAUCCAA
CGGAAUCGAUGACGGGCUGCAUGCUGAGGACGACC
AGCUGAGGGUGUAUUAUAUGCAGAAUUACAUAAAC
GAAGCUCUCAAAGCCCACAUACUGGAUGGUAUCAA
UCUUUGCGGAUACUUUGCUUAUUCGUUUAACGACC
GCACAGCUCCGAGGUUUGGCCUCUAUCGUUAUGCU
GCAGAUCAGUUUGAGCCCAAGGCAUCCAUGAAACA
UUACAGGAAAAUUAUUGACAGCAAUGGUUUCCCGG
GCCCAGAAACUCUGGAAAGAUUUUGUCCAGAAGAA
UUCACCGUGUGUACUGAGUGCAGUUUUUUUCACAC
CCGAAAGUCUUUACUGGCUUUCAUAGCUUUUCUAU
UUUUUGCUUCUAUUAUUUCUCUCUCCCUUAUAUUU
UACUACUCGAAGAAAGGCAGAAGAAGUUACAAAUA
GUUCUGAACAUUUUUCUAUUCAUUCAUUUUGAAAU
AAUUAUGCAGACACAUCAGCUGUUAACCAUUUGCA
CCUCUAAGUGUUGUGAAACUGUAAAUUUCAUACAU

-continued

UUGACUUCUAGAAAACAUUUUUGUGGCUUAUGACA
GAGGUUUUGAAAUGGGCAUAGGUGAUCGUAAAAUA
UUGAAUAAUGCGAAUAGUGCCUGAAUUUGUUCUCU
UUUUGGGUGAUUAAAAAACUGACAGGCACUAUAAU
UUCUGUAACACACUAACAAAAGCAUGAAAAAUAGG
AACCACACCAAUGCAACAUUUGUGCAGAAAUUUGA
AUGACAAGAUUAGGAAUAUUUUCUUCUGCACCCAC
UUCUAAAUUUAAUGUUUUUCUGGAAGUAGUAAUUG
CAAGAGUUCGAAUAGAAAGUUAUGUACCAAGUAAC
CAUUUCUCAGCUGCCAUAAUAAUGCCUAGUGGCUU
CCCCUCUGUCAAAUCUAGUUUCCUAUGGAAAAGAA
GAUGGCAGAUACAGGAGAGACGACAGAGGGUCCUA
GGCUGGAAUGUUCCUUUCGAAAGCAAUGCUUCUAU
CAAAUACUAGUAUUAAUUUAUGUAUCUGGUUAAUG
ACAUACUUGGAGAGCAAAUUAUGGAAAUGUGUAUU
UUAUAUGAUUUUUGAGGUCCUGUCUAAACCCUGUG
UCCCUGAGGGAUCUGUCUCACUGGCAUCUUGUUGA
GGGCCUUGCACAUAGGAAACUUUUGAUAAGUAUCU
GCGGAAAAACAAACAUGAAUCCUGUGAUAUUGGGC
UCUUCAGGAAGCAUAAAGCAAUUGUGAAAUACAGU
AUACCGCAGUGGCUCUAGGUGGAGGAAAGGAGGAA
AAAGUGCUUAUUAUGUGCAACAUUAUGAUUAAUCU
GAUUAUACACCAUUUUUGAGCAGAUCUUGGAAUGA
AUGACAUGACCUUUCCCUAGAGAAUAAGGAUGAAA
UAAUCACUCAUUCUAUGAACAGUGACACUACUUUC
UAUUCUUUAGCUGUACUGUAAUUUCUUUGAGUUGA
UAGUUUUACAAAUUCUUAAUAGGUUCAAAAGCAAU
CUGGUCUGAAUAACACUGGAUUUGUUUCUGUGAUC
UCUGAGGUCUAUUUUAUGUUUUUGCUGCUACUUCU
GUGGAAGUAGCUUUGAACUAGUUUUACUUUGAACU
UUCACGCUGAAACAUGCUAGUGAUAUCUAGAAAGG
GCUAAUUAGGUCUCAUCCUUUAAUGCCCCUUAAAU
AAGUCUUGCUGAUUUUCAGACAGGGAAGUCUCUCU
AUUACACUGGAGCUGUUUUAUAGAUAAGUCAAUAU
UGUAUCAGGCAAGAUAAACCAAUGUCAUAACAGGC
AUUGCCAACCUCACUGACACAGGGUCAUAGUGUAU
AAUAAUAUACUGUACUAUAUAAUAUAUCAUCUUUA
GAGGUAUGAUUUUUUCAUGAAAGAUAAGCUUUUGG
UAAUAUUCAUUUUAAAGUGGACUUAUUAAAAUUGG
AUGCUAGAGAAUCAAGUUUAUUUUAUGUAUAUAUU
UUUCUGAUUAUAAGAGUAAUAUAUGUUCAUUGUAA

-continued

AAAUUUUUAAAACACAGAAACUAUAUGCAAAGAAA

AAAUAAAAAUUAUCUAUAAUCUCAGAACCCAGAAA

UAGCCACUAUUAACAUUUCCUACGUAUUUUAUUUU

ACAUAGAUCAUAUUGUAUAUAGUUAGUAUCUUUAU

UAAUUUUUAUUAUGAAACUUUCCUUUGUCAUUAUU

AGUCUUCAAAAGCAUGAUUUUUAAUAGUUGUUGAG

-continued

UAUUCCACCACAGGAAUGUAUCACAACUUAACCGU

UCCCGUUUGUUAGACUAGUUUCUUAUUAAUGUUGA

UGAAUGUUGUUUAAAAAUAAUUUUGUUGCUACAUU

UACUUUAAUUUCCUUGACUGUAAAGAGAAGUAAUU

UUGCUCCUUGAUAAAGUAUUAUAUUAAUAAUAAAU

CUGCCUGCAACUUUUUGCCUUCUUUCAUAAUC

Other nucleic acid sequences relevant to the present disclosure are set forth in Table 1.

TABLE 1

| SEQ ID NO | Description | Sequence |
|---|---|---|
| 2 | 2,000 nt human genomic region immediately upstream of Klotho translation start site (−2,000 to −1) (sense) F1 RT primer underlined F2 RT primer double-underlined RV1 RT primer bold italics RV2 RT primer lower case | ACTGCTTTAAAATTTAAAAAATGCTGCTGGTCAAGTAAAAATA<br>GCAATAGATAAAATCTGCCCTGAGCAAACAGACCATACATCAA<br>TAAATGAATACTTAGCTTAAGCGATTTTCCATGAGACCCATGA<br>AGCATTTCTAATTGAAACTTAACAAGCTACAACCCAACAGACA<br>CTCCAATCTTCACTTCTAGAAGGGAAATGTGATACTCCATGTA<br>GACGTAGCTTTTTAAATTTAGCTGGAAGACAGCGTGACAGTGA<br>AGTTGTGTGCTGTAATTTTTTAAAATTGCTGAAGTGTCATGGT<br>TTGCTATTTCGTATTTATTGAAAAAATGTAAATGCTATATTTA<br>ACAGAATGGCAGTAACTCTGTTTCAATCTGAAGACTTAATCTT<br>ACTAATCATGGTAATATATGCTGGCTGGAGTTGGGAATATTTC<br>ATAAAATACTGGAATAAATTTGTGCTTATATTTCAGGGGAATT<br>AATAAAAGCACCTTCATCTGCAACATTTAAAATGTTATTGCCT<br>TTAAATTTGTATTAAATAATGCAGGGAGGATAGATCACTGGGG<br>GAGAATGGATGCACCTCTGTGAGGATCTTGGTCATTCAACACA<br>CGTGTACGGGTGAGGAAACTAAGGCACGACTTACTGGGTAGGG<br>AGGTAGGGATATTAGCAAGATCCTTCACTTGTCTGGGCTTTCT<br>GTCTTTGAGTCACCTTTGCGCAGTTTTTCACTGGACTTCACAA<br>GCCTCTGAGGCGGCAGGGCAGACAGGACATCCTTATTTTATAG<br>AGGAAAAAACTTAGGCTTACAGAGGTTTCCTGCCCCAAATCAC<br>AAAGGTGGAGCCTAGACCTTCTCAGTCTCCACCAACTGTATTT<br>CGGTTAGCCACAATCCTATCTACCCACATCCAAATGGACACCG<br>TGGCTCTGCAACTTCTGTCAAAAGGGCTCTTTGGCAACAGGAA<br>AAACGTCATGGCTCCATTGTATTGTAGAGGATGGGAATGGGTG<br>TTCCGGCTAAATTCTCCCTCCCCTTTCCCTCCACAGCTCAGAT<br>GGCAAATGTGCGACCCAGGGACCTCCCGCTCCAGCAGACCTGT<br>GCGCACAACTTTGCACAGATTACCTGCTAAGTCAGAGCCGAAA<br>GGTAACACAGATGCCAAAGGATAATAAAGGTGAATGAGATTTA<br>CTCAAAATTGGAAACTTGGTGTTTGGTTTTTCAGGAGAACAAT<br>CAACGACTGTGATTTGAAGTTCACCAGGGTATTCTGAGAGATC<br>TAATCAAAGATAGAGTGCTGGTTTGAAATTATTAAAAGGTAAC<br>AGTAAAAGGGAGAGCAAAACCCCAGTCCCAACGCAACCCATAA<br>ATCTACTTTGTCTTCCTCGAAAGAGGGGCGCGGGTGGGCGCGT<br>CTCCCCGCGAGCATCTCACCTAAGGGGGAATCCCTTTCAGCGC<br>ACGGCGAAGTTCCCCCTCGGCTGTCCCACCTGGCAGTCCCTCT<br>AGGATTTCGGCCAGTCCCTAATTGGCTCCAGCAATGTCCAGCC<br>GGAGCTTCTTTGGGCCTCCGAGTGGGAGAAAAGTGAGAGCAGG<br>TGCTTCCCCAGCGGCGCGCTCCGCTAGGGCCCGGCAGGATCCC<br>GCCCCCAAGTCGGGGAAAGTTGGTCGGCGCCTTTTCTCCCCGA<br>CGAAGCCGCTCCAGGGCTGCTCTCAGAGGACGCGCGGCAGGCA<br>***AAGAGAATGAACCTGAGCGTC***CACGAAACGTCCTGCACGGCTC<br>CCGGGAGCTGGGAGGAACAGGTGCCTTTCTCCGACGTCCGCGG<br>GCGACGCCTGCCGCACCTTGCCCGCTGCCGCGCCCCTCCCGGG<br>CACCCCTCGCCCTCGGCGCCCCTGCCCCCACCCCCAGTGCCAG<br>GGCGGAGGCAGTCCCGGCTCGCAGGTAattattgccagcggag<br>ccCGCCGGGGAGCGGGGGTGGGCGCGCCGGCGGTGGGCGGGCG<br>GGCGCGGCGGGGCGCGGGCATAAAGGGGCGCGGCGCGGGGCCC<br>CGGAGCCTGGCTCCCGCGCAGC |
| 3 | RNA sequence corresponding to 2,000 nt human genomic region immediately upstream of Klotho translation start site (sense) siRNA1 target sequence underlined | ACUGCUUUAAAAUUUAAAAAAUGCUGCUGGUCAAGUAAAAAUA<br>GCAAUAGAUAAAAUCUGCCCUGAGCAAACAGACCAUACAUCAA<br>UAAAUGAAUACUUAGCUUAAGCGAUUUUCCAUGAGACCCAUGA<br>AGCAUUUCUAAUUGAAACUUAACAAGCUACAACCCAACAGACA<br>CUCCAAUCUUCACUUCUAGAAGGGAAAUGUGAUACUCCAUGUA<br>GACGUAGCUUUUUAAAUUUAGCUGGAAGACAGCGUGACAGUGA<br>AGUUGUGUGCUGUAAUUUUUUAAAAUUGCUGAAGUGUCAUGGU<br>UUGCUAUUUCGUAUUUAUUGAAAAAAUGUAAAUGCUAUAUUUA<br>ACAGAAUGGCAGUAACUCUGUUUCAAUCUGAAGACUUAAUCUU<br>ACUAAUCAUGGUAAUAUAUGCUGGCUGGAGUUGGGAAUAUUUC<br>AUAAAAUACUGGAAUAAAUUUGUGCUUAUAUUUCAGGGGAAUU |

TABLE 1-continued

| SEQ ID NO | Description | Sequence |
|---|---|---|
| | P1 target sequence large font P2 target sequence target sequence bold P3 target sequence lower case P4 target sequence italics | AAUAAAAGCACCUUCAUCUGCAACAUUUAAAAUGUUAUUGCCU<br>UUAAAUUUGUAUUAAAUAAUGCAGGGAGGAUAGAUCACUGGGG<br>GAGAAUGGAUGCACCUCUGUGAGGAUCUUGGUCAUUCAACACA<br>CGUGUACGGGUGAGGAAACUAAGGCACGACUUACUGGGUAGGG<br>AGGUAGGGAUAUUAGCAAGAUCCUUCACUUGUCUGGGCUUUCU<br>GUCUUUGAGUCACCUUUGCGCAGUUUUUCACUGGACUUCACAA<br>GCCUCUGAGGCGGCAGGGCAGACAGGACAUCCUUAUUUUAUAG<br>AGGAAAAAACUUAGGCUUACAGAGGUUUCCUGCCCCAAAUCAC<br>AAAGGUGGAGCCUAGACCUUCUCAGUCUCCACCAACUGUAUUU<br>CGGUUAGCCACAAUCCUAUCUACCCACAUCCAAAUGGACACCG<br>UGGCUCUGCAACUUCUGUCAAAAGGGCUCUUUGGCAACAGGAA<br>AAACGUCAUGGCUCCAUUGUAUUGUAGAGGAUGGGAAUGGGUG<br>UUCCGGCUAAAUUCUCCCUCCCCUUUCCCUCCACAGCUCAGAU<br>GGCAAAUGUGCGACCCAGGGACCUCCCGCUCCAGCAGACCUGU<br>GCGCACAACUUUGCACAGAUUACCUGCUAAGUCAGAGCCGAAA<br>GGUAACACAGAUGCCAAAGGAUAAUAAAGGUGAAUGAGAUUUA<br>CUCAAAAUUGGAAACUUGGUGUUUGGUUUUUCAGGAGAACAAU<br>CAACGACUGUGAUUUGAAGUUCACCAGGGUAUUCUGAGAGAUC<br>UAAUCAAAGAUAGAGUGCUGGUUUGAAAUUAUUAAAAGGUAAC<br>AGUAAAAGGGAGAGCAAAACCCCAGUCCCAACGCAACCCAUAA<br>AUCUACUUUGUCUUCCUCGAAAGAGGGGCGCGGGUGGGCGCGU<br>CUCCCCGCGAGCAUCUCACCUAAGGGGGAAUCCCUUUCAGCGC<br>ACGGCGAAGUUCCCCCUCGGCUGUCCCACCUGGCAGUCCCUCU<br>AGGAUUUCGGCCAGUCCCUAAUUGGCUCCAGCAAUGUCCAGCC<br>GGAGCUUCUUUGGGCCUCCGAGUGGGAGAAAAGUGAGAGCAGG<br>UGCUUCCCCAGCGGCGCGCUCCGCUAGGGCCCGGCAGGAUCCC<br>GCCCCCAAGUCGGGGAAAGUUGGUCGGCGCCUUUUCUCCCCGA<br>CGAAGCCGCUCCAGGGCUGCUCUCAGAGGACGCGCGGCAGGCA<br>*AAGAGA**AUGAA*CCUGAGCGUCCACGAAACGUCCUGCA<br>C**GGCUCCCGGGAgcugggaggaa**caggugccuuuCUCCGACGU<br>CCGCGGGCGACGCCUGCCGCACCUUGCCCGCUGCCGCGCCCCU<br>CCCGGGCACCCCUCGCCCUCGGCGCCCCUGCCCCCACCCCCAG<br>UGCCAGGGCGGAGGCAGUCCCGGCUCGCAGGUAAUUAUUGCCA<br>GCGGAGCCCGCCGGGGAGCGGGGGUGGGCGCGCCGGCGGUGGG<br>CGGGCGGGCGCGGCGGGGCGCGGGCAUAAAGGGGCGCGGCGCG<br>GGGCCCCGGAGCCUGGCUCCCGCGCAGC |
| 4 | RNA sequence corresponding to 2,000 nt human genomic region immediately upstream of Klotho translation start site (antisense) | GCUGCGCGGGAGCCAGGCUCCGGGGCCCCGCGCCGCGCCCCUU<br>UAUGCCCGCGCCCCGCCGCGCCCGCCCGCCCACCGCCGGCGCG<br>CCCACCCCCGCUCCCCGGCGGGCUCCGCUGGCAAUAAUUACCU<br>GCGAGCCGGGACUGCCUCCGCCCUGGCACUGGGGGUGGGGGCA<br>GGGGCGCCGAGGGCGAGGGGUGCCCGGGAGGGGCGCGGCAGCG<br>GGCAAGGUGCGGCAGGCGUCGCCCGCGGACGUCGGAGAAAGGC<br>ACCUGUUCCUCCCAGCUCCCGGGAGCCGUGCAGGACGUUUCGU<br>GGACGCUCAGGUUCAUUCUCUUUGCCUGCCGCGCGUCCUCUGA<br>GAGCAGCCCUGGAGCGGCUUCGUCGGGGAGAAAAGGCGCCGAC<br>CAACUUUCCCCGACUUGGGGGCGGGAUCCUGCCGGGCCCUAGC<br>GGAGCGCGCCGCUGGGGAAGCACCUGCUCUCACUUUUCUCCCA<br>CUCGGAGGCCCAAAGAAGCUCCGGCUGGACAUUGCUGGAGCCA<br>AUUAGGGACUGGCCGAAAUCCUAGAGGGACUGCCAGGUGGGAC<br>AGCCGAGGGGGAACUUCGCCGUGCGCUGAAAGGGAUUCCCCCU<br>UAGGUGAGAUGCUCGCGGGGAGACGCGCCCACCCGCGCCCCUC<br>UUUCGAGGAAGACAAAGUAGAUUUAUGGGUUGCGUUGGGACUG<br>GGGUUUUGCUCUCCCUUUUACUGUUACCUUUUAAUAAUUUCAA<br>ACCAGCACUCUAUCUUUGAUUAGAUCUCUCAGAAUACCCUGGU<br>GAACUUCAAAUCACAGUCGUUGAUUGUUCUCCUGAAAAACCAA<br>ACACCAAGUUUCCAAUUUUGAGUAAAUCUCAUUCACCUUUAUU<br>AUCCUUUGGCAUCUGUGUUACCUUUCGGCUCUGACUUAGCAGG<br>UAAUCUGUGCAAAGUUGUGCGCACAGGUCUGCUGGAGCGGGAG<br>GUCCCUGGGUCGCACAUUUGCCAUCUGAGCUGUGGAGGGAAAG<br>GGGAGGGAGAAUUUAGCCGGAACACCCAUUCCCAUCCUCUACA<br>AUACAAUGGAGCCAUGACGUUUUUCCUGUUGCCAAAGAGCCCU<br>UUUGACAGAAGUUGCAGAGCCACGGUGUCCAUUUGGAUGUGGG<br>UAGAUAGGAUUGUGGCUAACCGAAAUACAGUUGGUGGAGACUG<br>AGAAGGUCUAGGCUCCACCUUUGUGAUUUGGGGCAGGAAACCU<br>CUGUAAGCCUAAGUUUUUUCCUCUAUAAAAUAAGGAUGUCCUG<br>UCUGCCCUGCCGCCUCAGAGGCUUGUGAAGUCCAGUGAAAAAC<br>UGCGCAAAGGUGACUCAAAGACAGAAAGCCCAGACAAGUGAAG<br>GAUCUUGCUAAUAUCCCUACCUCCCUACCCAGUAAGUCGUGCC<br>UUAGUUUCCUCACCCGUACACGUGUGUUGAAUGACCAAGAUCC<br>UCACAGAGGUGCAUCCAUUCUCCCCCAGUGAUCUAUCCUCCCU<br>GCAUUAUUUAAUACAAAUUUAAAGGCAAUAACAUUUUAAAUGU<br>UGCAGAUGAAGGUGCUUUUAUUAAUUCCCCUGAAAUAUAAGCA<br>CAAAUUUAUUCCAGUAUUUUAUGAAAUAUUCCCAACUCCAGCC<br>AGCAUAUAUUACCAUGAUUAGUAAGAUUAAGUCUUCAGAUUGA<br>AACAGAGUUACUGCCAUUCUGUUAAAUAUAGCAUUUACAUUUU |

TABLE 1-continued

| SEQ ID NO | Description | Sequence |
|---|---|---|
| | | UUCAAUAAAUACGAAAUAGCAAACCAUGACACUUCAGCAAUUU<br>UAAAAAAUUACAGCACACAACUUCACUGUCACGCUGUCUUCCA<br>GCUAAAUUUAAAAAGCUACGUCUACAUGGAGUAUCACAUUUCC<br>CUUCUAGAAGUGAAGAUUGGAGUGUCUGUUGGGUUGUAGCUUG<br>UUAAGUUUCAAUUAGAAAUGCUUCAUGGGUCUCAUGGAAAAUC<br>GCUUAAGCUAAGUAUUCAUUUAUUGAUGUAUGGUCUGUUUGCU<br>CAGGGCAGAUUUUAUCUAUUGCUAUUUUUACUUGACCAGCAGC<br>AUUUUUUAAAUUUUAAAGCAGU |
| 5 | Genomic region extending from F2 RT primer to RV1 RT primer<br>F2 RT primer double-underlined<br>RV1 RT primer bold italics | TGGCAGTCCCTCTAGGATTTCGGCCAGTCCCTAATTGGCTCCA<br>GCAATGTCCAGCCGGAGCTTCTTTGGGCCTCCGAGTGGGAGAA<br>AAGTGAGAGCAGGTGCTTCCCCAGCGGCGCGCTCCGCTAGGGC<br>CCGGCAGGATCCCGCCCCCAAGTCGGGGAAAGTTGGTCGGCGC<br>CTTTTCTCCCCGACGAAGCCGCTCCAGGGCTGCTCTCAGAGGA<br>CGCGCGGCAGGC***AAGAGAATGAACCTGAGCGTC*** |
| 6 | RNA sequence corresponding to genomic region extending from F2 RT primer to RV1 RT primer (sense) | UGGCAGUCCCUCUAGGAUUUCGGCCAGUCCCUAAUUGGCUCCA<br>GCAAUGUCCAGCCGGAGCUUCUUUGGGCCUCCGAGUGGGAGAA<br>AAGUGAGAGCAGGUGCUUCCCCAGCGGCGCGCUCCGCUAGGGC<br>CCGGCAGGAUCCCGCCCCCAAGUCGGGGAAAGUUGGUCGGCGC<br>CUUUUCUCCCCGACGAAGCCGCUCCAGGGCUGCUCUCAGAGGA<br>CGCGCGGCAGGCAAAGAGAAUGAACCUGAGCGUC |
| 7 | RNA sequence corresponding to genomic region extending from F2 RT primer to RV1 RT primer (antisense) | GACGCUCAGGUUCAUUCUCUUUGCCUGCCGCGCGUCCUCUGAG<br>AGCAGCCCUGGAGCGGCUUCGUCGGGGAGAAAAGGCGCCGACC<br>AACUUUCCCCGACUUGGGGGCGGGAUCCUGCCGGGCCCUAGCG<br>GAGCGCGCCGCUGGGGAAGCACCUGCUCUCACUUUUCUCCCAC<br>UCGGAGGCCCAAAGAAGCUCCGGCUGGACAUUGCUGGAGCCAA<br>UUAGGGACUGGCCGAAAUCCUAGAGGGACUGCCA |
| 8 | Genomic region extending from F1 RT primer to RV2 RT primer<br>F1 RT primer underlined<br>F2 RT primer double-underlined<br>RV1 RT primer bold italics<br>RV2 RT primer lower case | TCCCAACGCAACCCATAAATCTACTTTGTCTTCCTCGAAAGAG<br>GGGCGCGGGTGGGCGCGTCTCCCCGCGAGCATCTCACCTAAGG<br>GGGAATCCCTTTCAGCGCACGGCGAAGTTCCCCCTCGGCTGTC<br>CCACCTGGCAGTCCCTCTAGGATTTCGGCCAGTCCCTAATTGG<br>CTCCAGCAATGTCCAGCCGGAGCTTCTTTGGGCCTCCGAGTGG<br>GAGAAAAGTGAGAGCAGGTGCTTCCCCAGCGGCGCGCTCCGCT<br>AGGGCCCGGCAGGATCCCGCCCCCAAGTCGGGGAAAGTTGGTC<br>GGCGCCTTTTCTCCCCGACGAAGCCGCTCCAGGGCTGCTCTCA<br>GAGGACGCGCGGCAGGCA***AAGAGAATGAACCTGAGCGTC***CACG<br>AAACGTCCTGCACGGCTCCCGGGAGCTGGGAGGAACAGGTGCC<br>TTTCTCCGACGTCCGCGGGCGACGCCTGCCGCACCTTGCCCGC<br>TGCCGCGCCCCTCCCGGGCACCCCTCGCCCTCGGCGCCCCTGC<br>CCCCACCCCCAGTGCCAGGGCGGAGGCAGTCCCGGCTCGCAGG<br>TAattattgccagcggagcc |
| 9 | RNA sequence corresponding to genomic region extending from F1 RT primer to RV2 RT primer (sense) | UCCCAACGCAACCCAUAAAUCUACUUUGUCUUCCUCGAAAGAG<br>GGGCGCGGGUGGGCGCGUCUCCCCGCGAGCAUCUCACCUAAGG<br>GGGAAUCCCUUUCAGCGCACGGCGAAGUUCCCCCUCGGCUGUC<br>CCACCUGGCAGUCCCUCUAGGAUUUCGGCCAGUCCCUAAUUGG<br>CUCCAGCAAUGUCCAGCCGGAGCUUCUUUGGGCCUCCGAGUGG<br>GAGAAAAGUGAGAGCAGGUGCUUCCCCAGCGGCGCGCUCCGCU<br>AGGGCCCGGCAGGAUCCCGCCCCCAAGUCGGGGAAAGUUGGUC<br>GGCGCCUUUUCUCCCCGACGAAGCCGCUCCAGGGCUGCUCUCA<br>GAGGACGCGCGGCAGGCAAAGAGAAUGAACCUGAGCGUCCACG<br>AAACGUCCUGCACGGCUCCCGGGAGCUGGGAGGAACAGGUGCC<br>UUUCUCCGACGUCCGCGGGCGACGCCUGCCGCACCUUGCCCGC<br>UGCCGCGCCCCUCCCGGGCACCCCUCGCCCUCGGCGCCCCUGC<br>CCCCACCCCCAGUGCCAGGGCGGAGGCAGUCCCGGCUCGCAGG<br>UAAUUAUUGCCAGCGGAGCC |
| 10 | RNA sequence corresponding to genomic region extending from F1 RT primer to RV2 RT primer (antisense) | GGCUCCGCUGGCAAUAAUUACCUGCGAGCCGGGACUGCCUCCG<br>CCCUGGCACUGGGGGUGGGGGCAGGGGCGCCGAGGGCGAGGGG<br>UGCCCGGGAGGGGCGCGGCAGCGGGCAAGGUGCGGCAGGCGUC<br>GCCCGCGGACGUCGGAGAAAGGCACCUGUUCCUCCCAGCUCCC<br>GGGAGCCGUGCAGGACGUUUCGUGGACGCUCAGGUUCAUUCUC<br>UUUGCCUGCCGCGCGUCCUCUGAGAGCAGCCCUGGAGCGGCUU<br>CGUCGGGGAGAAAAGGCGCCGACCAACUUUCCCCGACUUGGGG<br>GCGGGAUCCUGCCGGGCCCUAGCGGAGCGCGCCGCUGGGGAAG<br>CACCUGCUCUCACUUUUCUCCCACUCGGAGGCCCAAAGAAGCU<br>CCGGCUGGACAUUGCUGGAGCCAAUUAGGGACUGGCCGAAAUC<br>CUAGAGGGACUGCCAGGUGGGACAGCCGAGGGGGAACUUCGCC<br>GUGCGCUGAAAGGGAUUCCCCCUUAGGUGAGAUGCUCGCGGGG |

TABLE 1-continued

| SEQ ID NO | Description | Sequence |
|---|---|---|
| | | AGACGCGCCCACCCGCGCCCCUCUUUCGAGGAAGACAAAGUAG<br>AUUUAUGGGUUGCGUUGGGA |
| 11 | Human genomic region extending 2,000 nt downstream from Klotho translation stop site (sense) | TTCTGAACATTTTTCTATTCATTCATTTTGAAATAATTATGCA<br>GACACATCAGCTGTTAACCATTTGCACCTCTAAGTGTTGTGAA<br>ACTGTAAATTTCATACATTTGACTTCTAGAAAACATTTTTGTG<br>GCTTATGACAGAGGTTTTGAAATGGGCATAGGTGATCGTAAAA<br>TATTGAATAATGCGAATAGTGCCTGAATTTGTTCTCTTTTTGG<br>GTGATTAAAAAACTGACAGGCACTATAATTTCTGTAACACACT<br>AACAAAAGCATGAAAAATAGGAACCACACCAATGCAACATTTG<br>TGCAGAAATTTGAATGACAAGATTAGGAATATTTTCTTCTGCA<br>CCCACTTCTAAATTTAATGTTTTTCTGGAAGTAGTAATTGCAA<br>GAGTTCGAATAGAAAGTTATGTACCAAGTAACCATTTCTCAGC<br>TGCCATAATAATGCCTAGTGGCTTCCCCTCTGTCAAATCTAGT<br>TTCCTATGGAAAAGAAGATGGCAGATACAGGAGAGACGACAGA<br>GGGTCCTAGGCTGGAATGTTCCTTTCGAAAGCAATGCTTCTAT<br>CAAATACTAGTATTAATTTATGTATCTGGTTAATGACATACTT<br>GGAGAGCAAATTATGGAAATGTGTATTTTATATGATTTTTGAG<br>GTCCTGTCTAAACCCTGTGTCCCTGAGGGATCTGTCTCACTGG<br>CATCTTGTTGAGGGCCTTGCACATAGGAAACTTTTGATAAGTA<br>TCTGCGGAAAAACAAACATGAATCCTGTGATATTGGGCTCTTC<br>AGGAAGCATAAAGCAATTGTGAAATACAGTATACCGCAGTGGC<br>TCTAGGTGGAGGAAAGGAGGAAAAAGTGCTTATTATGTGCAAC<br>ATTATGATTAATCTGATTATACACCATTTTTGAGCAGATCTTG<br>GAATGAATGACATGACCTTTCCCTAGAGAATAAGGATGAAATA<br>ATCACTCATTCTATGAACAGTGACACTACTTTCTATTCTTTAG<br>CTGTACTGTAATTTCTTTGAGTTGATAGTTTTACAAATTCTTA<br>ATAGGTTCAAAAGCAATCTGGTCTGAATAACACTGGATTTGTT<br>TCTGTGATCTCTGAGGTCTATTTTATGTTTTTGCTGCTACTTC<br>TGTGGAAGTAGCTTTGAACTAGTTTTACTTTGAACTTTCACGC<br>TGAAACATGCTAGTGATATCTAGAAAGGGCTAATTAGGTCTCA<br>TCCTTTAATGCCCCTTAAATAAGTCTTGCTGATTTTCAGACAG<br>GGAAGTCTCTCTATTACACTGGAGCTGTTTTATAGATAAGTCA<br>ATATTGTATCAGGCAAGATAAACCAATGTCATAACAGGCATTG<br>CCAACCTCACTGACACAGGGTCATAGTGTATAATAATATACTG<br>TACTATATAATATATCATCTTTAGAGGTATGATTTTTTCATGA<br>AAGATAAGCTTTTGGTAATATTCATTTTAAAGTGGACTTATTA<br>AAATTGGATGCTAGAGAATCAAGTTTATTTTATGTATATATTT<br>TTCTGATTATAAGAGTAATATATGTTCATTGTAAAAATTTTTA<br>AAACACAGAAACTATATGCAAAGAAAAAATAAAAATTATCTAT<br>AATCTCAGAACCCAGAAATAGCCACTATTAACATTTCCTACGT<br>ATTTTATTTTAGATAGATCATATTGTATATAGTTAGTATCTTT<br>ATTAATTTTTATTATGAAACTTTCCTTTGTCATTATTAGTCTT<br>CAAAAGCATGATTTTTAATAGTTGTTGAGTATTCCACCACAGG<br>AATGTATCACAACTTAACCGTTCCCGTTTGTTAGACTAGTTTC<br>TTATTAATGTTGATGAATGTTGTTTAAAAATAATTTTGTTGCT<br>ACATTTACTTTAATTTCCTTGACTGTAAAGAGAAGTAATTTTG<br>CTCCTTGATAAAGTATTATATTAATAATAAATCTGCCTGCAAC<br>TTTTTGCCTTCTTTCATAATCATATGAGTGGTTGCTAGCTAAT<br>TTTTTTGTAATTAAAAAAACTT |
| 12 | RNA sequence corresponding to genomic region extending 2,000 nt downstream from human Klotho translation stop site (sense) | UUCUGAACAUUUUUCUAUUCAUUCAUUUUGAAAUAAUUAUGCA<br>GACACAUCAGCUGUUAACCAUUUGCACCUCUAAGUGUUGUGAA<br>ACUGUAAAUUUCAUACAUUUGACUUCUAGAAAACAUUUUUGUG<br>GCUUAUGACAGAGGUUUUGAAAUGGGCAUAGGUGAUCGUAAAA<br>UAUUGAAUAAUGCGAAUAGUGCCUGAAUUUGUUCUCUUUUUGG<br>GUGAUUAAAAAACUGACAGGCACUAUAAUUUCUGUAACACACU<br>AACAAAAGCAUGAAAAAUAGGAACCACACCAAUGCAACAUUUG<br>UGCAGAAAUUUGAAUGACAAGAUUAGGAAUAUUUUCUUCUGCA<br>CCCACUUCUAAAUUUAAUGUUUUUCUGGAAGUAGUAAUUGCAA<br>GAGUUCGAAUAGAAAGUUAUGUACCAAGUAACCAUUUCUCAGC<br>UGCCAUAAUAAUGCCUAGUGGCUUCCCCUCUGUCAAAUCUAGU<br>UUCCUAUGGAAAAGAAGAUGGCAGAUACAGGAGAGACGACAGA<br>GGGUCCUAGGCUGGAAUGUUCCUUUCGAAAGCAAUGCUUCUAU<br>CAAAUACUAGUAUUAAUUUAUGUAUCUGGUUAAUGACAUACUU<br>GGAGAGCAAAUUAUGGAAAUGUGUAUUUUAUAUGAUUUUUGAG<br>GUCCUGUCUAAACCCUGUGUCCCUGAGGGAUCUGUCUCACUGG<br>CAUCUUGUUGAGGGCCUUGCACAUAGGAAACUUUUGAUAAGUA<br>UCUGCGGAAAAACAAACAUGAAUCCUGUGAUAUUGGGCUCUUC<br>AGGAAGCAUAAAGCAAUUGUGAAAUACAGUAUACCGCAGUGGC<br>UCUAGGUGGAGGAAAGGAGGAAAAAGUGCUUAUUAUGUGCAAC<br>AUUAUGAUUAAUCUGAUUAUACACCAUUUUUGAGCAGAUCUUG<br>GAAUGAAUGACAUGACCUUUCCCUAGAGAAUAAGGAUGAAAUA<br>AUCACUCAUUCUAUGAACAGUGACACUACUUUCUAUUCUUUAG<br>CUGUACUGUAAUUUCUUUGAGUUGAUAGUUUUACAAAUUCUUA<br>AUAGGUUCAAAAGCAAUCUGGUCUGAAUAACACUGGAUUUGUU |

TABLE 1-continued

| SEQ ID NO | Description | Sequence |
|---|---|---|
| | | UCUGUGAUCUCUGAGGUCUAUUUUAUGUUUUUGCUGCUACUUC<br>UGUGGAAGUAGCUUUGAACUAGUUUUACUUUGAACUUUCACGC<br>UGAAACAUGCUAGUGAUAUCUAGAAAGGGCUAAUUAGGUCUCA<br>UCCUUUAAUGCCCCUUAAAUAAGUCUUGCUGAUUUUCAGACAG<br>GGAAGUCUCUCUAUUACACUGGAGCUGUUUUAUAGAUAAGUCA<br>AUAUUGUAUCAGGCAAGAUAAACCAAUGUCAUAACAGGCAUUG<br>CCAACCUCACUGACACAGGGUCAUAGUGUAUAAUAAUAUACUG<br>UACUAUAUAAUAUAUCAUCUUUAGAGGUAUGAUUUUUUCAUGA<br>AAGAUAAGCUUUUGGUAAUAUUCAUUUUAAAGUGGACUUAUUA<br>AAAUUGGAUGCUAGAGAAUCAAGUUUAUUUUAUGUAUAUAUUU<br>UUCUGAUUAUAAGAGUAAUAUAUGUUCAUUGUAAAAAUUUUUA<br>AAACACAGAAACUAUAUGCAAAGAAAAAAUAAAAAUUAUCUAU<br>AAUCUCAGAACCCAGAAAUAGCCACUAUUAACAUUUCCUACGU<br>AUUUUAUUUUACAUAGAUCAUAUUGUAUAUAGUUAGUAUCUUU<br>AUUAAUUUUUAUUAUGAAACUUUCCUUUGUCAUUAUUAGUCUU<br>CAAAAGCAUGAUUUUUAAUAGUUGUUGAGUAUUCCACCACAGG<br>AAUGUAUGACAACUUAACCGUUCCCGUUUGUUAGACUAGUUUC<br>UUAUUAAUGUUGAUGAAUGUUGUUUAAAAAUAAUUUUGUUGCU<br>ACAUUUACUUUAAUUUCCUUGACUGUAAAGAGAAGUAAUUUUG<br>CUCCUUGAUAAAGUAUUAUAUUAAUAAUAAAUCUGCCUGCAAC<br>UUUUUGCCUUCUUUCAUAAUCAUAUGAGUGGUUGCUAGCUAAU<br>UUUUUUGUAAUUAAAAAAACUU |
| 13 | RNA sequence corresponding to human genomic region extending 2,000 nt downstream from Klotho translation stop site (antisense) siRNA2 target sequence underlined siRNA3 target sequence double-underlined siRNA4 target sequence lower case | AAGUUUUUUUAAUUACAAAAAAAUUAGCUAGCAACCACUCAUA<br>UGAUUAUGAAAGAAGGCAAAAAGUUGCAGGCAGAUUUAUUAUU<br>AAUAUAAUACUUUAUCAAGGAGCAAAAUUACUUCUCUUUACAG<br>UCAAGGAAAUUAAAGUAAAUGUAGCAACAAAAUUAUUUUUAAA<br>CAACAUUCAUCAACAUUAAUAAGAAACUAGUCUAACAAACGGG<br>AACGGUUAAGUUGUGAUACAUUCCUGUGGUGGAAUACUCAACA<br>ACUAUUAAAAAUCAUGCUUUUGAAGACUAAUAAUGACAAAGGA<br>AAGUUUCAUAAUAAAAAUUAAUAAAGAUACUAACUAUAUACAA<br>UAUGAUCUAUGUAAAAUAAAAUACGUAGGAAAUGUUAAUAGUG<br>GCUAUUUCUGGGUUCUGAGAUUAUAGAUAAUUUUUAUUUUUUC<br>UUUGCAUAUAGUUUCUGUGUUUUAAAAAUUUUUACAAUGAACA<br>UAUAUUACUCUUAUAAUCAGAAAAAUAUAUACAUAAAAUAAAC<br>UUGAUUCUCUAGCAUCCAAUUUUAAUAAGUCCACUUUAAAAUG<br>AAUAUUACCAAAAGCUUAUCUUUCAUGAAAAAAUCAUACCUCU<br>AAAGAUGAUAUAUUAUAUAGUACAGUAUAUUAUUAUACACUAU<br>GACCCUGUGUCAGUGAGGUUGGCAAUGCCUGUUAUGACAUUGG<br>UUUAUCUUGCCUGAUACAAUAUUGACUUAUCUAUAAAACAGCU<br>CCAGUGUAAUAGAGAGACUUCCCUGUCUGAAAAUCAGCAAGAC<br>UUAUUUAAGGGGCAUUAAAGGAUGAGACCUAAUUAGCCCUUUC<br>UAGAUAUGACUAGCAUGUUUCAGCGUGAAAGUUCAAAGUAAAA<br>CUAGUUCAAAGCUACUUCCACAGAAGUAGCAGCAAAAACAUAA<br>AAUAGACCUCAGAGAUCACAGAAACAAAUCCAGUGUUAUUCAG<br>ACCAGAUUGCUUUUGAACCUAUUAAGAAUUUGUAAAACUAUCA<br>ACUCAAAGAAAUUACAGUACAGCUAAAGAAUAGAAAGUAGUGU<br>CACUGUUCAUAGAAUGAGUGAUUAUUUCAUGCUUAUUCUCUAG<br>GGAAAGGUCAUGUCAUUCAUUCCAAGAUCUGCUCAAAAAUGGU<br>GUAUAAUCAGAUUAAUCAUAAUGUUGCACAUAAUAAGCACUUU<br>UUCCUCCUUUCCUCCACCUAGAGCCACUGCGGUAUACUGUAUU<br>UCACAAUUGCUUUAUGCUUCCUGAAGAGCCCAAUAUCACAGGA<br>UUCAUGUUUGUUUUUCCGCAGAUACUUAUCAAAAGUUUCCUAU<br>GUGCAAGGCCCUCAACAAGAUGCCAGUGAGACAGAUCCCUCAG<br>GGACACAGGGUUUAGACAGGACCUCAAAAAUCAUAUAAAAUAC<br>ACAUUUCCAUAAUUUGCUCUCCAAGUAUGUCAUUAACCAGAUA<br>CAUAAAUUAAUACUAGUAUUUGAUAGAAGCAUUGCUUUCGAAA<br>GGAACAUUCCAGCCUAGGACCCUCUGUCGUCUCUCCUGUAUCU<br>GCCAUCUUCUUUUCCAUAGGAAACUAGAUUUGACAGAGGGGAA<br>GCCACUAGGCAUUAUUAUGGCAGCUGAGAAAUGGUUACUUGGU<br>ACAUAACUUUCUAUUCGAACUCUUGCAAUUACUACUUCCAGAA<br>AAACAUUAAAUUUAGAAGUGGGUGCAGAAGAAAAUAUUCCUAA<br>UCUUGUCAUUCAAAUUUCUGCACAAAUGUUGCAUUGGUGUGGU<br>UCCUAUUUUUCAUGCUUUUGUUAGUGUGUUACAGAAAUUAUAG<br>UGCCUGUCAGUUUUUUAAUCACCCAAAAAGAGAACAAAUUCAG<br>GCACUAUUCGCAUUAUUCAAUAUUUUACGAUCACCUAUGCCCA<br>UUUCAAAACCUCUGUCAUAAGCCACAAAAAUGUUUUCUAGAAG<br>UCAAAUGUaugaaauuuacaguuucacaacacuuaGAGGUGCA<br>AAUGGUUAACAGCUGAUGUGUCUGCAUAAUUAUUUCAAAAUGA<br>AUGAAUAGAAAAAUGUUCAGAA |

TABLE 1-continued

| SEQ ID NO | Description | Sequence |
|---|---|---|
| 14 | Genomic region extending from S2 RT primer to AS2 primer<br>S2 RT primer bold and italics<br>AS2 RT primer lower case<br>Klotho translation stop codon bold and underlined | ***ACTACTCGAAGAAAGGCAGAAG***AAGTTACAAA**TAG**TTCTGAAC<br>ATTTTTCTATTCATTCATTTTGAAATAATTATGCAGACACATC<br>AGCTGTTAACCATTTGCACCTCTAAGTGTTGTGAAACTGTAAA<br>TTTCATACATTTGACTTCTAGAAAACATTTTTGTGGCTTATGA<br>CAGAGGTTTTGAAATGGGCATAGGTGATCGTAAAATATTGAAT<br>AATGCGAATAGTGCCTGAATTTGTTCTCTTTTTGGGTGATTAA<br>AAAACTGACAGGCACTATAATTTCTGTAACACACTAACAAAAG<br>CATGAAAAATAGGAACCACACCAATGCAACATTTGTGCAGAAA<br>TTTGAATGACAAGATTAGGAATATTTTCTTCTGCACCCACTTC<br>TAAATTTAATGTTTTTCTGGAAGTAGTAATTGCAAGAGTTCGA<br>ATAGAAAGTTATGTACCAAGTAACCATTTCTCAGCTGCCAtaa<br>taatgcctagtggcttccc |
| 15 | RNA sequence corresponding to genomic region extending from S2 RT primer to AS2 primer (sense) | ACUACUCGAAGAAAGGCAGAAGAAGUUACAAAUAGUUCUGAAC<br>AUUUUUCUAUUCAUUCAUUUUGAAAUAAUUAUGCAGACACAUC<br>AGCUGUUAACCAUUUGCACCUCUAAGUGUUGUGAAACUGUAAA<br>UUUCAUACAUUUGACUUCUAGAAAACAUUUUUGUGGCUUAUGA<br>CAGAGGUUUUGAAAUGGGCAUAGGUGAUCGUAAAAUAUUGAAU<br>AAUGCGAAUAGUGCCUGAAUUUGUUCUCUUUUUGGGUGAUUAA<br>AAAACUGACAGGCACUAUAAUUUCUGUAACACACUAACAAAAG<br>CAUGAAAAAUAGGAACCACACCAAUGCAACAUUUGUGCAGAAA<br>UUUGAAUGACAAGAUUAGGAAUAUUUUCUUCUGCACCCACUUC<br>UAAAUUUAAUGUUUUUCUGGAAGUAGUAAUUGCAAGAGUUCGA<br>AUAGAAAGUUAUGUACCAAGUAACCAUUUCUCAGCUGCCAUAA<br>UAAUGCCUAGUGGCUUCCC |
| 16 | RNA sequence corresponding to genomic region extending from S2 RT primer to AS2 primer (antisense) | GGGAAGCCACUAGGCAUUAUUAUGGCAGCUGAGAAAUGGUUAC<br>UUGGUACAUAACUUUCUAUUCGAACUCUUGCAAUUACUACUUC<br>CAGAAAAACAUUAAAUUUAGAAGUGGGUGCAGAAGAAAAUAUU<br>CCUAAUCUUGUCAUUCAAAUUUCUGCACAAAUGUUGCAUUGGU<br>GUGGUUCCUAUUUUUCAUGCUUUUGUUAGUGUGUUACAGAAAU<br>UAUAGUGCCUGUCAGUUUUUUAAUCACCCAAAAAGAGAACAAA<br>UUCAGGCACUAUUCGCAUUAUUCAAUAUUUUACGAUCACCUAU<br>GCCCAUUUCAAAACCUCUGUCAUAAGCCACAAAAAUGUUUUCU<br>AGAAGUCAAAUGUAUGAAAUUUACAGUUUCACAACACUUAGAG<br>GUGCAAAUGGUUAACAGCUGAUGUGUCUGCAUAAUUAUUUCAA<br>AAUGAAUGAAUAGAAAAAUGUUCAGAACUAUUUGUAACUUCUU<br>CUGCCUUUCUUCGAGUAGU |
| 17 | Genomic region extending from SI RT primer to ASI primer<br>S1 RT primer underlined<br>AS1 RT primer double-underlined<br>S2 RT primer bold and italics<br>AS2 RT primer lower case<br>Klotho translation stop codon bold and underlined | AGGTTTGGCCTCTATCGTTATGCTGCAGATCAGTTTGAGCCCA<br>AGGCATCCATGAAACATTACAGGAAAATTATTGACAGCAATGG<br>TTTCCCGGGCCCAGAAACTCTGGAAAGATTTTGTCCAGAAGAA<br>TTCACCGTGTGTACTGAGTGCAGTTTTTTTCACACCCGAAAGT<br>CTTTACTGGCTTTCATAGCTTTTCTATTTTTTGCTTCTATTAT<br>TTCTCTCTCCCTTATATTTT***ACTACTCGAAGAAAGGCAGAAG***A<br>AGTTACAAA**TAG**TTCTGAACATTTTTCTATTCATTCATTTTGA<br>AATAATTATGCAGACACATCAGCTGTTAACCATTTGCACCTCT<br>AAGTGTTGTGAAACTGTAAATTTCATACATTTGACTTCTAGAA<br>AACATTTTTGTGGCTTATGACAGAGGTTTTGAAATGGGCATAG<br>GTGATCGTAAAATATTGAATAATGCGAATAGTGCCTGAATTTG<br>TTCTCTTTTTGGGTGATTAAAAAACTGACAGGCACTATAATTT<br>CTGTAACACACTAACAAAAGCATGAAAAATAGGAACCACACCA<br>ATGCAACATTTGTGCAGAAATTTGAATGACAAGATTAGGAATA<br>TTTTCTTCTGCACCCACTTCTAAATTTAATGTTTTTCTGGAAG<br>TAGTAATTGCAAGAGTTCGAATAGAAAGTTATGTACCAAGTAA<br>CCATTTCTCAGCTGCCAtaataatgcctagtggcttcccCTCT<br>GTCAAATCTAGTTTCCTATGGAAAAGAAGATGGCAGATACAGG<br>AGAGACGACAGAG |
| 18 | RNA sequence corresponding to genomic region extending from S1 RT primer to AS1 primer (sense) | AGGUUUGGCCUCUAUCGUUAUGCUGCAGAUCAGUUUGAGCCCA<br>AGGCAUCCAUGAAACAUUACAGGAAAAUUAUUGACAGCAAUGG<br>UUUCCCGGGCCCAGAAACUCUGGAAAGAUUUUGUCCAGAAGAA<br>UUCACCGUGUGUACUGAGUGCAGUUUUUUUCACACCCGAAAGU<br>CUUUACUGGCUUUCAUAGCUUUUCUAUUUUUUGCUUCUAUUAU<br>UUCUCUCUCCCUUAUAUUUUACUACUCGAAGAAAGGCAGAAGA<br>AGUUACAAAUAGUUCUGAACAUUUUUCUAUUCAUUCAUUUUGA<br>AAUAAUUAUGCAGACACAUCAGCUGUUAACCAUUUGCACCUCU<br>AAGUGUUGUGAAACUGUAAAUUUCAUACAUUUGACUUCUAGAA<br>AACAUUUUUGUGGCUUAUGACAGAGGUUUUGAAAUGGGCAUAG<br>GUGAUCGUAAAAUAUUGAAUAAUGCGAAUAGUGCCUGAAUUUG<br>UUCUCUUUUUGGGUGAUUAAAAAACUGACAGGCACUAUAAUUU<br>CUGUAACACACUAACAAAAGCAUGAAAAAUAGGAACCACACCA<br>AUGCAACAUUUGUGCAGAAAUUUGAAUGACAAGAUUAGGAAUA<br>UUUUCUUCUGCACCCACUUCUAAAUUUAAUGUUUUUCUGGAAG<br>UAGUAAUUGCAAGAGUUCGAAUAGAAAGUUAUGUACCAAGUAA |

TABLE 1-continued

| SEQ ID NO | Description | Sequence |
|---|---|---|
| | | CCAUUUCUCAGCUGCCAUAAUAAUGCCUAGUGGCUUCCCCUCU<br>GUCAAAUCUAGUUUCCUAUGGAAAAGAAGAUGGCAGAUACAGG<br>AGAGACGACAGAG |
| 19 | RNA sequence corresponding to genomic region extending from S1 RT primer to AS1 primer (antisense) | CUCUGUCGUCUCUCCUGUAUCUGCCAUCUUCUUUUCCAUAGGA<br>AACUAGAUUUGACAGAGGGGAAGCCACUAGGCAUUAUUAUGGC<br>AGCUGAGAAAUGGUUACUUGGUACAUAACUUUCUAUUCGAACU<br>CUUGCAAUUACUACUUCCAGAAAAACAUUAAAUUUAGAAGUGG<br>GUGCAGAAGAAAAUAUUCCUAAUCUUGUCAUUCAAAUUUCUGC<br>ACAAAUGUUGCAUUGGUGUGGUUCCUAUUUUUCAUGCUUUUGU<br>UAGUGUGUUACAGAAAUUAUAGUGCCUGUCAGUUUUUUAAUCA<br>CCCAAAAAGAGAACAAAUUCAGGCACUAUUCGCAUUAUUCAAU<br>AUUUUACGAUCACCUAUGCCCAUUUCAAAACCUCUGUCAUAAG<br>CCACAAAAAUGUUUUCUAGAAGUCAAAUGUAUGAAAUUUACAG<br>UUUCACAACACUUAGAGGUGCAAAUGGUUAACAGCUGAUGUGU<br>CUGCAUAAUUAUUUCAAAAUGAAUGAAUAGAAAAAUGUUCAGA<br>ACUAUUUGUAACUUCUUCUGCCUUUCUUCGAGUAGUAAAAUAU<br>AAGGGAGAGAGAAAUAAUAGAAGCAAAAAAUAGAAAAGCUAUG<br>AAAGCCAGUAAAGACUUUCGGGUGUGAAAAAAACUGCACUCAG<br>UACACACGGUGAAUUCUUCUGGACAAAAUCUUUCCAGAGUUUC<br>UGGGCCCGGGAAACCAUUGCUGUCAAUAAUUUUCCUGUAAUGU<br>UUCAUGGAUGCCUUGGGCUCAAACUGAUCUGCAGCAUAACGAU<br>AGAGGCCAAACCU |
| 20 | Genomic DNA sequence of human Klotho from translation start site to translation stop site. | [See sequence listing] |
| 45 | Human Klotho protein (transmembrane form, 130 kDa) Signal sequence underlined Transmembrane domain double-underlined Cleavage sites in bold | MPASAPPRRPRPPPPSLSLLLVLLGLGGRRLR**AE**PGDGAQTWA<br>RFSRPPAPEAAGLFQGTFPDGFLWAVGSAAYQTEGGWQQHGKG<br>ASIWDTFTHHPLAPPGDSRNASLPLGAPSPLQPATGDVASDSY<br>NNVFRDTEALRELGVTHYRFSISWARVLPNGSAGVPNREGLRY<br>YRRLLERLRELGVQPVVTLYHWDLPQRLQDAYGGWANRALADH<br>FRDYAELCFRHFGGQVKYWITIDNPYVVAWHGYATGRLAPGIR<br>GSPRLGYLVAHNLLLAHAKVWHLYNTSFRPTQGGQVSIALSSH<br>WINPRRMTDHSIKECQKSLDFVLGWFAKPVFIDGDYPESMKNN<br>LSSILPDFTESEKKFIKGTADFFALCFGPTLSFQLLDPHMKFR<br>QLESPNLRQLLSWIDLEFNHPQIFIVENGWFVSGTTKRDDAKY<br>MYYLKKFIMETLKAIKLDGVDVIGYTAWSLMDGFEWHRGYSIR<br>RGLFYVDFLSQDKMLLPKSSALFYQKLIEKNGFPPLPENQPLE<br>GTFPCDFAWGVVDNYIQVDTTLSQFTDLNVYLWDVHHSKRLIK<br>VDGVVTKKRKSYCVDFAAIQPQIALLQEMHVTHFRFSLDWALI<br>LPLGNQSQVNHTILQYYRCMASELVRVNITPVVALWQPMAPNQ<br>GLPRLLARQGAWENPYTALAFAEYARLCFQELGHHVKLWITMN<br>EPYTRNMTYSAGHNLLKAHALAWHVYNEKFRHAQNGKISIALQ<br>ADWIEPACPFSQKDKEVAERVLEFDIGWLAEPIFGSGDYPWVM<br>RDWLNQRNNFLLPYFTEDEKKLIQGTFDFLALSHYTTILVDSE<br>KEDPIKYNDYLEVQEMTDITWLNSPSQVAVVPWGLRKVLNWLK<br>FKYGDLPMYIISNGIDDGLHAEDDQLRVYYMQNYINEALKAHI<br>LDGINLCGYFAYSFNDRTAPRFGLYRYAADQFEPKASMKHYRK<br>IIDSNGFPGPE**TL**ERFCPEEFTVCTECSFFHTRKSLLAFIAFL<br>FFASIISLSLIFYYSKKGRRSYK |
| 46 | Human Klotho (cleaved form) | **E**PGDGAQTWARFSRPPAPEAAGLFQGTFPDGFLWAVGSAAYQT<br>EGGWQQHGKGASIWDTFTHHPLAPPGDSRNASLPLGAPSPLQP<br>ATGDVASDSYNNVFRDTEALRELGVTHYRFSISWARVLPNGSA<br>GVPNREGLRYYRRLLERLRELGVQPVVTLYHWDLPQRLQDAYG<br>GWANRALADHFRDYAELCFRHFGGQVKYWITIDNPYVVAWHGY<br>ATGRLAPGIRGSPRLGYLVAHNLLLAHAKVWHLYNTSFRPTQG<br>GQVSIALSSHWINPRRMTDHSIKECQKSLDFVLGWFAKPVFID<br>GDYPESMKNNLSSILPDFTESEKKFIKGTADFFALCFGPTLSF<br>QLLDPHMKFRQLESPNLRQLLSWIDLEFNHPQIFIVENGWFVS<br>GTTKRDDAKYMYYLKKFIMETLKAIKLDGVDVIGYTAWSLMDG<br>FEWHRGYSIRRGLFYVDFLSQDKMLLPKSSALFYQKLIEKNGF<br>PPLPENQPLEGTFPCDFAWGVVDNYIQVDTTLSQFTDLNVYLW<br>DVHHSKRLIKVDGVVTKKRKSYCVDFAAIQPQIALLQEMHVTH<br>FRFSLDWALILPLGNQSQVNHTILQYYRCMASELVRVNITPVV<br>ALWQPMAPNQGLPRLLARQGAWENPYTALAFAEYARLCFQELG<br>HHVKLWITMNEPYTRNMTYSAGHNLLKAHALAWHVYNEKFRHA<br>QNGKISIALQADWIEPACPFSQKDKEVAERVLEFDIGWLAEPI<br>FGSGDYPWVMRDWLNQRNNFLLPYFTEDEKKLIQGTFDFLALS<br>HYTTILVDSEKEDPIKYNDYLEVQEMTDITWLNSPSQVAVVPW |

TABLE 1-continued

| SEQ ID NO | Description | Sequence |
|---|---|---|
| | | GLRKVLNWLKFKYGDLPMYIISNGIDDGLHAEDDQLRVYYMQN<br>YINEALKAHILDGINLCGYFAYSFNDRTAPRFGLYRYAADQFE<br>PKASMKHYRKIIDSNGFPGPE**T** |
| 47 | Human Klotho (secreted form by alternative splicing, 70 kD) | MPASAPPRRPRPPPPSLSLLLVLLGLGGRRLR**AE**PGDGAQTWA<br>RFSRPPAPEAAGLFQGTFPDGFLWAVGSAAYQTEGGWQQHGKG<br>ASIWDTFTHHPLAPPGDSRNASLPLGAPSPLQPATGDVASDSY<br>NNVFRDTEALRELGVTHYRFSISWARVLPNGSAGVPNREGLRY<br>YRRLLERLRELGVQPVVTLYHWDLPQRLQDAYGGWANRALADH<br>FRDYAELCFRHFGGQVKYWITIDNPYVVAWHGYATGRLAPGIR<br>GSPRLGYLVAHNLLLAHAKVWHLYNTSFRPTQGGQVSIALSSH<br>WINPRRMTDHSIKECQKSLDFVLGWFAKPVFIDGDYPESMKNN<br>LSSILPDFTESEKKFIKGTADFFALCFGPTLSFQLLDPHMKFR<br>QLESPNLRQLLSWIDLEFNHPQIFIVENGWFVSGTTKRDDAKY<br>MYYLKKFIMETLKAIKLDGVDVIGYTAWSLMDGFEWHRGYSIR<br>RGLFYVDFLSQDKMLLPKSSALFYQKLIEKNGFPPLPENQPLE<br>GTFPCDFAWGVVDNYIQVSQLTKPISSLTKPYH |
| 48 | NONHSAT166585.1 (antisense) Guide 1 target sequence underlined Guide 2 target sequence bold Guide 3 target sequence italics Guide 4 target sequence lower case Guide 5 target sequence double-underlined | CCUCCGUGUCGCGGAAGACGUUGUUGUAGCUGUCGCUGGCUAC<br>GUCCCCGGUGGCGGGCUGCAGCGGCGACGGGGCGCCCAACGGC<br>AGACUGGCGUUCCGGGAGUCUCCCGGGGGUGCCAGGGGGUGGU<br>GGGUGAACGUAUCCCAGAUGGACGCACCCUUGCCGUGCUGCUG<br>CCAGCCGCCCUCGGUCUGGUAGGCGGCGCUGCCCACGGCCCAG<br>AGGAAGCCGUCGGGGAAGGUGCCCUGGAAGAGGCCCGCGGCCU<br>CGGGGGCAGGAGGCCGCGAGAAACGGGCCCAGGUCUGCGCGCC<br>GUCGCCCGGCUCCGCACGCAGGCGGCGGCCGCCCAGGCCCAGC<br>AGCACCAGCAGCAGCGACAGCGACGGCGGCGGCGGCCGCGGGC<br>GGCGCGGCGGGGCGCUGGCGGGCAUGCUGCGCGGGAGCCAGGC<br>UCCGGGGCCCCGCGCCGCGCCCCUUUAUGCCCGCGCCCCGCCG<br>CGCCCGCCCGCCCACCGCCGGCGCGCCCACCCCCGCUCCCCGG<br>CGGGCUCCGCUGGCAAUAAUUACCUGCGAGCCGGGACUGCCUC<br>CGCCCUGGCACUGGGGGCGGGGGCAGGGGCGCCGAGGGCGAGG<br>GGUGCCCGGGAGGGGCGCGGCAGCGGGCAAGGUGCGGCAGGCG<br>UCGCCCGCGGA*CGUCGGAGAAAGGCACCUGUUU*CUCCCAGCUC<br>CCGGGAGCCGUGCAGGACGUUUCGUG**GACGCUCAGGUUCAUUC**<br>**UCUUU**GCCUGCCGCGCGUCCUCUGAGAGCAGCCCUGGAGCGGC<br>UUCGUCGGGGAGAAAAGGCGCCGACCAACUUUCCCCGAGUUGG<br>GGGCGGGAUCCUGCCGGGCCCUAGCGGAGCGCGCCGCUGGGGA<br>AGCACCUGCUCUCACUUUUCUCCCACUCGGAGGCCCAAAGAAG<br>CUCCGGCUGGACAUUGCUGGAgccaauuagggacuggccgaaa<br>UCCUAGAGGGACUGCCAGGUGGGACAGCCGAGGGGGAACUUCG<br>CCGUGCGCUGAAAGGGAUUCCCCCUUAGGACGAUGGGAGCCUU<br>UUAACACCAAUGGAGCAGGAGAUGCACUGAUUCACAUGCACCC<br>AAAUACAACACCAACCCCACAAGCUCUCAGCUCACCAGUCACA<br>GACAUCACCUUCUACGGACAUAUUUUUAUUUCACUGAGCUACA<br>ACUACGGGCAAGGCAACGACGAGCUGUGUGGAGACUUCAAAAC<br>AUAGAGGACAACCUCUGCCCUCAAAGACAACAUCCAACUGAAG<br>AAAGGAUCAAGAAAGAUGAAAAUAAAUAAGUUGUUUGAUUAUG<br>CUGUGUUAAUAAAUGACCCAUAGAAUAAUUGUCAG |
| 49 | NONHSAT166585.1 (sense) | CUGACAAUUAUUCUAUGGGUCAUUUAUUAACACAGCAUAAUCA<br>AACAACUUAUUUAUUUUCAUCUUUCUUGAUCCUUUCUUCAGUU<br>GGAUGUUGUCUUUGAGGGCAGAGGUUGUCCUCUAUGUUUUGAA<br>GUCUCCACACAGCUCGUCGUUGCCUUGCCCGUAGUUGUAGCUC<br>AGUGAAAUAAAAAUAUGUCCGUAGAAGGUGAUGUCUGUGACUG<br>GUGAGCUGAGAGCUUGUGGGGUUGGUGUUGUAUUUGGGUGCAU<br>GUGAAUCAGUGCAUCUCCUGCUCCAUUGGUGUUAAAAGGCUCC<br>CAUCGUCCUAAGGGGGAAUCCCUUUCAGCGCACGGCGAAGUUC<br>CCCCUCGGCUGUCCCACCUGGCAGUCCCUCUAGGAUUUCGGCC<br>AGUCCCUAAUUGGCUCCAGCAAUGUCCAGCCGGAGCUUCUUUG<br>GGCCUCCGAGUGGGAGAAAAGUGAGAGCAGGUGCUUCCCCAGC<br>GGCGCGCUCCGCUAGGGCCCGGCAGGAUCCCGCCCCCAAGUCG<br>GGGAAAGUUGGUCGGCGCCUUUUCUCCCCGACGAAGCCGCUCC<br>AGGGCUGCUCUCAGAGGACGCGCGGCAGGCAAAGAGAAUGAAC<br>CUGAGCGUCCACGAAACGUCCUGCACGGCUCCCGGGAGCUGGG<br>AGAAACAGGUGCCUUUCUCCGACGUCCGCGGGCGACGCCUGCC<br>GCACCUUGCCCGCUGCCGCGCCCCUCCCGGGCACCCCUCGCCC<br>UCGGCGCCCCUGCCCCCGCCCCCAGUGCCAGGGCGGAGGCAGU<br>CCCGGCUCGCAGGUAAUUAUUGCCAGCGGAGCCCGCCGGGGAG<br>CGGGGGUGGGCGCGCCGGCGGUGGGCGGGCGGGCGCGGCGGGG<br>CGCGGGCAUAAAGGGGCGCGGCGCGGGGCCCCGGAGCCUGGCU<br>CCCGCGCAGCAUGCCCGCCAGCGCCCCGCCGCGCCGCCCGCGG<br>CCGCCGCCGCCGUCGCUGUCGCUGCUGCUGGUGCUGCUGGGCC<br>UGGGCGGCCGCCGCCUGCGUGCGGAGCCGGGCGACGGCGCGCA<br>GACCUGGGCCCGUUUCUCGCGGCCUCCUGCCCCCGAGGCCGCG<br>GGCCUCUUCCAGGGCACCUUCCCCGACGGCUUCCUCUGGGCCG |

TABLE 1-continued

| SEQ ID NO | Description | Sequence |
|---|---|---|
| | | UGGGCAGCGCCGCCUACCAGACCGAGGGCGGCUGGCAGCAGCA<br>CGGCAAGGGUGCGUCCAUCUGGGAUACGUUCACCCACCACCCC<br>CUGGCACCCCCGGGAGACUCCCGGAACGCCAGUCUGCCGUUGG<br>GCGCCCCGUCGCCGCUGCAGCCCGCCACCGGGGACGUAGCCAG<br>CGACAGCUACAACAACGUCUUCCGCGACACGGAGG |
| 50 | Chromosomal region corresponding to NONHSAT166585.1 (sense) Klotho translation start codon underlined | CTGACAATTATTCTATGGGTCATTTATTAACACAGCATAATCAAACAACTTA<br>TTTATTTTCATCTTTCTTGATCCTTTCTTCAGTTGGATGTTGTCTTTGAGGG<br>CAGAGGTTGTCCTCTATGTTTTGAAGTCTCCACACAGCTCATCGTTGCCTTG<br>CCCGTAGTTGTAGCTCAGTGAAATAAAAATATGTCCGTAGAAGGTGATGTCT<br>GTGACTGGTGAGCCGAGAGCTTGTGGGGTTGGTGTTGTATTTGAGTGCATGT<br>GAATCAGTGCATCTCCTGCTCCATTGGTGTTAAAAGGCTCCCATCGTCCTGG<br>GAACACAATAGGAAAGAGAACAGGTGGGAAGGCACTGGATGAAGGAATGTGG<br>AGAATGGAGGAAAAGTTGATCAGATTGTTGACAACTTTCAGTGTTGAAATTG<br>TCACCAAAATCAAAGTCAGTAAATAAATTTACAATGTCCTTTTCTTCAATGC<br>ATCAATAACTTCACCTTCCTGTTCAAAGCACAGCAAGTAATTAATCTCTTAT<br>TTGCATTTGAAACCCAAGTTTCAGATGTTTGAAGGTGGTTGTAAAAAATAAA<br>AACCAAAATAAAGCCAAAATAAATAAGCAGCAGCACTAGGCCGGGCACAGTG<br>TCTCACACCTGTAATCCCAGCATTTTAGGAGACCGAGGTGGGTGGATCACAG<br>GAGATCAGGAGTTTGAGACCAGCCTGGTCAGCATGGTGAAACCCTGTCTCTA<br>CTAAAAATACAAAAATTAGCCAGGTGTGGTGGTGTGCCCTTATAATCCCAGC<br>TACTGGGGGGCTGAGACAGGAGAATTGCTTGAACCTGGGAGGCAGAGGTTGC<br>AGTGAGCAGAGACCATGCCACTGCACTCCAGCCTGGGCGACAGAGTGAGACT<br>CCGTCTCACACTTGTGGAACCCAGAACTTAGTAACCATGAACAGAACCTTAA<br>TAAACAGAAAGTTCTGGAAATAAAGTTTAATCATCATGCAATCTTTATCACT<br>GGGTTAAATGAACAATCATCTGGGAACATGTCTTGGAATGCTTAAAGCTTTG<br>AGATGCATGTGCCTATGTGGCAGACAAATTTCAAATGTGAAACGTTTAGTTA<br>ACTTGGTCTTGCTTTTTAATCACTGCTTTAAAATTTAAAAAATGCTGCTGGT<br>CAAGTAAAAATAGCAATAGATAAAATCTGCCCTGAGCAAACAGACCATACAT<br>CAATAAATGAATACTTAGCTTAAGCGATTTTCCATGAGACCCATGAAGCATT<br>TCTAATTGAAACTTAACAAGCTACAACCCAACAGACACTCCAATCTTCACTT<br>CTAGAAGGGAAATGTGATACTCCATGTAGACGTAGCTTTTTAAATTTAGCTG<br>GAAGACAGCGTGACAGTGAAGTTGTGTGCTGTAATTTTTTAAAATTGCTGAA<br>GTGTCATGGTTTGCTATTTCGTATTTATTGAAAAAATGTAAATGCTATATTT<br>AACAGAATGGCAGTAACTCTGTTTCAATCTGAAGACTTAATCTTACTAATCA<br>TGGTAATATATGCTGGCTGGAGTTGGGAATATTTCATAAAATACTGGAATAA<br>ATTTGTGCTTATATTTCAGGGGAATTAATAAAAGCACCTTCATCTGCAACAT<br>TTAAAATGTTATTGCCTTTAAATTTGTATTAAATAATGCAGGGAGGATAGAT<br>CACTGGGGGAGAATGGATGCACCTCTGTGAGGATCTTGGTCATTCAACACAC<br>GTGTACGGGTGAGGAAACTAAGGCACGACTTACTGGGTAGGGAGGTAGGGAT<br>ATTAGCAAGATCCTTCACTTGTCTGGGCTTTCTGTCTTTGAGTCACCTTTGC<br>GCAGTTTTTCACTGGACTTCACAAGCCTCTGAGGCGGCAGGGCAGACAGGAC<br>ATCCTTATTTTATAGAGGAAAAAACTTAGGCTTACAGAGGTTTCCTGCCCCA<br>AATCACAAAGGTGGAGCCTAGACCTTCTCAGTCTCCACCAACTGTATTTCGG<br>TTAGCCACAATCCTATCTACCCACATCCAAATGGACACCGTGGCTCTGCAAC<br>TTCTGTCAAAAGGGCTCTTTGGCAACAGGAAAAACGTCATGGCTCCATTGTA<br>TTGTAGAGGATGGGAATGGGTGTTCCGGCTAAATTCTCCCTCCCCTTTCCCT<br>CCACAGCTCAGATGGCAAATGTGCGACCCAGGGACCTCCCGCTCCAGCAGAC<br>CTGTGCGCACAACTTTGCACAGATTACCTGCTAAGTCAGAGCCGAAAGGTAA<br>CACAGATGCCAAAGGATAATAAAGGTGAATGAGATTTACTCAAAATTGGAAA<br>CTTGGTGTTTGGTTTTTCAGGAGAACAATCAACGACTGTGATTTGAAGTTCA<br>CCAGGGTATTCTGAGAGATCTAATCAAAGATAGAGTGCTGGTTTGAAATTAT<br>TAAAAGGTAACAGTAAAAGGGAGAGCAAAACCCCAGTCCCAACGCAACCCAT<br>AAATCTACTTTGTCTTCCTCGAAAGAGGGGCGCGGGTGGGCGCGTCTCCCCG<br>CGAGCATCTCACCTAAGGGGGAATCCCTTTCAGCGCACGGCGAAGTTCCCCC<br>TCGGCTGTCCCACCTGGCAGTCCCTCTAGGATTTCGGCCAGTCCCTAATTGG<br>CTCCAGCAATGTCCAGCCGGAGCTTCTTTGGGCCTCCGAGTGGGAGAAAAGT<br>GAGAGCAGGTGCTTCCCCAGCGGCGCGCTCCGCTAGGGCCCGGCAGGATCCC<br>GCCCCCAAGTCGGGGAAAGTTGGTCGGCGCCTTTTCTCCCCGACGAAGCCGC<br>TCCAGGGCTGCTCTCAGAGGACGCGCGGCAGGCAAAGAGAATGAACCTGAGC<br>GTCCACGAAACGTCCTGCACGGCTCCCGGGAGCTGGGAGGAACAGGTGCCTT<br>TCTCCGACGTCCGCGGGCGACGCCTGCCGCACCTTGCCCGCTGCCGCGCCCC<br>TCCCGGGCACCCCTCGCCCTCGGCGCCCCTGCCCCCACCCCCAGTGCCAGGG<br>CGGAGGCAGTCCCGGCTCGCAGGTAATTATTGCCAGCGGAGCCCGCCGGGGA<br>GCGGGGGTGGGCGCGCCGGCGGTGGGCGGGCGGGCGCGGCGGGGCGCGGGCA<br>TAAAGGGGCGCGGCGCGGGGCCCCGGAGCCTGGCTCCCGCGCAGC**ATG**CCCG<br>CCAGCGCCCCGCCGCGCCGCCCGCGGCCGCCGCCGCCGTCGCTGTCGCTGCT<br>GCTGGTGCTGCTGGGCCTGGGCGGCCGCCGCCTGCGTGCGGAGCCGGGCGAC<br>GGCGCGCAGACCTGGGCCCGTTTCTCGCGGCCTCCTGCCCCCGAGGCCGCGG<br>GCCTCTTCCAGGGCACCTTCCCCGACGGCTTCCTCTGGGCCGTGGGCAGCGC<br>CGCCTACCAGACCGAGGGCGGCTGGCAGCAGCACGGCAAGGGTGCGTCCATC<br>TGGGATACGTTCACCCACCACCCCCTGGCACCCCCGGGAGACTCCCGGAACG<br>CCAGTCTGCCGTTGGGCGCCCCGTCGCCGCTGCAGCCCGCCACCGGGGACGT<br>AGCCAGCGACAGCTACAACAACGTCTTCCGCGACACGGAGG |

TABLE 1-continued

| SEQ ID NO | Description | Sequence |
|---|---|---|
| 51 | lnc-STARD13-4:1 (antisense) Guide 1 target sequence underlined Guide 2 target sequence bold Guide 3 target sequence italics Guide 4 target sequence lower case Guide 5 target sequence double-underlined | GGCGAGGGGUGCCCGGGAGGGGCGCGGCAGCGGGCAAGGUGCG<br>GCAGGCGUCGCCCGCGGA*CGUCGGAGAAAGGCACCUGUUU*CUC<br>CCAGCUCCCGGGAGCCGUGCAGGACGUUUCGUG**GACGCUCAGG**<br>**UUCAUUCUCUUU**GCCUGCCGCGCGUCCUCUGAGAGCAGCCCUG<br>GAGCGGCUUCGUCGGGGAGAAAAGGCGCCGAGCAACUUUCCCC<br>GACUUGGGGGCGGGAUCCUGCCGGGCCCUAGCGGAGCGCGCCG<br>CUGGGGAAGCACCUGCUCUCACUUUUCUCCCACUCGGAGGCCC<br>AAAGAAGCUCCGGCUGGACAUUGCUGGAgccaauuagggacug<br>gccgaaaUCCUAGAGGGACUGCCAGGUGGGACAGCCGAGGGGG<br>AACUUCGCCGUGCGCUGAAAGGGAUUCCCCCUUAGGAAGGUGA<br>AGUUAUUGAUGCAUUGAAGAAAAGGAC |
| 52 | lnc-STARD13-4:1 (sense) | GUCCUUUUCUUCAAUGCAUCAAUAACUUCACCUUCCUAAGGGG<br>GAAUCCCUUUCAGCGCACGGCGAAGUUCCCCCUCGGCUGUCCC<br>ACCUGGCAGUCCCUCUAGGAUUUCGGCCAGUCCCUAAUUGGCU<br>CCAGCAAUGUCCAGCCGGAGCUUCUUUGGGCCUCCGAGUGGGA<br>GAAAAGUGAGAGCAGGUGCUUCCCCAGCGGCGCGCUCCGCUAG<br>GGCCCGGCAGGAUCCCGCCCCCAAGUCGGGGAAAGUUGGUCGG<br>CGCCUUUUCUCCCCGACGAAGCCGCUCCAGGGCUGCUCUCAGA<br>GGACGCGCGGCAGGCAAAGAGAAUGAACCUGAGCGUCCACGAA<br>ACGUCCUGCACGGCUCCCGGGAGCUGGGAGAAACAGGUGCCUU<br>UCUCCGACGUCCGCGGGCGACGCCUGCCGCACCUUGCCCGCUG<br>CCGCGCCCCUCCCGGGCACCCCUCGCC |
| 53 | Chromosomal region corresponding to lnc-STARD13-4:1 (sense) | GTCCTTTTCTTCAATGCATCAATAACTTCACCTTCCTGTTCAAAG<br>CACAGCAAGTAATTAATCTCTTATTTGCATTTGAAACCCAAGTTT<br>CAGATGTTTGAAGGTGGTTGTAAAAAATAAAAACCAAAATAAAGC<br>CAAAATAAATAAGCAGCAGCACTAGGCCGGGCACAGTGTCTCACA<br>CCTGTAATCCCAGCATTTTAGGAGACCGAGGTGGGTGGATCACAG<br>GAGATCAGGAGTTTGAGACCAGCCTGGTCAGCATGGTGAAACCCT<br>GTCTCTACTAAAAATACAAAAATTAGCCAGGTGTGGTGGTGTGCC<br>CTTATAATCCCAGCTACTGGGGGGCTGAGACAGGAGAATTGCTTG<br>AACCTGGGAGGCAGAGGTTGCAGTGAGCAGAGACCATGCCACTGC<br>ACTCCAGCCTGGGCGACAGAGTGAGACTCCGTCTCACACTTGTGG<br>AACCCAGAACTTAGTAACCATGAACAGAACCTTAATAAACAGAAA<br>GTTCTGGAAATAAAGTTTAATCATCATGCAATCTTTATCACTGGG<br>TTAAATGAACAATCATCTGGGAACATGTCTTGGAATGCTTAAAGC<br>TTTGAGATGCATGTGCCTATGTGGCAGACAAATTTCAAATGTGAA<br>ACGTTTAGTTAACTTGGTCTTGCTTTTTAATCACTGCTTTAAAAT<br>TTAAAAAATGCTGCTGGTCAAGTAAAAATAGCAATAGATAAAATC<br>TGCCCTGAGCAAACAGACCATACATCAATAAATGAATACTTAGCT<br>TAAGCGATTTTCCATGAGACCCATGAAGCATTTCTAATTGAAACT<br>TAACAAGCTACAACCCAACAGACACTCCAATCTTCACTTCTAGAA<br>GGGAAATGTGATACTCCATGTAGACGTAGCTTTTTAAATTTAGCT<br>GGAAGACAGCGTGACAGTGAAGTTGTGTGCTGTAATTTTTTAAAA<br>TTGCTGAAGTGTCATGGTTTGCTATTTCGTATTTATTGAAAAAAT<br>GTAAATGCTATATTTAACAGAATGGCAGTAACTCTGTTTCAATCT<br>GAAGACTTAATCTTACTAATCATGGTAATATATGCTGGCTGGAGT<br>TGGGAATATTTCATAAAATACTGGAATAAATTTGTGCTTATATTT<br>CAGGGGAATTAATAAAAGCACCTTCATCTGCAACATTTAAAATGT<br>TATTGCCTTTAAATTTGTATTAAATAATGCAGGGAGGATAGATCA<br>CTGGGGGAGAATGGATGCACCTCTGTGAGGATCTTGGTCATTCAA<br>CACACGTGTACGGGTGAGGAAACTAAGGCACGACTTACTGGGTAG<br>GGAGGTAGGGATATTAGCAAGATCCTTCACTTGTCTGGGCTTTCT<br>GTCTTTGAGTCACCTTTGCGCAGTTTTTCACTGGACTTCACAAGC<br>CTCTGAGGCGGCAGGGCAGACAGGACATCCTTATTTTATAGAGGA<br>AAAAACTTAGGCTTACAGAGGTTTCCTGCCCCAAATCACAAAGGT<br>GGAGCCTAGACCTTCTCAGTCTCCACCAACTGTATTTCGGTTAGC<br>CACAATCCTATCTACCCACATCCAAATGGACACCGTGGCTCTGCA<br>ACTTCTGTCAAAAGGGCTCTTTGGCAACAGGAAAAACGTCATGGC<br>TCCATTGTATTGTAGAGGATGGGAATGGGTGTTCCGGCTAAATTC<br>TCCCTCCCCTTTCCCTCCACAGCTCAGATGGCAAATGTGCGACCC<br>AGGGACCTCCCGCTCCAGCAGACCTGTGCGCACAACTTTGCACAG<br>ATTACCTGCTAAGTCAGAGCCGAAAGGTAACACAGATGCCAAAGG<br>ATAATAAAGGTGAATGAGATTTACTCAAAATTGGAAACTTGGTGT<br>TTGGTTTTTCAGGAGAACAATCAACGACTGTGATTTGAAGTTCAC<br>CAGGGTATTCTGAGAGATCTAATCAAAGATAGAGTGCTGGTTTGA<br>AATTATTAAAAGGTAACAGTAAAAGGGAGAGCAAAACCCCAGTCC<br>CAACGCAACCCATAAATCTACTTTGTCTTCCTCGAAAGAGGGGCG |

TABLE 1-continued

| SEQ ID NO | Description | Sequence |
|---|---|---|
| | | CGGGTGGGCGCGTCTCCCCGCGAGCATCTCACCTAAGGGGGAATC<br>CCTTTCAGCGCACGGCGAAGTTCCCCCTCGGCTGTCCCACCTGGC<br>AGTCCCTCTAGGATTTCGGCCAGTCCCTAATTGGCTCCAGCAATG<br>TCCAGCCGGAGCTTCTTTGGGCCTCCGAGTGGGAGAAAAGTGAGA<br>GCAGGTGCTTCCCCAGCGGCGCGCTCCGCTAGGGCCCGGCAGGAT<br>CCCGCCCCCAAGTCGGGGAAAGTTGGTCGGCGCCTTTTCTCCCCG<br>ACGAAGCCGCTCCAGGGCTGCTCTCAGAGGACGCGCGGCAGGCAA<br>AGAGAATGAACCTGAGCGTCCACGAAACGTCCTGCACGGCTCCCG<br>GGAGCTGGGAGGAACAGGTGCCTTTCTCCGACGTCCGCGGGCGAC<br>GCCTGCCGCACCTTGCCCGCTGCCGCGCCCCTCCCGGGCACCCCT<br>CGCC |

Klotho

Klotho plays important regulatory and protective roles in, inter alia, memory loss, stress, synaptic plasticity, biopolar disorder, epilepsy, Alzheimer's disease, Parkinson's disease, multiple sclerosis, myelin-related disease, neurogenic decline, neurodegeneration and kidney dysfunction (Vo et al., 2018. *Brain Plast.* 3: 183-194).

The human Klotho gene is located on chromosome 13 and comprises five exons. The Klotho protein primarily exists in one of three forms. Transmembrane Klotho is an approximately 130 kDa, glyclosylated, Type I transmembrane protein. The transmembrane Klotho can be shed from the cell surface by ADAM10/17 metalloproteinases into a soluble form that is detectable in serum and CSF (Bloch et al., 2009. *FEBS Lett.* 583(19): 3221-3224; Chen et al., 2007. *Proc. Natl Acad. Sci. USA.* 104(50): 19796-19801; Matsumura et al., 1998. *Biochem. Biophys. Res. Commun.* 242(3): 626-630). A third, secreted form of Klotho is generated by alternative splicing of exon 3 to produce a 70 kDa protein which is detectable in blood and CSF (Masso et al., 2015. *PLoS One.* 10(11): e0143623). Both the transmembrane and soluble forms of Klotho have important functions in many homeostatic processes.

Table 1 lists various Klotho sequences that are relevant to the present disclosure. Those skilled in the art will understand that several different Klotho alleles exist among humans, and all of those alleles are envisaged by the present disclosure. Skilled persons will also understand that greater levels of sequence variation may exist in genomic regions which do not directly encode amino acids.

RNA Transcripts

The present disclosure provides methods for increasing expression of a Klotho gene in a cell the method comprising administering to the cell a binding molecule (such as a nucleic acid) that binds to an RNA transcript transcribed from a chromosomal region within or near the Klotho gene. The RNA transcript preferably does not encode a Klotho protein. A chromosomal region will be considered "near" the Klotho gene if, despite not being located within the Klotho gene, the chromosomal region is sufficiently close to the Klotho gene such that a RNA transcript transcribed from the chromosomal region suppresses the expression of Klotho. Targeting that RNA transcript, eg, with a nucleic acid, should therefore increase expression of the Klotho gene.

RNA transcripts transcribed from a region within or near the Klotho gene can readily be identified by a person skilled in the art using one or more of a variety of known techniques. For example, a skilled person could perform reverse transcription using strand-specific primers or strand-unspecific primers. Priming reverse transcription using random short oligomers (eg, hexamers) would be an example of strand-unspecific reverse transcription as the oligomers would be expected to hybridise to, and prime reverse transcription of, sense and antisense RNA transcripts. Short random oligomers would be expected to hybridise to transcripts transcribed from chromosomal regions located anywhere or almost anywhere in the genome. Alternatively, primers may be designed to hybridise to, and prime reverse transcription of, either sense or antisense transcripts transcribed from a particular locus or loci (see, eg, Example 1). Still further, a person skilled in the art could readily perform genome-wide RNA sequencing (sometimes referred to as transcriptome sequencing, RNAseq or next-generation RNA sequencing).

The RNA transcript of the present disclosure is preferably non-coding in the sense that it does not encode a Klotho protein. Determining whether or not a RNA transcript encodes a Klotho protein can readily be determined by a person skilled in the art using one or more of a variety of known techniques. For instance, using strand-specific reverse transcription, it may be found that the RNA transcript is transcribed from the opposite DNA strand from that which the Klotho mRNA is transcribed. That is, the RNA transcript may be an antisense transcript as compared to the Klotho mRNA which is a sense transcript. Such an antisense transcript would not encode a Klotho protein. Alternatively, the RNA transcript may be a sense transcript, but may encompass sequences that are located far upstream or far downstream from known Klotho mRNA sequences such that it can readily be determined that the RNA transcript does not encode a Klotho protein. After sequencing a RNA transcript transcribed from a region within or near a Klotho gene, a skilled person could also translate the RNA transcript (or a portion thereof) in all three reading frames and determine whether any of the translated amino acid sequences correspond to a known Klotho protein. Those skilled in the art will be aware of other methods for determining whether a RNA transcript transcribed from a region within or near the Klotho gene encodes a Klotho protein without undue burden. Preferably, the RNA transcript of the present disclosure does not encompass the Klotho mRNA sequence (SEQ ID NO. 1).

In certain examples, the RNA transcript of the present disclosure is transcribed from a chromosomal region comprising a region of at least about 150 nucleotides upstream of the Klotho gene translation start site. It will be understood that in such examples, the RNA transcript is at least 150 nucleotides in length and that it is transcribed from a chromosomal region comprising at least 150 nucleotides which are located upstream of the Klotho gene translation start site, although the chromosomal region (and the RNA transcript derived therefrom) may, if it is longer than 150 nucleotides, extend downstream of the Klotho gene translation start site. In certain examples, the RNA transcript of the present disclosure is transcribed from a chromosomal region comprising a region of DNA of at least about 200 nucleotides, or at least about 250 nucleotides, or at least about 300 nucleotides, or at least about 350 nucleotides, or at least about 400 nucleotides, or at least about 450 nucleotides, or at least about 500 nucleotides, or at least about 550 nucleotides, or at least about 575 nucleotides upstream of the Klotho gene translation start site.

In some examples, the chromosomal region from which the RNA transcript is transcribed comprises the region between about 400 nucleotides and 500 nucleotides upstream of the Klotho gene translation start site. It will be understood that in such examples, the chromosomal region is at least 100 nucleotides in length. In some examples, the chromosomal region from which the RNA transcript is transcribed comprises a region between about 350 nucleotides and 550 nucleotides upstream of the Klotho gene translation start site, or between about 302 nucleotides and 552 nucleotides upstream of the Klotho gene translation start site, or between about 250 nucleotides and 650 nucleotides upstream of the Klotho gene translation start site, or between about 200 and 650 nucleotides upstream of the Klotho gene translation start site, or between about 150 and 650 nucleotides upstream of the Klotho gene translation start site, or between about 106 and 685 nucleotides upstream of the Klotho gene translation start site. In certain examples, the chromosomal region comprises the region between about 40 nucleotides and 65 nucleotides upstream of the Klotho gene translation start site, such as between about 35 nucleotides and 70 nucleotides upstream of the Klotho gene translation start site. Preferably, such transcripts are sense transcripts. That is, the transcripts are preferably transcribed in the same direction as the Klotho mRNA.

In certain examples, the chromosomal region from which the RNA transcript is transcribed comprises the region between about 1,000 nucleotides and 1,150 nucleotides upstream of the Klotho translation start site, such as between about 1,000 nucleotides and 1,500 nucleotides upstream of the Klotho gene translation start site, or between about 750 nucleotides and 1,750 nucleotides upstream of the Klotho gene translation start site, or between about 500 nucleotides and 2,000 nucleotides upstream of the Klotho gene translation start site, or between about 250 nucleotides and 2,500 nucleotides upstream of the Klotho gene translation start site, or between about 200 nucleotides and 2,600 nucleotides upstream of the Klotho gene translation start site, or between about 183 nucleotides and 2,662 nucleotides upstream of the Klotho gene translation start site. The chromosomal region from which the RNA transcript is transcribed may comprise the region between about 2,750 nucleotides upstream of the Klotho gene translation start site and the Klotho gene translation start site, such as between about 2,750 nucleotides upstream of the Klotho gene translation start site and 100 nucleotides downstream of the Klotho gene translation start site, or between about 3,000 nucleotides upstream of the Klotho gene translation start site and 250 nucleotides downstream of the Klotho gene translation start site, or between about 3,100 nucleotides upstream of the Klotho gene translation start site and 300 nucleotides downstream of the Klotho gene translation start site, or between about 3,133 nucleotides upstream of the Klotho gene translation start site and 412 nucleotides downstream of the Klotho gene translation start site. In certain examples, the chromosomal region from which the RNA transcript is transcribed comprises the region between about 81 nucleotides and 103 nucleotides upstream of the Klotho gene translation start site. In certain examples, the chromosomal region from which the RNA transcript is transcribed comprises the region between about 200 nucleotides and 222 nucleotides upstream of the Klotho gene translation start site. In certain examples, the chromosomal region from which the RNA transcript is transcribed comprises the region between about 235 nucleotides and 257 nucleotides upstream of the Klotho gene translation start site. In certain examples, the chromosomal region from which the RNA transcript is transcribed comprises the region between about 308 nucleotides and 330 nucleotides upstream of the Klotho gene translation start site. In certain examples, the chromosomal region from which the RNA transcript is transcribed comprises the region between about 81 nucleotides and 330 nucleotides upstream of the Klotho gene translation start site. Such RNA transcripts are preferably antisense transcripts (as compared to the Klotho mRNA transcript, which is a sense transcript).

In other examples, the chromosomal region from which the RNA transcript is transcribed comprises the region between about 10 nucleotides upstream of the Klotho gene translation stop site and 100 nucleotides downstream of the Klotho gene translation stop site, or between about 10 nucleotides upstream of the Klotho gene translation stop site and 200 nucleotides downstream of the Klotho gene translation stop site, or between about 20 nucleotides upstream of the Klotho gene translation stop site and 300 nucleotides downstream of the Klotho gene translation stop site, or between about 30 nucleotides upstream of the Klotho gene translation stop site and 400 nucleotides downstream of the Klotho gene translation stop site, between about 32 nucleotides upstream of the Klotho gene translation stop site and 457 nucleotides downstream of the Klotho gene translation stop site, between about 100 nucleotides upstream of the Klotho gene translation stop site and 500 nucleotides downstream of the Klotho gene translation stop site, or between about 200 nucleotides upstream of the Klotho gene translation stop site and 500 nucleotides downstream of the Klotho gene translation stop site, or between about 267 nucleotides upstream of the Klotho gene translation stop site and 517 nucleotides downstream of the Klotho gene translation stop site. Preferably, such RNA transcripts are antisense transcripts. That is, the RNA transcripts are preferably transcribed in the opposite (reverse) direction as the Klotho mRNA.

In some examples, the RNA transcript of the present disclosure is at least about 100 nucleotides in length, such as at least about 150 nucleotides in length, or at least about 200 nucleotides in length, or at least about 250 nucleotides in length, or at least about 300 nucleotides in length, or at least about 350 nucleotides in length, or at least about 400 nucleotides in length, or at least about 450 nucleotides in length, or at least about 500 nucleotides in length, or at least about 550 nucleotides in length, or at least about 600 nucleotides in length, or at least about 650 nucleotides in length, or at least about 700 nucleotides in length. In some examples, the RNA transcript of the present disclosure is between about 100 and 10,000 nucleotides in length, such as between about 100 and 5,000 nucleotides, or between about 100 and 3,000 nucleotides, or between about 100 and 2,500 nucleotides, or between about 100 and 2,000 nucleotides, or between about 200 and 2,000 nucleotides, or between about 500 and 2,000 nucleotides, or between about 500 and 1,500 nucleotides, or between about 700 and 1,500 nucleotides in length. Such RNA transcripts may be spliced, in which case, corresponding intron-containing (immature) transcripts will be longer.

In some examples, the chromosomal region from which the RNA transcript is transcribed comprises the sequence set forth in SEQ ID NO. 5, or a sequence having at least about 60% identity, or at least about 65% identity, or at least about 70% identity, or at least about 75% identity, or at least about 80% identity, or at least about 85% identity, or at least about 90% identity, or at least about 95% identity, or at least about 99% identity, to the sequence set forth in SEQ ID NO. 5. In some examples, the chromosomal region from which the RNA transcript is transcribed comprises the sequence set forth in SEQ ID NO. 8, or a sequence having at least about 60% identity, or at least about 65% identity, or at least about 70% identity, or at least about 75% identity, or at least about 80% identity, or at least about 85% identity, or at least about 90% identity, or at least about 95% identity, or at least about 99% identity, to the sequence set forth in SEQ ID NO. 8. In other examples, the chromosomal region from which the RNA transcript is transcribed comprises the sequence set forth in SEQ ID NO. 14, or a sequence having at least about 60% identity, or at least about 65% identity, or at least about 70% identity, or at least about 75% identity, or at least about 80% identity, or at least about 85% identity, or at least about 90% identity, or at least about 95% identity, or at least about 99% identity, to the sequence set forth in SEQ ID NO. 14. In some examples, the chromosomal region from which the RNA transcript is transcribed comprises the sequence set forth in SEQ ID NO. 17, or a sequence having at least about 60% identity, or at least about 65% identity, or at least about 70% identity, or at least about 75% identity, or at least about 80% identity, or at least about 85% identity, or at least about 90% identity, or at least about 95% identity, or at least about 99% identity, to the sequence set forth in SEQ ID NO. 17. In some examples, the chromosomal region from which the RNA transcript is transcribed comprises the sequence set forth in SEQ ID NO. 53 or a sequence having at least about 60% identity, or at least about 65% identity, or at least about 70% identity, or at least about 75% identity, or at least about 80% identity, or at least about 85% identity, or at least about 90% identity, or at least about 95% identity, or at least about 99% identity, to the sequence set forth in SEQ ID NO. 53. In some examples, the chromosomal region from which the RNA transcript is transcribed comprises the sequence set forth in SEQ ID NO. 50 or a sequence having at least about 60% identity, or at least about 65% identity, or at least about 70% identity, or at least about 75% identity, or at least about 80% identity, or at least about 85% identity, or at least about 90% identity, or at least about 95% identity, or at least about 99% identity, to the sequence set forth in SEQ ID NO. 50. It will be understood that the RNA transcript may be transcribed from either DNA strand of such chromosomal regions (eg, the template strand of the chromosome may comprise the sequence set forth in the particular SEQ ID NO., or the template strand may comprise the complement of that sequence).

In some examples, the RNA transcript of the present disclosure comprises the sequence set forth in SEQ ID NO. 6 or a sequence having at least about 60% identity, or at least about 65% identity, or at least about 70% identity, or at least about 75% identity, or at least about 80% identity, or at least about 85% identity, or at least about 90% identity, or at least about 95% identity, or at least about 99% identity, to the sequence set forth in SEQ ID NO. 6. In some examples, the RNA transcript of the present disclosure comprises the sequence set forth in SEQ ID NO. 9 or a sequence having at least about 60% identity, or at least about 65% identity, or at least about 70% identity, or at least about 75% identity, or at least about 80% identity, or at least about 85% identity, or at least about 90% identity, or at least about 95% identity, or at least about 99% identity, to the sequence set forth in SEQ ID NO. 9. In other examples, the RNA transcript of the present disclosure comprises the sequence set forth in SEQ ID NO. 16 or a sequence having at least about 60% identity, or at least about 65% identity, or at least about 70% identity, or at least about 75% identity, or at least about 80% identity, or at least about 85% identity, or at least about 90% identity, or at least about 95% identity, or at least about 99% identity, to the sequence set forth in SEQ ID NO. 16. In some examples, the RNA transcript of the present disclosure comprises the sequence set forth in SEQ ID NO. 19 or a sequence having at least about 60% identity, or at least about 65% identity, or at least about 70% identity, or at least about 75% identity, or at least about 80% identity, or at least about 85% identity, or at least about 90% identity, or at least about 95% identity, or at least about 99% identity, to the sequence set forth in SEQ ID NO. 19. In some examples, the RNA transcript of the present disclosure comprises the sequence set forth in SEQ ID NO. 51 or a sequence having at least about 60% identity, or at least about 65% identity, or at least about 70% identity, or at least about 75% identity, or at least about 80% identity, or at least about 85% identity, or at least about 90% identity, or at least about 95% identity, or at least about 99% identity, to the sequence set forth in SEQ ID NO. 51. In some examples, the RNA transcript of the present disclosure comprises the sequence set forth in SEQ ID NO. 48 or a sequence having at least about 60% identity, or at least about 65% identity, or at least about 70% identity, or at least about 75% identity, or at least about 80% identity, or at least about 85% identity, or at least about 90% identity, or at least about 95% identity, or at least about 99% identity, to the sequence set forth in SEQ ID NO. 48.

Binding Molecules Including Nucleic Acids

The present disclosure provides methods for increasing expression of a Klotho gene in a cell the method comprising administering to the cell a binding molecule that binds to an RNA transcript transcribed from a chromosomal region within or near the Klotho gene. The RNA transcript preferably does not encode a Klotho protein. It will be understood that the RNA transcript, or transcription of the RNA transcript, may reduce expression of the Klotho gene, for example, by hybridising to Klotho mRNA or by interfering with the transcription of Klotho mRNA (Core et al. 2008. Science. 322(5909): 1845-1848; Seila et al. 208. Science. 322(5909): 1849-1851; Sun et al. 2005. Nucleic Acids Res. 33(17): 5533-5543; Shearwin et al. 2005. 21(6): 339-345; Katayama et al. 2005. Science. 309(5740): 1564-1566). Binding molecules which bind to the RNA transcript may therefore at least partially relieve the Klotho gene from the suppressive effects of the RNA transcript (or transcription of the RNA transcript), and thereby increase expression of the Klotho gene.

The binding molecule may be a small organic molecule. A small organic molecule generally has a low molecular weight such as less than 5000 Daltons, less than 4000 Daltons, less than 3000 Daltons, less than 2000 Daltons or less than 1000 Daltons. Such binding molecules may be identified using a number of different methods (see, eg, Connelly et al. 2016. Cell Chem. Biol. 2016: 23(9): 1077-1090).

Preferably, the binding molecule is a nucleic acid comprising a sequence that is substantially complementary to the RNA transcript transcribed from a chromosomal region within or near the Klotho gene. The level of complementarity is preferably sufficient to enable the nucleic acid to hybridise to its target (eg, an antisense RNA transcript overlapping with the Klotho gene) and, for example, guide RNAi. The nucleic acid may be an RNAi agent such as a siRNA, a short hairpin RNA (also referred to as a small hairpin RNA) or a miRNA which targets the RNA transcript for degradation by RNAi. In other examples, the nucleic acid is an antisense oligonucleotide (ASO) or an antagoNAT (Rusk. 2012. Nat. Methods. 9(5): 437; Modarresi et al. 2012. Nat. Biotechnol. 30(5): 453-459; Modaressi et al. 2011. Int. J. Alzheimer's Dis. 2011 929042; Finkel et al. 2016. Lancet. 388(10063): 3017-3026). In examples where the nucleic acid is a small RNA (eg, siRNA or miRNA), mismatches in the centre of the small RNA-target duplex may be more likely to reduce the efficacy of the small RNA compared to mismatches at the 3' end. The nucleic acid may comprise a sense strand and an antisense strand which form a double stranded region, but which need not be perfectly complementary with each other.

In examples where the nucleic acid is dsRNA, the dsRNA may comprise one or two overhang regions. The overhang regions may be 1 to 6 nucleotides in length, such as 2 to 6 nucleotides, 1 to 5 nucleotides, 2 to 5 nucleotides, 1 to 4 nucleotides, 2 to 4 nucleotides, 1 to 3 nucleotides, 2 or 3 nucleotides or 1 or 2 nucleotides in length. The overhangs can be the result of one strand being longer than the other, or the result of two strands of the same length being staggered. In one example, the nucleotides in the overhang region of the RNA are each independently a modified or unmodified nucleotide including, but no limited to 2'-sugar modified, such as, 2-F,2'-O-methyl, thymidine (T), deoxythymine (dT), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, dTdT can be an overhang sequence for either end on either strand. In some examples, the overhang region(s) contains two nucleotides having a phosphorothioate between the two nucleotides, where the two nucleotides can be the same or different. In some examples, the nucleic acid binding molecule is RNA and contains only a single overhang, which can strengthen the interference activity of the RNA, without affecting its overall stability.

In certain examples, the nucleic acid of the present disclosure comprises at least 10 contiguous nucleotides, such as at least 11 contiguous nucleotides, or at least 12 contiguous nucleotides, or at least 13 contiguous nucleotides, or at least 14 contiguous nucleotides, or at least 15 contiguous nucleotides, or at least 16 contiguous nucleotides, or at least 17 contiguous nucleotides, or at least 18 contiguous nucleotides, or at least 19 contiguous nucleotides, or at least 20 contiguous nucleotides, or at least 21 contiguous nucleotides, or at least 22 contiguous nucleotides, or at least 23 contiguous nucleotides, or at least 24 contiguous nucleotides, or at least 25 contiguous nucleotides which are substantially complementary to a nucleotide sequence set forth in SEQ ID NO. 3. In certain examples, the nucleic acid of the present disclosure comprises at least 10 contiguous nucleotides, such as at least 11 contiguous nucleotides, or at least 12 contiguous nucleotides, or at least 13 contiguous nucleotides, or at least 14 contiguous nucleotides, or at least 15 contiguous nucleotides, or at least 16 contiguous nucleotides, or at least 17 contiguous nucleotides, or at least 18 contiguous nucleotides, or at least 19 contiguous nucleotides, or at least 20 contiguous nucleotides, or at least 21 contiguous nucleotides, or at least 22 contiguous nucleotides, or at least 23 contiguous nucleotides, or at least 24 contiguous nucleotides, or at least 25 contiguous nucleotides which are substantially complementary to a nucleotide sequence set forth in SEQ ID NO. 9. In certain examples, the nucleic acid of the present disclosure comprises at least 15 contiguous nucleotides differing by no more than 3 nucleotides, or preferably no more than 2 nucleotides, or more preferably no more than 1 nucleotide from a nucleotide sequence set forth in SEQ ID NO. 10. In certain examples, the nucleic acid of the present disclosure comprises at least 15 contiguous nucleotides which are at least about 60% identical, or at least about 65% identical, or at least about 70% identical, or at least about 75% identical, or at least about 80% identical, or at least about 85% identical, or at least about 90% identical, or at least about 95% identical, or at least about 99% identical to a nucleotide sequence set forth in SEQ ID NO. 10. In certain examples, the nucleic acid of the present disclosure comprises a sequence that is at least about 50% identical, or at least about 55% identical, or at least about 60% identical, or at least about 65% identical, or at least about 70% identical, or at least about 75% identical, or at least about 80% identical, or at least about 85% identical, or at least about 90% identical, or at least about 95% identical, or at least about 99% identical to a nucleotide sequence set forth in SEQ ID NO. 21, 23, 25, 27, 29, 72, 86, 88, 90 or 92 and preferably to a nucleotide sequence set forth in SEQ ID NO. 21, 23 or 27.

In certain examples, the nucleic acid of the present disclosure comprises at least 10 contiguous nucleotides, such as at least 11 contiguous nucleotides, or at least 12 contiguous nucleotides, or at least 13 contiguous nucleotides, or at least 14 contiguous nucleotides, or at least 15 contiguous nucleotides, or at least 16 contiguous nucleotides, or at least 17 contiguous nucleotides, or at least 18 contiguous nucleotides, or at least 19 contiguous nucleotides, or at least 20 contiguous nucleotides, or at least 21 contiguous nucleotides, or at least 22 contiguous nucleotides, or at least 23 contiguous nucleotides, or at least 24 contiguous nucleotides, or at least 25 contiguous nucleotides which are substantially complementary to a nucleotide sequence set forth in SEQ ID NO. 51. In certain examples, the nucleic acid of the present disclosure comprises at least 10 contiguous nucleotides, such as at least 11 contiguous nucleotides, or at least 12 contiguous nucleotides, or at least 13 contiguous nucleotides, or at least 14 contiguous nucleotides, or at least 15 contiguous nucleotides, or at least 16 contiguous nucleotides, or at least 17 contiguous nucleotides, or at least 18 contiguous nucleotides, or at least 19 contiguous nucleotides, or at least 20 contiguous nucleotides, or at least 21 contiguous nucleotides, or at least 22 contiguous nucleotides, or at least 23 contiguous nucleotides, or at least 24 contiguous nucleotides, or at least 25 contiguous nucleotides which are substantially complementary to a nucleotide sequence set forth in SEQ ID NO. 48. In certain examples, the nucleic acid of the present disclosure comprises at least 15 contiguous nucleotides differing by no more than 3 nucleotides, or preferably no more than 2 nucleotides, or more preferably no more than 1 nucleotide from a nucleotide sequence set forth in SEQ ID NO. 52. In certain examples, the nucleic acid of the present disclosure comprises at least 15 contiguous nucleotides differing by no more than 3 nucleotides, or preferably no more than 2 nucleotides, or more preferably no more than 1 nucleotide from a nucleotide sequence set forth in SEQ ID NO. 49. In certain examples, the nucleic acid of the present disclosure comprises at least 15 contiguous nucleotides which are at least about 60% identical, or at least about 65% identical, or at least about 70% identical, or at least about 75% identical, or at least about 80% identical, or at least about 85% identical, or at least about 90% identical, or at least about 95% identical, or at least about 99% identical to a nucleotide sequence set forth in SEQ ID NO. 52. In certain examples, the nucleic acid of the present disclosure comprises at least 15 contiguous nucleotides which are at least about 60% identical, or at least about 65% identical, or at least about 70% identical, or at least about 75% identical, or at least about 80% identical, or at least about 85% identical, or at least about 90% identical, or at least about 95% identical, or at least about 99% identical to a nucleotide sequence set forth in SEQ ID NO. 49. In certain examples, the nucleic acid of the present disclosure comprises a sequence that is at least about 60% identical, or at least about 65% identical, or at least about 70% identical, or at least about 75% identical, or at least about 80% identical, or at least about 85% identical, or at least about 90% identical, or at least about 95% identical, or at least about 99% identical to a nucleotide sequence set forth in SEQ ID NO. 54, 55, 56, 57 or 58, and preferably to a nucleotide sequence set forth in SEQ ID NO. 56, 57 or 58.

In certain examples, the nucleic acid of the present disclosure comprises at least 10 contiguous nucleotides, such as at least 11 contiguous nucleotides, or at least 12 contiguous nucleotides, or at least 13 contiguous nucleotides, or at least 14 contiguous nucleotides, or at least 15 contiguous nucleotides, or at least 16 contiguous nucleotides, or at least 17 contiguous nucleotides, or at least 18 contiguous nucleotides, or at least 19 contiguous nucleotides, or at least 20 contiguous nucleotides, or at least 21 contiguous nucleotides, or at least 22 contiguous nucleotides, or at least 23 contiguous nucleotides, or at least 24 contiguous nucleotides, or at least 25 contiguous nucleotides which are substantially complementary to a nucleotide sequence set forth in SEQ ID NO. 19. In certain examples, the nucleic acid of the present disclosure comprises at least 15 contiguous nucleotides differing by no more than 3 nucleotides, or preferably no more than 2 nucleotides, or more preferably no more than 1 nucleotide from a nucleotide sequence set forth in SEQ ID NO. 18. In certain examples, the nucleic acid of the present disclosure comprises at least 15 contiguous nucleotides which are at least about 60% identical, or at least about 65% identical, or at least about 70% identical, or at least about 75% identical, or at least about 80% identical, or at least about 85% identical, or at least about 90% identical, or at least about 95% identical, or at least about 99% identical to a nucleotide sequence set forth in SEQ ID NO. 18. In certain examples, the nucleic acid of the present disclosure comprises a sequence that is at least about 60% identical, or at least about 65% identical, or at least about 70% identical, or at least about 75% identical, or at least about 80% identical, or at least about 85% identical, or at least about 90% identical, or at least about 95% identical, or at least about 99% identical to a nucleotide sequence set forth in SEQ ID NO. 31, 33 or 35, and preferably to a nucleotide sequence set forth in SEQ ID NO. 35.

In certain examples, the nucleic acid comprises a sequence that is substantially complementary to an antisense RNA transcript transcribed from a chromosomal region within or near the Klotho gene. For example, the nucleic acid may comprise a sequence that is substantially complementary to an antisense RNA transcript transcribed from a chromosomal region that overlaps with the Klotho coding sequence.

The nucleic acid of the present disclosure may be between about 10 nucleotides and 1,000 nucleotides in length, such as between about 15 nucleotides and 900 nucleotides, or between about 15 nucleotides and 750 nucleotides, or between about 15 nucleotides and 600 nucleotides, or between about 15 nucleotides and 500 nucleotides, or between about 15 nucleotides and 350 nucleotides, or between about 15 nucleotides and 250 nucleotides, or between about 15 nucleotides and 150 nucleotides, or between about 15 nucleotides and 100 nucleotides, or between about 15 nucleotides and 75 nucleotides, or between about 15 nucleotides and 50 nucleotides, or between about 15 nucleotides and 40 nucleotides, or between about 15 nucleotides and 30 nucleotides, or between about 20 nucleotides and 30 nucleotides in length. It will be understood that the nucleic acid may be double stranded and formed from separate complementary strands, in which case, the length of the nucleic acid is made with reference to one strand. For example, in examples where the nucleic acid is between 10 and 50 nucleotides in length, one strand will be between 10 and 50 nucleotides in length. The nucleic acid may be, or each stand of a double stranded nucleic acid may independently be, for example, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides or 30 nucleotides in length.

In certain examples, the present disclosure provides a method of increasing expression of a Klotho gene in a cell the method comprising administering to the cell a nucleic acid (eg, an siRNA, a miRNA, an ASO or an antagoNAT) comprising a sequence that is substantially complementary to a sense RNA transcript transcribed from a chromosomal region commencing at least 10 nucleotides upstream of the Klotho translation start site, wherein the RNA transcript does not encode a Klotho protein. In certain examples, the present disclosure provides a method of increasing expression of a Klotho gene in a cell the method comprising administering to the cell a nucleic acid comprising a sequence that is substantially complementary to a sense RNA transcript, wherein the sense RNA transcript is transcribed from a chromosomal region comprising the region between 302 nucleotides and 551 nucleotides, such as between 106 nucleotides and 685 nucleotides, upstream of the Klotho gene translation start site. In certain examples, the present disclosure provides a method of increasing expression of a Klotho gene in a cell the method comprising administering to the cell a nucleic acid comprising a sequence that is substantially complementary to a sense RNA transcript transcribed from a chromosomal region within or near the Klotho gene, wherein the RNA transcript comprises the sequence set forth in SEQ ID NO. 6 or a sequence having at least about 90% identity to SEQ ID NO. 6. In certain examples, the present disclosure provides a method of increasing expression of a Klotho gene in a cell the method comprising administering to the cell a nucleic acid comprising a sequence that is substantially complementary to a sense RNA transcript transcribed from a chromosomal region within or near the Klotho gene, wherein the nucleic acid comprises at least 15 contiguous nucleotides which are substantially complementary to a nucleotide sequence located upstream of the Klotho translation start site. In certain examples, the present disclosure provides a method of increasing expression of a Klotho gene in a cell the method comprising administering to the cell a nucleic acid comprising a sequence that is substantially complementary to a sense RNA transcript transcribed from a chromosomal region within or near the Klotho gene, wherein the nucleic acid comprises at least 15 contiguous nucleotides which are substantially complementary to a nucleotide sequence set forth in SEQ ID NO. 3. In certain examples, the present disclosure provides a method of increasing expression of a Klotho gene in a cell the method comprising administering to the cell a nucleic acid comprising a sequence that is substantially complementary to a sense RNA transcript transcribed from a chromosomal region within or near the Klotho gene, wherein the nucleic acid comprises a sequence that is at least about 90% identical to the sequence set forth in SEQ ID NO. 21, 23 or 27.

In some examples, the present disclosure provides an isolated, recombinant or synthesised nucleic acid that binds to an RNA transcript transcribed from a chromosomal region within or near a Klotho gene. In certain examples, the chromosomal region comprises a region of at least 200 nucleotides upstream of the Klotho gene translation start site. In certain examples, the chromosomal region comprises the region between 302 nucleotides and 551 nucleotides upstream of the Klotho gene translation start site. In certain examples, the chromosomal region comprises the region between 106 nucleotides and 685 nucleotides upstream of the Klotho gene translation start site. In certain examples, the chromosomal region comprises the sequence set forth in SEQ ID NO. 5 or a sequence having at least about 90% identity to SEQ ID NO. 5. In certain examples, the chromosomal region comprises the sequence set forth in SEQ ID NO. 8 or a sequence having at least about 90% identity to SEQ ID NO. 8. In certain examples, the RNA transcript comprises the sequence set forth in SEQ ID NO. 6 or a sequence having at least about 90% identity to SEQ ID NO. 6. In certain examples, the RNA transcript comprises the sequence set forth in SEQ ID NO. 9 or a sequence having at least about 90% identity to SEQ ID NO. 9. In certain examples, the nucleic acid comprises at least 15 contiguous nucleotides which are substantially complementary to a nucleotide sequence set forth in SEQ ID NO. 3. In certain examples, the nucleic acid comprises at least 15 contiguous nucleotides which are substantially complementary to a nucleotide sequence set forth in SEQ ID NO. 9. In certain examples, the nucleic acid comprises at least 15 contiguous nucleotides differing by no more than 3 nucleotides from a nucleotide sequence set forth in SEQ ID NO. 10. In certain examples, the nucleic acid comprises at least 15 contiguous nucleotides which are at least about 90% identical to a nucleotide sequence set forth in SEQ ID NO. 10. In certain examples, the nucleic acid comprises a sequence that is at least about 90% identical to the sequence set forth in SEQ ID NO. 21, SEQ ID NO. 23, SEQ ID NO. 25, SEQ ID NO. 27 or SEQ ID NO. 29. In certain examples, the nucleic acid comprises a sequence that is at least about 90% identical to the sequence set forth in SEQ ID NO. 21, SEQ ID NO. 23 or SEQ ID NO. 27. In certain examples, the RNA transcript is a sense RNA transcript. In certain examples, the chromosomal region comprises the region between 183 nucleotides and 2,662 nucleotides upstream of the Klotho gene translation start site. In certain examples, the chromosomal region comprises the sequence set forth in SEQ ID NO. 53 or a sequence having at least about 90% identity to SEQ ID NO. 53. In certain examples, the RNA transcript comprises the sequence set forth in SEQ ID NO. 51 or a sequence having at least about 90% identity to SEQ ID NO. 51. In certain examples, the nucleic acid comprises at least 15 contiguous nucleotides which are substantially complementary to a nucleotide sequence set forth in SEQ ID NO. 51. In certain examples, the nucleic acid comprises at least 15 contiguous nucleotides differing by no more than 3 nucleotides from a nucleotide sequence set forth in SEQ ID NO. 52. In certain examples, the nucleic acid comprises at least 15 contiguous nucleotides which are at least about 90% identical to a nucleotide sequence set forth in SEQ ID NO. 52. In certain examples, the chromosomal region comprises the region between 3,133 nucleotides upstream of the Klotho gene translation start site and 412 nucleotides downstream of the Klotho gene translation start site. In certain examples, the chromosomal region comprises the sequence set forth in SEQ ID NO. 50 or a sequence having at least about 90% identity to SEQ ID NO. 50. In certain examples, the RNA transcript comprises the sequence set forth in SEQ ID NO. 48 or a sequence having at least about 90% identity to SEQ ID NO. 48. In certain examples, the nucleic acid comprises at least 15 contiguous nucleotides which are substantially complementary to a nucleotide sequence set forth in SEQ ID NO. 48. In certain examples, the nucleic acid comprises at least 15 contiguous nucleotides differing by no more than 3 nucleotides from a nucleotide sequence set forth in SEQ ID NO. 49. In certain examples, the nucleic acid comprises at least 15 contiguous nucleotides which are at least about 90% identical to a nucleotide sequence set forth in SEQ ID NO. 49. In certain examples, the nucleic acid comprises a sequence that is at least about 90% identical to the sequence set forth in SEQ ID NO. 54, SEQ ID NO. 55, SEQ ID NO. 56, SEQ ID NO. 57 or SEQ ID NO. 58. In certain examples, the nucleic acid comprises a sequence that is at least about 90% identical to the sequence set forth in SEQ ID NO. 56, SEQ ID NO. 57 or SEQ ID NO. 58. In certain examples, the chromosomal region comprises the region between 32 nucleotides upstream of the Klotho gene translation stop site and 457 nucleotides downstream of the Klotho gene translation stop site. In certain examples, the chromosomal region comprises the region between 267 nucleotides upstream of the Klotho gene translation stop site and 517 nucleotides downstream of the Klotho gene translation stop site. In certain examples, the chromosomal region comprises the sequence set forth in SEQ ID NO. 14 or a sequence having at least about 90% identity to SEQ ID NO. 14. In certain examples, the chromosomal region comprises the sequence set forth in SEQ ID NO. 17 or a sequence having at least about 90% identity to SEQ ID NO. 17. In certain examples, the RNA transcript comprises the sequence set forth in SEQ ID NO. 16 or a sequence having at least about 90% identity to SEQ ID NO. 16. In certain examples, the RNA transcript comprises the sequence set forth in SEQ ID NO. 19 or a sequence having at least about 90% identity to SEQ ID NO. 19. In certain examples, the nucleic acid comprises at least 15 contiguous nucleotides which are substantially complementary to a nucleotide sequence set forth in SEQ ID NO. 19. In certain examples, the nucleic acid comprises at least 15 contiguous nucleotides differing by no more than 3 nucleotides from a nucleotide sequence set forth in SEQ ID NO. 18. In certain examples, the nucleic acid comprises at least 15 contiguous nucleotides which are at least about 90% identical to a nucleotide sequence set forth in SEQ ID NO. 18. In certain examples, the nucleic acid comprises a sequence that is at least about 90% identical to the sequence set forth in SEQ ID NO. 31, SEQ ID NO. 33 or SEQ ID NO. 35. In certain examples, the nucleic acid comprises a sequence that is at least about 90% identical to the sequence set forth in SEQ ID NO. 35. In certain examples, the RNA transcript is an antisense RNA transcript. In certain examples, the nucleic acid is between 15 and 50 nucleotides in length. In certain examples, the nucleic acid is RNA. In certain examples, the nucleic acid is a siRNA or a nucleic acid encoding a siRNA. In certain examples, the siRNA is conjugated to N-acetylgalactosamine.

In certain examples, the present disclosure provides a method of increasing expression of a Klotho gene in a cell the method comprising administering to the cell a nucleic acid (eg, an siRNA, a miRNA, an ASO or an antagoNAT) comprising a sequence that is substantially complementary to an antisense RNA transcript transcribed from a chromosomal region within or near the Klotho gene. For example, the present disclosure provides a method of increasing expression of a Klotho gene in a cell the method comprising administering to the cell a nucleic acid comprising a sequence that is substantially complementary to an antisense RNA transcript transcribed from a chromosomal region commencing downstream (eg, at least 10 nucleotides downstream) of the Klotho translation stop site and extending upstream of the Klotho translation stop site. It will be understood that in such examples, transcription of the RNA transcript progresses towards the Klotho translation stop codon and into the Klotho coding sequence. In certain examples, the present disclosure provides a method of increasing expression of a Klotho gene in a cell the method comprising administering to the cell a nucleic acid comprising a sequence that is substantially complementary to an antisense RNA transcript transcribed from a chromosomal region within or near the Klotho gene, wherein the chromosomal region comprises the region between 32 nucleotides upstream of the Klotho gene translation stop site and 457 nucleotides downstream of the Klotho gene translation stop site. In certain examples, the present disclosure provides a method of increasing expression of a Klotho gene in a cell the method comprising administering to the cell a nucleic acid comprising a sequence that is substantially complementary to an antisense RNA transcript transcribed from a chromosomal region within or near the Klotho gene, wherein the nucleic acid comprises at least 15 contiguous nucleotides which are substantially complementary to a nucleotide sequence set forth in SEQ ID NO. 19. In certain examples, the present disclosure provides a method of increasing expression of a Klotho gene in a cell the method comprising administering to the cell a nucleic acid comprising a sequence that is substantially complementary to an antisense RNA transcript transcribed from a chromosomal region within or near the Klotho gene, wherein the RNA transcript comprises the sequence set forth in SEQ ID NO. 16 or a sequence having at least about 90% identity to SEQ ID NO. 16. In certain examples, the present disclosure provides a method of increasing expression of a Klotho gene in a cell the method comprising administering to the cell a nucleic acid comprising a sequence that is substantially complementary to an antisense RNA transcript transcribed from a chromosomal region within or near the Klotho gene, wherein the nucleic acid comprises at least 15 contiguous nucleotides which are at least about 90% identical to a nucleotide sequence set forth in SEQ ID NO. 18. In certain examples, the present disclosure provides a method of increasing expression of a Klotho gene in a cell the method comprising administering to the cell a nucleic acid comprising a sequence that is substantially complementary to an antisense RNA transcript transcribed from a chromosomal region within or near the Klotho gene, wherein the nucleic acid comprises a sequence that is at least about 90% identical to the sequence set forth in SEQ ID NO. 35.

In some examples, the present disclosure provides a method of increasing expression of a Klotho gene in a cell the method comprising administering to the cell a nucleic acid (eg, an SIRNA, a miRNA, an ASO or an antagoNAT) comprising a sequence that is substantially complementary to an antisense RNA transcript transcribed from a chromosomal region comprising the region between 183 nucleotides and 2,662 nucleotides upstream of the Klotho gene translation start site. In some examples, the present disclosure provides a method of increasing expression of a Klotho gene in a cell the method comprising administering to the cell a nucleic acid (eg, an siRNA, a miRNA, an ASO or an antagoNAT) comprising a sequence that is substantially complementary to an antisense RNA transcript transcribed from a region commencing downstream of the Klotho gene translation start site, such as about 412 nucleotides downstream of the Klotho gene translation start site, and ending about 3,133 nucleotides upstream of the Klotho gene translation start site. In certain examples, the present disclosure provides a method of increasing expression of a Klotho gene in a cell the method comprising administering to the cell a nucleic acid comprising a sequence that is substantially complementary to an antisense RNA transcript transcribed from a chromosomal region within or near the Klotho gene, wherein the nucleic acid comprises at least 15 contiguous nucleotides which are substantially complementary to a nucleotide sequence set forth in SEQ ID NO. 51 or SEQ ID NO. 48. In certain examples, the present disclosure provides a method of increasing expression of a Klotho gene in a cell the method comprising administering to the cell a nucleic acid comprising a sequence that is substantially complementary to an antisense RNA transcript transcribed from a chromosomal region within or near the Klotho gene, wherein the RNA transcript comprises the sequence set forth in SEQ ID NO. 51 or 48, or a sequence having at least about 90% identity to SEQ ID NO. 51 or 48. In certain examples, the present disclosure provides a method of increasing expression of a Klotho gene in a cell the method comprising administering to the cell a nucleic acid comprising a sequence that is substantially complementary to an antisense RNA transcript transcribed from a chromosomal region within or near the Klotho gene, wherein the nucleic acid comprises at least 15 contiguous nucleotides which are at least about 90% identical to a nucleotide sequence set forth in SEQ ID NO. 52 or 49.

In certain examples, the nucleic acid of the present disclosure comprises modifications, for example, end modifications, eg, 5'-end modifications (phosphorylation, conjugation, inverted linkages) or 3'-end modifications (conjugation, DNA nucleotides, inverted linkages, etc.); base modifications, eg, replacement with stabilizing bases, destabilizing bases, or bases that base pair with an expanded repertoire of partners, removal of bases (abasic nucleotides), or conjugated bases; sugar modifications (eg, at the 2'-position or 4'-position) or replacement of the sugar; and/or backbone modifications, including modification or replacement of the phosphodiester linkages. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In peptide nucleic acid (PNA) compounds, the sugar backbone of a RNA is replaced with an amide containing backbone, in particular an aminoethylglycine backbone. The nucleobases are retained and are bound directly or indirectly to aza nitrogen atoms of the amide portion of the backbone. Modified RNAs can also contain one or more substituted sugar moieties. The RNA may include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. A RNA can also comprise nucleobase (base) modifications. Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deasaguanine and 3-deazaadenine.

In examples where the nucleic acid of the present disclosure is RNA, the RNA may be modified to include one or more locked nucleic acids (LNA). A locked nucleic acid is a nucleotide having a modified ribose moiety in which the ribose moiety comprises an extra bridge connecting the 2' and 4' carbons. This structure effectively “locks” the ribose in the 3'-endo structural conformation. The addition of locked nucleic acids to siRNAs has been shown to increase siRNA stability in serum, and to reduce off-target effects (Elmen, et al., 2005. Nucleic Acids Research 33(1):439-447). Potentially stabilizing modifications to the ends of RNA can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), inverted base dT(idT) and others. In preferred examples, the nucleic acid of the present disclosure is conjugated to N-acetylgalactosamine (GalNAc) or a GalNAc derivative. The GalNAc may be attached to the nucleic acid via a monovalent linker, a bivalent linker or a trivalent linker.

The nucleic acid may be modified or unmodified, RNA or DNA, isolated, synthesised or recombinant. In examples where the nucleic acid is RNA, that RNA may be administered to a cell either directly or as a DNA molecule which is transcribed to produce the RNA. In either case, a binding molecule that binds to an RNA transcript is considered to have been administered to the cell. The RNA may be single stranded (ss) or double stranded (ds).

The level of complementarity between the nucleic acid and the RNA transcript is preferably sufficient to enable the nucleic acid to hybridise to the transcript and, for example, guide RNAi, which results in degradation of the transcript. Those skilled in the art will be aware of various techniques that may be used to measure RNA accumulation, for example, qPCR, Northern blotting, microarray, nucleic acid sequencing etc. In some examples, administration of a nucleic acid of the present disclosure reduces accumulation of the RNA transcript by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more. The reduction in transcript levels may be measured, for example, by comparing two populations of cells; one control (untreated) population and one population which is treated with the nucleic acid, such that the level of transcript reduction is measured as: [(transcript in control cells)−(transcript in treated cells)]+(transcript in control cells)×100%.

The nucleic acid of the present disclosure may be a siRNA or a nucleic acid encoding a siRNA. RNAi constructs may be produced by chemical synthetic methods or by recombinant nucleic acid techniques. Endogenous RNA polymerase of a treated cell may mediate transcription in vivo, or cloned RNA polymerase may be used for in vitro transcription. The RNAi constructs may include modifications to either the phosphate-sugar backbone or the nucleoside, for example, to reduce susceptibility to cellular nucleases, improve bioavailability, improve formulation characteristics, or to change other pharmacokinetic properties. The RNAi construct may encode a long dsRNA. In certain examples, the RNAi construct encodes a dsRNA that is at least 20, 25, 30, 50, 100, 200, 300 or 400 nucleotides in length. Long dsRNAs produced by such constructs may be digested intracellularly to produce small RNAs in the cell. In certain examples, the RNAi construct may encode a hairpin RNA.

Administration

The delivery of a nucleic acid of the present disclosure to a cell, eg, a cell within a subject, such as a human subject, can be achieved in a number of different ways. In vivo delivery may be performed directly by administering to a subject a composition comprising a nucleic acid of the present disclosure. Alternatively, in examples where the nucleic acid of the disclosure is RNA, in vivo delivery may be performed indirectly by administering one or more DNA vectors that encode and direct the expression of the RNA.

Factors to consider for in vivo delivery include biological stability of the delivered nucleic acid, prevention of non-specific effects and accumulation of the nucleic acid in the target tissue. The non-specific effects of the nucleic acid can be minimized by local administration, for example, by direct injection or implantation into a tissue. Modification of the nucleic acid or the pharmaceutical carrier can also permit tissue-specific targeting and reduced off-target effects. Nucleic acid molecules can be modified by chemical conjugation to lipophilic groups such as cholesterol to enhance cellular uptake and to prevent degradation (see, eg, Soutschek, et al. 2004. *Nature* 432:173-178).

In some examples, the nucleic acid may be delivered using drug delivery systems such as a nanoparticle, a dendrimer, a polymer, liposomes, or a cationic delivery system. Cationic delivery systems facilitate binding of a nucleic acid molecule and also enhance interactions at the negatively charged cell membrane to permit efficient uptake of the nucleic acid by the cell. Cationic lipids, dendrimers, or polymers can either be bound to a nucleic acid, or induced to form a vesicle or micelle (see eg, Kim, et al. 2008. *J Controlled Release* 129(2): 107-116) that encases a nucleic acid. The formation of vesicles or micelles further prevents degradation of the nucleic acid when administered systemically. Methods for making and administering cationic nucleic acid complexes can readily be performed by those skilled in the art (see eg, Sorensen, et al. 2003. *J. Mal. Biol.* 327:761-766; Verma, et al. 2003. *Clin. Cancer Res.* 9:1291-1300; Arnold, et al. 2007. *J. Hypertens.* 25: 197-205). Some non-limiting examples of drug delivery systems useful for systemic delivery of RNA include DOTAP (Sorensen, et al. 2003. *J. Mal. Biol.* 327:761-766; Verma, et al. 2003. *Clin. Cancer Res.* 9:1291-1300), oligofectamine, solid nucleic acid lipid particles (Zimmermann, et al. 2006. *Nature* 441: 111-114), cardiolipin (Chien, et al. 2005. *Cancer Gene Ther.* 12:321-328; Pal, et al. 2005. *Int J. Oneal.* 26: 1087-1091), polyethyleneimine (Aigner, 2006. *J. Biomed. Biotechnol.* 71659), Arg-Gly-Asp (RGD) peptides (Liu, 2006. *Mal. Pharm.* 3:472-487), and polyamidoamines (Tomalia, et al. 2007. *Biochem. Soc. Trans.* 35:61-67). In some examples, the nucleic acid forms a complex with cyclodextrin for systemic administration. In some examples, the nucleic acid of the present disclosure is formulated with a lipid nanoparticle composition comprising a cationic lipid/Cholesterol/PEG-C-DMA/DSPC (eg, in a 40/48/2/10 ratio), a cationic lipid/Cholesterol/PEG-DMG/DSPC (eg, in a 40/48/2/10 ratio), ora cationic lipid/Cholesterol/PEG-DMG (eg, in a 60/38/2 ratio). In some examples, the cationic lipid is Octyl CL in DMA, DL in DMA, L-278, DLinKC2DMA or MC3. In certain examples, the nucleic acid is conjugated to, or complexed with, another compound, eg, to facilitate delivery of the nucleic acid (eg, CDM-LBA, CDM-Pip-LBA, CDM-PEG, CDM-NAG etc.). In certain examples, polyethylene glycol (PEG) is covalently attached to the nucleic acid. In further examples, the nucleic acid is formulated or complexed with polyethyleneimine or a derivative thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-tri-GAL) derivatives.

In examples where the nucleic acid of the present disclosure is an RNA molecule, that molecule may be expressed from a DNA vector. Expression can be transient (in the order of hours to weeks) or sustained (weeks to months or longer), depending upon the specific construct used and the target tissue or cell type. Transgenes expressing the RNA can be introduced as a linear construct, a circular plasmid, or a viral vector, which can be an integrating or non-integrating vector. The transgene can also be constructed to permit inheritance as an extrachromosomal plasmid (Gassmann, et al. 1995. *Proc. Natl. Acad. Sci.* USA 92:1292). The individual strand or strands of a RNA can be transcribed from a promoter on an expression vector. Where two separate strands are to be expressed to generate, for example, a dsRNA, two separate expression vectors can be co-introduced (eg, by transfection or infection) into a target cell. Alternatively, transcription of each individual strand of a dsRNA can be directed by promoters, both of which are located on the same expression plasmid. In one example, a dsRNA is expressed as inverted repeat polynucleotides joined by a linker polynucleotide sequence such that the dsRNA has a stem and loop structure.

RNA expression vectors are generally DNA plasmids or viral vectors. Expression vectors compatible with eukaryotic cells, preferably those compatible with vertebrate cells, can be used to produce recombinant constructs for the expression of a RNA molecule as described herein. Classes of viral systems that are used in gene therapy can be categorized into two groups according to whether their genomes integrate into host cellular chromatin (oncoretroviruses and lentiviruses) or persist in the cell nucleus predominantly as extrachromosomal episomes (adeno-associated virus, adenoviruses and herpesviruses). In certain examples, the viral vector is an adenoviral (AdV) vector. Adenoviruses are medium sized double-stranded, non-enveloped DNA viruses with linear genomes that are between 26-48 Kbp. In other examples, the viral vector is from the Parvoviridae family. The Parvoviridae is a family of small single-stranded, non-enveloped DNA viruses with genomes approximately 5000 nucleotides long. Included among the family members is adeno-associated virus (AAV). In some examples, the viral vector of the present disclosure is an AAV. In other examples, the viral vector is from the family Retroviridae. Retroviruses comprise single-stranded RNA animal viruses that are characterized by two unique features. First, the genome of a retrovirus is diploid. Second, this RNA is transcribed by the virion-associated enzyme reverse transcriptase into double-stranded DNA. This dsDNA or provirus can then integrate into the host genome and be passed from parent cell to progeny cells as a stably-integrated component of the host genome. In certain examples, the viral vector is a lentivirus. Lentivirus vectors are often pseudotyped with vesicular steatites virus glycoprotein (VSV-G), and have been derived from the human immunodeficiency virus (HIV); visan-maedi, which causes encephalitis (visna) or pneumonia in sheep; equine infectious anemia virus (EIAV), which causes autoimmune hemolytic anemia and encephalopathy in horses; feline immunodeficiency virus (FIV), which causes immune deficiency in cats; bovine immunodeficiency virus (BIV) which causes lymphadenopathy and lymphocytosis in cattle; and simian immunodeficiency virus (SIV), which causes immune deficiency and encephalopathy in non-human primates. A lentiviral-based construct used to express RNA of the disclosure preferably comprises sequences from the 5' and 3' long terminal repeats (LTRs) of a lentivirus. In some examples, the viral construct comprises an inactivated or self-inactivating 3' LTR from a lentivirus. The 3' LTR may be made self-inactivating by any method known in the art. Viral vector systems which can be used in the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, eg, vaccinia virus vectors or avipox, eg, canary pox or fowl pox; and (j) a helper-dependent or gutless adenovirus.

In some examples, the nucleic acid of the present disclosure is administered via a route such as, but not limited to, enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration, which is then covered by a dressing that occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, nerve block, biliary perfusion, cardiac perfusion, photopheresis and spinal.

Modes of administration include injection, infusion, instillation, and/or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some examples, the route is intravenous. For the delivery of cells, administration by injection or infusion can be performed.

In addition, components may be formulated to permit release over a prolonged period of time. A release system can include a matrix of a biodegradable material or a material which releases the incorporated components by diffusion. The components can be homogeneously or heterogeneously distributed within the release system. A variety of release systems may be useful, however, the choice of the appropriate system will depend upon the rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). The release system material can be selected so that components having different molecular weights are released by diffusion or through degradation of the material. Representative synthetic, biodegradable polymers include, for example: polyamides such as poly (amino acids) and poly(peptides); polyesters such as poly (lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly(ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof. Poly(lactide-co-glycolide) microspheres can also be used.

The nucleic acids of the present disclosure may be administered as a composition which includes materials for increasing the biological stability of the nucleic acid and/or materials that increase the ability of the composition to penetrate a particular cell type. The nucleic acid is preferably administered with a pharmaceutically acceptable carrier (eg, physiological saline), which is selected on the basis of the mode and route of administration, and standard pharmaceutical practice. In some examples, an isotonic formulation is used. Generally, additives for isotonicity can include sodium chloride, dextrose, mannitol, sorbitol and lactose. In some cases, isotonic solutions such as phosphate buffered saline are preferred. Stabilizers include gelatin and albumin. In some examples, a vasoconstriction agent is added to the formulation. The compositions according to the present disclosure are preferably sterile and pyrogen free.

Dosages may vary with the type and severity of the condition to be treated, and may include single or multiple dosses. Specific dosage regimens may be adjusted over time according to the individual need and the professional judgment of the practitioner administering the composition. When administered to a human subject, the dosage regimen may vary depending on a variety of factors including the type and severity of the condition, the age, sex, weight or medical condition of the subject and the route of administration. A suitable dose may be in the range of about 0.001 to about 200 milligrams per kilogram body weight of the recipient per day, generally in the range of about 1 to 50 mg per kilogram body weight per day. For example, the nucleic acid may be administered at about 0.01 mg/kg, about 0.05 mg/kg, about 0.5 mg/kg, about 1 mg/kg, about 1.5 mg/kg, about 2 mg/kg, about 3 mg/kg, about 10 mg/kg, about 20 mg/kg, about 30 mg/kg, about 40 mg/kg, or about 50 mg/kg per dose.

Compositions comprising the binding molecules described herein may be administered over a period of hours, days, weeks, or months, depending on several factors, including the severity of the condition being treated, whether a recurrence is considered likely, etc. The administration may be constant, eg, constant infusion over a period of hours, days, weeks, months, etc. Alternatively, the administration may be intermittent, eg, once per day over a period of days, once per hour over a period of hours, or any other such schedule as deemed suitable.

Treatments

The present disclosure provides methods for treating a neurological disorder in a subject the method comprising administering to the subject a therapeutically effective amount of a binding molecule, such as a nucleic acid, that binds to an RNA transcript transcribed from a chromosomal region within or near the Klotho gene. The RNA transcript preferably does not encode a Klotho protein, and administration of the binding molecule preferably increases expression of the Klotho gene in the subject. The neurological disorder may be associated with memory loss, psychological dysfunction, stress, biopolar disorder, epilepsy, dementia (eg, post stroke dementia, post-traumatic dementia, senile dementia), Alzheimer's disease, Parkinson's disease, Huntington's disease, Creutzfeldt-Jakob disease, ataxia telangiectasia, craniocerebral trauma, amyotrophic lateral sclerosis (ALS), depression, schizophrenia, multiple sclerosis, myelin-related disease, oxidative stress, neurogenic decline or neurodegeneration. Symptoms of neurological disorders may include memory loss, anxiety, depression, insomnia, disorientation, irrational fear, decline of motor skills or locomotor activity, neophobia, apathy, agitation, tremors, loss of balance, irritability or agoraphobia.

The method may further comprise administering to the subject an active agent suitable for the treatment of a neurological disorder such as donepezil hydrochloride, memantine, rivastigmine, ligustilide, aripiprazole, asenapine, cariprazine, clozapine, lurasidone, olanzapine, quetiapine, risperidone, ziprasidone, xenazine, tetrabenazine, baclofen, lioresal, kemstro, deutetrabenazine, austedo, *cannabis* extract, a cannabinoid or cannabinol, an antidepressant, memantine, a cholinesterase inhibitor, an antipsychotic, antioxidants, levodopa, carbidopa, trazodone or dibenzoylmethane. Those skilled in the art will be aware of other active agents that may be suitable for treatment of neurological disorders.

Klotho also plays important regulatory and protective roles in the kidney. In that regard, the present disclosure provides a method of treating renal dysfunction in a subject the method comprising administering to the subject a therapeutically effective amount of a binding molecule, such as a nucleic acid, that binds to an RNA transcript transcribed from a chromosomal region within or near a Klotho gene in the subject. The RNA transcript preferably does not encode a Klotho protein, and administration of the binding molecule preferably increases expression of the Klotho gene in the subject. In certain examples, the renal dysfunction is associated with renal fibrosis, acute kidney injury or a kidney disease such as chronic kidney disease.

Studies have also shown that Klotho plays important roles in regulating fertility. In that regard, the present disclosure provides a method of treating infertility in a subject the method comprising administering to the subject a therapeutically effective amount of a binding molecule, such as a nucleic acid, that binds to an RNA transcript transcribed from a chromosomal region within or near a Klotho gene in the subject. The RNA transcript preferably does not encode a Klotho protein, and administration of the binding molecule preferably increases expression of the Klotho gene in the subject.

Klotho has also been identified as a regulator of various tumorigenesis and cancer signalling pathways. In that regard, the present disclosure provides methods for treating cancer in a subject comprising administering to the subject a therapeutically effective amount of a binding molecule, such as a nucleic acid, that binds to an RNA transcript transcribed from a chromosomal region within or near a Klotho gene in the subject. The RNA transcript preferably does not encode a Klotho protein, and administration of the binding molecule preferably increases expression of the Klotho gene in the subject. In certain examples the cancer is mediated by IGF-1, WNT, bFGF or TGF-β. The cancer may be colon cancer, prostate cancer, lung cancer, cervical cancer, pancreatic cancer, ovarian cancer or breast cancer. Further, non-limiting examples of cancer include leukemias (e.g., acute leukemia, acute lymphocytic leukemia, acute myelocytic leukemia, acute myeloblastic leukemia, acute promyclocytic leukemia, acute myclomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, Squamous cell carcinoma, basal cell carcinoma, adenocarcinoma, Sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, Small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, Schwannoma, meningioma, melanoma, neuroblastoma, and retinoblastoma). In some examples, the cancer is metastatic cancer.

The present disclosure also provides methods of suppressing tumorigenesis, such as breast tumorigenesis and pancreatic tumorigenesis in a subject comprising administering to the subject a therapeutically effective amount of a binding molecule, such as a nucleic acid, that binds to an RNA transcript transcribed from a chromosomal region within or near a Klotho gene in the subject. The RNA transcript preferably does not encode a Klotho protein, and administration of the binding molecule preferably increases expression of the Klotho gene in the subject.

The present disclosure also provides methods for treating an age-related condition in a subject comprising administering to the subject a therapeutically effective amount of a binding molecule, such as a nucleic acid, that binds to an RNA transcript transcribed from a chromosomal region within or near a Klotho gene in the subject. The RNA transcript preferably does not encode a Klotho protein, and administration of the binding molecule preferably increases expression of the Klotho gene in the subject. The age-related condition may be sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, memory loss, wrinkles, impaired kidney function or hearing loss.

The present disclosure also provides methods for treating a muscular disorder such as muscle atrophy and muscular dystrophy (eg, duchene muscular dystrophy) in a subject comprising administering to the subject a therapeutically effective amount of a binding molecule, such as a nucleic acid, that binds to an RNA transcript transcribed from a chromosomal region within or near a Klotho gene in the subject. The RNA transcript preferably does not encode a Klotho protein, and administration of the binding molecule preferably increases expression of the Klotho gene in the subject. Muscle atrophy is associated with numerous neuromuscular, metabolic, immunological and neurological disorders and diseases as well as starvation, nutritional deficiency, metabolic stress, diabetes, aging, muscular dystrophy or myopathy. Symptoms include a decline in skeletal muscle tissue mass. In human males, muscle mass declines by one-third between the ages of 50 and 80. Some molecular features of muscle atrophy include the upregulation of ubiquitin ligases, and the loss of myofibrillar proteins (Furuno et al. 1990. J. Biol. Chem. 265: 8550-8557). The degradation of these proteins can be detected, eg, by measuring 3-methyl-histidine production, which is a specific component of actin, and in certain muscles of myosin. Release of creatine kinase can also be indicative.

The present disclosure also provides methods for treating a metabolic disorder in a subject comprising administering to the subject a therapeutically effective amount of a binding molecule, such as a nucleic acid, that binds to an RNA transcript transcribed from a chromosomal region within or near a Klotho gene in the subject. The RNA transcript preferably does not encode a Klotho protein, and administration of the binding molecule preferably increases expression of the Klotho gene in the subject. In certain examples, the metabolic disorder is selected from Type II Diabetes, Metabolic Syndrome, hyperglycemia and obesity.

Methods, Compositions and Uses

Method 1. A method of increasing expression of a Klotho gene in a cell the method comprising administering to the cell a binding molecule that binds to an RNA transcript transcribed from a chromosomal region within or near the Klotho gene, wherein the RNA transcript does not encode a Klotho protein.

Method 2. The method of method 1 wherein the binding molecule is a nucleic acid comprising a sequence that is substantially complementary to the RNA transcript.

Method 3. The method of method 2 wherein the chromosomal region comprises a region of at least 200 nucleotides upstream of the Klotho gene translation start site.

Method 4. The method of method 2 or method 3 wherein the chromosomal region comprises the region between 302 nucleotides and 551 nucleotides upstream of the Klotho gene translation start site.

Method 5. The method of any one of methods 2 to 4 wherein the chromosomal region comprises the region between 106 nucleotides and 685 nucleotides upstream of the Klotho gene translation start site.

Method 6. The method of any one of methods 2 to 4 wherein the chromosomal region comprises the sequence set forth in SEQ ID NO. 5 or a sequence having at least about 90% identity to SEQ ID NO. 5.

Method 7. The method of any one of methods 2 to 6 wherein the chromosomal region comprises the sequence set forth in SEQ ID NO. 8 or a sequence having at least about 90% identity to SEQ ID NO. 8.

Method 8. The method of any one of methods 2 to 4 wherein the RNA transcript comprises the sequence set forth in SEQ ID NO. 6 or a sequence having at least about 90% identity to SEQ ID NO. 6.

Method 9. The method of any one of methods 2 to 8 wherein the RNA transcript comprises the sequence set forth in SEQ ID NO. 9 or a sequence having at least about 90% identity to SEQ ID NO. 9.

Method 10. The method of any one of methods 2 to 9 wherein the nucleic acid comprises at least 15 contiguous nucleotides which are substantially complementary to a nucleotide sequence set forth in SEQ ID NO. 3.

Method 11. The method of any one of methods 2 to 10 wherein the nucleic acid comprises at least 15 contiguous nucleotides which are substantially complementary to a nucleotide sequence set forth in SEQ ID NO. 9.

Method 12. The method of any one of methods 2 to 11 wherein the nucleic acid comprises at least 15 contiguous nucleotides differing by no more than 3 nucleotides from a nucleotide sequence set forth in SEQ ID NO. 10.

Method 13. The method of any one of methods 2 to 12 wherein the nucleic acid comprises at least 15 contiguous nucleotides which are at least about 90% identical to a nucleotide sequence set forth in SEQ ID NO. 10.

Method 14. The method of any one of methods 2 to 13 wherein the nucleic acid comprises a sequence that is at least about 90% identical to the sequence set forth in SEQ ID NO. 21, SEQ ID NO. 23, SEQ ID NO. 25, SEQ ID NO. 27 or SEQ ID NO. 29.

Method 15. The method of any one of methods 2 to 14 wherein the nucleic acid comprises a sequence that is at least about 90% identical to the sequence set forth in SEQ ID NO. 21, SEQ ID NO. 23 or SEQ ID NO. 27.

Method 16. The method of any one of methods 2 to 15 wherein the RNA transcript is a sense RNA transcript.

Method 17. The method of method 2 or method 3 wherein the chromosomal region comprises the region between 183 nucleotides and 2,662 nucleotides upstream of the Klotho gene translation start site.

Method 18. The method of any one of methods 2, 3 or 17 wherein the chromosomal region comprises the sequence set forth in SEQ ID NO. 53 or a sequence having at least about 90% identity to SEQ ID NO. 53.

Method 19. The method of any one of methods 2, 3, 17 or 18 wherein the RNA transcript comprises the sequence set forth in SEQ ID NO. 51 or a sequence having at least about 90% identity to SEQ ID NO. 51.

Method 20. The method of any one of methods 2, 3 or 17 to 19 wherein the nucleic acid comprises at least 15 contiguous nucleotides which are substantially complementary to a nucleotide sequence set forth in SEQ ID NO. 51.

Method 21. The method of any one of methods 2, 3 or 17 to 20 wherein the nucleic acid comprises at least 15 contiguous nucleotides differing by no more than 3 nucleotides from a nucleotide sequence set forth in SEQ ID NO. 52.

Method 22. The method of any one of methods 2, 3 or 17 to 21 wherein the nucleic acid comprises at least 15 contiguous nucleotides which are at least about 90% identical to a nucleotide sequence set forth in SEQ ID NO. 52.

Method 23. The method of method 2 or method 3 wherein the chromosomal region comprises the region between 3,133 nucleotides upstream of the Klotho gene translation start site and 412 nucleotides downstream of the Klotho gene translation start site.

Method 24. The method of any one of methods 2, 3 or 23 wherein the chromosomal region comprises the sequence set forth in SEQ ID NO. 50 or a sequence having at least about 90% identity to SEQ ID NO. 50.

Method 25. The method of any one of methods 2, 3, 23 or 24 wherein the RNA transcript comprises the sequence set forth in SEQ ID NO. 48 or a sequence having at least about 90% identity to SEQ ID NO. 48.

Method 26. The method of any one of methods 2, 3 or 23 to 25 wherein the nucleic acid comprises at least 15 contiguous nucleotides which are substantially complementary to a nucleotide sequence set forth in SEQ ID NO. 48.

Method 27. The method of any one of methods 2, 3 or 23 to 26 wherein the nucleic acid comprises at least 15 contiguous nucleotides differing by no more than 3 nucleotides from a nucleotide sequence set forth in SEQ ID NO. 49.

Method 28. The method of any one of methods 2, 3 or 23 to 27 wherein the nucleic acid comprises at least 15 contiguous nucleotides which are at least about 90% identical to a nucleotide sequence set forth in SEQ ID NO. 49.

Method 29. The method of any one of methods 2, 3 or 17 to 28 wherein the nucleic acid comprises a sequence that is at least about 90% identical to the sequence set forth in SEQ ID NO. 54, SEQ ID NO. 55, SEQ ID NO. 56, SEQ ID NO. 57 or SEQ ID NO. 58.

Method 30. The method of method 29 wherein the nucleic acid comprises a sequence that is at least about 90% identical to the sequence set forth in SEQ ID NO. 56, SEQ ID NO. 57 or SEQ ID NO. 58.

Method 31. The method of method 2 wherein the chromosomal region comprises the region between 32 nucleotides upstream of the Klotho gene translation stop site and 457 nucleotides downstream of the Klotho gene translation stop site.

Method 32. The method of method 2 or method 31 wherein the chromosomal region comprises the region between 267 nucleotides upstream of the Klotho gene translation stop site and 517 nucleotides downstream of the Klotho gene translation stop site.

Method 33. The method of method 2 or method 31 wherein the chromosomal region comprises the sequence set forth in SEQ ID NO. 14 or a sequence having at least about 90% identity to SEQ ID NO. 14.

Method 34. The method of method 2 or any one of methods 31 to 33 wherein the chromosomal region comprises the sequence set forth in SEQ ID NO. 17 or a sequence having at least about 90% identity to SEQ ID NO. 17.

Method 35. The method of method 2 or method 31 wherein the RNA transcript comprises the sequence set forth in SEQ ID NO. 16 or a sequence having at least about 90% identity to SEQ ID NO. 16.

Method 36. The method of method 2 or any one of methods 31 to 35 wherein the RNA transcript comprises the sequence set forth in SEQ ID NO. 19 or a sequence having at least about 90% identity to SEQ ID NO. 19.

Method 37. The method of method 2 or any one of methods 31 to 36 wherein the nucleic acid comprises at least 15 contiguous nucleotides which are substantially complementary to a nucleotide sequence set forth in SEQ ID NO. 19.

Method 38. The method of method 2 or any one of methods 31 to 37 wherein the nucleic acid comprises at least 15 contiguous nucleotides differing by no more than 3 nucleotides from a nucleotide sequence set forth in SEQ ID NO. 18.

Method 39. The method of method 2 or any one of methods 31 to 38 wherein the nucleic acid comprises at least 15 contiguous nucleotides which are at least about 90% identical to a nucleotide sequence set forth in SEQ ID NO. 18.

Method 40. The method of method 2 or any one of methods 31 to 39 wherein the nucleic acid comprises a sequence that is at least about 90% identical to the sequence set forth in SEQ ID NO. 31, SEQ ID NO. 33 or SEQ ID NO. 35.

Method 41. The method of method 2 or any one of methods 31 to 40 wherein the nucleic acid comprises a sequence that is at least about 90% identical to the sequence set forth in SEQ ID NO. 35.

Method 42. The method of method 2 or any one of methods 17 to 41 wherein the RNA transcript is an antisense RNA transcript.

Method 43. The method of any one of methods 2 to 42 wherein the nucleic acid is between 15 and 50 nucleotides in length.

Method 44. The method of any one of methods 2 to 43 wherein the nucleic acid is RNA.

Method 45. The method of any one of methods 2 to 44 wherein the nucleic acid is a siRNA or a nucleic acid encoding a siRNA.

Method 46. The method of method 45 wherein the siRNA is conjugated to N-acetylgalactosamine.

Method 47. The method of any one of methods 2 to 46 wherein the method comprises administering to the cell two nucleic acids wherein each nucleic acid is independently selected from the nucleic acid defined in any one of methods 2 to 46.

Method 48. The method of any one of methods 1 to 47 wherein the cell is a human cell.

Method 49. A method of treating cancer in a subject the method comprising administering to the subject a therapeutically effective amount of a binding molecule that binds to an RNA transcript transcribed from a chromosomal region within or near a Klotho gene, wherein the RNA transcript does not encode a Klotho protein, and wherein administration of the binding molecule increases expression of the Klotho gene in the subject.

Method 50. The method of method 49 wherein the cancer is selected from the group consisting of colon cancer, prostate cancer, lung cancer, cervical cancer, pancreatic cancer, ovarian cancer and breast cancer.

Method 51. A method of treating a muscle disorder in a subject the method comprising administering to the subject a therapeutically effective amount of a binding molecule that binds to an RNA transcript transcribed from a chromosomal region within or near a Klotho gene, wherein the RNA transcript does not encode a Klotho protein, and wherein administration of the binding molecule increases expression of the Klotho gene in the subject.

Method 52. The method of method 51 wherein the muscle disorder is selected from the group consisting of muscle atrophy and muscular dystrophy such as duchene muscular dystrophy.

Method 53. A method of treating a kidney disorder in a subject the method comprising administering to the subject a therapeutically effective amount of a binding molecule that binds to an RNA transcript transcribed from a chromosomal region within or near a Klotho gene, wherein the RNA transcript does not encode a Klotho protein, and wherein administration of the binding molecule increases expression of the Klotho gene in the subject.

Method 54. The method of method 53 wherein the kidney disorder is selected from the group consisting of renal dysfunction, acute kidney injury and kidney disease such as chronic kidney disease.

Method 55. A method of enhancing cognition in a subject the method comprising administering to the subject a therapeutically effective amount of a binding molecule that binds to an RNA transcript transcribed from a chromosomal region within or near a Klotho gene, wherein the RNA transcript does not encode a Klotho protein, and wherein administration of the binding molecule increases expression of the Klotho gene in the subject.

Method 56. A method of treating a neurological disorder in a subject the method comprising administering to the subject a therapeutically effective amount of a binding molecule that binds to an RNA transcript transcribed from a chromosomal region within or near a Klotho gene, wherein the RNA transcript does not encode a Klotho protein, and wherein administration of the binding molecule increases expression of the Klotho gene in the subject.

Method 57. The method of method 56 wherein the neurological disorder is selected from the group consisting of memory loss, stress, biopolar disorder, epilepsy, dementia, Alzheimer's disease, Parkinson's disease, Huntington's disease, Creutzfeldt-Jakob disease, ataxia telangiectasia, craniocerebral trauma, amyotrophic lateral sclerosis, depression, schizophrenia, multiple sclerosis, myelin-related disease, oxidative stress and neurodegeneration.

Method 58. The method of any one of methods 49 to 57 wherein the binding molecule is a nucleic acid comprising a sequence that is substantially complementary to the RNA transcript.

Method 59. The method of method 58 wherein the chromosomal region comprises a region of at least 200 nucleotides upstream of the Klotho gene translation start site.

Method 60. The method of method 58 or method 59 wherein the chromosomal region comprises the region between 302 nucleotides and 551 nucleotides upstream of the Klotho gene translation start site.

Method 61. The method of any one of methods 58 to 60 wherein the chromosomal region comprises the region between 106 nucleotides and 685 nucleotides upstream of the Klotho gene translation start site.

Method 62. The method of any one of methods 58 to 60 wherein the chromosomal region comprises the sequence set forth in SEQ ID NO. 5 or a sequence having at least about 90% identity to SEQ ID NO. 5.

Method 63. The method of any one of methods 58 to 62 wherein the chromosomal region comprises the sequence set forth in SEQ ID NO. 8 or a sequence having at least about 90% identity to SEQ ID NO. 8.

Method 64. The method of any one of methods 58 to 60 wherein the RNA transcript comprises the sequence set forth in SEQ ID NO. 6 or a sequence having at least about 90% identity to SEQ ID NO. 6.

Method 65. The method of any one of methods 58 to 64 wherein the RNA transcript comprises the sequence set forth in SEQ ID NO. 9 or a sequence having at least about 90% identity to SEQ ID NO. 9.

Method 66. The method of any one of methods 58 to 65 wherein the nucleic acid comprises at least 15 contiguous nucleotides which are substantially complementary to a nucleotide sequence set forth in SEQ ID NO. 3.

Method 67. The method of any one of methods 58 to 66 wherein the nucleic acid comprises at least 15 contiguous nucleotides which are substantially complementary to a nucleotide sequence set forth in SEQ ID NO. 9.

Method 68. The method of any one of methods 58 to 67 wherein the nucleic acid comprises at least 15 contiguous nucleotides differing by no more than 3 nucleotides from a nucleotide sequence set forth in SEQ ID NO. 10.

Method 69. The method of any one of methods 58 to 68 wherein the nucleic acid comprises at least 15 contiguous nucleotides which are at least about 90% identical to a nucleotide sequence set forth in SEQ ID NO. 10.

Method 70. The method of any one of methods 58 to 69 wherein the nucleic acid comprises a sequence that is at least about 90% identical to the sequence set forth in SEQ ID NO. 21, SEQ ID NO. 23, SEQ ID NO. 25, SEQ ID NO. 27 or SEQ ID NO. 29.

Method 71. The method of any one of methods 58 to 70 wherein the nucleic acid comprises a sequence that is at least about 90% identical to the sequence set forth in SEQ ID NO. 21, SEQ ID NO. 23 or SEQ ID NO. 27.

Method 72. The method of any one of methods 58 to 71 wherein the RNA transcript is a sense RNA transcript.

Method 73. The method of method 58 or method 59 wherein the chromosomal region comprises the region between 183 nucleotides and 2,662 nucleotides upstream of the Klotho gene translation start site.

Method 74. The method of any one of methods 58, 59 or 73 wherein the chromosomal region comprises the sequence set forth in SEQ ID NO. 53 or a sequence having at least about 90% identity to SEQ ID NO. 53.

Method 75. The method of any one of methods 58, 59, 73 or 74 wherein the RNA transcript comprises the sequence set forth in SEQ ID NO. 51 or a sequence having at least about 90% identity to SEQ ID NO. 51.

Method 76. The method of any one of methods 58, 59 or 73 to 75 wherein the nucleic acid comprises at least 15 contiguous nucleotides which are substantially complementary to a nucleotide sequence set forth in SEQ ID NO. 51.

Method 77. The method of any one of methods 58, 59 or 73 to 76 wherein the nucleic acid comprises at least 15 contiguous nucleotides differing by no more than 3 nucleotides from a nucleotide sequence set forth in SEQ ID NO. 52.

Method 78. The method of any one of methods 58, 59 or 73 to 77 wherein the nucleic acid comprises at least 15 contiguous nucleotides which are at least about 90% identical to a nucleotide sequence set forth in SEQ ID NO. 52.

Method 79. The method of method 58 or method 59 wherein the chromosomal region comprises the region between 3,133 nucleotides upstream of the Klotho gene translation start site and 412 nucleotides downstream of the Klotho gene translation start site.

Method 80. The method of any one of methods 58, 59 or 79 wherein the chromosomal region comprises the sequence set forth in SEQ ID NO. 50 or a sequence having at least about 90% identity to SEQ ID NO. 50.

Method 81. The method of any one of methods 58, 59, 79 or 80 wherein the RNA transcript comprises the sequence set forth in SEQ ID NO. 48 or a sequence having at least about 90% identity to SEQ ID NO. 48.

Method 82. The method of any one of methods 58, 59 or 79 to 81 wherein the nucleic acid comprises at least 15 contiguous nucleotides which are substantially complementary to a nucleotide sequence set forth in SEQ ID NO. 48.

Method 83. The method of any one of methods 58, 59 or 79 to 82 wherein the nucleic acid comprises at least 15 contiguous nucleotides differing by no more than 3 nucleotides from a nucleotide sequence set forth in SEQ ID NO. 49.

Method 84. The method of any one of methods 58, 59 or 79 to 83 wherein the nucleic acid comprises at least 15 contiguous nucleotides which are at least about 90% identical to a nucleotide sequence set forth in SEQ ID NO. 49.

Method 85. The method of any one of methods 58, 59 or 73 to 84 wherein the nucleic acid comprises a sequence that is at least about 90% identical to the sequence set forth in SEQ ID NO. 54, SEQ ID NO. 55, SEQ ID NO. 56, SEQ ID NO. 57 or SEQ ID NO. 58.

Method 86. The method of method 85 wherein the nucleic acid comprises a sequence that is at least about 90% identical to the sequence set forth in SEQ ID NO. 56, SEQ ID NO. 57 or SEQ ID NO. 58.

Method 87. The method of method 58 wherein the chromosomal region comprises the region between 32 nucleotides upstream of the Klotho gene translation stop site and 457 nucleotides downstream of the Klotho gene translation stop site.

Method 88. The method of method 58 or method 87 wherein the chromosomal region comprises the region between 267 nucleotides upstream of the Klotho gene translation stop site and 517 nucleotides downstream of the Klotho gene translation stop site.

Method 89. The method of method 58 or method 87 wherein the chromosomal region comprises the sequence set forth in SEQ ID NO. 14 or a sequence having at least about 90% identity to SEQ ID NO. 14.

Method 90. The method of method 58 or any one of methods 87 to 89 wherein the chromosomal region comprises the sequence set forth in SEQ ID NO. 17 or a sequence having at least about 90% identity to SEQ ID NO. 17.

Method 91. The method of method 58 or method 87 wherein the RNA transcript comprises the sequence set forth in SEQ ID NO. 16 or a sequence having at least about 90% identity to SEQ ID NO. 16.

Method 92. The method of method 58 or any one of methods 87 to 91 wherein the RNA transcript comprises the sequence set forth in SEQ ID NO. 19 or a sequence having at least about 90% identity to SEQ ID NO. 19.

Method 93. The method of method 58 or any one of methods 87 to 92 wherein the nucleic acid comprises at least 15 contiguous nucleotides which are substantially complementary to a nucleotide sequence set forth in SEQ ID NO. 19.

Method 94. The method of method 58 or any one of methods 87 to 93 wherein the nucleic acid comprises at least 15 contiguous nucleotides differing by no more than 3 nucleotides from a nucleotide sequence set forth in SEQ ID NO. 18.

Method 95. The method of method 58 or any one of methods 87 to 94 wherein the nucleic acid comprises at least 15 contiguous nucleotides which are at least about 90% identical to a nucleotide sequence set forth in SEQ ID NO. 18.

Method 96. The method of method 58 or any one of methods 87 to 95 wherein the nucleic acid comprises a sequence that is at least about 90% identical to the sequence set forth in SEQ ID NO. 31, SEQ ID NO. 33 or SEQ ID NO. 35.

Method 97. The method of method 58 or any one of methods 87 to 96 wherein the nucleic acid comprises a sequence that is at least about 90% identical to the sequence set forth in SEQ ID NO. 35.

Method 98. The method of method 58 or any one of methods 73 to 97 wherein the RNA transcript is an antisense RNA transcript.

Method 99. The method of any one of methods 58 to 98 wherein the nucleic acid is between 15 and 50 nucleotides in length.

Method 100. The method of any one of methods 58 to 99 wherein the nucleic acid is RNA.

Method 101. The method of any one of methods 58 to 100 wherein the nucleic acid is a siRNA or a nucleic acid encoding a siRNA.

Method 102. The method of method 101 wherein the siRNA is conjugated to N-acetylgalactosamine.

Method 103. The method of any one of methods 58 to 102 wherein the method comprises administering to the subject two nucleic acids wherein each nucleic acid is independently selected from the nucleic acid defined in any one of methods 2 to 46.

Method 104. The method of any one of methods 58 to 103 wherein the subject is a human.

Composition 1. An isolated or recombinant nucleic acid molecule as defined in any one of methods 2 to 46.

Composition 2. A vector comprising the nucleic acid of composition 1.

Use 1. Use of a binding molecule that binds to an RNA transcript transcribed from a chromosomal region within or near a Klotho gene in the manufacture of a medicament for increasing expression of the Klotho gene in a cell, wherein the RNA transcript does not encode a Klotho protein.

Use 2. Use of a binding molecule that binds to an RNA transcript transcribed from a chromosomal region within or near a Klotho gene in the manufacture of a medicament for the treatment of cancer in a subject, wherein the RNA transcript does not encode a Klotho protein, and wherein administration of the binding molecule increases expression of the Klotho gene in the subject.

Use 3. Use of a binding molecule that binds to an RNA transcript transcribed from a chromosomal region within or near a Klotho gene in the manufacture of a medicament for the treatment of a muscle disorder in a subject, wherein the RNA transcript does not encode a Klotho protein, and wherein administration of the binding molecule increases expression of the Klotho gene in the subject.

Use 4. Use of a binding molecule that binds to an RNA transcript transcribed from a chromosomal region within or near a Klotho gene in the manufacture of a medicament for the treatment of a kidney disorder in a subject, wherein the RNA transcript does not encode a Klotho protein, and wherein administration of the binding molecule increases expression of the Klotho gene in the subject.

Use 5. Use of a binding molecule that binds to an RNA transcript transcribed from a chromosomal region within or near a Klotho gene in the manufacture of a medicament for enhancing cognition in a subject, wherein the RNA transcript does not encode a Klotho protein, and wherein administration of the binding molecule increases expression of the Klotho gene in the subject.

Use 6. Use of a binding molecule that binds to an RNA transcript transcribed from a chromosomal region within or near a Klotho gene in the manufacture of a medicament for the treatment of a neurological disorder in a subject, wherein the RNA transcript does not encode a Klotho protein, and wherein administration of the binding molecule increases expression of the Klotho gene in the subject.

EXAMPLES

Nucleic Acid Sequences

Nucleic acid sequences relevant to the present examples are listed in Table 2.

TABLE 2

| SEQ | Description | Sequence |
|---|---|---|
| 21 | siRNA1 guide sequence | UCGUGGACGCUCAGGUUCAUUCUCUUU |
| 22 | siRNA1 passenger sequence | AGAGAAUGAACCUGAGCGUCCACGA |
| 23 | shRNA P1 guide sequence | UUUCGUGGACGCUCAGGUUCAU |
| 24 | P1 guide sequence (DNA) | TTTCGTGGACGCTCAGGTTCAT |
| 25 | shRNA P2 guide sequence | UUCCUCCCAGCUCCCGGGAGCC |
| 26 | P2 guide sequence (DNA) | TTCCTCCCAGCTCCCGGGAGCC |
| 27 | shRNA P3 guide sequence | AAAGGCACCUGUUCCUCCCAGC |
| 28 | P3 guide sequence (DNA) | AAAGGCACCTGTTCCTCCCAGC |
| 29 | shRNA P4 guide sequence | UUCAUUCUCUUUGCCUGCCGCG |
| 30 | P4 guide sequence (DNA) | TTCATTCTCTTTGCCTGCCGCG |
| 31 | siRNA2 guide sequence | UAUUCUUUAGCUGUACUGUAAUUUCUU |
| 32 | siRNA2 passenger sequence | GAAAUUACAGUACAGCUAAAGAATA |
| 33 | siRNA3 guide sequence | GAAAGAUAAGCUUUUGGUAAUAUUCAU |
| 34 | siRNA3 passenger sequence | GAAUAUUACCAAAAGCUUAUCUUTC |
| 35 | siRNA4 guide sequence | UAAGUGUUGUGAAACUGUAAAUUUCAU |
| 36 | siRNA4 passenger sequence | GAAAUUUACAGUUUCACAACACUTA |
| 37 | F1 RT primer | TCCCAACGUAACCCATAAA |
| 38 | RV1 RT primer | GACGCTCAGGTTCATTCTCTT |
| 39 | F2 RT primer | TGGCAGTCCCTCTAGGATTT |
| 40 | RV2 RT primer | GGCTCCGCTGGCAATAAT |
| 41 | S1 RT primer | AGGTTTGGCCTCTATCGTTATG |
| 42 | AS1 RT primer | CTCTGTCGTCTCTCCTGTATCT |
| 43 | S2 RT primer | ACTACTCGAAGAAAGGCAGAAG |
| 44 | AS2 RT primer | GGGAAGCCACTAGGCATTATTA |
| 54 | Short hairpin RNA - guide 1 | AAAGUGAGAGCAGGUGCUUCCC |
| 55 | Short hairpin RNA - guide 2 | AAAGAGAAUGAACCUGAGCGUC |

TABLE 2-continued

| SEQ | Description | Sequence |
|---|---|---|
| 56 | Short hairpin RNA - guide 3 | AAACAGGUGCCUUUCUCCGACG |
| 57 | Short hairpin RNA - guide 4 | UUUCGGCCAGUCCCUAAUUGGC |
| 58 | Short hairpin RNA - guide 5 | UUUCUCCCCGACGAAGCCGCUC |
| 59 | mP1 (DNA) | TATTCCACATCGCACAATCCTG |
| 60 | mP1 (RNA) | UAUUCCACAUCGCACAAUCCUG |
| 61 | mP2 (DNA) | AATCCTGTGGCCTCCATCCTGA |
| 62 | mP2 (RNA) | AAUCCUGUGGCCUCCAUCCUGA |
| 63 | mP3 (DNA) | TCAGGGAGCAGACTATTCCACA |
| 64 | mP3 (RNA) | UCAGGGAGCAGACUAUUCCACA |
| 65 | mP4 (DNA) | ATGTCCCCGCGTCGCCCACTCC |
| 66 | mP4 (RNA) | AUGUCCCCGCGUCGCCCACUCC |
| 67 | mP5 (DNA) | AATGATTATCCAGAGCAGGCGC |
| 68 | mP5 (RNA) | AAUGAUUAUCCAGAGCAGGCGC |
| 69 | mP6 (DNA) | ATAGGGACGTCGGAGAACAAGC |
| 70 | mP6 (RNA) | AUAGGGACGUCGGAGAACAAGC |
| 71 | mP7 (DNA) | TATGCCCGCGCCCCGCCGCCCT |
| 72 | mP7 (RNA) | UAUGCCCGCGCCCCGCCGCCCU |
| 73 | mP8 (DNA) | TACGCGGTGCCCACCCCCGCTC |
| 74 | mP8 (RNA) | UACGCGGUGCCCACCCCCGCUC |
| 75 | mP9 (DNA) | TTATCCAGAGCAGGCGCCGCCC |
| 76 | mP9 (RNA) | UUAUCCAGAGCAGGCGCCGCCC |
| 77 | mP10 (DNA) | ACTCCGGCCTGGCACGGGGGCG |
| 78 | mP10 (RNA) | ACUCCGGCCUGGCACGGGGGCG |
| 79 | mSense1 (DNA) | TATGACCCCTGCTGTGCTCTCT |
| 80 | mSense1 (RNA) | UAUGACCCCUGCUGUGCUCUCU |
| 81 | mSense2 (DNA) | ATAATCATTGCTCGTGGGGCGG |
| 82 | mSense2 (RNA) | AUAAUCAUUGCUCGUGGGGCGG |
| 83 | mSense3 (DNA) | TATAGGGGCGCGGCGCGGTGCC |
| 84 | mSense3 (RNA) | UAUAGGGGCGCGGCGCGGUGCC |
| 85 | mSense4 (DNA) | AAAGGGAGTGGACGCGGGGAGT |
| 86 | mSense4 (RNA) | AAAGGGAGUGGACGCGGGGAGU |
| 87 | mSense5 (DNA) | AATAGTCTGCTCCCTGAGCTGG |
| 88 | mSense5 (RNA) | AAUAGUCUGCUCCCUGAGCUGG |
| 89 | mSense6 (DNA) | TTGTTCTCCGACGTCCCTATGA |
| 90 | mSense6 (RNA) | UUGUUCUCCGACGUCCCUAUGA |

TABLE 2-continued

| SEQ | Description | Sequence |
|---|---|---|
| 91 | mSense7 (DNA) | ATTGCTCGTGGGGCGGCGGGAG |
| 92 | mSense7 (RNA) | AUUGCUCGUGGGGCGGCGGGAG |

Example 1: Detection of Human RNA Transcripts

Strand-Specific RT-PCR

RNA was isolated from HK-2 cells and Caco-2 cells using a Qiagen RNeasy Kit. RT-PCR was performed using iScript RT (Bio-Rad), ClonAmpHiFi PCR kit (Clontech) and strand specific primers. The primers used were as follows:

F1: (SEQ ID NO. 37)
TCCCAACGCAACCCATAAA

RV1: (SEQ ID NO. 38)
GACGCTCAGGTTCATTCTCTT

F2: (SEQ ID NO. 39)
TGGCAGTCCCTCTAGGATTT

RV2: (SEQ ID NO. 40)
GGCTCCGCTGGCAATAAT

UTR S1: (SEQ ID NO. 41)
AGGTTTGGCCTCTATCGTTATG

UTR AS1: (SEQ ID NO. 42)
CTCTGTCGTCTCTCCTGTATCT

UTR S2: (SEQ ID NO. 43)
ACTACTCGAAGAAAGGCAGAAG

UTR AS2: (SEQ ID NO. 44)
GGGAAGCCACTAGGCATTATTA

The relative position of each primer is indicated in FIGS. 1A and 1B.

Cell lysates were collected using lysis buffer (same as that used for protein samples) with the addition of mercapto-ethanol. RNA was purified from the lysates, and samples were stored at −80° C. RNA concentration was measured using NanoDrop, and the samples were diluted as appropriate to equal concentrations using nuclease-free water. SuperScript IV VILO protocol was used for reverse transcription. qRT-PCR was carried out using human TaqMan Gene Expression Assays (Life Technologies), a Bio-Rad CFX96 Real-Time PCR system and Fast Advanced Master Mix (Life Technologies), according to the manufacturer's protocol. Transcripts within or near the Klotho gene were normalized to the endogenous controls, Actin B and PPIA. Samples were run in triplicates using 1 μg of cDNA per reaction.

Using strand-specific primers for RT-PCR, a sense RNA transcript was detected commencing upstream of the Klotho translation start site, and a downstream (3'UTR) antisense RNA transcript was also detected in the HK-2 and Caco-2 cells (FIGS. 1C and 1D).

Example 2: Suppression of Human RNA Transcripts

Nucleic Acid Construction

Nucleic acids, including siRNAs, were purchased from Integrated DNA Technologies, Inc. One siRNA (siRNA1) targeting the upstream RNA transcript, and three siRNAs (siRNA2-4) targeting the downstream RNA transcript were designed (FIG. 2A).

Figure 2A:
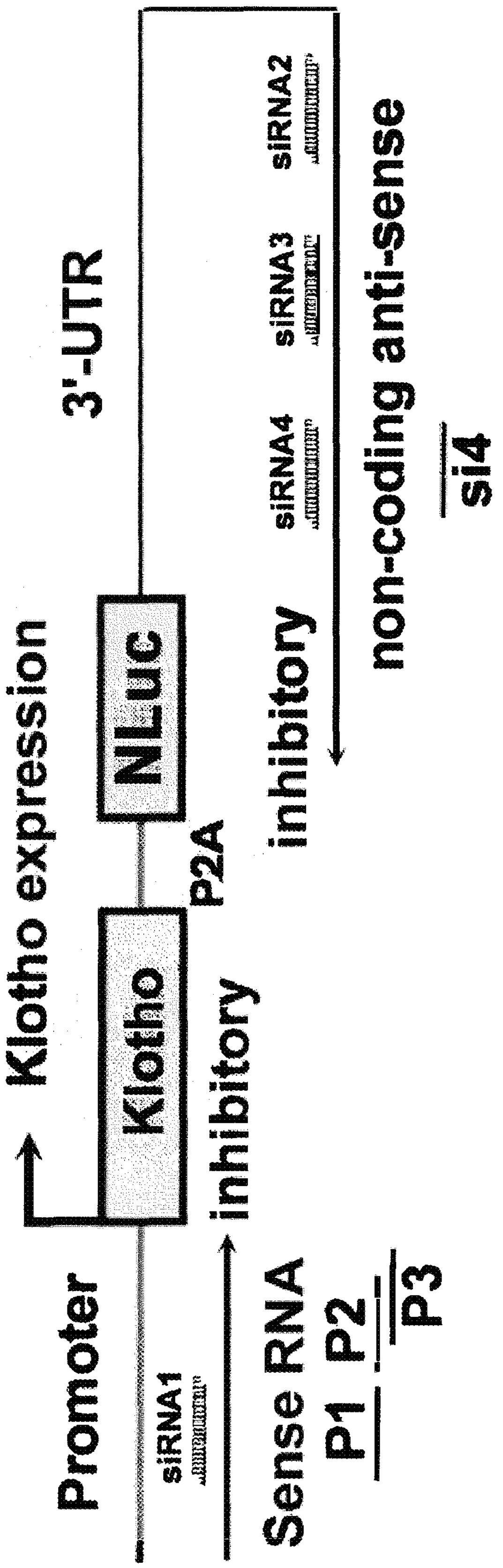
FIG. 2: A) Schematic diagram of Klotho-NLuc and associated noncoding RNAs. B) 350 bp region of Klotho promoter including siRNA and short hairpin (shRNA) targets. C) Klotho activation by siRNA measured using NLuc knock-in HEK239 cell line. D) Klotho activation by shRNA constructs in HK-2 cells measured by ELISA. * $p<0.05$. Results normalised to total protein.
Figure 2B:
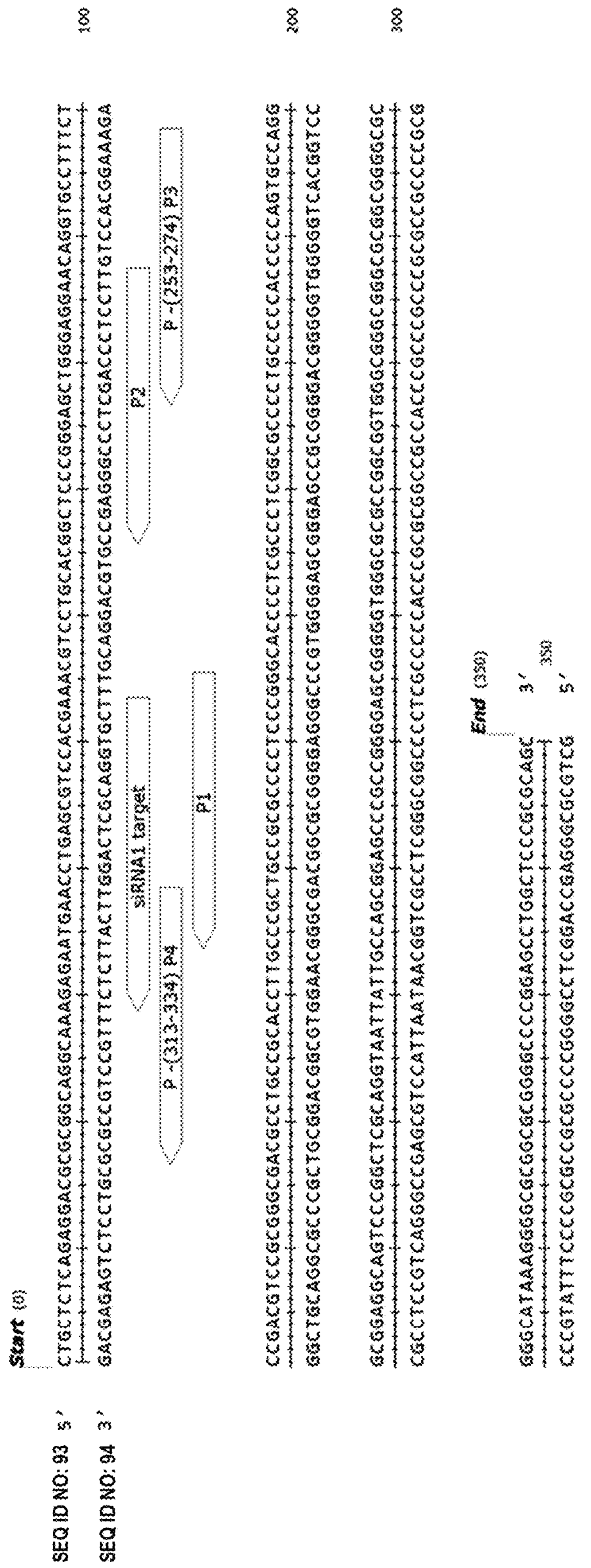

In addition, plasmids were constructed which express one of four short hairpin RNA molecules (P1, P2, P3 and P4) that target the upstream RNA transcript near the siRNA1 target site (FIGS. 2A and 2B). The shRNA constructs were generated using the OshR workflow Excel Spreadsheet (Zeng et al. 2013. Methods. 63(2): 101-109). Oligonucleotide designs were validated and checked for off-target effects using BLAST-N searches against the human genome. CloneAmp HiFi PCR Premix was used for extension of the oligonucleotides. Agarose gel electrophoresis was used to confirm size and concentration of the PCR products. Relevant bands were cut from the gel and purified using a standard gel extraction and DNA cleanup kit. Digestion with SalI and SphI enabled ligation into the pGSHO vector using the In-Fusion protocol. The product was then transformed into Stellar Competent cells. Transformed Stellar Competent cells were plated on ampicillin media and grown overnight. Colonies were harvested and inoculated (shaken at 37° C.) overnight. Cultures were purified the next day using the ZymoPURE Plasmid MiniPrep/MidiPrep protocol. To confirm that the insertion was successful, plasmids were digested with SphI and/or SalI, and the products were run on an agarose gel using the empty vector as a negative control. Sanger sequencing was further used to confirm successful insertion. Once samples were confirmed to have the appropriate insert, DNA was quantified using NanoDrop with elution buffer as a blank control.

In addition, a plasmid expressing a short hairpin targeting the downstream RNA transcript at the siRNA4 target site (si4) was also constructed (FIG. 2A).

Cell Transfection

Transfection was performed in HK-2 and HEK NLuc knock-in cell lines which were previously described by Chen et al. (2018. J. Mol. Neurosci. 64(2): 175-184). Cell culture and transfections were performed as described by Chen et al. (2018. J. Mol. Neurosci. 64(2): 175-184). HK-2 lines were passaged weekly, using trypsin for re-suspension, and were discarded after 20+ passages to ensure no mutations were present during transfection. Media was changed twice per week, even if the cells were not passaged. Both 12-well and 6-well plates were used, and cells were checked for minimum 70% confluency before proceeding with transfection protocols. Transfection was performed in the morning. Medium was changed about 5 hours post-transfection to reduce toxicity. Cells were transfected using Attractene and Opti-MEM reagents. 2 μg of DNA was used per well. All cell lysates were collected 48 hours post-transfection.

Transfection with an empty vector (EV) served for normalization. A sequence taken from the literature, shown to achieve significant downregulation, was formatted to OshR and used as a negative control, named human knockout (hKO) (Zeng et al. 2013. Methods. 63(2): 101-109). Egr1 was used as a positive control (Choi et al. 2010. Gene. 450(1-2): 121-127).

Klotho Expression

NLuc expression under control of the Klotho promoter in the coincidence reporter vector was measured using a NLuciferase kit (Promega) as described by Chen et al. (2018. J.

Figure 2C:
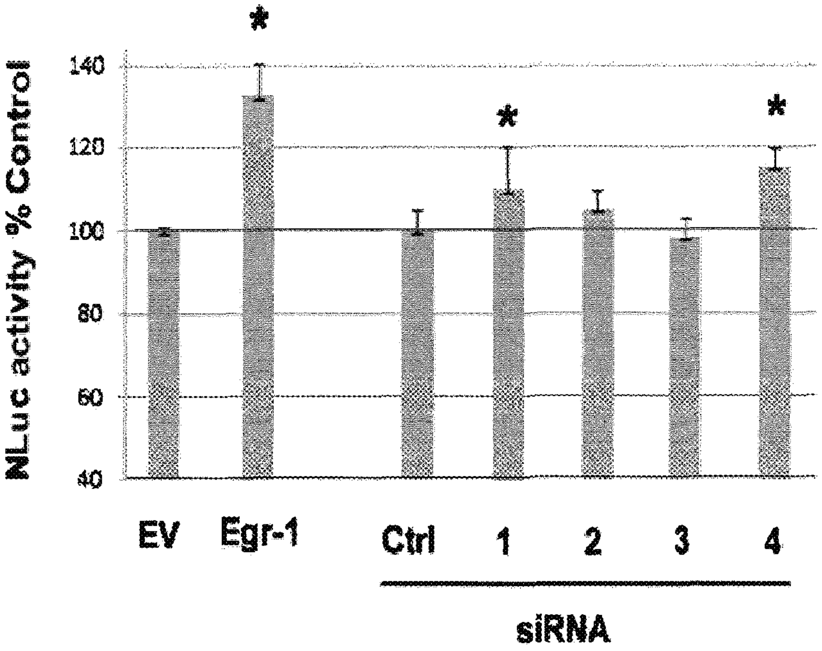
Figure 2D:
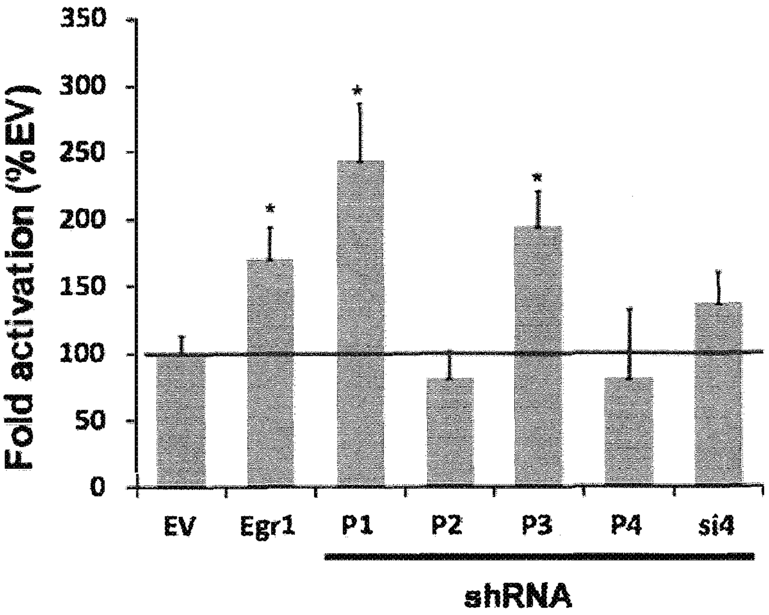

Mol. Neurosci. 64(2): 175-184). Klotho protein also was assayed using an enzyme-linked immunosorbent assay (ELISA) kit purchased from IBL according to the manufacturer's instructions. Referring to FIG. 2C, siRNA1 and siRNA4 significantly increased Klotho gene expression as measured using the HEK NLuc knock-in line. Referring to FIG. 2D, transfection with P1, P3 and si4 in HK-2 cells also increased Klotho expression as measured by ELISA.

qPCR analysis also demonstrated that P1 enhanced Klotho mRNA expression by 2-fold (p=0.043572) (Table 3).

TABLE 3 qPCR results from HK-2 cells

| Target | Sample | Mean Cq | Mean Efficiency Corrected Cq | Normalized Expression | Relative Normalized Expression | Regulation | Compared to Regulation Threshold | P-Value | Exceeds P-Value Threshold |
|---|---|---|---|---|---|---|---|---|---|
| KL | egr1-hk2 | 32.75 | 32.75 | 0.00271 | 1.01622 | 1.01622 | No change | 0.985571 | Yes |
| KL | EV-hk2 | 32.72 | 32.72 | 0.00267 | 1.00000 | 1.00000 | No change | | No |
| KL | hKO-hk2 | 32.60 | 32.60 | 0.00240 | 0.90062 | −1.11034 | No change | 0.956224 | Yes |
| KL | P1-hk2 | 32.30 | 32.30 | 0.00522 | 1.95640 | 1.95640 | No change | 0.043572 | Yes |
| KL | P2-hk2 | 33.92 | 33.92 | 0.00426 | 1.59550 | 1.59550 | No change | 0.295232 | Yes |

Example 3: In Silico Detection of Human RNA Transcripts

Figure 3:
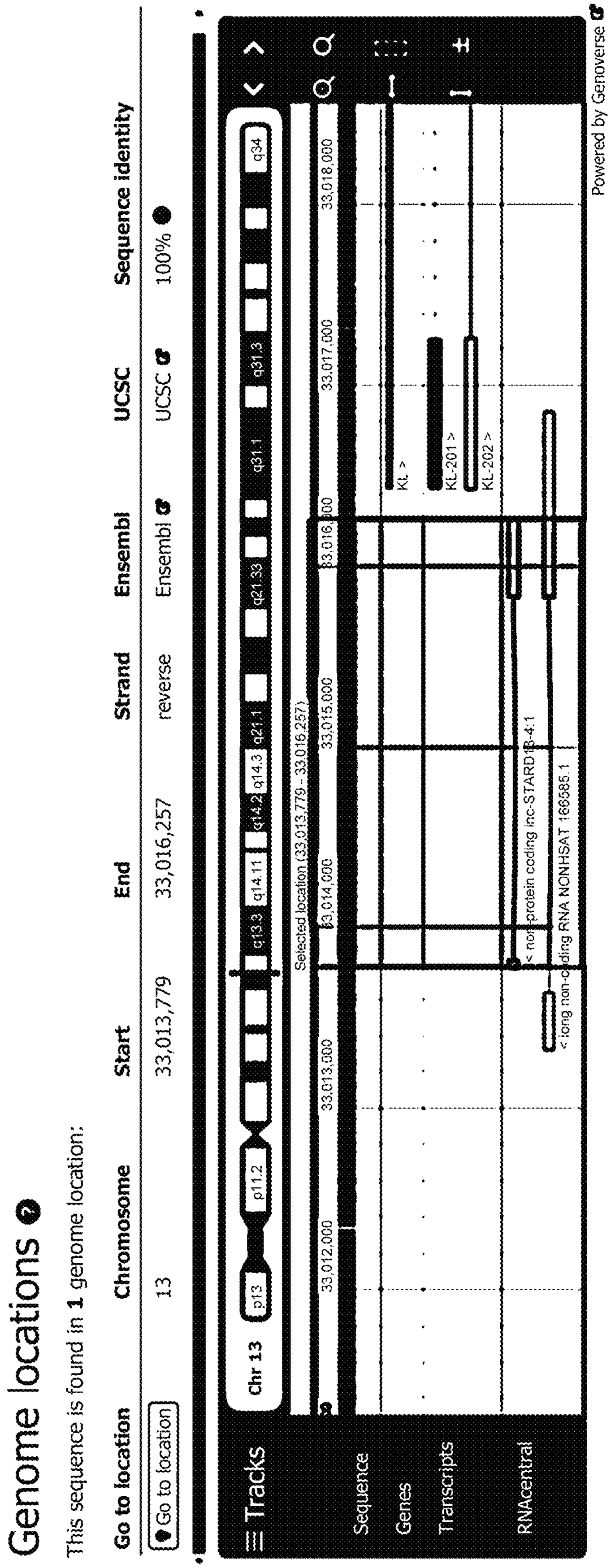
FIG. 3: Illustration of the location and splicing of NONHSAT166585.1 and lnc-STARD13-4:1 relative to Klotho (world wide web address: rnacentral.org).

The RNA sequence database, RNAcentral (world wide web address: rnacentral.org), was searched using the region −350 to −1 of the Klotho anti-sense strand. Two long, non-coding RNA transcripts were identified, namely, Inc-STARD13-4:1, which is 457 nucleotides in length (SEQ ID NO. 51), and NONHSAT166585.1, which is 1,325 nucleotides in length (SEQ ID NO. 48). The two RNA transcripts share a common 424-nucleotide sequence, and have different tail sequences due to their respective introns (FIG. 3). Inc-STARD13-4:1 starts at the −184 position of Klotho, whereas NONHSAT166585.1 starts within the coding sequence. Inc-STARD13-4:1 is transcribed from a chromosomal region between about 183 nucleotides and 2,662 nucleotides upstream of the Klotho gene translation start site, whereas NONHSAT166585.1 is transcribed from a chromosomal region between about 3,133 nucleotides upstream of the Klotho gene translation start site and 412 nucleotides downstream of the Klotho gene translation start site.

Figure 4:
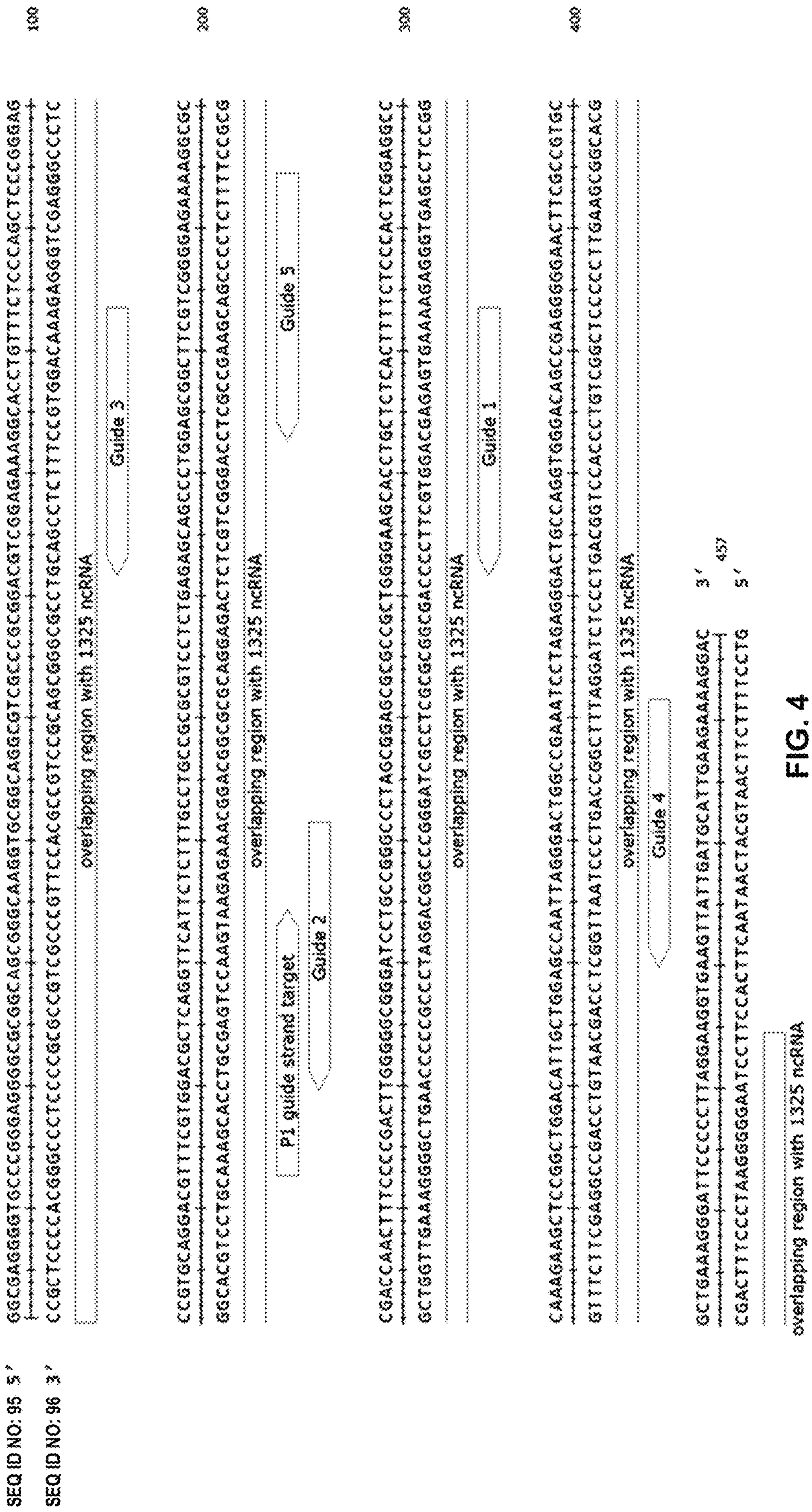
FIG. 4: Schematic diagram showing the binding positions of guide 1, guide 2, guide 3, guide 4 and guide 5 on NONHSAT 166585.1 and lnc-STARD13-4:1.
Figure 5:
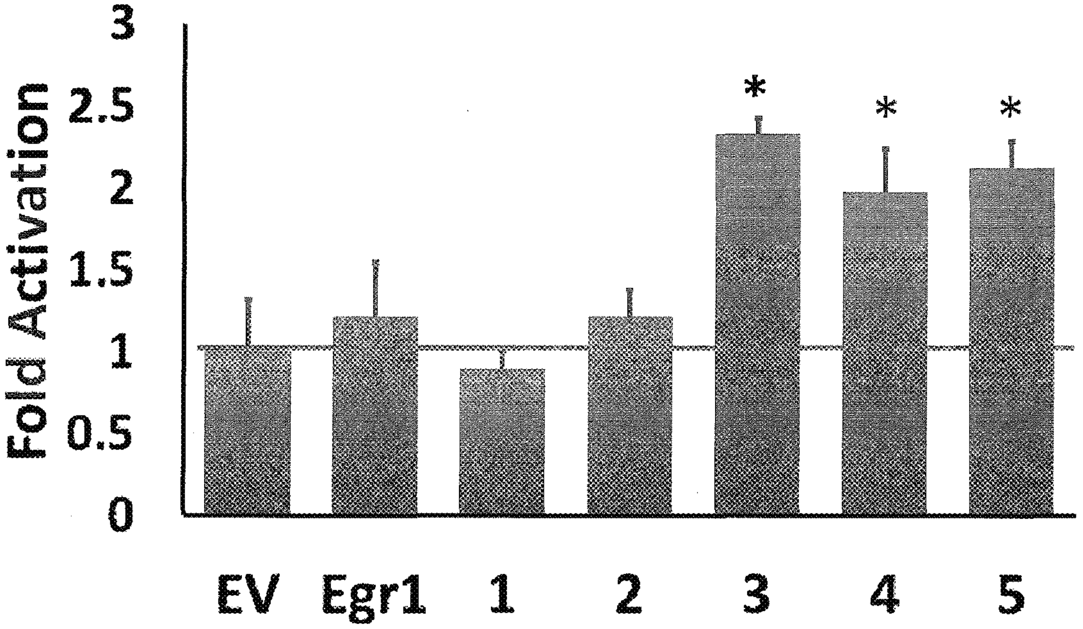
FIG. 5: Klotho activation in HK-2 cells using short hairpin RNA constructs measured using a Klotho ELISA kit. * $p<0.05$. Results normalised to total protein.

Five short hairpin RNAs were then designed to target both of the non-coding RNA transcripts. The guide strand of each short RNA targets a specific sequence within the 424-nucleotide sequence shared between both transcripts (FIG. 4). The sequence of each guide strand is set forth in SEQ ID NOs. 54 to 58. Each short hairpin RNA was transfected into HK-2 cells, and those corresponding to guide 3, guide 4 and guide 5 were found to significantly increase Klotho gene expression (FIG. 5).

Example 4: Suppression of Mouse RNA Transcripts

Figure 6:
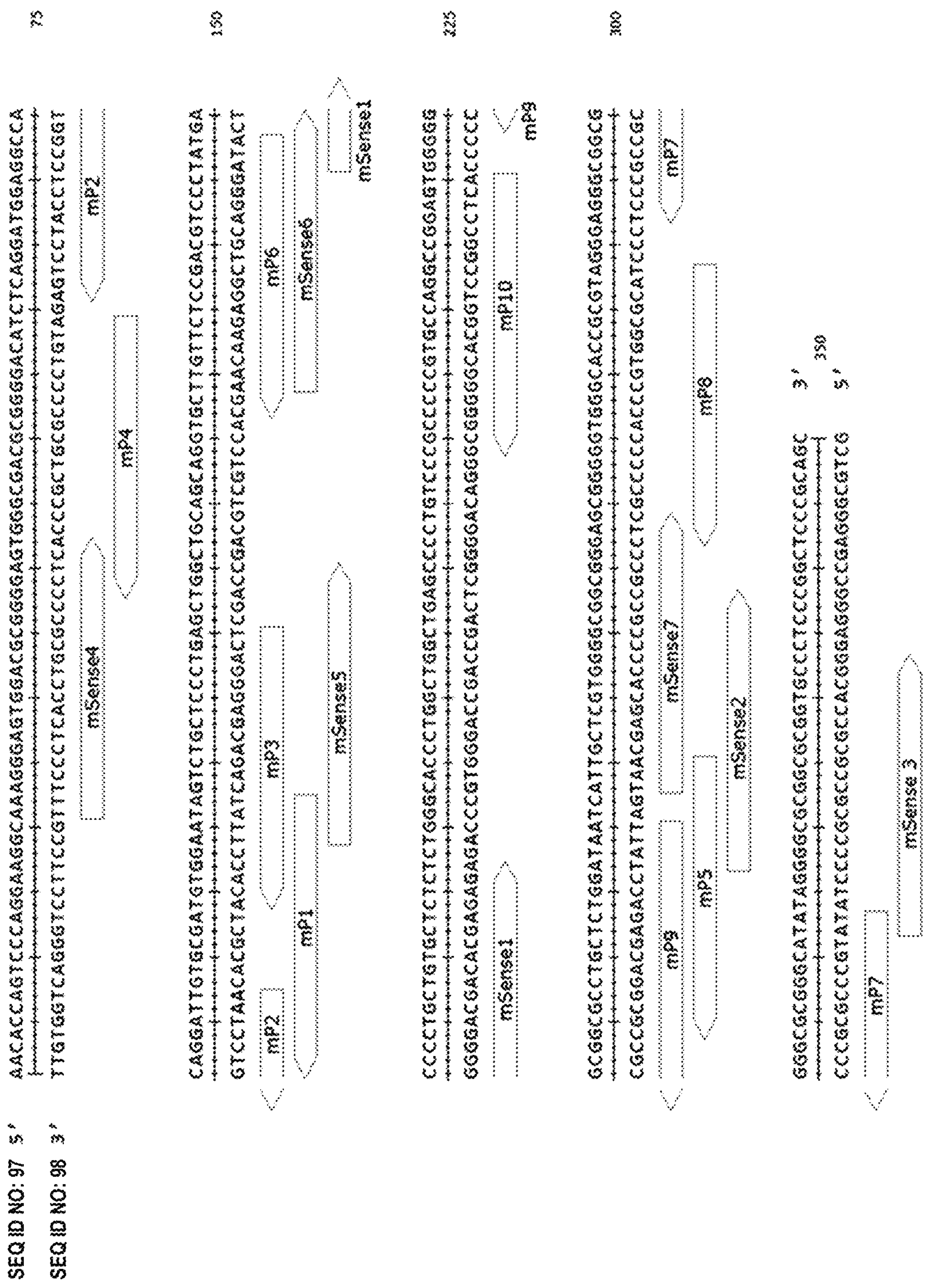
FIG. 6: Schematic diagram showing the chromosomal region extending 350 bp upstream from the mouse Klotho gene translation start site. Binding positions of short RNAs are indicated.

To test whether non-coding RNA transcripts reduce Klotho gene expression in other organisms, a set of plasmids was designed to express short hairpin RNAs (shRNAs) which target either sense (mP1 to mP10) or antisense (mSense1 to mSense7) RNA transcripts derived from a chromosomal region upstream of the mouse Klotho translation start site (Table 2 and FIG. 6). Each shRNA was separately transfected into mouse N2a cells and qPCR was used to measure Klotho gene expression. An empty vector served as a negative control for normalisation, while a plasmid encoding a Klotho-specific zinc finger protein fused to the VP64, p65 and RTA transcriptional activation domains (ZFP3VPR) served as a positive control.

Figure 7:
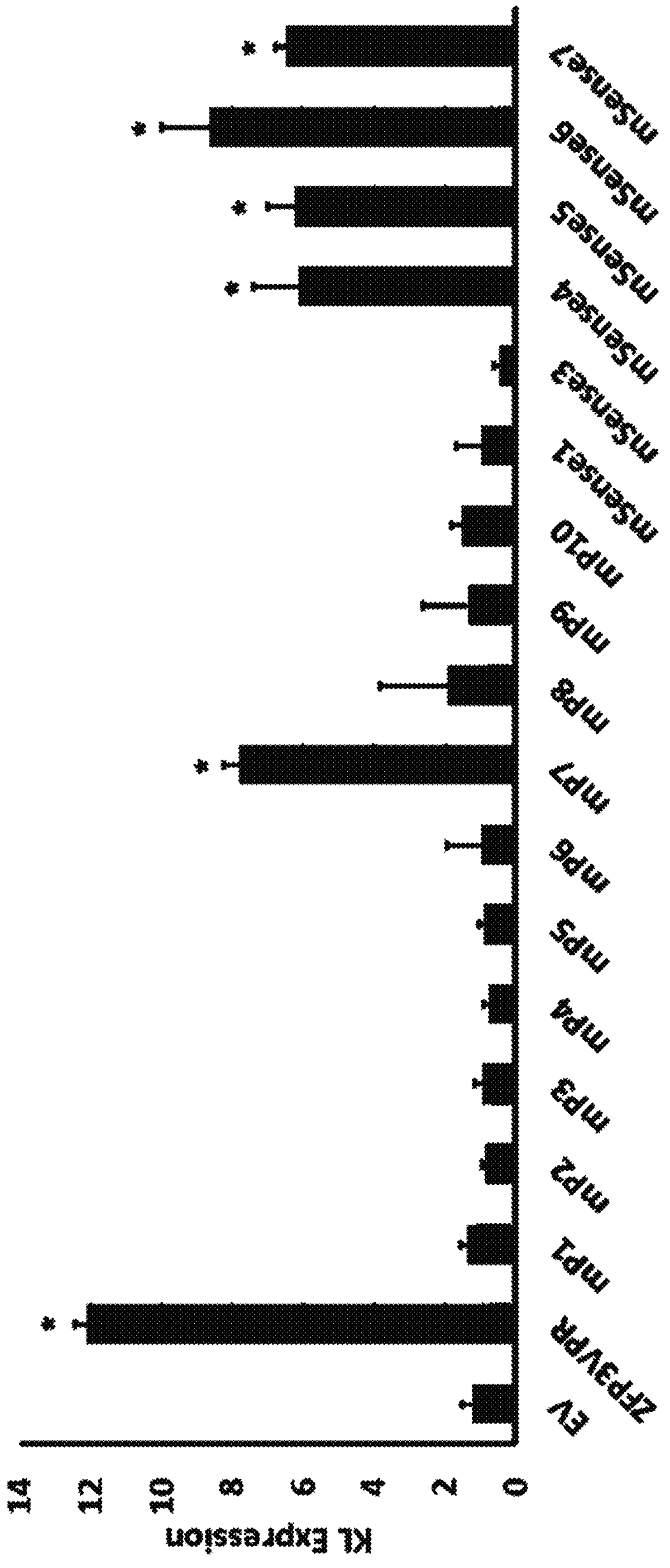
FIG. 7: Quantitative PCR measurements of Klotho gene expression in transfected N2a cells. * $p<0.05$. Results normalised to empty vector (EV) control.

Referring to FIG. 7, administration of mP7, mSense4, mSense5, mSense6 and mSense7 was found to significantly increase Klotho gene expression.

It will be appreciated by those skilled in the art that the present disclosure may be embodied in many other forms.

The invention claimed is:

1. A method of increasing expression of a Klotho gene in a cell, the method comprising administering to the cell a nucleic acid that hybridizes to an RNA transcript transcribed from a chromosomal region within or near the Klotho gene, wherein the RNA transcript does not encode a Klotho protein, and wherein the nucleic acid is between about 15 and 50 nucleotides in length and comprises a region of at least 15 nucleotides that is substantially complementary to the RNA transcript.

2. The method of claim 1 wherein the chromosomal region comprises the region between 302 nucleotides and 551 nucleotides upstream of the Klotho gene translation start site.

3. The method of claim 1 wherein the RNA transcript comprises the sequence set forth in SEQ ID NO. 6 or a sequence having at least about 90% identity to SEQ ID NO. 6.

4. The method of claim 1 wherein the nucleic acid comprises a sequence that is at least about 90% identical to the sequence set forth in SEQ ID NO. 21, SEQ ID NO. 23, SEQ ID NO. 25, SEQ ID NO. 27 or SEQ ID NO. 29.

5. The method of claim 1 wherein the RNA transcript is a sense RNA transcript.

6. The method of claim 1 wherein the chromosomal region comprises the region between 183 nucleotides and 2,662 nucleotides upstream of the Klotho gene translation start site.

7. The method of claim 1 wherein the RNA transcript comprises the sequence set forth in SEQ ID NO. 51 or a sequence having at least about 90% identity to SEQ ID NO. 51.

8. The method of claim 1 wherein the chromosomal region comprises the region between 3,133 nucleotides upstream of the Klotho gene translation start site and 412 nucleotides downstream of the Klotho gene translation start site.

9. The method of claim 1 wherein the RNA transcript comprises the sequence set forth in SEQ ID NO. 48 or a sequence having at least about 90% identity to SEQ ID NO. 48.

10. The method of claim 1 wherein the nucleic acid comprises a sequence that is at least about 90% identical to the sequence set forth in SEQ ID NO. 54, SEQ ID NO. 55, SEQ ID NO. 56, SEQ ID NO. 57 or SEQ ID NO. 58.

11. The method of claim 1 wherein the chromosomal region comprises the region between 32 nucleotides upstream of the Klotho gene translation stop site and 457 nucleotides downstream of the Klotho gene translation stop site.

12. The method of claim 1 wherein the RNA transcript comprises the sequence set forth in SEQ ID NO. 16 or a sequence having at least about 90% identity to SEQ ID NO. 16.

13. The method of claim 1 wherein the nucleic acid comprises a sequence that is at least about 90% identical to the sequence set forth in SEQ ID NO. 31, SEQ ID NO. 33 or SEQ ID NO. 35.

14. The method of claim 1 wherein the RNA transcript is an antisense RNA transcript.

15. A method of treating cancer, a muscle disorder, a kidney disorder, or neurological disorder in a subject, the method comprising administering to the subject a therapeutically effective amount of a nucleic acid that hybridizes to an RNA transcript transcribed from a chromosomal region within or near a Klotho gene, wherein the RNA transcript does not encode a Klotho protein, wherein the nucleic acid is between about 15 and 50 nucleotides in length and comprises a region of at least 15 nucleotides that is substantially complementary to the RNA transcript, and wherein administration of the nucleic acid increases expression of the Klotho gene in the subject.

16. The method of claim 15 wherein the chromosomal region comprises a region of at least 200 nucleotides upstream of the Klotho gene translation start site.

17. The method of claim 15 wherein the chromosomal region comprises the region between 32 nucleotides upstream of the Klotho gene translation stop site and 457 nucleotides downstream of the Klotho gene translation stop site.

18. A method of enhancing cognition in a subject having a neurological disorder, the method comprising administering to the subject a therapeutically effective amount of a nucleic acid that hybridizes to an RNA transcript transcribed from a chromosomal region within or near a Klotho gene, wherein the RNA transcript does not encode a Klotho protein, wherein the nucleic acid is between about 15 and 50 nucleotides in length and comprises a region of at least 15 nucleotides that is substantially complementary to the RNA transcript, and wherein administration of the nucleic acid increases expression of the Klotho gene in the subject.

* * * * *

SEQUENCE LISTING

```
<160> NUMBER OF SEQ ID NOS: 98

<210> SEQ ID NO 1
<211> LENGTH: 5003
<212> TYPE: RNA
<213> ORGANISM: Homo sapiens

<400> SEQUENCE: 1

cgcgcagcau gcccgccagc gccccgccgc gccgcccgcg gccgccgccg ccgucgcugu      60

cgcugcugcu ggugcugcug ggccugggcg gccgccgccu gcgugcggag ccgggcgacg     120

gcgcgcagac cugggcccgu uucucgcggc cuccugcccc cgaggccgcg ggccucuucc     180
```

-continued agggcaccuu ccccgacggc uuccucuggg ccgugggcag cgccgccuac cagaccgagg 240
gcggcuggca gcagcacggc aagggugcgu ccaucuggga uacguucacc caccaccccc 300
uggcaccccc gggagacucc cggaacgcca gucugccguu gggcgccccg ucgccgcugc 360
agcccgccac cggggacgua gccagcgaca gcuacaacaa cgucuuccgc gacacggagg 420
cgcugcgcga gcucggggtc acucacuacc gcuucuccau cucgugggcg cgagugcucc 480
ccaauggcag cgcgggcguc cccaaccgcg aggggcugcg cuacuaccgg cgccugcugg 540
agcggcugcg ggagcugggc gugcagcccg uggucacccu guaccacugg gaccugcccc 600
agcgccugca ggacgccuac ggcggcuggg ccaaccgcgc ccuggccgac cacuucaggg 660
auuacgcgga gcucugcuuc cgccacuucg gcggucaggu caaguacugg aucaccaucg 720
acaaccccua cgugguggcc uggcacggcu acgccaccgg gcgccuggcc cccggcaucc 780
ggggcagccc gcggcucggg uaccuggugg cgcacaaccu ccuccuggcu caugccaaag 840
ucuggcaucu cuacaauacu ucuuuccguc ccacucaggg aggucaggug uccauugccc 900
uaagcucuca cuggaucaau ccucgaagaa ugaccgacca cagcaucaaa gaaugucaaa 960
aaucucugga cuuuguacua gguugguuug ccaaacccgu auuuauugau ggugacuauc 1020
ccgagagcau gaagaauaac cuuucaucua uucugccuga uuuuacugaa ucugagaaaa 1080
aguucaucaa aggaacugcu gacuuuuuug cucuuugcuu uggacccacc uugaguuuuc 1140
aacuuuugga cccucacaug aaguuccgcc aauuggaauc ucccaaccug aggcaacugc 1200
uuuccuggau ugaccuugaa uuuaaccauc cucaaauauu uauuguggaa aauggcuggu 1260
uugucucagg gaccaccaag agagaugaug ccaaauauau guauuaccuc aaaaaguuca 1320
ucauggaaac cuuaaaagcc aucaagcugg augggguggga ugucaucggg uauaccgcau 1380
ggucccucau ggaugguuuc gaguggcaca gagguuacag caucaggcgu ggacucuucu 1440
auguugacuu ucuaagccag gacaagaugu uguugccaaa gucuucagcc uuguucuacc 1500
aaaagcugau agagaaaaau ggcuucccuc cuuuaccuga aaaucagccc cuagaaggga 1560
cauuucccug ugacuuugcu uggggaguug uugacaacua cauucaagua gauaccacuc 1620
ugucucaguu uaccgaccug aauguuuacc ugugggaugu ccaccacagu aaaaggcuua 1680
uuaaagugga uggggguugug accaagaaga ggaaauccua cuguguugac uuugcugcca 1740
uccagcccca gaucgcuuua cuccaggaaa ugcacguuac acauuuucgc uucucccugg 1800
acugggcccu gauucucccu cuggguaacc agucccaggu gaaccacacc auccugcagu 1860
acuaucgcug cauggccagc gagcuugucc gugucaacau caccccagug guggcccugu 1920
ggcagccuau ggccccgaac caaggacugc cgcgccuccu ggccaggcag ggcgccuggg 1980
agaaccccua cacugcccug gccuuugcag aguaugcccg acugugcuuu caagagcucg 2040
gccaucacgu caagcuuugg auaacgauga augagccgua uacaaggaau augacauaca 2100
gugcuggcca caaccuucug aaggcccaug cccuggcuug gcauguguac aaugaaaagu 2160
uuaggcaugc ucagaauggg aaaauaucca uagccuugca ggcugauugg auagaaccug 2220
ccugcccuuu cucccaaaag gacaaagagg uggccgagag aguuuuggaa uuugacauug 2280
gcuggcuggc ugagcccauu uucggcucug gagauuaucc augggugaug agggacuggc 2340
ugaaccaaag aaacaauuuu cuucuuccuu auuucacuga agaugaaaaa aagcuaaucc 2400
aggguaccuu ugacuuuuug gcuuuaagcc auuauaccac cauccuugua gacucagaaa 2460
aagaagaucc aauaaaaauac aaugauuacc uagaagugca agaaaugacc gacaucacgu 2520
ggcucaacuc ccccagucag guggcgguag ugcccugggg guugcgcaaa gugcugaacu 2580

-continued

```
ggcugaaguu caaguacgga gaccucccca uguacauaau auccaacgga aucgaugacg   2640
ggcugcaugc ugaggacgac cagcugaggg uguauuauau gcagaauuac auaaacgaag   2700
cucucaaagc ccacauacug gaugguauca aucuuugcgg auacuuugcu uauucguuua   2760
acgaccgcac agcuccgagg uuuggccucu aucguuaugc ugcagaucag uuugagccca   2820
aggcauccau gaaacauuac aggaaaauua uugacagcaa ugguuucccg ggcccagaaa   2880
cucuggaaag auuuugucca gaagaauuca ccguguguac ugagugcagu uuuuuucaca   2940
cccgaaaguc uuuacuggcu uucauagcuu uucuauuuuu ugcuucuauu auuucucucu   3000
cccuuauauu uuacuacucg aagaaaggca gaagaaguua caaauaguuc ugaacauuuu   3060
ucuauucauu cauuuugaaa uaauuaugca gacacaucag cuguuaacca uuugcaccuc   3120
uaaguguugu gaaacuguaa auuucauaca uuugacuucu agaaaacauu uuuguggcuu   3180
augacagagg uuuugaaaug ggcauaggug aucguaaaau auugaauaau gcgaauagug   3240
ccugaauuug uucucuuuuu gggugauuaa aaaacugaca ggcacuauaa uuucuguaac   3300
acacuaacaa aagcaugaaa aauaggaacc acaccaaugc aacauuugug cagaaauuug   3360
aaugacaaga uuaggaauau uuucuucugc acccacuucu aaauuuaaug uuuuucugga   3420
aguaguaauu gcaagaguuc gaauagaaag uuauguacca aguaaccauu ucucagcugc   3480
cauaaauaaug ccuaguggcu uccccucugu caaaucuagu uuccuaugga aaagaagaug   3540
gcagauacag gagagacgac agagggucc u aggcuggaau guuccuuucg aaagcaaugc   3600
uucuaucaaa uacuaguauu aauuuaugua ucugguuaau gacauacuug gagagcaaau   3660
uauggaaaug uguauuuuau augauuuuug agguccuguc uaaacccugu gucccugagg   3720
gaucugucuc acuggcaucu uguugagggc cuugcacaua ggaaacuuuu gauaaguauc   3780
ugcggaaaaa caaacaugaa uccugugaua uugggcucuu caggaagcau aaagcaauug   3840
ugaaauacag uauaccgcag uggcucuagg uggaggaaag gaggaaaaag ugcuuauuau   3900
gugcaacauu augauuaauc ugauuauaca ccauuuuuga gcagaucuug gaaugaauga   3960
caugaccuuu cccuagagaa uaaggaugaa auaaucacuc auucuaugaa cagugacacu   4020
acuuucuauu cuuuagcugu acuguaauuu cuuugaguug auaguuuuac aaauucuuaa   4080
uagguucaaa agcaaucugg ucugaauaac acuggauuug uuucugugau cucugagguc   4140
uauuuuaugu uuuugcugcu acuucugugg aaguagcuuu gaacuaguuu uacuuugaac   4200
uuucacgcug aaacaugcua gugauaucua gaaagggcua auuaggucuc auccuuuaau   4260
gccccuuaaa uaagucuugc ugauuuucag acagggaagu cucucuauua cacuggagcu   4320
guuuuauaga uaagucaaua uuguaucagg caagauaaac caaugucaua acaggcauug   4380
ccaaccucac ugacacaggg ucauagugua uaauaauaua cuguacuaua uaauauauca   4440
ucuuuagagg uaugauuuuu ucaugaaaga uaagcuuuug guaauauuca uuuuaaagug   4500
gacuuauuaa aauuggaugc uagagaauca aguuuauuuu auguauauau uuuucugauu   4560
auaagaguaa uauauguuca uuguaaaaau uuuuaaaaca cagaaacuau augcaaagaa   4620
aaaauaaaaa uuaucuauaa ucucagaacc cagaaauagc cacuauuaac auuuccuacg   4680
uauuuuauuu uacauagauc auauuguaua uaguuaguau cuuuauuaau uuuuauuaug   4740
aaacuuuccu uugucauuau uagucuucaa aagcaugauu uuuaauaguu guugaguauu   4800
ccaccacagg aauguaucac aacuuaaccg uucccguuug uuagacuagu uucuuauuaa   4860
uguugaugaa uguuguuuaa aaauaauuuu guugcuacau uuacuuuaau uuccuugacu   4920
```

-continued guaaagagaa guaauuuugc uccuugauaa aguauuauau uaauaauaaa ucugccugca 4980
acuuuuugcc uucuuucaua auc 5003

<210> SEQ ID NO 2
<211> LENGTH: 2000
<212> TYPE: DNA
<213> ORGANISM: Homo sapiens

<400> SEQUENCE: 2
actgctttaa aatttaaaaa atgctgctgg tcaagtaaaa atagcaatag ataaaatctg 60
ccctgagcaa acagaccata catcaataaa tgaatactta gcttaagcga ttttccatga 120
gacccatgaa gcatttctaa ttgaaactta acaagctaca acccaacaga cactccaatc 180
ttcacttcta gaagggaaat gtgatactcc atgtagacgt agctttttaa atttagctgg 240
aagacagcgt gacagtgaag ttgtgtgctg taattttta aaattgctga agtgtcatgg 300
tttgctattt cgtatttatt gaaaaaatgt aaatgctata tttaacagaa tggcagtaac 360
tctgtttcaa tctgaagact taatcttact aatcatggta atatatgctg gctggagttg 420
ggaatatttc ataaaatact ggaataaatt tgtgcttata tttcagggga attaataaaa 480
gcaccttcat ctgcaacatt taaaatgtta ttgcctttaa atttgtatta aataatgcag 540
ggaggataga tcactggggg agaatggatg cacctctgtg aggatcttgg tcattcaaca 600
cacgtgtacg ggtgaggaaa ctaaggcacg acttactggg tagggaggta gggatattag 660
caagatcctt cacttgtctg ggctttctgt ctttgagtca cctttgcgca gtttttcact 720
ggacttcaca agcctctgag gcggcagggc agacaggaca tccttatttt atagaggaaa 780
aaacttaggc ttacagaggt ttcctgcccc aaatcacaaa ggtggagcct agaccttctc 840
agtctccacc aactgtattt cggttagcca caatcctatc tacccacatc caaatggaca 900
ccgtggctct gcaacttctg tcaaaagggc tctttggcaa caggaaaaac gtcatggctc 960
cattgtattg tagaggatgg gaatgggtgt tccggctaaa ttctccctcc cctttccctc 1020
cacagctcag atggcaaatg tgcgacccag ggacctcccg ctccagcaga cctgtgcgca 1080
caactttgca cagattacct gctaagtcag agccgaaagg taacacagat gccaaaggat 1140
aataaaggtg aatgagattt actcaaaatt ggaaacttgg tgtttggttt ttcaggagaa 1200
caatcaacga ctgtgatttg aagttcacca gggtattctg agagatctaa tcaaagatag 1260
agtgctggtt tgaaattatt aaaaggtaac agtaaaaggg agagcaaaac cccagtccca 1320
acgcaaccca taaatctact ttgtcttcct cgaaagaggg gcgcgggtgg gcgcgtctcc 1380
ccgcgagcat ctcacctaag ggggaatccc tttcagcgca cggcgaagtt ccccctcggc 1440
tgtcccacct ggcagtccct ctaggatttc ggccagtccc taattggctc cagcaatgtc 1500
cagccggagc ttctttgggc ctccgagtgg gagaaaagtg agagcaggtg cttccccagc 1560
ggcgcgctcc gctagggccc ggcaggatcc cgcccccaag tcggggaaag ttggtcggcg 1620
ccttttctcc ccgacgaagc cgctccaggg ctgctctcag aggacgcgcg gcaggcaaag 1680
agaatgaacc tgagcgtcca cgaaacgtcc tgcacggctc ccgggagctg ggaggaacag 1740
gtgcctttct ccgacgtccg cgggcgacgc ctgccgcacc ttgcccgctg ccgcgcccct 1800
cccgggcacc cctcgccctc ggcgcccctg cccccacccc cagtgccagg gcggaggcag 1860
tcccggctcg caggtaatta ttgccagcgg agcccgccgg ggagcggggg tgggcgcgcc 1920
ggcggtgggc gggcgggcgc ggcggggcgc gggcataaag gggcgcggcg cggggccccg 1980
gagcctggct cccgcgcagc 2000

<210> SEQ ID NO 3
<211> LENGTH: 2000
<212> TYPE: RNA
<213> ORGANISM: Homo sapiens

<400> SEQUENCE: 3
acugcuuuaa aauuuaaaaa augcugcugg ucaaguaaaa auagcaauag auaaaaucug 60
cccugagcaa acagaccaua caucaauaaa ugaauacuua gcuuaagcga uuuuccauga 120
gacccaugaa gcauuucuaa uugaaacuua acaagcuaca acccaacaga cacuccaauc 180
uucacuucua gaagggaaau gugauacucc auguagacgu agcuuuuuaa auuuagcugg 240
aagacagcgu gacagugaag uugugugcug uaauuuuuua aaauugcuga agugucaugg 300
uuugcuauuu cguauuuauu gaaaaaaugu aaaugcuaua uuuaacagaa uggcaguaac 360
ucuguuucaa ucugaagacu uaaucuuacu aaucauggua auauaugcug gcuggaguug 420
ggaauauuuc auaaaauacu ggaauaaauu ugugcuuaua uuucagggga auuaauaaaa 480
gcaccuucau cugcaacauu uaaaauguua uugccuuuaa auuuguauua aauaaugcag 540
ggaggauaga ucacuggggg agaauggaug caccucugug aggaucuugg ucauucaaca 600
cacguguacg ggugaggaaa cuaaggcacg acuuacuggg uagggaggua gggauauuag 660
caagauccuu cacuugucug ggcuuucugu cuuugaguca ccuuugcgca guuuuucacu 720
ggacuucaca agccucugag gcggcagggc agacaggaca uccuuauuuu auagaggaaa 780
aaacuuaggc uuacagaggu uuccugcccc aaaucacaaa gguggagccu agaccuucuc 840
agucuccacc aacuguauuu cgguuagcca caauccuauc uacccacauc caaauggaca 900
ccguggcucu gcaacuucug ucaaaagggc ucuuuggcaa caggaaaaac gucauggcuc 960
cauuguauug uagaggaugg gaaugggugu uccggcuaaa uucucccucc ccuuucccuc 1020
cacagcucag auggcaaaug ugcgacccag ggaccucccg cuccagcaga ccugugcgca 1080
caacuuugca cagauuaccu gcuaagucag agccgaaagg uaacacagau gccaaaggau 1140
aauaaaggug aaugagauuu acucaaaauu ggaaacuugg uguuugguuu uucaggagaa 1200
caaucaacga cugugauuug aaguucacca ggguauucug agagaucuaa ucaaagauag 1260
agugcugguu ugaaauuauu aaaagguaac aguaaaaggg agagcaaaac cccaguccca 1320
acgcaaccca uaaaucuacu uugucuuccu cgaaagaggg gcgcgggugg gcgcgucucc 1380
ccgcgagcau cucaccuaag ggggaauccc uuucagcgca cggcgaaguu cccccucggc 1440
ugucccaccu ggcagucccu cuaggauuuc ggccaguccc uaauuggcuc cagcaauguc 1500
cagccggagc uucuuugggc cuccgagugg gagaaaagug agagcaggug cuuccccagc 1560
ggcgcgcucc gcuagggccc ggcaggaucc cgcccccaag ucggggaaag uuggucggcg 1620
ccuuuucucc ccgacgaagc cgcuccaggg cugcucucag aggacgcgcg gcaggcaaag 1680
agaaugaacc ugagcgucca cgaaacgucc ugcacggcuc ccgggagcug ggaggaacag 1740
gugccuuucu ccgacguccg cgggcgacgc cugccgcacc uugcccgcug ccgcgccccu 1800
cccgggcacc ccucgcccuc ggcgccccug cccccacccc cagugccagg gcggaggcag 1860
ucccggcucg cagguaauua uugccagcgg agcccgccgg ggagcggggg ugggcgcgcc 1920
ggcggugggc gggcgggcgc ggcggggcgc gggcauaaag gggcgcggcg cggggccccg 1980
gagccuggcu cccgcgcagc 2000

<210> SEQ ID NO 4

-continued

<211> LENGTH: 2000
<212> TYPE: RNA
<213> ORGANISM: Homo sapiens

<400> SEQUENCE: 4
gcugcgcggg agccaggcuc cggggccccg cgccgcgccc cuuuaugccc gcgccccgcc 60
gcgcccgccc gcccaccgcc ggcgcgccca cccccgcucc ccggcgggcu ccgcuggcaa 120
uaauuaccug cgagccggga cugccuccgc ccuggcacug ggggugggggg caggggcgcc 180 gagggcgagg ggugcccggg aggggcgcgg cagcgggcaa ggugcggcag gcgucgcccg 240
cggacgucgg agaaaggcac cuguuccucc cagcuccccgg gagccgugca ggacguuucg 300
uggacgcuca gguucauucu cuuugccugc cgcgcguccu cugagagcag cccuggagcg 360
gcuucgucgg ggagaaaagg cgccgaccaa cuuuccccga cuugggggcg ggauccugcc 420
gggcccuagc ggagcgcgcc gcuggggaag caccugcucu cacuuuucuc ccacucggag 480
gcccaaagaa gcuccggcug gacauugcug gagccaauua gggacuggcc gaaauccuag 540
agggacugcc aggugggaca gccgaggggg aacuucgccg ugcgcugaaa gggauucccc 600
cuuaggugag augcucgcgg ggagacgcgc ccacccgcgc cccucuuucg aggaagacaa 660
aguagauuua uggguugcgu ugggacuggg guuuugcucu cccuuuuacu guuaccuuuu 720
aauaauuuca aaccagcacu cuaucuuuga uuagaucucu cagaauaccc uggugaacuu 780
caaaucacag ucguugauug uucuccugaa aaaccaaaca ccaaguuucc aauuuugagu 840
aaaucucauu caccuuuauu auccuuuggc aucuguguua ccuuucggcu cugacuuagc 900
agguaaucug ugcaaaguug ugcgcacagg ucugcuggag cgggaggucc cugggucgca 960
cauuugccau cugagcugug gagggaaagg ggagggagaa uuuagccgga acacccauuc 1020
ccauccucua caauacaaug gagccaugac guuuuuccug uugccaaaga gcccuuuuga 1080
cagaaguugc agagccacgg uguccauuug gaugugggua gauaggauug uggcuaaccg 1140
aaauacaguu gguggagacu gagaaggucu aggcuccacc uuugugauuu ggggcaggaa 1200
accucuguaa gccuaaguuu uuuccucuau aaaauaagga uguccugucu gcccugccgc 1260
cucagaggcu ugugaagucc agugaaaaac ugcgcaaagg ugacucaaag acagaaagcc 1320
cagacaagug aaggaucuug cuaauauccc uaccucccua cccaguaagu cgugccuuag 1380
uuuccucacc cguacacgug uguugaauga ccaagauccu cacagaggug cauccauucu 1440
cccccaguga ucuauccucc cugcauuauu uaauacaaau uuaaaggcaa uaacauuuua 1500
aauguugcag augaaggugc uuuuauuaau uccccugaaa uauaagcaca aauuuauucc 1560
aguauuuuau gaaauauucc caacuccagc cagcauauau uaccaugauu aguaagauua 1620
agucuucaga uugaaacaga guuacugcca uucuguuaaa uauagcauuu acauuuuuuc 1680
aauaaauacg aaauagcaaa ccaugacacu ucagcaauuu uaaaaaauua cagcacacaa 1740
cuucacuguc acgcugucuu ccagcuaaau uuaaaaagcu acgucuacau ggaguaucac 1800
auuucccuuc uagaagugaa gauuggagug ucuguugggu uguagcuugu uaaguuucaa 1860
uuagaaaugc uucauggguc ucauggaaaa ucgcuuaagc uaaguauuca uuuauugaug 1920
uauggucugu uugcucaggg cagauuuuau cuauugcuau uuuuacuuga ccagcagcau 1980
uuuuuaaauu uuaaagcagu 2000

<210> SEQ ID NO 5
<211> LENGTH: 249
<212> TYPE: DNA
<213> ORGANISM: Homo sapiens

<400> SEQUENCE: 5
tggcagtccc tctaggattt cggccagtcc ctaattggct ccagcaatgt ccagccggag 60
cttctttggg cctccgagtg ggagaaaagt gagagcaggt gcttccccag cggcgcgctc 120
cgctagggcc cggcaggatc ccgcccccaa gtcggggaaa gttggtcggc gccttttctc 180
cccgacgaag ccgctccagg gctgctctca gaggacgcgc ggcaggcaaa gagaatgaac 240
ctgagcgtc 249

<210> SEQ ID NO 6
<211> LENGTH: 249
<212> TYPE: RNA
<213> ORGANISM: Homo sapiens

<400> SEQUENCE: 6
uggcaguccc ucuaggauuu cggccagucc cuaauuggcu ccagcaaugu ccagccggag 60
cuucuuuggg ccuccgagug ggagaaaagu gagagcaggu gcuuccccag cggcgcgcuc 120
cgcuagggcc cggcaggauc ccgcccccaa gucggggaaa guuggucggc gccuuuucuc 180
cccgacgaag ccgcuccagg gcugcucuca gaggacgcgc ggcaggcaaa gagaaugaac 240
cugagcguc 249

<210> SEQ ID NO 7
<211> LENGTH: 249
<212> TYPE: RNA
<213> ORGANISM: Homo sapiens

<400> SEQUENCE: 7
gacgcucagg uucauucucu uugccugccg cgcguccucu gagagcagcc cuggagcggc 60
uucgucgggg agaaaaggcg ccgaccaacu uuccccgacu ugggggcggg auccugccgg 120
gcccuagcgg agcgcgccgc uggggaagca ccugcucuca cuuuucuccc acucggaggc 180
ccaaagaagc uccggcugga cauugcugga gccaauuagg gacuggccga aauccuagag 240
ggacugcca 249

<210> SEQ ID NO 8
<211> LENGTH: 579
<212> TYPE: DNA
<213> ORGANISM: Homo sapiens

<400> SEQUENCE: 8
tcccaacgca acccataaat ctactttgtc ttcctcgaaa gaggggcgcg ggtgggcgcg 60
tctccccgcg agcatctcac ctaaggggga atccctttca gcgcacggcg aagttccccc 120
tcggctgtcc cacctggcag tccctctagg atttcggcca gtccctaatt ggctccagca 180
atgtccagcc ggagcttctt tgggcctccg agtgggagaa aagtgagagc aggtgcttcc 240
ccagcggcgc gctccgctag ggcccggcag gatcccgccc ccaagtcggg gaaagttggt 300
cggcgccttt tctccccgac gaagccgctc cagggctgct ctcagaggac gcgcggcagg 360
caaagagaat gaacctgagc gtccacgaaa cgtcctgcac ggctcccggg agctgggagg 420
aacaggtgcc tttctccgac gtccgcgggc gacgcctgcc gcaccttgcc cgctgccgcg 480
cccctcccgg gcacccctcg ccctcggcgc ccctgccccc acccccagtg ccagggcgga 540
ggcagtcccg gctcgcaggt aattattgcc agcggagcc 579

<210> SEQ ID NO 9

-continued

<211> LENGTH: 579
<212> TYPE: RNA
<213> ORGANISM: Homo sapiens

<400> SEQUENCE: 9

```
ucccaacgca acccauaaau cuacuuuguc uuccucgaaa gaggggcgcg ggugggcgcg     60

ucuccccgcg agcaucucac cuaaggggga aucccuuuca gcgcacggcg aaguuccccc    120

ucggcugucc caccuggcag ucccucuagg auuucggcca gucccuaauu ggcuccagca    180

auguccagcc ggagcuucuu ugggccuccg agugggagaa aagugagagc aggugcuucc    240

ccagcggcgc gcuccgcuag ggcccggcag gaucccgccc ccaagucggg gaaaguuggu    300

cggcgccuuu ucuccccgac gaagccgcuc cagggcugcu cucagaggac gcgcggcagg    360

caaagagaau gaaccugagc guccacgaaa cguccugcac ggcucccggg agcugggagg    420

aacaggugcc uuucuccgac guccgcgggc gacgccugcc gcaccuugcc cgcugccgcg    480

ccccucccgg gcaccccucg cccucggcgc cccugccccc acccccagug ccagggcgga    540

ggcagucccg gcucgcaggu aauuauugcc agcggagcc                           579
```

<210> SEQ ID NO 10
<211> LENGTH: 579
<212> TYPE: RNA
<213> ORGANISM: Homo sapiens

<400> SEQUENCE: 10

```
ggcuccgcug gcaauaauua ccugcgagcc gggacugccu ccgcccuggc acugggggug     60

ggggcagggg cgccgagggc gaggggugcc cgggaggggc gcggcagcgg gcaaggugcg    120

gcaggcgucg cccgcggacg ucggagaaag gcaccuguuc cucccagcuc ccgggagccg    180

ugcaggacgu uucguggacg cucagguuca uucucuuugc cugccgcgcg uccucugaga    240

gcagcccugg agcggcuucg ucggggagaa aaggcgccga ccaacuuucc ccgacuuggg    300

ggcgggaucc ugccgggccc uagcggagcg cgccgcuggg gaagcaccug cucucacuuu    360

ucucccacuc ggaggcccaa agaagcuccg gcuggacauu gcuggagcca auuagggacu    420

ggccgaaauc cuagagggac ugccaggugg gacagccgag ggggaacuuc gccgugcgcu    480

gaaagggauu cccccuuagg ugagaugcuc gcggggagac gcgcccaccc gcgccccucu    540

uucgaggaag acaaaguaga uuuaugggau gcguuggga                           579
```

<210> SEQ ID NO 11
<211> LENGTH: 2000
<212> TYPE: DNA
<213> ORGANISM: Homo sapiens

<400> SEQUENCE: 11

```
ttctgaacat ttttctattc attcattttg aaataattat gcagacacat cagctgttaa     60

ccatttgcac ctctaagtgt tgtgaaactg taaatttcat acatttgact tctagaaaac    120

atttttgtgg cttatgacag aggttttgaa atgggcatag gtgatcgtaa aatattgaat    180

aatgcgaata gtgcctgaat ttgttctctt tttgggtgat taaaaaactg acaggcacta    240

taatttctgt aacacactaa caaaagcatg aaaaatagga accacaccaa tgcaacattt    300

gtgcagaaat ttgaatgaca agattaggaa tattttcttc tgcacccact tctaaattta    360

atgtttttct ggaagtagta attgcaagag ttcgaataga aagttatgta ccaagtaacc    420

atttctcagc tgccataata atgcctagtg gcttcccctc tgtcaaatct agtttcctat    480

ggaaaagaag atggcagata caggagagac gacagagggt cctaggctgg aatgttcctt    540
```

-continued

```
tcgaaagcaa tgcttctatc aaatactagt attaatttat gtatctggtt aatgacatac    600

ttggagagca aattatggaa atgtgtattt tatatgattt ttgaggtcct gtctaaaccc    660

tgtgtccctg agggatctgt ctcactggca tcttgttgag ggccttgcac ataggaaact    720

tttgataagt atctgcggaa aaacaaacat gaatcctgtg atattgggct cttcaggaag    780

cataaagcaa ttgtgaaata cagtataccg cagtggctct aggtggagga aaggaggaaa    840

aagtgcttat tatgtgcaac attatgatta atctgattat acaccatttt tgagcagatc    900

ttggaatgaa tgacatgacc tttccctaga gaataaggat gaaataatca ctcattctat    960

gaacagtgac actactttct attctttagc tgtactgtaa tttctttgag ttgatagttt   1020

tacaaattct taataggttc aaaagcaatc tggtctgaat aacactggat ttgtttctgt   1080

gatctctgag gtctatttta tgtttttgct gctacttctg tggaagtagc tttgaactag   1140

ttttactttg aactttcacg ctgaaacatg ctagtgatat ctagaaaggg ctaattaggt   1200

ctcatccttt aatgcccctt aaataagtct tgctgatttt cagacaggga agtctctcta   1260

ttacactgga gctgttttat agataagtca atattgtatc aggcaagata aaccaatgtc   1320

ataacaggca ttgccaacct cactgacaca gggtcatagt gtataataat atactgtact   1380

atataatata tcatctttag aggtatgatt ttttcatgaa agataagctt ttggtaatat   1440

tcattttaaa gtggacttat taaaattgga tgctagagaa tcaagtttat tttatgtata   1500

tatttttctg attataagag taatatatgt tcattgtaaa aatttttaaa acacagaaac   1560

tatatgcaaa gaaaaaataa aaattatcta taatctcaga acccagaaat agccactatt   1620

aacatttcct acgtatttta ttttacatag atcatattgt atatagttag tatctttatt   1680

aatttttatt atgaaacttt cctttgtcat tattagtctt caaaagcatg atttttaata   1740

gttgttgagt attccaccac aggaatgtat cacaacttaa ccgttcccgt ttgttagact   1800

agtttcttat taatgttgat gaatgttgtt taaaaaataat tttgttgcta catttacttt   1860

aatttccttg actgtaaaga gaagtaattt tgctccttga taaagtatta tattaataat   1920

aaatctgcct gcaacttttt gccttctttc ataatcatat gagtggttgc tagctaattt   1980

ttttgtaatt aaaaaaactt                                               2000
```

<210> SEQ ID NO 12
<211> LENGTH: 2000
<212> TYPE: RNA
<213> ORGANISM: Homo sapiens

<400> SEQUENCE: 12

```
uucugaacau uuuucuauuc auucauuuug aaauaauuau gcagacacau cagcuguuaa     60

ccauuugcac cucuaagugu ugugaaacug uaaauuucau acauuugacu ucuagaaaac    120

auuuuugugg cuuaugacag agguuuugaa augggcauag gugaucguaa aauauugaau    180

aaugcgaaua gugccugaau uuguucucuu uuugggugau uaaaaaacug acaggcacua    240

uaauuucugu aacacacuaa caaaagcaug aaaaauagga accacaccaa ugcaacauuu    300

gugcagaaau uugaaugaca agauuaggaa uauuuucuuc ugcacccacu ucuaaauuua    360

auguuuuucu ggaaguagua auugcaagag uucgaauaga aaguuaugua ccaaguaacc    420

auuucucagc ugccauaaua augccuagug gcuuccccuc ugucaaaucu aguuuccuau    480

ggaaaagaag auggcagaua caggagagac gacagagggu ccuaggcugg aauguucccuu    540

ucgaaagcaa ugcuucuauc aaauacuagu auuaauuuau guaucugguu aaugacauac    600
```

-continued uuggagagca aauuauggaa auguguauuu uauaugauuu uugaggaccu gucuaaaccc 660
ugugucccug agggaucugu cucacuggca ucuuguugag ggccuugcac auaggaaacu 720
uuugauaagu aucugcggaa aaacaaacau gaauccugug auauugggcu cuucaggaag 780
cauaaagcaa uugugaaaua caguauaccg caguggcucu agguggagga aaggaggaaa 840
aagugcuuau uaugugcaac auuaugauua aucugauuau acaccauuuu ugagcagauc 900
uuggaaugaa ugacaugacc uuucccuaga gaauaaggau gaaauaauca cucauucuau 960
gaacagugac acuacuuucu auucuuuagc uguacuguaa uuucuuugag uugauaguuu 1020
uacaaauucu uaauagguuc aaaagcaauc uggucugaau aacacuggau uuguuucugu 1080
gaucucugag gucuauuuua uguuuuugcu gcuacuucug uggaaguagc uuugaacuag 1140
uuuuacuuug aacuuucacg cugaaacaug cuagugauau cuagaaaggg cuaauuaggu 1200
cucauccuuu aaugccccuu aaauaagucu ugcugauuuu cagacaggga agucucucua 1260
uuacacugga gcuguuuuau agauaaguca auauuguauc aggcaagaua aaccaauguc 1320
auaacaggca uugccaaccu cacugacaca gggucauagu guauaauaau auacuguacu 1380
auauaauaua ucaucuuuag agguaugauu uuuucaugaa agauaagcuu uugguaauau 1440
ucauuuuaaa guggacuuau uaaaauugga ugcuagagaa ucaaguuuau uuuauguaua 1500
uauuuuucug auuauaagag uaauauaugu ucauuguaaa aauuuuuaaa acacagaaac 1560
uauaugcaaa gaaaaaauaa aaauuaucua uaaucucaga acccagaaau agccacuauu 1620
aacauuuccu acguauuuua uuuuacauag aucauauugu auauaguuag uaucuuuauu 1680
aauuuuuauu augaaacuuu ccuuugucau uauuagucuu caaaagcaug auuuuuaaua 1740
guuguugagu auuccaccac aggaauguau cacaacuuaa ccguucccgu uuguuagacu 1800
aguuucuuau uaauguugau gaauguuguu uaaaaaauaau uuuguugcua cauuuacuuu 1860
aauuuccuug acuguaaaga gaaguaauuu ugcuccuuga uaaaguauua uauuaauaau 1920
aaaucugccu gcaacuuuuu gccuucuuuc auaaucauau gagugguugc uagcuaauuu 1980
uuuuguaauu aaaaaaacuu 2000

<210> SEQ ID NO 13
<211> LENGTH: 2000
<212> TYPE: RNA
<213> ORGANISM: Homo sapiens

<400> SEQUENCE: 13
aaguuuuuuu aauuacaaaa aaauuagcua gcaaccacuc auaugauuau gaaagaaggc 60
aaaaaguugc aggcagauuu auuauuaaua uaauacuuua ucaaggagca aaauuacuuc 120
ucuuuacagu caaggaaauu aaaguaaaug uagcaacaaa auuauuuuua aacaacauuc 180
aucaacauua auaagaaacu agucuaacaa acgggaacgg uuaaguugug auacauuccu 240
gugguggaau acucaacaac uauuaaaaau caugcuuuug aagacuaaua augacaaagg 300
aaaguuucau aauaaaaauu aauaaagaua cuaacuauau acaauaugau cuauguaaaa 360
uaaaauacgu aggaaauguu aauaguggcu auuucugggu ucugagauua uagauaauuu 420
uuauuuuuuc uuugcauaua guuucugugu uuuaaaaauu uuuacaauga acauauauua 480
cucuuauaau cagaaaaaua uauacauaaa auaaacuuga uucucuagca uccaauuuua 540
auaaguccac uuuaaaauga auauuaccaa aagcuuaucu uucaugaaaa aaucauaccu 600
cuaaagauga uauauuauau aguacaguau auuauuauac acuaugaccc ugugucagug 660
agguuggcaa ugccuguuau gacauugguu uaucuugccu gauacaauau ugacuuaucu 720
auaaaacagc uccaguguaa uagagagacu ucccugucug aaaaucagca agacuuauuu 780
aaggggcauu aaaggaugag accuaauuag cccuuucuag auaucacuag cauguuucag 840
cgugaaaguu caaaguaaaa cuaguucaaa gcuacuucca cagaaguagc agcaaaaaca 900
uaaaauagac cucagagauc acagaaacaa auccaguguu auucagacca gauugcuuuu 960
gaaccuauua agaauuugua aaacuaucaa cucaaagaaa uuacaguaca gcuaaagaau 1020
agaaaguagu gucacuguuc auagaaugag ugauuauuuc auccuuauuc ucuagggaaa 1080
ggucauguca uucauuccaa gaucugcuca aaaauggugu auaaucagau uaaucauaau 1140
guugcacaua auaagcacuu uuuccuccuu uccuccaccu agagccacug cgguauacug 1200
uauuucacaa uugcuuuaug cuuccugaag agcccaauau cacaggauuc auguuuguuu 1260
uuccgcagau acuuaucaaa aguuuccuau gugcaaggcc cucaacaaga ugccagugag 1320
acagaucccu cagggacaca ggguuuagac aggaccucaa aaaucauaua aaauacacau 1380
uuccauaauu ugcucuccaa guaugucauu aaccagauac auaaaauuaau acuaguauuu 1440 gauagaagca uugcuuucga aaggaacauu ccagccuagg acccucuguc gucucuccug 1500
uaucugccau cuucuuuucc auaggaaacu agauuugaca gaggggaagc cacuaggcau 1560
uauuauggca gcugagaaau gguuacuugg uacauaacuu ucuauucgaa cucuugcaau 1620
uacuacuucc agaaaaacau uaaauuuaga agugggugca gaagaaaaua uuccuaaucu 1680
ugucauucaa auuucugcac aaauguugca uugguguggu uccuauuuuu caugcuuuug 1740 uuagugguguu acagaaauua uagugccugu caguuuuuua aucacccaaa aagagaacaa 1800
auucaggcac uauucgcauu auucaauauu uuacgaucac cuaugcccau uucaaaaccu 1860
cugucauaag ccacaaaaau guuuucuaga agucaaaugu augaaauuua caguuucaca 1920
acacuuagag gugcaaaugg uuaacagcug augugucugc auaauuauuu caaaaugaau 1980
gaauagaaaa auguucagaa 2000

<210> SEQ ID NO 14
<211> LENGTH: 492
<212> TYPE: DNA
<213> ORGANISM: Homo sapiens

<400> SEQUENCE: 14
actactcgaa gaaaggcaga agaagttaca aatagttctg aacatttttc tattcattca 60
ttttgaaata attatgcaga cacatcagct gttaaccatt tgcacctcta agtgttgtga 120
aactgtaaat ttcatacatt tgacttctag aaaacatttt tgtggcttat gacagaggtt 180
ttgaaatggg cataggtgat cgtaaaatat tgaataatgc gaatagtgcc tgaatttgtt 240
ctctttttgg gtgattaaaa aactgacagg cactataatt tctgtaacac actaacaaaa 300
gcatgaaaaa taggaaccac accaatgcaa catttgtgca gaaatttgaa tgacaagatt 360
aggaatattt tcttctgcac ccacttctaa atttaatgtt tttctggaag tagtaattgc 420
aagagttcga atagaaagtt atgtaccaag taaccatttc tcagctgcca taataatgcc 480
tagtggcttc cc 492

<210> SEQ ID NO 15
<211> LENGTH: 492
<212> TYPE: RNA
<213> ORGANISM: Homo sapiens

<400> SEQUENCE: 15

-continued

```
acuacucgaa gaaaggcaga agaaguuaca aauaguucug aacauuuuuc uauucauuca     60

uuuugaaaua auuaugcaga cacaucagcu guuaaccauu ugcaccucua aguguuguga    120

aacuguaaau uucauacauu ugacuucuag aaaacauuuu uguggcuuau gacagagguu    180

uugaaauggg cauaggugau cguaaaauau ugaauaaugc gaauagugcc ugaauuuguu    240

cucuuuuugg gugauuaaaa aacugacagg cacuauaauu ucuguaacac acuaacaaaa    300

gcaugaaaaa uaggaaccac accaaugcaa cauuugugca gaaauuugaa ugacaagauu    360

aggaauauuu ucuucugcac ccacuucuaa auuuaauguu uuucuggaag uaguaauugc    420

aagaguucga auagaaaguu auguaccaag uaaccauuuc ucagcugcca uaauaaugcc    480

uaguggcuuc cc                                                        492
```

```
<210> SEQ ID NO 16
<211> LENGTH: 492
<212> TYPE: RNA
<213> ORGANISM: Homo sapiens

<400> SEQUENCE: 16

gggaagccac uaggcauuau uauggcagcu gagaaauggu uacuugguac auaacuuucu     60

auucgaacuc uugcaauuac uacuuccaga aaaacauuaa auuuagaagu gggugcagaa    120

gaaaauauuc cuaaucuugu cauucaaauu ucugcacaaa uguugcauug gugugguucc    180

uauuuuucau gcuuuuguua guguguuaca gaaauuauag ugccugucag uuuuuuaauc    240

acccaaaaag agaacaaauu caggcacuau ucgcauuauu caauauuuua cgaucaccua    300

ugcccauuuc aaaaccucug ucauaagcca caaaaauguu uucuagaagu caaauguaug    360

aaauuuacag uuucacaaca cuuagaggug caaaugguua acagcugaug ugucugcaua    420

auuauuucaa aaugaaugaa uagaaaaaug uucagaacua uuuguaacuu cuucugccuu    480

ucuucgagua gu                                                        492
```

```
<210> SEQ ID NO 17
<211> LENGTH: 787
<212> TYPE: DNA
<213> ORGANISM: Homo sapiens

<400> SEQUENCE: 17

aggtttggcc tctatcgtta tgctgcagat cagtttgagc ccaaggcatc catgaaacat     60

tacaggaaaa ttattgacag caatggtttc ccgggcccag aaactctgga aagattttgt    120

ccagaagaat tcaccgtgtg tactgagtgc agttttttttc acacccgaaa gtctttactg    180

gctttcatag cttttctatt ttttgcttct attatttctc tctcccttat attttactac    240

tcgaagaaag gcagaagaag ttacaaatag ttctgaacat tttttctattc attcattttg    300

aaataattat gcagacacat cagctgttaa ccatttgcac ctctaagtgt tgtgaaactg    360

taaatttcat acatttgact tctagaaaac atttttgtgg cttatgacag aggttttgaa    420

atgggcatag gtgatcgtaa aatattgaat aatgcgaata gtgcctgaat ttgttctctt    480

tttgggtgat taaaaaactg acaggcacta taatttctgt aacacactaa caaaagcatg    540

aaaaatagga accacaccaa tgcaacattt gtgcagaaat ttgaatgaca agattaggaa    600

tattttcttc tgcacccact tctaaattta atgtttttct ggaagtagta attgcaagag    660

ttcgaataga aagttatgta ccaagtaacc atttctcagc tgccataata atgcctagtg    720

gcttcccctc tgtcaaatct agtttcctat ggaaaagaag atggcagata caggagagac    780

gacagag                                                              787
```

<210> SEQ ID NO 18
<211> LENGTH: 787
<212> TYPE: RNA
<213> ORGANISM: Homo sapiens

<400> SEQUENCE: 18
agguuuggcc ucuaucguua ugcugcagau caguuugagc ccaaggcauc caugaaacau 60
uacaggaaaa uuauugacag caaugguuuc ccgggcccag aaacucugga aagauuuugu 120
ccagaagaau ucaccgugug uacugagugc aguuuuuuuc acacccgaaa gucuuuacug 180
gcuuucauag cuuuucuauu uuuugcuucu auuauuucuc ucucccuuau auuuuacuac 240
ucgaagaaag gcagaagaag uuacaaauag uucugaacau uuuucuauuc auucauuuug 300
aaauaauuau gcagacacau cagcuguuaa ccauuugcac cucuaagugu ugugaaacug 360
uaaauuucau acauuugacu ucuagaaaac auuuuugugg cuuaugacag agguuuugaa 420
augggcauag gugaucguaa aauauugaau aaugcgaaua gugccugaau uuguucucuu 480
uuugggugau uaaaaaacug acaggcacua uaauuucugu aacacacuaa caaaagcaug 540
aaaaauagga accacaccaa ugcaacauuu gugcagaaau uugaaugaca agauuaggaa 600
uauuuucuuc ugcacccacu ucuaaauuua auguuuuucu ggaaguagua auugcaagag 660
uucgaauaga aaguuaugua ccaaguaacc auuucucagc ugccauaaua augccuagug 720
gcuuccccuc ugucaaaucu aguuuccuau ggaaaagaag auggcagaua caggagagac 780
gacagag 787

<210> SEQ ID NO 19
<211> LENGTH: 787
<212> TYPE: RNA
<213> ORGANISM: Homo sapiens

<400> SEQUENCE: 19
cucugucguc ucuccuguau cugccaucuu cuuuuccaua ggaaacuaga uuugacagag 60
gggaagccac uaggcauuau uauggcagcu gagaaauggu uacuugguac auaacuuucu 120
auucgaacuc uugcaauuac uacuuccaga aaaacauuaa auuuagaagu gggugcagaa 180
gaaaauauuc cuaaucuugu cauucaaauu ucugcacaaa uguugcauug gugugguucc 240
uauuuuucau gcuuuuguua guguguuaca gaaauuauag ugccugucag uuuuuuaauc 300
acccaaaaag agaacaaauu caggcacuau ucgcauuauu caauauuuua cgaucaccua 360
ugcccauuuc aaaaccucug ucauaagcca caaaaauguu uucuagaagu caaauguaug 420
aaauuuacag uuucacaaca cuuagaggug caaaugguua acagcugaug ugucugcaua 480
auuauuucaa aaugaaugaa uagaaaaaug uucagaacua uuuguaacuu cuucugccuu 540
ucuucgagua guaaaauaua agggagagag aaauaauaga agcaaaaaau agaaaagcua 600
ugaaagccag uaaagacuuu cgggugugaa aaaaacugca cucaguacac acggugaauu 660
cuucuggaca aaaucuuucc agaguuucug ggcccgggaa accauugcug ucaauaauuu 720
uccuguaaug uuucauggau gccuugggcu caaacugauc ugcagcauaa cgauagaggc 780
caaaccu 787

<210> SEQ ID NO 20
<211> LENGTH: 47745
<212> TYPE: DNA
<213> ORGANISM: Homo sapiens -continued

<400> SEQUENCE: 20

```
atgcccgcca gcgccccgcc gcgccgcccg cggccgccgc cgccgtcgct gtcgctgctg     60
ctggtgctgc tgggcctggg cggccgccgc ctgcgtgcgg agccgggcga cggcgcgcag    120
acctgggccc gtttctcgcg gcctcctgcc cccgaggccg cgggcctctt ccagggcacc    180
ttccccgacg gcttcctctg ggccgtgggc agcgccgcct accagaccga gggcggctgg    240
cagcagcacg gcaagggtgc gtccatctgg gatacgttca cccaccaccc cctggcaccc    300
ccgggagact cccggaacgc cagtctgccg ttgggcgccc cgtcgccgct gcagcccgcc    360
accggggacg tagccagcga cagctacaac aacgtcttcc gcgacacgga ggcgctgcgc    420
gagctcgggg tcactcacta ccgcttctcc atctcgtggg cgcgagtgct ccccaatggc    480
agcgcgggcg tccccaaccg cgaggggctg cgctactacc ggcgcctgct ggagcggctg    540
cgggagctgg gcgtgcagcc cgtggtcacc ctgtaccact gggacctgcc ccagcgcctg    600
caggacgcct acggcggctg ggccaaccgc gccctggccg accacttcag ggattacgcg    660
gagctctgct tccgccactt cggcggtcag gtcaagtact ggatcaccat cgacaacccc    720
tacgtggtgg cctggcacgg ctacgccacc gggcgcctgg cccccggcat ccggggcagc    780
ccgcggctcg ggtacctggt ggcgcacaac ctcctcctgg tgagtgcgag ggccaggcg     840
gagggccacg caggggagac agagggcctc cacaggggcc agggggaagt gtgggaactg    900
agtctccccc agacgaggct tcacttggac acgtgtatgt ggtcaccggg ggaaactgag    960
cagttctgac ttcccttgga aggcgtggaa ttaggagaga aatcccttag tgggcacacg   1020
agtgagtgcc ccttggagtc catctgtgga aaggaagcgg tgataggttt ccgcagtgag   1080
gaaagaaact cctttctctg ggtgtagagg aattcctaga ggtgagggcg gggaggattt   1140
gctaggagta actgcaggaa gagaatgagc agggtggatg aaagaaacac gtttgttctt   1200
aagccgcaca gatagcatta ctctctggag ctgtcacgag ttcagtgtta atccaataag   1260
atctgtcttg cttgtggcac aagttcacac tgttgtgaaa gtgtcaaaac acaactcccg   1320
gagagtcaga tttaaactgt gtttggaggt cccttctgcg gcagggcagg gaactgcatc   1380
caccaatctt attcaccggg gtgtgaagac cgctttatac aatctcaaac aaagctagtc   1440
atagaaacac agaaacaact gcagggtgat atagattgtt ctaccacatc tatatttcca   1500
cagtgctctc tacagttgaa agggttcctc acttatgaca ttgttagcct gataaaatta   1560
attgtaacac ccttgtgcaa aatattttat taattttgac agcaggaaat attgctatgc   1620
catggtaaag ttgtctcaag tatttcttcc tcctttttc tccttagtgt tcaaatttag    1680
gcaccattgt tttggggatt catttataat catgtcagtt gttagtacac tttgtacaga   1740
gttttgtatc acaataaaat attttatgta catgtataaa cattttaata aaagtgttta   1800
aatgtacaac ttttggtacc caattctgat cacttgtggg cctactggaa gacttatttt   1860
taaatttaga attcagccac atattctgaa caaagtcagt actaaaacca tttctaaaca   1920
cttttaatta aagccataga taatatgggc agagcagtac tgggttattg aggtgactta   1980
gtgctctgag ctgctggtaa tgttgtaata atggctaaat tagattttat gtcagttcca   2040
caaaacctgt ttgctgctac tggccataaa agaatgttgg atttgtttgg aaacacattg   2100
tgatttttgt gatttcatac ttatgtatgt cttttcataa ggatgtttta gagcggtgat   2160
tcttatactt tttcaatcct tttatggatc tgaaaaactc taaagaccac cagtgtatgg   2220
ctggtgatag aaaaactatg ggaagaatgg tctcactttt tgaagaaaac ataagcaagt   2280
tatcagttca tactggaagc aaataaatgg atcagctgga ggatctaata gatcatgccc   2340
```

-continued ataaaatctt tactttagat ttaaatccta caagttctat ttttagagtc cctaggataa 2400
acttgcatat acaaagtagt caattgttat tatagtgact tataggatca ttttattata 2460
agataaagac ttgcgtgctc tctggtgctc tggtgtttta aataatcaac atgttttaga 2520
tctttttgcc cactcatggc cctctgatta acttctcagt tatatttttc aatgcttaca 2580
caaaaaattt gccaaacact aaccatcctt cctagaaatg cagtggactt tgtatttagg 2640
gaaattagta acaggtgaat gctccatttg ctgatgttgc aaacaaactg ttagttggtg 2700
taaagtatta attttgcttt cacatttctt ttggtttggt gtttagtcat tcttgtatct 2760
tatttagaag cgagttccca ttgtcaaaga aagtatcttg aattaatttt gttgtatgag 2820
atactttcat tctgttttca atgacctttc tcggtgtgta tataggggtt gggggaagcg 2880
agaatagaaa aatttgagct tacctgaaaa agataaaaca ttctgcagat tttgataaaa 2940
gggcatttta gctggggctt agatattgct gctgtacaga tataggggcc agttgtgttc 3000
cgggatctga tgttggtgaa ggataaagac tggctagcac ccttccctca ctccctctgt 3060
gtttccacta acttacaaat gggctaagga gatcccctgg gatgatggga agcttgaccc 3120
ctcctagaga gtcaagaatc attgatggcc tggaggacag gaggcagaac aaacaaacag 3180
caggacaaat aatggaggcc ctgctcagaa tggaggtctt ggtgttcttt gtgggttcct 3240
catactggag tgagccttgg caaaaatggt gtgtgtgtgt gtgtgtgtgt gtgagagaga 3300
gagagagaga gagagaggag acagaagaga aggagaagag gggagagggg aggagggaca 3360
gagagagaga ggtctcctac aaagagcttg gagctcaggc tgctttgctc atttgagtgt 3420
aatccaggag gatgcacctt ttctctcgga cttgaagacc aactgctcag ccttcacagc 3480
tcttgaaaca aagttcttaa tgtcccctga aatcagcact agggactgta gttggggagt 3540
tcagccccag cagtgcctct gagtctttgt tctgtatatg ggttctaaga ggattagaat 3600
caagttggaa atacacgtgt tcccatttcc caccttcaac tcccctcacc gcctgagatt 3660
cttgcaaaca tttgtgcaag gaacctgtga aaaagacttc tttcacgtaa ggaagtaggg 3720
ctaggagata ttaatctggg cattgttgag cattagcatc agtgtgcagg tctcagccca 3780
tctgtctgca atgtttgttg aagccatcac ttcttgtccc ttgaatcctt cctcaacttg 3840
gatttcaggc cctggctctc ccttgcttct cctctcagct ccctggcgat tccctcttag 3900
tctcctttgc ttgttcctcc tcaccttgcc tgtaaatagt ggagggctca gggctctgtc 3960
tagattcact ccaggccatt gctttgaata ctgctgcatc ccgatgactg gagattttga 4020
gtctccaccc aggtttcccc gagcatcaga ctggcataga caaccgcctt ctccacgtgg 4080
atgtctaatg ggcatgtcac atcgaacaca tcccaaacca aacccctgct tccccttctc 4140
tattatgatg actttttact cttccagttg ttggaccccg aatcttaact actccccttt 4200
ttcatgtctt gtttctaatc catcaacaaa tcctgcagct ctacctacct ccaggatgtg 4260
tccagaatca aaccacttct ccccttatct atgactacga tggaggtgca agacaccatc 4320
caaccttgcc tgggtaatgg gaacagcctc actgctgggg ttcttatttc tgccttgccc 4380
cctgcagtgt gccatgatgg atgctctaca gggtgacatt atgtgtggac aagacagagt 4440
ccttgctttt tcaaatccca cctgttcttc tggagccagc taacacgctc ccttgggccc 4500
catgcctgaa tgccatctct tccttctatg gcatcctgca caggacttcg ctttgctcag 4560
atgcctcctc ccgcgctctt ccctttattt aaccatttgt ctccatttta ccccttcgct 4620
atctggggta atcctgttcc cttcatctgt atctctgaaa atggcatctt gccctccctt 4680

-continued ggtgctcaga aggtggcttc tggtttaccg aatagcctga tttcaccttt ataaactcat 4740
gctactagaa ttttctctcc ttgtcagtct ttctagccac tttccaatgg aacagagact 4800
accaaatcct aatctgataa ggaaaaatag gtaaacataa cgtggcagac tctgacatct 4860
gcagtgaaaa tttaaggttc atcatcaaat gtatgattcc attgtgaaaa tgtccagtta 4920
aaagctatct gtagtcacca tgcagcatta tgaagaagtt ttcagaataa gggcaggtgg 4980
taaagtctcc tggccagctt taggagtata tattggaagg ggctttgtta gctgattgaa 5040
tttttattcc ccaagtaatt agtatgagcg atttgtctac tgtatatatg ctcaaattac 5100
atatactatg cacttttgag aaatacttta caagtttttc tttcattaaa atgtatttgg 5160
ggccgggcgc agtggctcac acctgtaatc ccagcacttt gggaggctga ggcgggtgga 5220
tcacctgaga tcaggagttt gagaacagcc tggccaacat ggtgaaaccc cgtctctact 5280
aaaaatatgg aaaattcacc agacgtggtg gcaggtgcct gtaatcccag ctacttggga 5340
ggctgaggca ggagaatcgt ttgaacatgg gaggcagagg ttgtagtgag ctgagatcgc 5400
accattgcac tccatcctga gcaacaagag cgaaactcca tctcaaaaaa atgtattttg 5460
tacataacta gaataatcaa ctggattgaa agttaatata aattttagaa tactactgaa 5520
ttcaatagtg catttagtca gaaatagtta aaatatctcc caaacagctt gaatcactcc 5580
tttttgaaca cattgttttt tgaaggttac agtcaagtcc aagaaaaaat tttaaaatag 5640
gaaaagaatt aatcaaatca tttcaaaatc atagcagtgt tttaacaatg ccaattattt 5700
tgagttgaag aaaagaagga aaatgtaaac tatgcattca agtaatgtca atgcaccttc 5760
tcaggtgcaa aatgaatgaa caattaactg tgccagctga atatgtagca atcacggctt 5820
ttgcacatag aagccttctg aattatctta tattctcaaa aatatcattg ctctaaacta 5880
gaattttatt ataattaatt tgtgcaaaag ttgtctttct ttcaatgaat gttgtctttt 5940
tgaggcataa aggaaatttt aggtggagga ggagaataga atacatgctt actgggagga 6000
caagtaataa taggtgagta aaaacacaca gcttattgaa ttgtctcaga tccacatttt 6060
ctccagaaat gcaaagttat acttgaaatc tatatttaaa cagataagca gaatgtgact 6120
tttatatgct ctattttgat gtattctgag tatgaagata acctgaagga tgcctttttc 6180
ccctctttat cttggggtaa actcttactt acccttcaga gacttgactc aaatattttc 6240
attctgcaat aaccacaggt agaatggatc atttactcag ttgtggctct cttaagagca 6300
cagactacct atcatattta tttcaaaatt tgtagtgctt atctcagtgc ttggcacaga 6360
ggaaagaaat acaattttta ataaaggcat aagtggagag gtaaaataca tatttctggt 6420
ttcaacgtgt ccatattctt tcttgtaaat ggaatattgc gcttgcagtc tgctctcaca 6480
caatatctgg gaaggagttt taaagagtga ggaagaacag taaagatttt cctaggcaga 6540
tacgttatgt gacctttgtt gatttccaga gcacataata tcccaatttc atccagtgga 6600
caggaaaaga gaggaagagg gaaaaggtgg cctctcaagt gcctgacctg gaagctgcac 6660
ctatcactgt cccttgggca gaactcagtc acatggtcaa aaggagtctg caaataattg 6720
tcccctgagg agccgggtgc tcagtgaatg attctattaa gttgaaatca gatgggaaca 6780
gatcatttag gataaccagc aggctctacc acattgccta actcccaggc atattgtgag 6840
aattaaaagc accttatata tgtcaacgtg ttttgaaaaa atacaaaaag ctctacaaaa 6900
gtgagctata aatttatcat taataataat agtaataata gcaaaatact tgagaaatgg 6960
tcctcttgag ctgtttagaa ggaatcatac aaatgcatta gacatggtag cctcacttaa 7020
ctacttaatt tgcctcttct ttgaaattat ttcaatagca tttgaccaaa aactatcaaa 7080

```
tcatttttga aataacgtat ttttacataa aacacattat caaatatctt tctggatcca   7140
gcttggtggt aaaaagatac atactaaagt ttatgactga tataacttta tatattgact   7200
aaaccaaaga taaatattga ttgaactttt gtggccccag tttcaataga ttttttttatt   7260
aacatttttt gtttgaagta cagatgtcac gtcatccatg aaccggtatc attatagctt   7320
gataaaatac tcaaactgaa agcagtgatg tacattaatt ttaaatataa tggttaagca   7380
aatgttattt ccatatctat aagtgcattt tatttgataa ttagaatgtt agaatcagaa   7440
ggaatttgga aaatcccagg ttacacttct ctccaggacg aactccttac agtggctctc   7500
ctggggtcag ctagcttttg cttgaccctt tgaagcagga ggaactcagt tccactcaag   7560
ttgcccccctt gattttctct ttcatattga acctgctgct gcacaggact cctccgtgac   7620
tgtctctttg ccttcctaaa tctcaaagaa taaagcaagt cactttttga caagacatct   7680
ttcacatatt tgaaaagaca tctttcacat atttgaaaag accagtacgt tttgttcttc   7740
ctagaatttt ctccttcatg ctaatgtctg ctccaagaag acatggaggt gactggacat   7800
ttagtcagga acatttcttg agagcttacc ctgtggcagg caggtgcaat gttgaattct   7860
gagaatatga atgtaacctt tgaacaggtg gctctgtctt ctgacgtttc aggataaggt   7920
ggaggagagg agaggggaaa gtcgacctat ctccccagcg gggagggttt agggttgtct   7980
gtgggacctg cctctgtctc atcatccatc accattgtcc tgctgatggg tgcagaggac   8040
tgaggacgag tggttggagt tctccctgtg ccggaccctg tagagagtcc agagccctgg   8100
ctcccaaagg aggcatattt gtagggctct tttcgtgagg gtccagagga cggctgcaaa   8160
gctgcagggg aggatggggg catgggaggc aagcccgttg ccctgtcaga gcctcttggg   8220
gatgctgctc ttccccgcct gtcctctctt ctctttgatt tctcatcatg tggtcctctt   8280
tcctctgcct tttcctctct tcggtgtccc aagttcttcc atagagacct gtgtcccctt   8340
gttcccatca ggcctttatg ccagccctgc acaggtgcgg ggacagtggt aggggcgtct   8400
cactcccgac tcaactacat tctcccagaa attgtctgca gtcaaacaca actcagcgtg   8460
gacattgctc accaaaggta tactgcttgg gctgcacgag agattcagtt ttctcctatc   8520
tatctggcat gggctgtgag gggctcctta acctaggggg ccttttttact ccttcctggc   8580
cagagctgcc atttccaagt ttctgcactg tcagaaaaga gggataaggt aagattcctg   8640
ccctcatgtc acagattagt aggggagagg taattgtcaa ataattacag taaaatgtat   8700
aaatgcctta agagaaataa gtacttgctt aggaacctat ttcaagaaag gagagatagg   8760
ttagcgtttt ggggaggtag tacgggagca gtcagggaaa gcaatacttg taagatcaga   8820
ggctggcaat ctttttctgt agagggctaa gttttggact ttgcagatcc tacagtgtct   8880
gttgcaacta ttacacagtt ctgtggttgc agcatgaatg cagccatggg caatgtgtta   8940
atgaatgggc acagctgtgt ttcaataaaa ctttatttac aaaaataggt agtgggccct   9000
gctgctgggc ttggcttgct gggcacacaa agtgagaagg gcattgtgcc tttctaggaa   9060
acatcccttg caaagtcagt acaggtgaga cagtgtggcc attcccacca cagcatgagg   9120
tcttttgaat ggctgaagcg tcaggtggga aaggatgagg agctgaagaa gaaagcctgg   9180
gaatttccaa ggcctctctt aacatttgct gtgcagaacc aagcagtgcc ccaggtgttc   9240
agagtaggct tcagcgatta catttcttgt tagacactga attttgttca tgccgcccaa   9300
gattgcatta acaattttgg ctgtcacctt accgcggact caaattagtt tgcagtcagc   9360
taaaacctct caggtttttt ccccccagct tgtgaattgc tgtgaagcca aacatccctg   9420
```

-continued

```
tcatctcttt ggtagtttat tttcaaactt tcaatcttat taaatttcat ctccaatgtg   9480
caaagataag aggaagttta ccgctgatgg tggtttattc tttaaaactg gacatcagct   9540
aaatgtgtta aggtaatccg ttagaggaat gttggtacgc ttatacagtg gaatactaat   9600
tggttattaa aatgttgatg tatgattatt aaaaggcagc ccatgttatg tctcttctgt   9660
atgaataagt atgtaaaaag tatgtaaaga ttactgtata gttcatgggt gggactgggc   9720
tctctctagc ctctgtcctt cattctccct gccagtgcct tttcccttgc agtgtccctt   9780
ccctggctgc atactcaaga ctggatttgc ccagccaaac cccattaact cacagaagca   9840
agaggaaaaa aataaattct tattagttca attctccaaa ttgggggcgg tctatttcac   9900
agcaataggt aactgacgta aaaggaaagg aaacaatgaa gtaattccag aaaatttcct   9960
atagctggag gacatgcatt ttcatattga atgggaagaa tggggtgggg gggtcatacc  10020
tctgtgttat tgcagggtcc tggctcctag ggacctaggc acctcttcag tcagtgaatt  10080
atagcttgga aaattggcta agtcggggaa ctgtacaagg ggtcatcact ttttatgtag  10140
ccatgctcta tgaaccatct ttataactcc ctggcttctg gcagttaagc accactcact  10200
atctggcctc tgtaatttca acttctgacc atccccgtgg gtggcaacaa gcccagctct  10260
gtgacacctc tgctaccagc agccctggcc tggagagcgg tgcccccact gaatgtctca  10320
gtgagattgg cacccccatg agcatattcc tgagggtgca gtgaatgctc tttctcccta  10380
cttgggactt ctgggaaaca ctgtcctctg gtgggttgtt tgacctcaca taatatactg  10440
gttcttgcat gccagcttct ctctgcttct tgattctttt atcagctgtt agggcaacaa  10500
tgtcaggcat ttccgcctgc tcagcattgg gcatcccttt ttacaggctt ctcagagcca  10560
ccctagcagc aactttaccg cgtctcctgg ggtccttgct ggatcgtgaa aacatacttc  10620
cggagaaagt gttccctaga taatgaatta tttcttgtcc tgtgttaagt tccagttcct  10680
tggtcaagga ccccagcgct actcctcagg atttgcagtg catgctcaat cttgaagcaa  10740
tgttgggata tagtatcttt tcttctctat caggcccagc tgtctccagg tgggttatac  10800
taggatttaa tcctcgttag tgccgggtca gctcctgagg ggtgcacctg ttgcttttta  10860
gggacgaggc ctcttcagca taaagaagtg ctatctctta ctagggaaga atgggccacc  10920
tctgtaagct ccaaatattc ccaggtttcc ccaaccgggg ccttgacctt ggcataactg  10980
atctgccttg gctgagcatt taaacatccc taaatctctg caagtctatc aggtcctagg  11040
cctgctgcta agtttctcta ctcttccact gtaggagaga aggctgtggc tcttatattg  11100
agcctttaac tgtttgttat tggccctcag tttctcatta gctctctgta gagtctcaat  11160
acaatatatc agaaagcatt caattccatc tccttgtagg cagggaatgc ctaaatcatt  11220
gcacctacaa tgacattctc caccaggata tttcccaggt tactgctgtt gaaatattta  11280
gcaattgaag caccatttgt gcaaggggac tatctgcccc tacacaacac tcagaatggc  11340
attctctttg ctttccagaa agtgaatgag ctggttcccc aacccctctt gtgttagttt  11400
gagtcctgaa agaagtaaat gtcaagatag gattagatgt acaagaaatt tattggggaa  11460
agaattgtga aggataaagg ggaaggagct aggggaggca ttgaaccttt ggatcatgat  11520
gtgtgtccaa caactatgaa ggagagtggg cagggagaag gatgggctgg gaagagtttc  11580
agttggcact gtgggtctca gaacaaccca ggcataggct gatggggacg ccttgagcca  11640
atgttgccca ttggcggagt ccacatcttg ctgaaatggg cctgcattag ttcccctgcc  11700
atgtttagtc atctgggagt agccgatgag aatcatgatc ttaggatcaa ctgcaatggc  11760
agattcaaag ggtagcaacc tgatggcctc agtcaactgt gctccttata gcaggaacac  11820
```

-continued

```
tgagcagtgc atttcttggc catcacaaag actagtgagg agtgcccttc agagaaggga  11880
atgaaaatta tttccagcct agaatttgat acttatctaa actgtcaatc attcatgaga  11940
gtcaaagtcc caaaaaataa atcttccata aaccctttct caggaagtta ttggagggta  12000
accgccacat aacatgagga agacaaggag gaagacatgg gatctatgaa agggcaggtc  12060
taacccagga aaaggatgat gaactgtaga cccatgatgt cagatgtgca gcagactaag  12120
atcagccagt gcagaatggg ggagattcca gaagtgtgtc cccccaaaat attggaggct  12180
catgtgactt ccctggggaa gtttctgctg agaggctatt ggaaattgag ggaagaatta  12240
gccacagtcc caaagaaaac agagccaatc aaaaagcaat gcaattatga acttcaaaga  12300
aaacaaaaat aagaaggaaa acagtcttac ttactacatt acaaggtcca gctgtgaatg  12360
atattcatgt tggcagaata atgtcaatac caaatgtcgg ttaaacccaa aactattgta  12420
taactaaatt gcctgtgtaa gagagctaaa cccttatcta gcataatagg aagtcagtgg  12480
atacttcctg aagtgtggat gtgtggagat gtaaattcca aaagaaaacg tcttaagagt  12540
caaaagtggt tgcctctaga gagaactggg ggaattgtag ggcaatgtag gacagggaac  12600
tgtgattttt cttgtaagtt gttctgacat tttaaaccat gaacatatat tacttgtatt  12660
tttaatttta aaaagacata aatatttttt ctatcacttt aaatattaat tttgctagtt  12720
atagcacata tttatagcat tacactctgt agagctcttt tggattcaag ttttggagaa  12780
ttttcaaagt tttagattaa tgcctttgtg agttttcatc cctttgatga taacaagtta  12840
caaagaaata gggttatgaa taaaccttgt gggatattgt tagtcacctt ctctcaagtc  12900
gatctgtccc atgaatcaat gtttcaaaca ttgaccagca tttgatactt aataagcaac  12960
gagtaagttt ttgttgaacc aatgaatact cttaaaatat attttttcaa gtggcaacag  13020
tactatctta tttgcactct acttttcttt ttgaccctaa gaatgtcaca aaaatgttta  13080
gcaactgtca agattattac atacagagat gactattgtg ttctcagata tgctgtatgt  13140
cttagttcat tttgtacagc tataagagta gctgagacta ggttatttat ttatttattt  13200
atttattttt tgagacggag tcttgctgtg ttgcccaggc tggagtgcag tggcacaatc  13260
tcggctcact ccaagctccg cctcccaggt tcacgccatt ctcctgcctc agcctcccga  13320
gtagctggga ctacaggcac ctgccgccat gcctggctaa tttttgtat ttttagtaga  13380
gacggggttt caccgtgtta gtcgggatgg tctcgatctc ctgaccttgt gatccactca  13440
cctcggcctc ccaaagtgct gggattacag gcgtgagcca ccgcgcctgg ccctattttt  13500
ttttttttta aaggaattta tttcctcaca gttctgttgg ctgggaagtc caagggcaag  13560
tctctggcat ctggtgagag acttcttgct gctttctccc atggtggaag gtgagagggc  13620
aagagagaga caaaaggagg ctgaactcat ccttttacaa ggaacccatg cctgagatat  13680
tgaacccact tctatgataa cagcattaat tcattgatga ggacagagac ctcattgcct  13740
aattggccta aagtgagacc tcttaaaggt ctcgcttaat actattacaa tggcaattaa  13800
atttcaacat gagttttgga ggggcaagca ttcaaatcat agcaccatat aatacaataa  13860
aaattttctg agctaagttt ggtaaattta ttctaggaat ccatgttgtc tcctagttat  13920
cttcccttcc atagtactga tgcatttttg ttaaccatta cctaattttg cttgagtcta  13980
ttatttctga aattcacatt atcttccctt ttaaagttga gaaaattttc attcttcaag  14040
cgccttattt tctataatct ctcaaagtaa ctgatggctg ttgcatgatc ataagtgcaa  14100
attattttgc tagaccacac ttggagatga tgaatttgga atggcatgca gactcccgac  14160
```

-continued atcaggagtc ttgtctcctg caataatcag gaacccaggc ttaaaaggga gcaggtacaa 14220
cagaagggca aggggtgaca atgctggtga aagacatttg aggaaagcta tcaacatgaa 14280
acagaataaa ataaacagaa aagcaaacca gggaaaataa attatgcagg aattaaacac 14340
atacacaaac tgaaacagga accatcagaa catataaaaa attcttgaac atcagtaaca 14400
caatagttga aacaaaatat ttagtaaaat atttgaaaag taaggtcaaa gcaatgctgt 14460
aaaagtagta caagatgata aagaaataga acacattttt gaaagggaaa aagatttaaa 14520
ggatattcat aaagatccaa catcagacta atagaagttc tggaaagaga gaataaggaa 14580
atacaggtca ggaaatttgt aaagaaataa tataataaaa tgccccagaa ctgaagaaca 14640
tgagctttta actttaaaga gccgactgag ttcctagctc aatgaatgta tagacatgta 14700
agggtattga aagttcacct tcagtgtcat gtttcctaag aagctaatgg aagatatgca 14760
ccagcaaaat tgtagtaaat acataggaag aaatagtata tagaaaaagt atggtttcaa 14820
tccataagaa ataaaggaaa ctcccaggac gagagcagct cttgacagca tctagtccaa 14880
actggacttg gaggctggaa acttctagca gggaaggaag agctctgggt gaaaaagtag 14940
actcaacaga atagatacga tcatagaaaa catgatagag aatcactaac acattgaaaa 15000
aatcacatat agaatattct gcacgcttaa taatgaggtc attatttatt caagggaaaa 15060
ttaaaagctg tttagaaaag ggaaatgtta tagtgcccta tttggctcta aaatgaacat 15120
ttatatagga atcttcatgt aaatactaac aatgatttaa ataagaacag acatttcgga 15180
aaataaggga agaaaatggg gcatgtaaaa gagctaactc ctcattatcc taatgaatta 15240
ttaaatttca caatagcata gtatttagaa atatgatagt tattacgaga agaaagagct 15300
aaaaggttgc cagtggggag caggagtgag ggttagagac gggattgggg gagatgctta 15360
ctgttttcat gataagcctt tggtactatt tgattttaaa ctatataaat gcatttatta 15420
atttaaagta atttaaaaaa cccataccac tggataatgc ttgataattt ctagagtcct 15480 tttttttgt attttggggc aggtaaattc attgagagac ccagagagtt tagctgactt 15540
tcctgtgggt accaagggtc agagctgggg tcaaaactca ggttttctga acccctattc 15600
ccagtgtaca ttccatgact ccaggctgcc tcccgcattg cacaggttac atctaggggt 15660
gtgctagcaa atgcctagac catcctcgtc cacatcagca tctgaaatgg acaagaatgt 15720
tagtcatgac ttgccactaa cgtctttaac cttaattgac atctgagagt gtcatcatta 15780
catcattaca aaaacactaa cccagataca tctgttccca ttactatttc tgcgtaattc 15840
ccccagactt aattgcttta aataaccatt ttatttggtt tacaaactta tgggtcagga 15900
ttaggggagg gctcacccac gcagtttttc tctggtccgc agtcatctga agcttgaacg 15960
gggtggggca tgcaagacgg ctcacacatg tgatccgcgg ttgagcctgg ctgtggacca 16020
gagcatctct gttggcctcg cttacacaag tggtctcaga ttagtagcct ctgtacatgg 16080
aaactagctt ccctcccggc aagcatccca agagaactag gaggaagtgg tatggacttc 16140
ttttcttctt cttcttcttc ttttcactta ttcttgatat catgtagctt catttctatc 16200
agagcagtca catgcccaca gattcaaggg ggagggtcca cagatccgcc aatgggagga 16260
acagccaggt tatatcgtaa aagatcatgg ggcatgggag atacccatct attttctgta 16320
aaaaatacat tttgccacag catcactggc tttccagctc acagtgatct gcctggaatg 16380
cctttttccg tctctccagg atctacatct ttcaatataa ggtttagaaa ctacctccta 16440
caggaagact tccttgattt ccctcagcaa gaaagaatct ttccttcctc tgaatcgcca 16500
ttgcattaaa aaaaaaatcc atcttctggc gttttcactt tcagacttat actgtaatta 16560

-continued

```
ttctatgtac ctatgtttga cccctcacga tgcccagcat aataatttgt ctattgagta  16620
aatatttgct taatgaaata atcattacat gataactcaa atagcagtcc tgaaaaagtg  16680
catttcaatt cagatctctc ttttttcttc cttcacaatt ctcatttccg aaaaatgaaa  16740
gaagccagag gatcctttat gaggagttac agtataactt atgcgtggct gtttcctgtg  16800
tttactgcta ctcagtgaga aatacgggag atgggagagt gaaaaaccat gtcatttaca  16860
atttgattaa aaagcttttt atcttttcct ttcacgttta agccttgccg ttttaaaaat  16920
ttccctttcg tcacagggga tcaagcagca gttaacgctg cagttccctg ttctggaaac  16980
actctcaaag gtgtttcaac acattttgtc tcaactctga ctcctgcccc gctgccccac  17040
gccatccagc cacactgaag gtcttgcatt tgtgccttgg ggcattattt tttttactc  17100
ttctccctgc ctggaaggtt cttcccaacc tgccctaccg ccatagccac agaaccaacc  17160
cttcactttc cttaagtcta tggtcacaag ctccttctca aaggaggcac acctctaacc  17220
acccccattt ggtgacttcc tgtctcctgg aggcccccgg aactagtctt ctctacttcc  17280
agcaacccac tttacgagca gcggagaaga ctgactactt ctgggggcct cgaggagaca  17340
ggaagtcacc aaatttacag gtgctgtgga tgaaactgtg tgataatgaa tttattgggc  17400
ttgttttttt agcttctgaa tagaagaacc aataagatca tttttttaaa aaagataaaa  17460
acagacaaac acaaaccctc tagtataaaa gcattttttt ttaaaaaaga tgaacacaca  17520
ccctcagatt gccttctttt gaaaaggcaa tctgagattc cttatgaaat ccccagacag  17580
aagctgtttc tttgaattta atatgctgta cactgtagag ccaagaggct tatagagtgt  17640
taattaacac cccttgtcaa acatttgtaa atgaatctgg ctaaagctca aggaaaccag  17700
gtttttctgt gtgataaaat ataatctttg gagattattt atgatcacaa agggagactg  17760
tacagaaaat tttcctagac ttggaaatga ggcaggatta ttggtgtcca tctggactga  17820
ggcctcaggc aggcctgcct agttaatccc attctcctat cctcattctc tgggggtgaa  17880
gaaggcagtg cacctttgtt caatttgctg cttaccatgg attagggcat tttaaattct  17940
gtaagggtag tttttaactt gtagaaaact gatagcgatg ggaaggattc ttgcctaata  18000
gggacacaaa cggattttgt tctgtagaga tgtaaatgaa aagatgaaaa tcacaacaca  18060
tttaatgaaa ggaaaataaa gactcttgtg agtgccacca aaaaaaaaaa taaataaaat  18120
gtatctcctc tccgtggcac cccaggcctt ccttacctca ctctatttct tcatagcact  18180
tattgcctta gaacattctt tataatttac atttattatg tttgttgttg gttgtcgctc  18240
ctcctgctaa aatggaatct ccgtgagggc acgggttttt ctttgatttg ttccctgttg  18300
tgccccaaag tgctagaatc atgccaggca cacaatagat gctcaataaa tacttctgga  18360
atgaaaatcc ccctccactt agaccagtga gttccaaact tttttgatct tgacccatag  18420
taagaaaggc attttccatg ttgaatatac accattgaaa caaaattttc acagaaaaaa  18480
cttaccatta ttacaggcag tgcactgtga tatttcctaa tctcttctat tttgattttc  18540
aaaattgctg aggctactca taggttgatt tcacaagtgg agtttgtgtt atgaaaaact  18600
ttgacttaac accatgtcga aactgctacc acaaaaaggc aaatgcgaaa gaagggggaa  18660
agagcaggcc gatgactttc cgctatccac cactccataa agcatatttc attttcctgt  18720
aattgtatcc tgttcaatga tgtagaaatc ctcacacact cacatgccac tttttctttg  18780
ggtgaaaagc gttctctact gcaagatgaa ttgagttatt tcaaaagcaa agagctataa  18840
atgagcctgt taaagaaagt ctcaaggaga gtctgttggc atctgctgtt gataacttaa  18900
```

-continued agcaggagaa ttagataagg aggcagaagt agaatgttta gaaaataaaa gtgaccatta 18960
tagaggaaaa actgcttgtc tcagttttgt tgatattgga gagtagctct ttcatgaggg 19020
tattgtggaa ttattggcaa ttatactaat agatgtttac tgaaaaaatc ctatttgact 19080
gatgaaccat ggaatacttt tgctgacctt gtggaaaaca tcacttatct gagttcctta 19140
tcttcttgtc tctttttct catctagcct atgcctccct acctgttccc tcatggttct 19200
cattttgttg ctattagaaa aacagagata caaaaaccag gaattggaac ccctctgtgt 19260
ctccagtaat aattctgtga ttaatgggtt agatggattc tggtcacaag ctggatattt 19320
tgttaacaac ctagcgtcaa tgacttggaa tgattttcac cgcagcatga tttagtattg 19380
aatagaatga tttaactaat gttaattagt tctgtacaga taaattaatg aagcaagaag 19440
ctcaatctct gatttattga tgtatttacc cagtgtaagt tatgaaatct tttttatttc 19500
atttgaagga agtttttatt taaatacaaa taaataagcc ctttattgtc acctactttg 19560
gaaaagtcca gataaaacaa tcttaagtaa caaaactcca aaattacaac atgattttca 19620
aaaactaccc tgacctttgt cttgcctggt tgttacagtg tacttttaac taaacggatt 19680
cttatagaat ctcaagtttg gttatatttg tattaaggaa ctctatattt gcatttgacc 19740
agccctaact aaaacaagct taaggaagaa aagggacttt acgacaagga caaaggattg 19800
aagaagaact ccagggactt tagatgttaa caactgtatt tgtcactaaa gtaaccatta 19860
ctgtcaaggt gggttctcct tctccctcac taaacacatg cacacacacc acacacacat 19920
acacatacca catacatacc acacacatgc acacacacca cacacacacc acaccacaca 19980
cacagaaata cacacagaca tacacacatg cacttatgct tgggtcagtt tggcttttat 20040
catcccagag agtctcttcc catgtcagca actccagatt cacttcctct cctaatatag 20100
gacagtcaca tgtctctatt ccagcaaaac aatctcaggg aaggtatctc attggcctgg 20160
cttgggtcat tcaacttgaa gtacaagaag agaaaacagt attcttttat ttttatagat 20220
ttcctgtaaa atcagtggat aatggtaaaa atttcatgac agcaggtgtt ttaccttatt 20280
tatgtttact atctctagaa cccagtatga tagttcataa taaatgctta ctaaaacaat 20340
tatcaaactg tacacttaaa aattaaaaga gtaaatttta agttgtgtat gttttaccac 20400
agtaaaacaa aataaaataa acctattatt gatcttattg tctatttctc aaaagtagca 20460
tacgtcataa tttcatgtga tttctaaagg agatctaatc tcaaacttag ttcttagagt 20520
aaaataaaag gttttggcaa tcatatacag cagtagactt taccttgaag atttaacaaa 20580
ggtttgaaag caaaatgcta tgatactgaa tatactaatg tttgagggct tgtgaaaagg 20640
tcttaatata ggaatcatat atcttctttt agattgtgtc ttggggaaca ttgggggtca 20700
gtttttctat cagtgttagt atgtagtaag taatggcata catctaagct tgagattttg 20760
ctcatttctg tattcttagc acttatatat ccaacatata ataggtgttg gataatattt 20820
gttgaataaa tgactaaata aatgtcttgg catgagaatt atgccatcta caaaaccgtc 20880
acttttaaaa aaaacaacaa agatttttga acctgtagat ccagccagaa agcaagaaat 20940
atcttcacct ttccagactg acttattttt tggtctagct gtgtactatg catgagctgt 21000
caactttaat actttatttt ttaatgccta ggtctagtga gttacaatgt gatgtagact 21060
gattgaatta aaggccccaa tgttgtcctc tcttcattgt atccatgcct tttgtcatgt 21120
aactttgcag tgtcctctac tctaggtgtc cattcagctt atcctttgac tctggccttc 21180
ttctcctttg actctggctt tatccatgtg acttacttta gccaacaatc ataatgctgg 21240
caaacactga gaaaatgctt attagtgtct gcttagtctc ttgcttctct gcaattgcca 21300

-continued

```
tgagaaaatg cccaagctag tacactggag gatgagacat gtggggcaga agcaacctgt  21360
cccatttgtc ccagccaaca ccatcctaga ttaaccagat gagaccagag cagaagacat  21420
gttcagtgga gcccaaccca gctcacgaat aatatttctt catgagcatg tgagcaatgt  21480
gtaactaatg caccatgctc tttttattct gcacttccaa acatctctca gattgccctg  21540
ttgttttgct tttcagtagt catcaccttt gtccagaacc ttaattgtat ctgcattttg  21600
gcagtatcct gccaatttc cacatccagc tgttcacatt ctaatgcatt ctgcaatgga  21660
tgattttgag catatgactg atcatcactg tctcagaaat ttatgctaat ctattgtgac  21720
ctattctgtc aaatccaaat aactttacat tcaaaacttt tcatattctg gccccatact  21780
gtctattgta atcttatttt ctaaaagcca caaactatta atcctgtagc ctaattaggt  21840
tgatatcatc attttcacaa cacgttgggt aaattcttat atctgttcct ttaatcatag  21900
tttccatgct tagacactcc attgccctcc ctaagcacca gccagagtcc actatggggg  21960
gatattttaa aggctctttt cccctaaccc atctgcccca gaggtggcac aggctagaaa  22020
agatagtcca attatttggc ttaattattt ggatcttaca gtttttttgg gagagttcca  22080
gatgatttga tgaaatgcaa catggtcaaa aacattttgg tggagaataa tttaatcaac  22140
tagaccattt ggtgaaaaat aaatcccagt tactagactt cccagtatta ataattttgg  22200
tatgccagga atttttaaaa catttctaac aaattttttc agaaatcaga atgactgaaa  22260
ggtataacaa taggaaatta ggaaatcaat aagtaatcat tgaaaagtga gtgattgaat  22320
tagttggaac aatctatgcc atccatcctg tgggggaaaa aatgaaaaca gctaaacaag  22380
cagagcagac atcatcaact tagaaaaaca atatagtaaa taatttgaac tagaaaattt  22440
tccaaaattg aaaattccag ttttaaaaaa tttgtgtttt cttattcaaa aagcaataca  22500
tatttcgtta cataaaagtc agaaaatcag agaagcagaa gaacataata aatgcccact  22560
gtcctactca atagagacta taactgctat ctctgtacaa atcctttaaa atcctgtctt  22620
atgtgtattt attttacatc tgtacatatg attccaaaat taggtaatac tgtacgtggt  22680
ctatctatag ctaactatag tttgtaattt aataagctat atttgtccat ggtgatcatt  22740
tattgctcat aaaattaata aattataatt tatttatcaa cactgatcat ttgttgctaa  22800
taatttattt catttaatgt cttattcctg ggttatttta actaatccct attgttagcc  22860
ctttaggttg tttcaactaa tttaagaatt ataaatggcc catagtagtt acttaataaa  22920
tatttgagtg aaaggataaa tgaatgaata attccacatt attggatgtt caagttgttt  22980
ccattcaact ttattgttgt gggggagtat aatacaatct tggtgaagag ccaccaactt  23040
aggaagaact atgaagaagc atgttattta ctcctgcttg tgggtggggt gcattgggaa  23100
aggaatgcct aaatgcacgt ggggagccaa acaagacttc acaggggaga tgggaattga  23160
gccaaatttg gaagaagtga gaattttcag ttgataattg gggaagatag tactaagagt  23220
aagtggggtt cattaggaac tacttcttag aagaggcaag tccagaacag aaggcagaaa  23280
gggatatgga tatgaaggaa aagtagaatg caacttcagg gctagtaggt tggcatccaa  23340
cgtaggtaca gccctggatg aggagtaatg agaaactgac ctggctgtag caaaacagct  23400
aggctgggaa gtgatgctgt ttacatttat atgcgattct actggtcttc ctgttacttt  23460
gtagaagact gtaaggcttg gtgctcagag ctagaaatgc aacttatttg atttgctaag  23520
aagtccaaag caggtagggg tgccaagctg ctgcctgttc acacatattc gtctaactgg  23580
gtgtcaggga aagcagatat gagccccctt gcattggtta aatcctgagc aacttttaag  23640
```

gaactgcaca cagagactac tggctatttt ttgtggataa agttgtagat agttattttt 23700
gggaaattat ttatgtgttc tattaggtgg ttgttttgtg ggaggctgtt tgaaattctg 23760
tcttaaggaa ctgcagctta taaaccatag tgctgataga aataagagaa ataatttggt 23820
ctgcgagcac aaacatcagg ctagttggca tgcttatgta aacaccacac agtagcagtg 23880
acttttaagg aagtcctcag acaatgtaat cccaatactc ttcttgaagt tgaggtaata 23940
gggtgccaga aagaaaaaga aaataaatct ctagtgcctt ctaaaatttt ttcaatcctt 24000
tgaccttttt gaaaacggtc acctttaatt cagaactaaa gtaacatctg gagggccctt 24060
ttcttagata gggagaagac ataaatgagc tatttgaatt attttctgct tatgggctgc 24120
atttcatttc ttccaccatt ggtctcagtc catttaatta agattatttg taggattaaa 24180
ttaatccttt aagaattatt ccatttcaat ttttaaaaaa tctaatgaat gatagataac 24240
aaaaagcggt ccattcagta ttacccctga aacatatttg ggtgattggt gataccatcc 24300
atgtctctcc aacttcagct tcatatactc agctgagtac caggcatctt cattgaaagc 24360
tagacttgtg acctaaatag aacttgatcc cttcccttcc ccaactcctt attttttgtt 24420
ttctttgagt tccttgattc ctcttcccct cctcacatgc aacatgtaac atccaattca 24480
tcagcaggtt ctacagattc tgccttcaat aatagcctaa atctagccac ttgttactat 24540
ctttttggt ccaaaccatc atgatctttt gcctggacca ttgcaatagt tgtctaactg 24600
gtatccttgc tcccatttg tcctcctaga tcctattttc cacgtagtag ccactgattt 24660
ttggaaactt atcaatcatt acccagacac aatgagtaca tttacatagt tgtttgattc 24720
catttacata aagtcccaca atcactctat gtactgggaa tcacaacagt ggtctcctat 24780
gttgagaatt gattaagagt cacaaggaaa caaggagtaa tattccattg tattaacaga 24840
ccacactgtt catacattct cctgtaaatg gacatttatg ttgttttcag tttttttgct 24900
attgtgatta aagctattag gttggtgcca aagtaattgc agtttttgcc attacttttt 24960
aaatggcaaa aactgcaatt actttggcac caacctaata ctgtaagtat ctttgaactt 25020
accaatcaaa cattactaca acacttgaat aagaaacact tccatagcat ttacaattct 25080
aagtgctttc catgtattga cttagttaat cctcacaagg atataaccat gaggtgctat 25140
tactatccct actttacaga tgaggaaata gaggcacaga cttcagataa tttgcccaag 25200
gtcccacagc taataagggg gcagaattag gaaagcctgg ctgagtctat gctctcatca 25260
cttgctcaac tctgcctgga atgcccttcc cgtaccctct accgcctctg cccaatcctc 25320
cgggttctct gctccttcca cacaccccca tctcaggtcc cagtcttttt tagcattctt 25380
cactttttct gttacagatc ctcagacaat gcttccttga agaagacttg cctgtctaaa 25440
ctgccttccc atcccaatcc ctgttacctt ctatcctttc tctgctttgt tttcatttgt 25500
tatctctctt cttcccaaga atgtaagctc cataagaaca ggatcatatt ttgaatcccc 25560
tagaaaagtg cctagtgtaa tatttgttga atgaatatga tccctgcaat taaaagctaa 25620
atatatatat ttttttaact aacagattac tgtagtagtt tcaaagatga atttatgttt 25680
cggagaaaat cagtattctc ttgccacata aattgtaggt aattatattt ctatacctga 25740
atagctttgc caatgactaa gatattaatc tattatatat ttattaatct atagatcttt 25800
aaaattgatg cacatgtttt ataagcaatt tgatgaattt tgatgactac atacacctgt 25860
atgtgtatgg atatctgtaa caaatatcca agtaaagata tagaatattc tcattacccc 25920
agaaagtttc tttgtgactt ctaatcaatt ctcacctccg taggaaaccg ctgttgtgat 25980
tcccatcacc acagactgat tttgggactt tatgtaaatg gaatcaaaca actctgtgaa 26040

-continued tgtactctgt gtctgagttc tttcaatcta cacaatcttt ttgacattaa tccatattac 26100
tgcctagaag agtagttcac tctttgcatt aatgaatagt attccattgt ataaacaaac 26160
cacactgttt atacattctc ctgtgaatgg acatttgtgt tgttttcagt tttctgctat 26220
tgcgatttaa gctactataa gcattttttt ttaattgtga tggggtttcg ctcttgttcc 26280
ccaggctgga gtgcagtggc agcgatctca gctcactgca gcttctgcca cgtgggtcca 26340
agcgattctc ctgcctcagc ctcccgagta cctgggatta caggcatgtg ccaccacacc 26400
tggctaagtt tcgtattttc agtagagacg gggtttcacc atgttggtca ggctggtctc 26460
gaagtcctga cctcaggtga tccacccacc tcggcctccc aaagtgctgg gattacagtc 26520
ttgagccact gtgcccggcc agcatctttg aacatatcaa tttgtaagtt ttatcttaat 26580
attgtacaag tcttttgggg ggcttatgtt gtcatttctc ttggtaaata cctaggtatg 26640
aacttgctag attatagaga aaatctatct ttaattttat aagaaactgt caaatagttt 26700
tccaaagtgg tggtactatt tatactccca ccatcaatgt atgaaatttc cgttgtttta 26760
cgtccttgcc agaatttgtt ggtagtcttt tttttttttt gaggcagcat ctcactgtgt 26820
tgcccaggca tacaatggtg tgatctcggc tcactgcaac ctctgcctcc caggttcaag 26880
ggattttcat gcctcagcat cccaagcagc tgggactaca gaggcgtgcc accacaccca 26940
gctaattttt gtatttttag tagagatggg gtttcaccat gttgcccaag ttggtctcga 27000
actcctggct tcaagtgatt cgcccgcctc agcctcccaa attgctggga ttataggcgt 27060
gagtcactgt acccagcctg ttgccagtat ttttagttgt aggcatctta gtgggtgtga 27120
gtgctcgttg ggttttaat ttgcattttc ctgatagtgt tgatgttgag gacatttcta 27180
tgtgtttact gagcattggt gaagattctc ttgtgaaata tctattcaaa tattttgctc 27240
atggtgggaa ggggagttat ttttctttta ctactgatag gtaggcttac gtatttattt 27300
cggatataat tattttgtca attatatact aatcataaac aaaaactgat aaattggacg 27360
acgtcaaaat taaaacctgc tcatcaaatg ttagcgaaat gtaaaggcaa atcacatact 27420
gaggggagat attttaatat atgtatattt atatagtgct ttctgtgttc taagaagtat 27480
tttcctactc caagataaag agactattct cttacatttt gttctataag ttttatagtt 27540
ttagctttta gctttggatc tatgatctgt ctcaaatttt tatgcaagat tggggtttaa 27600
ttttttcata cacttttcca gttgtcaagg atcatttgtt gaaacgtctt tcctgttgcc 27660
acataattgc tttgatgcat tcgttagaaa tcagttggct gtgggtttat tttggaattt 27720
tctgttctgc tcctttgatg tatttgtcta tccttatgcc aatatcaccc tatattaaat 27780
aattatagct ttataataag tcttgaaatc aggtaatgtg aatgtttcaa ctgtgttttt 27840
ccttttteta gttattttag ctgttttatg ttcttattgt atatatttta gaatcaactt 27900
attcatttct acaaaaagtt tattgggatt ctggatgaga tggtgttgat tcagtaggtc 27960
aatctgggga aatctgataa caatattgac tcttccaatc catgaaaatg gtatctcatt 28020
ctttatttac atattcttta atttctgtta gcaatgtgtt ataattgtag caaacttgca 28080
catcttttgt taaattattt tctaagtatt ttacgatttt ggtaccactg taagtggcat 28140
tgtatttaaa atttattttc tgtttgtttt ctgttcatat ataaatgcaa ttgattttct 28200
ttttttttt ttttttttt tttttttgag acagaggctt actttgtcac ccaggctgga 28260
gtgcagtggc gtgatcagca ctcactgcag acttgaactc ctgggctgaa gggagcctct 28320
cacctcagcc tcccaagtag ctgggactat gggtgtgagc cagtgttcct ggccaaatgc 28380

-continued

```
agctgatttt tgtattgaca ttgtattctg ccaacttgct aaattaactt attcgtttta  28440
atagttttc tgtttttta aaaatcttag gatttctaca cagacaatca tgtttttaat  28500
gaacaacaaa gtttgtttt ttgtttgttt gttttccct tttcaatcaa catgcctttt  28560
atgtttttat ttgccttact gcactggcta ggacctccag tacaatttta atagcaatgg  28620
tgagagtgtt taaatgtact cctgtgtata ttttattctt ttggaactta ttataaatgg  28680
aattgttttc ttaattttct ttttggactg ttcattgcta ttgtacagaa atacaactga  28740
ctattgtgtg ttgatcttgt accttgcaat tttgctgaaa tcgtttattt tttgcaatag  28800
atttttgtga attctttagg attttccata tgtagaatca tgttatctgt gaatagggat  28860
agttttactt cttttctaac ttggatagtt ttttccttcc taattgctct ggcaagaact  28920
tctagtacaa tgttagagag caatagtgaa agcaggcatc ttcctttcaa tcctgatgtt  28980
aggggtgaag ctctcagcct ttcactgtaa tgttggctgt ggattttcat aattttttgt  29040
ttgtttgttt ttttgtttga gacggagttt ctcttgttgc ctgggctgga gtgcagtggc  29100
gtgatctcgg ctcatcacaa cctctgcctc ctgggttcaa gcgattctcc tgcctcagcc  29160
tccagagtag ctgggattac aggtgcctgc caccacaccg actaattttg tatttttagt  29220
agagacgggg tttctcgatg ttggtcaggc tgctctcgaa ctcctgacct cagatgatcc  29280
gcccgcctcg gcctcccaaa gtgctgggat tacaggcatg agccaccacg cccggcccat  29340
aaatgctttt cttaatcata ttaaggaagt tcctttctag tcgtagtttt ctgagtgttt  29400
ttattatgaa agactttcag atttttgtaa aatgcttttc ctgcgttaat tgagataatc  29460
atatgggttt tctcccccttt tactctattg atgtaatgca ttacaacgat tttttttaat  29520
gtttacccat ctttgcattc ctggaataaa tactagttga ttgtgctgta taattcttaa  29580
aatatgctgc tggatttgtt ttgttagtat ttggttgcat tcttttgcat ctatattcat  29640
aagggatatt gatctgtaac tattattttc ttgtggtggc tttatctggc tttggtatca  29700
agataatgct ggccacattg gctaagttag aaagtgttct ttcttctatt ttttgaagag  29760
cttgaaaaga gtcgtgttaa ttcttcttta aatatttggt acaattcact attaaagcca  29820
ctagtcctgg gcttttctta gtttgaaagt ttttgattac taattcaatc tcttttacac  29880
ctagattaga ttttgtattt tttccttagc cacttttggt aatgtgtgtg cttccgggaa  29940
tttggccagg tcatctctgt tatctaattt gctggcatcc aaatgttcat aatgttctct  30000
tgtaatcctt tttattatag aaatgatata cagaaaaggt cagttaccac tttcttttat  30060
gattgcatta atttgcttct tttctctttt tttctctagt cagtcttgct aaaggttggt  30120
ctgttttgtt gattttttc aaagaaccaa cttttgattt tgttgattct ataattttc  30180
tgctctgtat tttgtgtata tccattctaa ttttattag ttcctttatt ctgttagctg  30240
tgagtttagt tggctcttct tttttatttt cttaaggtgg aagactaagt tattgagata  30300
tatcttgttt ttttttttga tgtaggtatt taaagctata aaatttcctc tgagcattgc  30360
ttttgctgca atttataagt attggtatgt tacatattca gttagttttt tatatacaca  30420
tttaagcttt tgctaatcta ccttgtgatt tcttcattga cttattgctt gtttgagtgt  30480
gtcaacaatt tccacgtatt tgtgaatatt ctagttttcc ttttgttatt gatttctagt  30540
ttcatttcat tgtggtaaga aacaatactt tttatgatct caacagttta aaatttatta  30600
agacttattt tctggtctaa catatgatct atcctggaaa atgtatcatg tgcacttgag  30660
aaaaatgtat attctgattt ttttaggtgg gtggcatgtt ctattaatat atatgtctgt  30720
tagctctagg tgaattatag tgatgttcaa agcctccatt ttgttattaa tataaccatg  30780
```

-continued

```
ccagattttt aatgctgtcc atttgcataa tatgtctctt tccattcttt ttcttttaca  30840
tgatcacttt atatttatag tatatttctt gcacacagaa tgtaattgaa acttactttt  30900
ctaaaatcta ctttcttttt tttttttttg agatggagtc ttgctctgtt gcccaggctg  30960
gagtgcagtg gcacaatctt ggctcactgc aatctctgct tcccgggttc aagcaattct  31020
cctgtctcag cctcccgagt agctgggatt acaggcacct gtatttttag tagagacggg  31080
gtttcaccat gttggtcagg ctggtcttga actcctgacc tcgtgatcca cctgccttgg  31140
cctcccaaag tgctgggatt acaggcgtga gccactgcac ccagccccta aaatctgctt  31200
tcatagcatc tgtcttgtac ttggaacatt tagtccatgt gtatttgaat atttattgat  31260
atgtttgggt ttatgtttac aatcctgcta tttgttttct ttttgttcca tgtgtttttt  31320
gtttttttatt tctgcatctt ttggaaaaat cagatttttt ggtaattcat ttttcttatt  31380
ttattggctt tttagagaaa ccttttaata tctttgtgag ttttagggat tacattattt  31440
attcttatta ttattccatt tagaattaat attgttaatc ccattcaaaa atttgtttat  31500
ttcgcttttc agttctagaa ttttcatgtt ttcttcagtt gttgtttctc tgttgttatt  31560
ctccatttgt tcattatatc tatcttttct ttgaaatcct taaaaatatt tataatagct  31620
attttaaagt cctctgctaa tcccaatgtc tgggacatct tggcttctgt tgatattgaa  31680
tacttctttt tttcccctta attaagggtt tcattttcct gctttttcac atatctagta  31740
gatttttatt atgctctgtg tgctatgaat gagatattat aggaagcctg gtcaatattg  31800
tctcttttta aagggtgttg tatttagttc tgccaagaag ttaaattacc agatttactt  31860
gatgtggctt tagtctttgt tagagctggt ctattcctgc tttgttctta cttctcaggt  31920
aatgaccttc ctgagtttca gctggatgcc tgaagtgctc agctgcattt ttctactctg  31980
gctattctga aatgcaatat tttccagacc tacccaacct ttggtattca tctcccagac  32040
ctgtggctgc ttctctttgc tgagcctcac aaaatcttgt cctgtgcatg gacagccaag  32100
gatccttggg aaatctcatg cagacttcta ggtccttcct ttgtgtagat ttcttctctc  32160
cagtacgttg acctgcttca gagtcctcat cattgctttc ttccttttca gctcagcaat  32220
actgctgtgt attgtgtggg cttcatttgc ctcagccata cctagaacac aacccaaggc  32280
agaaagctgg agtggacctg aggctcatca cctgtttcct tccacccacc atttaaaagc  32340
agcttatttg tgtgaaactt tttgttgggt tctgtggggg atacgtatag gcaaatgaca  32400
gggagcttat aatttagcca aagagaaaat gtctatatgt tctgtggaat tcagagtatt  32460
ttcctcgact tccaaaatta ttttcctcga cttccaaaat ttggggctac tagctagttg  32520
gtaggaagga attccagatc cattttttctt ctagattttt ttcagactcc atgtttcaaa  32580
atctagatgg aaggtaagaa ggaagcaagg agggcatcac atacgagaga gacttatacc  32640
ccaaagtgga tcattagcac attatgagat aatatggtat tattctcaga ggcctgccat  32700
ataaaattcc ttctaattta ttttttaatg gtatgtgcct gaaagttttc tgtctttcat  32760
gatcttgaaa gcaaaataag aaccagagta gcttatgaga gagttttcct gcttcagccc  32820
agaaaaatgt tgcttctgtc ctagaccctt tgatctggtt cttagtgcca gccttcattc  32880
ctctagatct gtttattgaa tactggctct gttgcagaga ctttgctaga atctgagaga  32940
taaaagactc aatgccttca aaacacctac aatccagaca cttaaataaa tgcaataata  33000
tatggttaag gtcttggata gaggaccatc atagaaacac atagaacaga catttagtcc  33060
atgctaggga gagggaagat gtcaaggaat gcttcctgga ggtggcgaca tctaagctga  33120
```

-continued

```
gttttaaagt gggtgtaaga gtgaaggaac tgggaatagg caaaacatac cttagagagc  33180
tgcacctcca aagcatggaa ggctagataa tcttagaact tcaagtgggg ttcaatgtgc  33240
ctgggacttg gatttcaggc agagaccata gggcaagttg gagaacaggt gggcagggtg  33300
agatgaagca gagactttta ataaccatca aacaggcctg ccatccaact gctatcagcc  33360
attttccctt tttgaatttt attttttaa tctctagagc aatacatgtt tatggtagga  33420
aatgaaaaaa atatatagat gggtaaaatg aagtgaatta taccacccac aatcctgctg  33480
taaaacaggt tttaacaagt tataaatccc tccagatcaa agtgctacta aactctactt  33540
gctattttat aaccttttc tgttcagagt attttagaaa cgtttttaca tgttaattga  33600
tattcttttg cattatcctg aataatggta tttctttagt tatactatca tgtattaaaa  33660
cattcataca tggtaaacat atttgaatat tagacatttc aattgttttc aatgtttggc  33720
tattaaaaat agtatttaga tgaatgttct tggccataca gttaataact tcactgagtc  33780
cttgtcaata actttattaa atcccaatct taagacaaca agcctataag attaacatac  33840
caggaataat tagaaagcat tgcaagacta tatgtaacca tctccctgtt aatcatcctt  33900
atttgttgca acatcctaaa tagcgacctt cccacactct gcctcataat atttaatctg  33960
tcaaatgtac catccgcaaa gggagtgaac tggctcgtga agaggtggtg aagctggttc  34020
aactcagttt aacagacaat gagggcctcc gtgtgccagg gagggagtga gggaactcca  34080
cagggagctc attctgggga gggatgcccc tcattatctg cagtaaatga tattagagaa  34140
gtatgtgtga gactcttggt gtccagagga ggggcatgca gcacagtatg gggggtccatg  34200
gggttgcagc gatttcttag agacggtgcc atgcctggga tgaccaccaa gttaggatgc  34260
tgtaaagagt aatcaaataa gtttcaacag ggttttggca tgaggtgagc agttaatcca  34320
aatgatatct gaaatgcttt ctaatgctgc aagtgtattc ctctgtaaaa taatcaacta  34380
cttaaaagac actctcactt gcattatgtc atttaatcct cacagtgtcc ctacgggaca  34440
atagatgtca ttcccacttg tacagagcag taagtgaggc tcacaccggt catagttaga  34500
ggagtaggga atctaaacct aagtctcttc tactccaaac cccaagtttt atcagtatgt  34560
cacatcgcta ctgtgggctg aattccttag caggggttgt ttcctccacc tgcaatattc  34620
ttccttttgg tttgttcatc ctctagagag agaagggata cgcattcatg gagatcctac  34680
tgttgcaaac tctgcattag gagttttaca tgaattgtct catttagtcc tcacaacagt  34740
cctgtgaggc acaggaaagt tagatttacc tgcccaaatt aaggaatgtg gccaactcaa  34800
gagtgacgaa ggccaggtgc ggtggctcat gcctgtaatc tcagcacttt gggaggctga  34860
ggtgggaggc tgaggatcgc ttgagcccag gagtttaaga ccagccaggg caacacagca  34920
agatttaatc tctactagaa ataaaaaaga aattagccag gtgcctgtag tcccagttac  34980
ttgggaggtt gaagtgggac gattgcttga gcctgggagg tagaggctgc agtgagccat  35040
gatcccatca cttcactcca gtcagggtga cagagtgaga cccagtctta aaacaaaaca  35100
aaacaaaaaa gagtgatgga gcaggaactt tatctgccat cagagaccat atatgtcttt  35160
ccttatggcc caggtcattt atcatgtcct tgctaaacct cctcctctga gccttgttaa  35220
agtcctcaag gttagaagag tggtctataa ttataaaaaa ttccattgta tgacttcagc  35280
tacctgcaaa actgaccgag attaatgcat tctttgtttg ctttcactct ttcattccct  35340
gttcagcgct tattctacag aaaggtgcct ggtagattta ggacatgact gttcataggc  35400
ctcaaatgcg gtcaaattag gaaagtcccc tggtttttgg tctcaagagg ttaattgctg  35460
agtactagcc tggactgctc aatggatttt atgtttaact gttgtgttta tttgtttgtt  35520
```

-continued

```
tgtttttgtt ttgtgagaca tatctttctc tgtcacctgg gctggaggtc agtggtgtga  35580
acatggctca ccgaagcctc catctcctgg gctcaagtga tcctcctgcc tcagccttcc  35640
tagtagctgg gactacaggc acacagcacc atgactggtt aagttttgga ttttttggta  35700
gaaatggggt ctcactcttt gcgcaggcta gttgtgaact cctggtatca agggattctc  35760
ccaatgtgct gggatttcgg cctcccaaag tgctgggact gcaggcatga gccatcatgc  35820
ccagcctctg tttaactgtt aacatcatga ggtttccttt caatgaggaa gggaggcctg  35880
gggaggtgtg atggggaaga tggagaaggg taggagacat cataaaactg acagaagtgt  35940
ggcacgatta agaccctggt ttcttagacc acataagcaa gtgccactat tcttttgatc  36000
aacatttgat tctctatttc cttcttagca tatagatagc tgcttcaggt cgtgaaaaaa  36060
tacatttagt gaaatgaaac atagtagata tgttcaccaa gaaactaaaa agaaaagtta  36120
gccacaaact atcttatttc attgaaatgt ttggctgaac ccataagaat gttgatgagg  36180
ccattcttgg atgcctgtac tgaaatgaac cacgagagga atatttagga tatgttgaag  36240
aggctgtttg gcttaatgaa caaaggagtt tctgcaggcc cagggagtgg aatgaaaatt  36300
ggcatgatca ttttggagaa tatatggagt caaacagaga atttgaatgg agttttcaaa  36360
gaggatatgt taggggaata aaggctgata aacaacactt gtatttgtag gaaaataggg  36420
agagtaaatc aaggaattca aagagaaaga gaaactcact tcaagtaggg gagaaaaaac  36480
ccctataatt ttcactcttc cttgtaaata aaaaggaaac aaatgaaaat aagatattag  36540
aagtcagtaa gaatttatgg gagtataaag ttggttttat ggatgcaaag cccttttcac  36600
tgctgtacga aactcctggc tgcatgctaa caatggacaa ctgatttcct tgcagctgta  36660
ttttgctgtt ttttgctctt ggcttggacc tagcaccctg ggtctgtggg aaaccagaac  36720
tgtcccagag ttctggaggg taggccaagg ttagatgctg gagtgggttc tttaatttat  36780
tgtactgatt cttcttggga agaaagaaga ttgcttgtta gaattttagc tacgagagat  36840
gactatgaaa cagtaaatta actccaacga cctgagtcat tttgaaaact cccagtctca  36900
ggataaaaaa tataatccta tttagaaatt cctggtgtga tcacagatgt agcattggtt  36960
cttttcatga aacccgtaaa ttaaaaagta cataatccaa agtcaattaa atagtaagct  37020
attataacaa attcttttat ttcattagct tttcaaaatg tggataacta cacactcaac  37080
ccaaggaatc tacatttttc cactgactgc taaagaccaa tggaaataac tctagtcccc  37140
gtagcacctc actgtggggt gacctacctt tgaaataatg tattggttct agctgatttt  37200
tatattgtta gtcattaagt taggcttgat gagaaacaga tataatctga tttggggatt  37260
caagtattat attgcatttc tcctcacaac tagagataaa tttgccatgg tttttctctt  37320
cataggctca tgccaaagtc tggcatctct acaatacttc tttccgtccc actcagggag  37380
gtcaggtgtc cattgcccta agctctcact ggatcaatcc tcgaagaatg accgaccaca  37440
gcatcaaaga atgtcaaaaa tctctggact ttgtactagg ttggtttgcc aaacccgtat  37500
ttattgatgg tgactatccc gagagcatga agaataacct ttcatctatt ctgcctgatt  37560
ttactgaatc tgagaaaaag ttcatcaaag gaactgctga ctttttttgct ctttgctttg  37620
gacccacctt gagttttcaa cttttggacc ctcacatgaa gttccgccaa ttggaatctc  37680
ccaacctgag gcaactgctt tcctggattg accttgaatt taaccatcct caaatattta  37740
ttgtggaaaa tggctggttt gtctcaggga ccaccaagag agatgatgcc aaatatatgt  37800
attacctcaa aaagttcatc atggaaacct taaaaggtat gattgtgggt aaagttctca  37860
```

-continued

```
tttcctgcca aaatcttctg gaaaaaaatc tctaagatta tctaacataa atgatgtgaa  37920
tttatatttt taaatcctaa tggagacatt cattttggca atagtagaat gcattcattt  37980
aacacctttc tcatttggag tcttgaggaa cttgaattaa tttttaaaaa cccatttgta  38040
aatgagaaac tgggttataa tatttgtaat tacttaactt tcagttatta atctagattt  38100
ttagattaaa ttgaacataa aacaaatccc aggatatcta gctctctgca catgtttttc  38160
agttcttgtt attttggttg aataaaacac tttaaagaaa aaggaatgtc catgttttct  38220
agagaaaata gtataaatag atcatgcttt taaagccttc atttatttat ttattgcatc  38280
agacacaaag ctgggtgtct aggatggaaa gtggtacaag acatctttcc agccctgtag  38340
aatatctatt ataaataagg aactattttt tcaaggtgct cagaaatcca aaaaacatat  38400
tagataggcc aattttgagg gcatttattt gtagagttat ataggtttga ttagagtctt  38460
tcgtcaagaa gaaaaatcat tggcttacca aacgagaagc attacacttt atttatttaa  38520
gtaggaaacg ctcagctgct cttgaaccat gatgcaagtg cccagcgaag ggtcatgttg  38580
ctcttgtccc ctcttccctt tgcagccatc aagctggatg gggtggatgt catcgggtat  38640
accgcatggt ccctcatgga tggtttcgag tggcacagag gttacagcat caggcgtgga  38700
ctcttctatg ttgactttct aagccaggac aagatgttgt tgccaaagtc ttcagccttg  38760
ttctaccaaa agctgataga gaaaaatggc ttccctcctt tacctgaaaa tcagccccta  38820
gaagggacat ttccctgtga ctttgcttgg ggagttgttg acaactacat tcaagtaagt  38880
cagctgacaa aaccaatcag cagtctcacc aagccctatc actagtaagt agtgcttcct  38940
tcctaggctg attgtcatgg cacattgtcc gttctttgag ccaaaaacaa ttccttatga  39000
gtacactaag ggcacaattt ggaatgctgc acccttctct ccaaaactct tccaatcttc  39060
atcttgttta agttagatcc aaagataaat aaatttaaag catatcaata tttaagatcc  39120
gattaagaca gtaaaaagat aaaacactct cttttcatac tgtggttttt gatccttttt  39180
aaggcagttg agtttttttca tgaacaggat ctaacacaga actccaaagc ctctgagttt  39240
cagtggtgct gctgagactg aggcaggaac attaggcaga gtcctccaga ggcacaactg  39300
tgggctccac aaatgtgcag aaataccccta agaaagtaaa ccctagatcc aatgattcac  39360
tggtcagaat gtcttttttta gcaatagtca ttgaaatgat acgaaatttc ttcagaatga  39420
tcaaccaata tttattgagc atcttctcag tagtaagccc ttaacattct ttcagacttc  39480
ctaaattttg aaggggcttg ttttccagca tttgactgga tactctagta agcacttatt  39540
ggatgtctag tgtgtccgaa gccttgtgtt agttgctcgg gtcgcttggt taaggggagt  39600
gcaggtagag ggtatactga gatgagtaag ggtaaccttt gctttcaaag gagcaaagga  39660
gtctactgag cgaaaacaat gtatgcacaa atgatgcaat ggagtgaagc gggcatggtg  39720
gtaagtaaca agggcggggc tgggggattg ctgctgatag agtcccaagt gtgaaaatag  39780
ccctcaagac agagacagag ttcagtgtcc atagacaagc agttggcttt gacatgttgg  39840
gttatggtag ccaattaatt ggttctgcaa atcacagctt gaaaggaaac acttggaaga  39900
atgtgaaatg ggttgctgtt ttcttgtaaa tatccaattg aaatctttta tttataagga  39960
aataaattaa caccatcctt agtacatttt ttgctggttg ggattattct tctttttcag  40020
accacccagt tcattttaca ggcagtctca gacttaaacc ctcgccttcc atttaaaaga  40080
tgactggctc acgcctgtaa tcccagcact ttgggaggcc gaggcgggcg gatcatgagg  40140
tcaggagatc aagaccatcc tgaataacac ggtgaaaccc cgtctctact aaaaatacaa  40200
aaaaaaaaaa aaaaattatc cgggtgtggt ggcgggcacc tgtagtccca gctactctgg  40260
```

-continued

```
aggctggggc aggagaatgg catgaaccca ggaggcggag cttgcagtga gccgagattg  40320
cgccactgca ctccagcctg ggtgacagag caagagtccg tctcttaaaa aaaaaaatga  40380
ctggatgtgt catcttttat gccaggatat gtgagcccag gagaaaggct tctgagctcc  40440
ctcctgctcg gtgtgcaatt ttctgccctg ccccgactct ctccttctct cccagcctcc  40500
tgctatttga aatctcctta tcctaatttc cctcctcaga gtggattcca ctgtggggtt  40560
cagagaggat ctgaggtggg agaagtgagg ctggtgagga agaaggggag gagaaaggga  40620
agaagacctc cgtagccttc cttcctcctc ctctttactg ggttggggga tagatcggat  40680
ggtccctggt ccttgttcta tctcttgacc ttctgcctgc tccctgctga gcacggatct  40740
ctgatagcag cctgagtctg gcaggttcag tcctttgtat gcggcacaat ctcccagcca  40800
gcattgctgt gcagatcatg ggaacgaatg cagaacaaga gtgggggtgt cggagggagc  40860
cctacttctc ctgttctatt cctcatcagg gggctgtgcg ctggctttgg gaattggtaa  40920
atagtgagaa agtcttaagg gtacatccta tttccttgag ggagaagaga aaacgctggt  40980
cagaagcaat aagtatagca gtgaatagca agggagatgg gagataattc cttttcctac  41040
tacactctag aagctattgt tttagaatct gacctaaggt cagccactaa ttggccccag  41100
aggtctctct ctcagatcac acggtccttt tttcctcatc agcttgggga ccccacccct  41160
cctcctggca gtctcctcct gtgcagaacc caacaaacac aaaattaagt cactctcaaa  41220
cccacagcag atgagagctt ctctggaagc tccctggtgg ggaaaggctg caattgctat  41280
tttcttcttc tggttttcac ctcaggcttt gtgttatatt gacagtaccc ttctcaagct  41340
aactccctaa ctgacctgac gtagtcaaaa taagttcttt gtatgtcagt tctgaggtgt  41400
gtgtgttttc acttacaaac agtactctac agctttaaga cattatatta aagtcctgag  41460
aagtgatttt taaaccactg aacttcatct tttccctcct ggctagtatt tcagactttc  41520
agtgtttgag gcatgcattt cacctgaaca acttgaaaaa taatatccta agaagcacac  41580
aacctgactt taggctcatt cacatggatt gtcactttac ttggacccac tttctcggct  41640
gagaggtttg ttttcccata accacggatg ctcatagtta atataaatat tgaactcact  41700
atgtagtgag gacatagagc ctctttaaca ttggtccctg ttaggagaaa gtttctccca  41760
taacatacta aatacatgtt ttaatagccg ttccttctga aaggtccaac ttcactattt  41820
tatttttta gtaaaatctt agttaacaaa ttaatggagg ttaggtggaa ttttgcccca  41880
aaagtcctgt attttctttt ttttttttc ttttttttg acagagtctt gctctgtcgc  41940
ccaggctgga gtgcagtggc gtgatctcgg ctcactgcaa gctccgcctc ctaaggtcac  42000
gccattctcc tgcctcagcc tcctgagtag ctggggctac aggtgcccgc caccgcaccc  42060
ggctaatttt ttgtattttt agtagagacc gggtttcact gtgttagcca ggatggtctc  42120
aatctcctga cctcgggatc cacccacctc ggcctcccaa agtgctggga ttacaggcgt  42180
gagccaccat gcccggcctg tcctgtattt tcaagaaact tttttttcc tccagaaatg  42240
ataccctagt ctttcatatt tgttttcaga tggactgaat aaaagctgtt gttttggaac  42300
aatcacggtt aaaaaaaaaa gttatgaatt tagtcaactc agagctctat aaaaataatc  42360
caaaaaattc cttcaaactc tgaacgcttc aaaagagcgt gcaaatattc tgtccttcaa  42420
agctaaggaa acatgatttg tggggtgcat cacagtggaa aaatactctg acagcattcc  42480
cacagcatta ggggaagtgc atgtgtgggt gttctgcaag ggacaattct ccagaaaagg  42540
caatttccct ttgacatgct gtttttaatg acttttcttt ataaacacac ttatctctcc  42600
```

-continued agagaaatag cagtgcattt gcaacaggcc cgtaaaatgc aacaaaacct ctgctatggt 42660
ttctgacccc tgcttttata cagagcatca gaccaaggaa cctgttctaa caggattatt 42720
tcagagggga acacaggctt agggtgcaga tcttccagct ggatttttca ctttgcattc 42780
cctccacagc agacacatga aggaatgatt ttgtgatttt gattttataa tttgcacact 42840
tttcctaaat actttttta aatttttatt tgggaggatt ttatagcata tgattgagaa 42900
ctataatcat catcattgtt acagaagaat aatttagaaa aattttttaa ctacgttaaa 42960
aattccacta tgggtggatg acaatattgt tctttccttc cacattctcc ctccttagac 43020
tttcttttct ttttttctat tttttttttg agatgaagtc tcgctctgtc actcaggctg 43080
gagtgcagtg ccatgatcct ggctcactgc aacctctgcc tcccgggttc aagtgattct 43140
cccgcctcag cttcctgagt agctgggatt acaggtgtgc accaccacac ctggctactt 43200
tttgtatttt tagtagagat ggggtttcac catgttggtc aggctggtct caaactcctg 43260
atctcatgat ctgcccgcct tggccccgca aagtgccggg attacaggcg tgagccactg 43320
cgcctggcct ctctctcgga ctttctacca tcagtcagat tgaatttgtt aaattctgtc 43380
actgacccta aacccaacaa aaggcaagag ttatgtttat ttagcacttc ctctacctat 43440
agcaaacctc aatttagagc gtaattttaa gcacaattta attataaata tcttttcatt 43500
ttcttactta actcactcag ttttttaaat cttctttttt gagacaagat cttgctctgt 43560
cactgaggcc gatgtacagt gatgtgatca tgacttactg cagccttgac ctcccaggct 43620
taggtgatcc tcatacctca gcctcccgag caactaggac tacaggcccg tgccaccatg 43680
ccgggccaag acggggtttg gacgtgttgc cccagctggt ctccaactcc tggcctcaag 43740
tgaccctccc gcctcggcct ctcaaagtgc tgggattata ggcatgagcc accgcacctg 43800
gccaactcac tcacatttta agtttttctt tttttcatc tagtttttt tctttttaaa 43860 tttgaaagcc tcatgacatt aatgatttct tacattaaaa gaaaaacacc caaaaatact 43920
ctgcttacat aacaccgaca agtagtgtgc aagactcatt agcatttgtc atctgaagtg 43980
accaaatcca gacttttggg ggtcacatta aagaaacagt tgaagagtta gaactatggg 44040
taaagcgagt gtgcatatca gaaagtggaa tattgtcttc ctcaggagct gacaatttat 44100
gaaaaatagt tcacattctc agctagaaag gcttctattt ttgctcatat tcctggctag 44160
ttttgctgaa ataattgctt tgaattactt cctcaggact gcccaggtga cgctaatgtt 44220
tactctgccc ttcacaggta gataccactc tgtctcagtt taccgacctg aatgtttacc 44280
tgtgggatgt ccaccacagt aaaaggctta ttaaagtgga tggggttgtg accaagaaga 44340
ggaaatccta ctgtgttgac tttgctgcca tccagcccca gatcgcttta ctccaggaaa 44400
tgcacgttac acattttcgc ttctccctgg actgggccct gattctccct ctgggtaacc 44460
agtcccaggt gaaccacacc atcctgcagt actatcgctg catggccagc gagcttgtcc 44520
gtgtcaacat caccccagtg gtggccctgt ggcagcctat ggccccgaac caaggactgc 44580
cgcgcctcct ggccaggcag ggcgcctggg agaaccccta cactgccctg gcctttgcag 44640
agtatgcccg actgtgcttt caagagctcg gccatcacgt caagctttgg ataacgatga 44700
atgagccgta tacaaggaat atgacataca gtgctggcca caaccttctg aaggcccatg 44760
ccctggcttg gcatgtgtac aatgaaaagt ttaggcatgc tcagaatggg aaaatatcca 44820
tagccttgca ggctgattgg atagaacctg cctgcccttt ctcccaaaag gacaaagagg 44880
tggctgagag agttttggaa tttgacattg gctggctggc tgagcccatt ttcggctctg 44940
gagattatcc atgggtgatg agggactggc tgaaccaaag aaacaatttt cttcttcctt 45000

-continued

```
atttcactga agatgaaaaa aagctaatcc agggtacctt tgactttttg gctttaagcc  45060
attataccac catccttgta gactcagaaa aagaagatcc aataaaatac aatgattacc  45120
tagaagtgca agaaatgacc gacatcacgt ggctcaactc cccagtcag gtggcggtag  45180
tgccctgggg gttgcgcaaa gtgctgaact ggctgaagtt caagtacgga gacctcccca  45240
tgtacataat atccaatgga atcgatgacg ggctgcatgc tgaggacgac cagctgaggg  45300
tgtattatat gcagaattac ataaacgaag ctctcaaagg taaggagccc tagctgcggc  45360
tatctcctga aggttatgtc accagagggc atgacacttg attaaatctc caacatcaac  45420
acacactgcc acccttggaa tggagggcta tccattttgt gcctcactga aacagtccaa  45480
gagatatcta gcatttcccc aaggataaag gagtgtagct aaaagtagaa gaccagaaat  45540
ccctagcccc tactctggat ctatgcaagc ctagattctt gtcttccatc ttggatggct  45600
ccacagcagt cttaactgtt tcatgtacat aaagcagtac ataaagattt aaccttgctg  45660
ggcatggtgg ctcacacctg taatcccagc attttggaag gccaaggcag gaggattgct  45720
tgagcctaga agtttgagac cagcctgggc aacatagtga gaccttgtct ctactaaaaa  45780
tcacaaaaat tagctgggca cggtggcata tacgcctgca gattcagtta cttgggagga  45840
gaggcgggag gattgcttga gcttgggagg tccagctgca gtgaatcatg atcacagcac  45900
tgcaatctgg cctgggtgac agagcaagac actatttcaa aaaaaaaaag accaagcatg  45960
gtggctcatg cctgtaatcc cagcactttg ggaggctgag gcaggtggat catctgaggt  46020
cagaagttca agaccagcct gaccaacatg gtgaaacccc gtctctactg aaaatacgaa  46080
aattatccag gtgtagtgat gcacacctgt aatctcagct actcgggagg ctgaggcaga  46140
agaatcactt gaactgggga cgtggaggct gcagtgagcc aagattgcac cattgcactc  46200
cagcctgggt gacagagcaa gactccatct caaaaaaaaa aaaaaaaaaa aaaggattta  46260
acccaagtat atcatagtag attgaattat gtaaaacacc catttaacaa ccaggtccag  46320
gtttgttctc tctgtgtagt aaatcaatca ctgtgacaca ggttttgcaa aagagaaaag  46380
atttatttgt aaggggacca agcgaggggg tgggagaata acttccaatc ctgcctctct  46440
gaagacaagg cttaggaata tgtatgggtt agggaatggg tggtctaagg catggtgaag  46500
agtgattggc aggggggggaa aatgaagtaa caggttagac acatgcacag aaaatggtgg  46560
tgttagcatg atctgagggc agagttttgg gccctctgac gtcaaaagac cacctctcag  46620
gcacttgtgc aggcccagtg gaagggtcag tggtcttaac tagtttgaac tggacaggag  46680
ctgccccaag ttcttggaaa aacaactgaa gtgaccattg ccatggtaac ctatgaatgt  46740
catcagtaaa gtagccagtg aaggttaagt ttcagcatac aatgggacaa ccttcagctt  46800
catggaaaaa ggaaaaaaaa aaaacacata cacacacgaa aagcaagtga ccaaaagcaa  46860
gcaggacagg cagacctgat ccaattaacc cctgggtttc aaccctgcta aatgcagctc  46920
aatatttgtc ttgataattt gcctatttgg ctttacataa aataaagcct tttctgatga  46980
aatctaattg agtctgaagt tgtattaaat ggtatcggaa acttcccagc aggaaggcta  47040
cgtaaaagtg gccgggcgtg gtgactcacg cctgtaatcc cagcactttg ggaggctgag  47100
gcaggcagat cacaaggtca agaaatcgag accatcctgg ccaacatggc gaaatcccat  47160
ctctactaaa aaaaaaaata caaaaatttg ccaggtgtgg tggtgctcac ctgtagtccc  47220
agctactcag gaggctgagg caggagaatc tgttgaacct gggaggcgga ggttgcagtg  47280
agtcaagatg gtgccattgc actccagcct gtgtgacaga gcaagactcc gtctcaaaaa  47340
```

-continued aaaaaaaaag tgatgtgttg tgtgcaaaat acgtaataac tactctccta tccttttgtt 47400
tttccagccc acatactgga tggtatcaat ctttgcggat actttgctta ttcgtttaac 47460
gaccgcacag ctccgaggtt tggcctctat cgttatgctg cagatcagtt tgagcccaag 47520
gcatccatga aacattacag gaaaattatt gacagcaatg gtttcccggg cccagaaact 47580
ctggaaagat tttgtccaga agaattcacc gtgtgtactg agtgcagttt ttttcacacc 47640
cgaaagtctt tactggcttt catagctttt ctatttttttg cttctattat ttctctctcc 47700
cttatatttt actactcgaa gaaaggcaga agaagttaca aatag 47745

<210> SEQ ID NO 21
<211> LENGTH: 27
<212> TYPE: RNA
<213> ORGANISM: Artificial Sequence
<220> FEATURE:
<223> OTHER INFORMATION: siRNA1 guide sequence

<400> SEQUENCE: 21
ucguggacgc ucagguucau ucucuuu 27

<210> SEQ ID NO 22
<211> LENGTH: 25
<212> TYPE: RNA
<213> ORGANISM: Artificial Sequence
<220> FEATURE:
<223> OTHER INFORMATION: siRNA1 passenger sequence

<400> SEQUENCE: 22
agagaaugaa ccugagcguc cacga 25

<210> SEQ ID NO 23
<211> LENGTH: 22
<212> TYPE: RNA
<213> ORGANISM: Artificial Sequence
<220> FEATURE:
<223> OTHER INFORMATION: shRNA P1 guide sequence

<400> SEQUENCE: 23
uuucguggac gcucagguuc au 22

<210> SEQ ID NO 24
<211> LENGTH: 22
<212> TYPE: DNA
<213> ORGANISM: Artificial Sequence
<220> FEATURE:
<223> OTHER INFORMATION: P1 guide sequence (DNA)

<400> SEQUENCE: 24
tttcgtggac gctcaggttc at 22

<210> SEQ ID NO 25
<211> LENGTH: 22
<212> TYPE: RNA
<213> ORGANISM: Artificial Sequence
<220> FEATURE:
<223> OTHER INFORMATION: shRNA P2 guide sequence

<400> SEQUENCE: 25
uuccucccag cucccgggag cc 22

<210> SEQ ID NO 26
<211> LENGTH: 22
<212> TYPE: DNA
<213> ORGANISM: Artificial Sequence
<220> FEATURE:
<223> OTHER INFORMATION: P2 guide sequence (DNA)

<400> SEQUENCE: 26
ttcctcccag ctcccgggag cc 22

<210> SEQ ID NO 27
<211> LENGTH: 22
<212> TYPE: RNA
<213> ORGANISM: Artificial Sequence
<220> FEATURE:
<223> OTHER INFORMATION: shRNA P3 guide sequence

<400> SEQUENCE: 27
aaaggcaccu guuccuccca gc 22

<210> SEQ ID NO 28
<211> LENGTH: 22
<212> TYPE: DNA
<213> ORGANISM: Artificial Sequence
<220> FEATURE:
<223> OTHER INFORMATION: P3 guide sequence (DNA)

<400> SEQUENCE: 28
aaaggcacct gttcctccca gc 22

<210> SEQ ID NO 29
<211> LENGTH: 22
<212> TYPE: RNA
<213> ORGANISM: Artificial Sequence
<220> FEATURE:
<223> OTHER INFORMATION: shRNA P4 guide sequence

<400> SEQUENCE: 29
uucauucucu uugccugccg cg 22

<210> SEQ ID NO 30
<211> LENGTH: 22
<212> TYPE: DNA
<213> ORGANISM: Artificial Sequence
<220> FEATURE:
<223> OTHER INFORMATION: P4 guide sequence (DNA)

<400> SEQUENCE: 30
ttcattctct ttgcctgccg cg 22

<210> SEQ ID NO 31
<211> LENGTH: 27
<212> TYPE: RNA
<213> ORGANISM: Artificial Sequence
<220> FEATURE:
<223> OTHER INFORMATION: siRNA2 guide sequence

<400> SEQUENCE: 31
uauucuuuag cuguacugua auuucuu 27

<210> SEQ ID NO 32
<211> LENGTH: 25
<212> TYPE: DNA
<213> ORGANISM: Artificial Sequence
<220> FEATURE:
<223> OTHER INFORMATION: siRNA2 passenger sequence

<400> SEQUENCE: 32
gaaauuacag uacagcuaaa gaata 25

-continued

<210> SEQ ID NO 33
<211> LENGTH: 27
<212> TYPE: RNA
<213> ORGANISM: Artificial Sequence
<220> FEATURE:
<223> OTHER INFORMATION: siRNA3 guide sequence

<400> SEQUENCE: 33
gaaagauaag cuuuugguaa uauucau 27

<210> SEQ ID NO 34
<211> LENGTH: 25
<212> TYPE: DNA
<213> ORGANISM: Artificial Sequence
<220> FEATURE:
<223> OTHER INFORMATION: siRNA3 passenger sequence

<400> SEQUENCE: 34
gaauauuacc aaaagcuuau cuutc 25

<210> SEQ ID NO 35
<211> LENGTH: 27
<212> TYPE: RNA
<213> ORGANISM: Artificial Sequence
<220> FEATURE:
<223> OTHER INFORMATION: siRNA4 guide sequence

<400> SEQUENCE: 35
uaaguguugu gaaacuguaa auuucau 27

<210> SEQ ID NO 36
<211> LENGTH: 25
<212> TYPE: DNA
<213> ORGANISM: Artificial Sequence
<220> FEATURE:
<223> OTHER INFORMATION: siRNA4 passenger sequence

<400> SEQUENCE: 36
gaaauuuaca guuucacaac acuta 25

<210> SEQ ID NO 37
<211> LENGTH: 19
<212> TYPE: DNA
<213> ORGANISM: Artificial Sequence
<220> FEATURE:
<223> OTHER INFORMATION: F1 RT primer

<400> SEQUENCE: 37
tcccaacgca acccataaa 19

<210> SEQ ID NO 38
<211> LENGTH: 21
<212> TYPE: DNA
<213> ORGANISM: Artificial Sequence
<220> FEATURE:
<223> OTHER INFORMATION: RV1 RT primer

<400> SEQUENCE: 38
gacgctcagg ttcattctct t 21

<210> SEQ ID NO 39
<211> LENGTH: 20
<212> TYPE: DNA
<213> ORGANISM: Artificial Sequence
<220> FEATURE:
<223> OTHER INFORMATION: F2 RT primer

<400> SEQUENCE: 39
tggcagtccc tctaggattt 20

<210> SEQ ID NO 40
<211> LENGTH: 18
<212> TYPE: DNA
<213> ORGANISM: Artificial Sequence
<220> FEATURE:
<223> OTHER INFORMATION: RV2 RT primer

<400> SEQUENCE: 40
ggctccgctg gcaataat 18

<210> SEQ ID NO 41
<211> LENGTH: 22
<212> TYPE: DNA
<213> ORGANISM: Artificial Sequence
<220> FEATURE:
<223> OTHER INFORMATION: S1 RT primer

<400> SEQUENCE: 41
aggtttggcc tctatcgtta tg 22

<210> SEQ ID NO 42
<211> LENGTH: 22
<212> TYPE: DNA
<213> ORGANISM: Artificial Sequence
<220> FEATURE:
<223> OTHER INFORMATION: AS1 RT primer

<400> SEQUENCE: 42
ctctgtcgtc tctcctgtat ct 22

<210> SEQ ID NO 43
<211> LENGTH: 22
<212> TYPE: DNA
<213> ORGANISM: Artificial Sequence
<220> FEATURE:
<223> OTHER INFORMATION: S2 RT primer

<400> SEQUENCE: 43
actactcgaa gaaaggcaga ag 22

<210> SEQ ID NO 44
<211> LENGTH: 22
<212> TYPE: DNA
<213> ORGANISM: Artificial Sequence
<220> FEATURE:
<223> OTHER INFORMATION: AS2 RT primer

<400> SEQUENCE: 44
gggaagccac taggcattat ta 22

<210> SEQ ID NO 45
<211> LENGTH: 1012
<212> TYPE: PRT
<213> ORGANISM: Homo sapiens

<400> SEQUENCE: 45

Met Pro Ala Ser Ala Pro Pro Arg Arg Pro Arg Pro Pro Pro Pro Ser
1 5 10 15

Leu Ser Leu Leu Leu Val Leu Leu Gly Leu Gly Gly Arg Arg Leu Arg
20 25 30

-continued

```
Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
```

-continued

```
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880
```

```
Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile  Phe Tyr Tyr Ser Lys  Lys Gly Arg
        995                 1000                1005

Arg Ser  Tyr Lys
    1010


<210> SEQ ID NO 46
<211> LENGTH: 925
<212> TYPE: PRT
<213> ORGANISM: Homo sapiens

<400> SEQUENCE: 46

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
```

-continued

```
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
        355                 360                 365

Asp Leu Glu Phe Asn His Pro Gln Ile Phe Ile Val Glu Asn Gly Trp
    370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
        435                 440                 445

Leu Ser Gln Asp Lys Met Leu Leu Pro Lys Ser Ser Ala Leu Phe Tyr
    450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
            500                 505                 510

Val Tyr Leu Trp Asp Val His His Ser Lys Arg Leu Ile Lys Val Asp
        515                 520                 525

Gly Val Val Thr Lys Lys Arg Lys Ser Tyr Cys Val Asp Phe Ala Ala
    530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
                565                 570                 575

Gln Val Asn His Thr Ile Leu Gln Tyr Tyr Arg Cys Met Ala Ser Glu
            580                 585                 590

Leu Val Arg Val Asn Ile Thr Pro Val Val Ala Leu Trp Gln Pro Met
        595                 600                 605

Ala Pro Asn Gln Gly Leu Pro Arg Leu Leu Ala Arg Gln Gly Ala Trp
    610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
                645                 650                 655
```

```
Pro Tyr Thr Arg Asn Met Thr Tyr Ser Ala Gly His Asn Leu Leu Lys
            660                 665                 670

Ala His Ala Leu Ala Trp His Val Tyr Asn Glu Lys Phe Arg His Ala
        675                 680                 685

Gln Asn Gly Lys Ile Ser Ile Ala Leu Gln Ala Asp Trp Ile Glu Pro
    690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
                725                 730                 735

Tyr Pro Trp Val Met Arg Asp Trp Leu Asn Gln Arg Asn Asn Phe Leu
            740                 745                 750

Leu Pro Tyr Phe Thr Glu Asp Glu Lys Lys Leu Ile Gln Gly Thr Phe
        755                 760                 765

Asp Phe Leu Ala Leu Ser His Tyr Thr Thr Ile Leu Val Asp Ser Glu
    770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Lys Phe Lys Tyr Gly Asp
            820                 825                 830

Leu Pro Met Tyr Ile Ile Ser Asn Gly Ile Asp Asp Gly Leu His Ala
        835                 840                 845

Glu Asp Asp Gln Leu Arg Val Tyr Tyr Met Gln Asn Tyr Ile Asn Glu
    850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr
        915                 920                 925


<210> SEQ ID NO 47
<211> LENGTH: 549
<212> TYPE: PRT
<213> ORGANISM: Homo sapiens

<400> SEQUENCE: 47

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
```

```
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525
```

```
Asp Asn Tyr Ile Gln Val Ser Gln Leu Thr Lys Pro Ile Ser Ser Leu
    530                 535                 540

Thr Lys Pro Tyr His
545


<210> SEQ ID NO 48
<211> LENGTH: 1325
<212> TYPE: RNA
<213> ORGANISM: Homo sapiens

<400> SEQUENCE: 48

ccuccguguc gcggaagacg uuguuguagc ugucgcuggc uacgucccccg guggcgggcu     60

gcagcggcga cggggcgccc aacggcagac uggcguuccg ggagucuccc gggggugcca    120

gggggugug ggugaacgua ucccagaugg acgcacccuu gccgugcugc ugccagccgc    180

ccucggucug guaggcggcg cugcccacgg cccagaggaa gccgucgggg aaggugcccu    240

ggaagaggcc cgcggccucg ggggcaggag gccgcgagaa acgggcccag gucugcgcgc    300

cgucgcccgg cuccgcacgc aggcggcggc cgcccaggcc cagcagcacc agcagcagcg    360

acagcgacgg cggcggcggc cgcgggcggc gcggcggggc gcuggcgggc augcugcgcg    420

ggagccaggc uccggggccc cgcgccgcgc cccuuuaugc ccgcgccccg ccgcgcccgc    480

ccgcccaccg ccggcgcgcc cacccccgcu ccccggcggg cuccgcuggc aauaauuacc    540

ugcgagccgg gacugccucc gcccuggcac ugggggcggg ggcaggggcg ccgagggcga    600

ggggugcccg ggaggggcgc ggcagcgggc aaggugcggc aggcgucgcc cgcggacguc    660

ggagaaaggc accuguuucu cccagcuccc gggagccgug caggacguuu cguggacgcu    720

cagguucauu cucuuugccu gccgcgcguc cucugagagc agcccuggag cggcuucguc    780

ggggagaaaa ggcgccgacc aacuuucccc gacuuggggg cgggauccug ccgggcccua    840

gcggagcgcg ccgcugggga agcaccugcu cucacuuuuc ucccacucgg aggcccaaag    900

aagcuccggc uggacauugc uggagccaau uagggacugg ccgaaauccu agagggacug    960

ccagguggga cagccgaggg ggaacuucgc cgugcgcuga aagggauucc cccuuaggac   1020

gaugggagcc uuuuaacacc aauggagcag gagaugcacu gauucacaug cacccaaaua   1080

caacaccaac cccacaagcu cucagcucac cagucacaga caucaccuuc uacggacaua   1140

uuuuuauuuc acugagcuac aacuacgggc aaggcaacga cgagcugugu ggagacuuca   1200

aaacauagag gacaaccucu gcccucaaag acaacaucca acugaagaaa ggaucaagaa   1260

agaugaaaau aaauaaguug uuugauuaug cuguguuaau aaaugaccca uagaauaauu   1320

gucag                                                               1325


<210> SEQ ID NO 49
<211> LENGTH: 1325
<212> TYPE: RNA
<213> ORGANISM: Homo sapiens

<400> SEQUENCE: 49

cugacaauua uucuaugggu cauuuauuaa cacagcauaa ucaaacaacu uauuuauuuu     60

caucuuucuu gauccuuucu ucaguuggau guugucuuug agggcagagg uuguccucua    120

uguuuugaag ucuccacaca gcucgucguu gccuugcccg uaguuguagc ucagugaaau    180

aaaaauaugu ccguagaagg ugaugucugu gacuggugag cugagagcuu gugggguugg    240

uguuguauuu gggugcaugu gaaucagugc aucuccugcu ccauuggugu uaaaaggcuc    300
```

-continued

```
ccaucguccu aagggggaau cccuuucagc gcacggcgaa guucccccuc ggcuguccca    360
ccuggcaguc ccucuaggau uucggccagu cccuaauugg cuccagcaau guccagccgg    420
agcuucuuug ggccuccgag ugggagaaaa gugagagcag gugcuucccc agcggcgcgc    480
uccgcuaggg cccggcagga ucccgccccc aagucgggga aaguuggucg gcgccuuuuc    540
ucccegacga agccgcucca gggcugcucu cagaggacgc gcggcaggca aagagaauga    600
accugagcgu ccacgaaacg uccugcacgg cucccgggag cugggagaaa caggugccuu    660
ucuccgacgu ccgcgggcga cgccugccgc accuugcccg cugccgcgcc ccucccgggc    720
accccucgcc cucggcgccc cugcccccgc ccccagugcc agggcggagg caguccccggc    780
ucgcagguaa uuauugccag cggagcccgc cggggagcgg gggugggcgc gccggcggug    840
ggcgggcggg cgcggcgggg cgcgggcaua aaggggcgcg gcgcggggcc ccggagccug    900
gcucccgcgc agcaugcccg ccagcgcccc gccgcgccgc ccgcggccgc cgccgccguc    960
gcugucgcug cugcuggugc ugcugggccu gggcggccgc cgccugcgug cggagccggg   1020
cgacggcgcg cagaccuggg cccguuucuc gcggccuccu gcccccgagg ccgcgggccu   1080
cuuccagggc accuuccccg acggcuuccu cugggccgug ggcagcgccg ccuaccagac   1140
cgagggcggc uggcagcagc acggcaaggg ugcguccauc ugggauacgu ucacccacca   1200
cccccuggca cccccgggag acucccggaa cgccagucug ccguugggcg ccccgucgcc   1260
gcugcagccc gccaccgggg acguagccag cgacagcuac aacaacgucu uccgcgacac   1320
ggagg                                                               1325
```

<210> SEQ ID NO 50
<211> LENGTH: 3525
<212> TYPE: DNA
<213> ORGANISM: Homo sapiens

<400> SEQUENCE: 50

```
ctgacaatta ttctatgggt catttattaa cacagcataa tcaaacaact tatttatttt     60
catctttctt gatcctttct tcagttggat gttgtctttg agggcagagg ttgtcctcta    120
tgttttgaag tctccacaca gctcatcgtt gccttgcccg tagttgtagc tcagtgaaat    180
aaaaatatgt ccgtagaagg tgatgtctgt gactggtgag ccgagagctt gtggggttgg    240
tgttgtattt gagtgcatgt gaatcagtgc atctcctgct ccattggtgt taaaaggctc    300
ccatcgtcct gggaacacaa taggaaagag aacaggtggg aaggcactgg atgaaggaat    360
gtggagaatg gaggaaaagt tgatcagatt gttgacaact ttcagtgttg aaattgtcac    420
caaaatcaaa gtcagtaaat aaatttacaa tgtccttttc ttcaatgcat caataacttc    480
accttcctgt tcaaagcaca gcaagtaatt aatctcttat ttgcatttga aacccaagtt    540
tcagatgttt gaaggtggtt gtaaaaaata aaaaccaaaa taaagccaaa ataaataagc    600
agcagcacta ggccgggcac agtgtctcac acctgtaatc ccagcatttt aggagaccga    660
ggtgggtgga tcacaggaga tcaggagttt gagaccagcc tggtcagcat ggtgaaaccc    720
tgtctctact aaaaatacaa aaattagcca ggtgtggtgg tgtgccctta taatcccagc    780
tactgggggg ctgagacagg agaattgctt gaacctggga ggcagaggtt gcagtgagca    840
gagaccatgc cactgcactc cagcctgggc gacagagtga gactccgtct cacacttgtg    900
gaacccagaa cttagtaacc atgaacagaa ccttaataaa cagaaagttc tggaaataaa    960
gtttaatcat catgcaatct ttatcactgg gttaaatgaa caatcatctg ggaacatgtc   1020
ttggaatgct taaagctttg agatgcatgt gcctatgtgg cagacaaatt tcaaatgtga   1080
```

```
aacgtttagt taacttggtc ttgcttttta atcactgctt taaaatttaa aaaatgctgc   1140
tggtcaagta aaaatagcaa tagataaaat ctgccctgag caaacagacc atacatcaat   1200
aaatgaatac ttagcttaag cgattttcca tgagacccat gaagcatttc taattgaaac   1260
ttaacaagct acaacccaac agacactcca atcttcactt ctagaaggga aatgtgatac   1320
tccatgtaga cgtagctttt taaatttagc tggaagacag cgtgacagtg aagttgtgtg   1380
ctgtaatttt ttaaaattgc tgaagtgtca tggtttgcta tttcgtattt attgaaaaaa   1440
tgtaaatgct atatttaaca gaatggcagt aactctgttt caatctgaag acttaatctt   1500
actaatcatg gtaatatatg ctggctggag ttgggaatat ttcataaaat actggaataa   1560
atttgtgctt atatttcagg ggaattaata aaagcacctt catctgcaac atttaaaatg   1620
ttattgcctt taaatttgta ttaaataatg cagggaggat agatcactgg gggagaatgg   1680
atgcacctct gtgaggatct tggtcattca acacacgtgt acgggtgagg aaactaaggc   1740
acgacttact gggtagggag gtagggatat tagcaagatc cttcacttgt ctgggctttc   1800
tgtctttgag tcacctttgc gcagtttttc actggacttc acaagcctct gaggcggcag   1860
ggcagacagg acatccttat tttatagagg aaaaaactta ggcttacaga ggtttcctgc   1920
cccaaatcac aaaggtggag cctagacctt ctcagtctcc accaactgta tttcggttag   1980
ccacaatcct atctacccac atccaaatgg acaccgtggc tctgcaactt ctgtcaaaag   2040
ggctctttgg caacaggaaa aacgtcatgg ctccattgta ttgtagagga tgggaatggg   2100
tgttccggct aaattctccc tcccctttcc ctccacagct cagatggcaa atgtgcgacc   2160
cagggacctc ccgctccagc agacctgtgc gcacaacttt gcacagatta cctgctaagt   2220
cagagccgaa aggtaacaca gatgccaaag gataataaag gtgaatgaga tttactcaaa   2280
attggaaact tggtgtttgg tttttcagga gaacaatcaa cgactgtgat ttgaagttca   2340
ccagggtatt ctgagagatc taatcaaaga tagagtgctg gtttgaaatt attaaaaggt   2400
aacagtaaaa gggagagcaa aaccccagtc ccaacgcaac ccataaatct actttgtctt   2460
cctcgaaaga ggggcgcggg tggcgcgtc tccccgcgag catctcacct aagggggaat   2520
ccctttcagc gcacggcgaa gttccccctc ggctgtccca cctggcagtc cctctaggat   2580
ttcggccagt ccctaattgg ctccagcaat gtccagccgg agcttctttg ggcctccgag   2640
tgggagaaaa gtgagagcag gtgcttcccc agcggcgcgc tccgctaggg cccggcagga   2700
tcccgccccc aagtcgggga aagttggtcg gcgccttttc tccccgacga agccgctcca   2760
gggctgctct cagaggacgc gcggcaggca aagagaatga acctgagcgt ccacgaaacg   2820
tcctgcacgg ctcccgggag ctgggaggaa caggtgcctt tctccgacgt ccgcgggcga   2880
cgcctgccgc accttgcccg ctgccgcgcc cctcccgggc acccctcgcc ctcggcgccc   2940
ctgcccccac ccccagtgcc agggcggagg cagtcccggc tcgcaggtaa ttattgccag   3000
cggagcccgc cggggagcgg gggtgggcgc gccggcggtg ggcgggcggg cgcggcgggg   3060
cgcgggcata aaggggcgcg gcgcggggcc ccggagcctg gctcccgcgc agcatgcccg   3120
ccagcgcccc gccgcgccgc ccgcggccgc cgccgccgtc gctgtcgctg ctgctggtgc   3180
tgctgggcct gggcggccgc cgcctgcgtg cggagccggg cgacggcgcg cagacctggg   3240
cccgtttctc gcggcctcct gcccccgagg ccgcgggcct cttccagggc accttccccg   3300
acggcttcct ctgggccgtg ggcagcgccg cctaccagac cgagggcggc tggcagcagc   3360
acggcaaggg tgcgtccatc tgggatacgt tcacccacca ccccctggca cccccgggag   3420
```

-continued actcccggaa cgccagtctg ccgttgggcg ccccgtcgcc gctgcagccc gccaccgggg 3480
acgtagccag cgacagctac aacaacgtct tccgcgacac ggagg 3525

<210> SEQ ID NO 51
<211> LENGTH: 457
<212> TYPE: RNA
<213> ORGANISM: Homo sapiens

<400> SEQUENCE: 51
ggcgaggggu gcccgggagg ggcgcggcag cgggcaaggu gcggcaggcg ucgcccgcgg 60
acgucggaga aaggcaccug uuucucccag cucccgggag ccgugcagga cguuucgugg 120
acgcucaggu ucauucucuu ugccugccgc gcguccucug agagcagccc uggagcggcu 180
ucgucgggga gaaaaggcgc cgaccaacuu ucccccgacuu gggggcggga uccugccggg 240
cccuagcgga gcgcgccgcu ggggaagcac cugcucucac uuuucuccca cucggaggcc 300
caaagaagcu ccggcuggac auugcuggag ccaauuaggg acuggccgaa auccuagagg 360
gacugccagg ugggacagcc gagggggaac uucgccgugc gcugaaaggg auuccccuu 420 aggaaggua aguuauugau gcauugaaga aaaggac 457

<210> SEQ ID NO 52
<211> LENGTH: 457
<212> TYPE: RNA
<213> ORGANISM: Homo sapiens

<400> SEQUENCE: 52
guccuuuucu ucaaugcauc aauaacuuca ccuuccuaag ggggaauccc uuucagcgca 60
cggcgaaguu ccccucggc ugucccaccu ggcagucccu cuaggauuuc ggccaguccc 120
uaauuggcuc cagcaauguc cagccggagc uucuuugggc cuccgagugg gagaaaagug 180
agagcaggug cuuccccagc ggcgcgcucc gcuagggccc ggcaggaucc cgcccccaag 240
ucggggaaag uuggucggcg ccuuuucucc ccgacgaagc cgcuccaggg cugcucucag 300
aggacgcgcg gcaggcaaag agaaugaacc ugagcgucca cgaaacgucc ugcacggcuc 360
ccgggagcug ggagaaacag gugccuuucu ccgacguccg cgggcgacgc cugccgcacc 420
uugcccgcug ccgcgccccu cccgggcacc ccucgcc 457

<210> SEQ ID NO 53
<211> LENGTH: 2479
<212> TYPE: DNA
<213> ORGANISM: Homo sapiens

<400> SEQUENCE: 53
gtccttttct tcaatgcatc aataacttca ccttcctgtt caaagcacag caagtaatta 60
atctcttatt tgcatttgaa acccaagttt cagatgtttg aaggtggttg taaaaaataa 120
aaaccaaaat aaagccaaaa taaataagca gcagcactag gccgggcaca gtgtctcaca 180
cctgtaatcc cagcatttta ggagaccgag gtgggtggat cacaggagat caggagtttg 240
agaccagcct ggtcagcatg gtgaaaccct gtctctacta aaaatacaaa aattagccag 300
gtgtggtggt gtgcccttat aatcccagct actgggggc tgagacagga gaattgcttg 360
aacctgggag gcagaggttg cagtgagcag agaccatgcc actgcactcc agcctgggcg 420
acagagtgag actccgtctc acacttgtgg aacccagaac ttagtaacca tgaacagaac 480
cttaataaac agaaagttct ggaaataaag tttaatcatc atgcaatctt tatcactggg 540
ttaaatgaac aatcatctgg gaacatgtct tggaatgctt aaagctttga gatgcatgtg 600

```
cctatgtggc agacaaattt caaatgtgaa acgtttagtt aacttggtct tgctttttaa    660

tcactgcttt aaaatttaaa aaatgctgct ggtcaagtaa aaatagcaat agataaaatc    720

tgccctgagc aaacagacca tacatcaata aatgaatact tagcttaagc gattttccat    780

gagacccatg aagcatttct aattgaaact taacaagcta caacccaaca gacactccaa    840

tcttcacttc tagaagggaa atgtgatact ccatgtagac gtagcttttt aaatttagct    900

ggaagacagc gtgacagtga agttgtgtgc tgtaattttt taaaattgct gaagtgtcat    960

ggtttgctat ttcgtattta ttgaaaaaat gtaaatgcta tatttaacag aatggcagta   1020

actctgtttc aatctgaaga cttaatctta ctaatcatgg taatatatgc tggctggagt   1080

tgggaatatt tcataaaata ctggaataaa tttgtgctta tatttcaggg gaattaataa   1140

aagcaccttc atctgcaaca tttaaaatgt tattgccttt aaatttgtat taaataatgc   1200

agggaggata gatcactggg ggagaatgga tgcacctctg tgaggatctt ggtcattcaa   1260

cacacgtgta cgggtgagga aactaaggca cgacttactg ggtagggagg tagggatatt   1320

agcaagatcc ttcacttgtc tgggctttct gtctttgagt cacctttgcg cagtttttca   1380

ctggacttca caagcctctg aggcggcagg gcagacagga catccttatt ttatagagga   1440

aaaaacttag gcttacagag gtttcctgcc ccaaatcaca aaggtggagc ctagaccttc   1500

tcagtctcca ccaactgtat ttcggttagc cacaatccta tctacccaca tccaaatgga   1560

caccgtggct ctgcaacttc tgtcaaaagg gctctttggc aacaggaaaa acgtcatggc   1620

tccattgtat tgtagaggat gggaatgggt gttccggcta aattctccct cccctttccc   1680

tccacagctc agatggcaaa tgtgcgaccc agggacctcc cgctccagca gacctgtgcg   1740

cacaactttg cacagattac ctgctaagtc agagccgaaa ggtaacacag atgccaaagg   1800

ataataaagg tgaatgagat ttactcaaaa ttggaaactt ggtgtttggt ttttcaggag   1860

aacaatcaac gactgtgatt tgaagttcac cagggtattc tgagagatct aatcaaagat   1920

agagtgctgg tttgaaatta ttaaaaggta acagtaaaag ggagagcaaa accccagtcc   1980

caacgcaacc cataaatcta ctttgtcttc ctcgaaagag gggcgcgggt gggcgcgtct   2040

ccccgcgagc atctcaccta agggggaatc cctttcagcg cacggcgaag ttccccctcg   2100

gctgtcccac ctggcagtcc ctctaggatt tcggccagtc cctaattggc tccagcaatg   2160

tccagccgga gcttctttgg gcctccgagt gggagaaaag tgagagcagg tgcttcccca   2220

gcggcgcgct ccgctagggc ccggcaggat cccgccccca agtcggggaa agttggtcgg   2280

cgccttttct ccccgacgaa gccgctccag ggctgctctc agaggacgcg cggcaggcaa   2340

agagaatgaa cctgagcgtc cacgaaacgt cctgcacggc tcccgggagc tgggaggaac   2400

aggtgccttt ctccgacgtc cgcgggcgac gcctgccgca ccttgcccgc tgccgcgccc   2460

ctcccgggca cccctcgcc                                                2479
```

```
<210> SEQ ID NO 54
<211> LENGTH: 22
<212> TYPE: RNA
<213> ORGANISM: Artificial Sequence
<220> FEATURE:
<223> OTHER INFORMATION: Short hairpin RNA

<400> SEQUENCE: 54

aaagugagag caggugcuuc cc                                              22


<210> SEQ ID NO 55
```

-continued

<211> LENGTH: 22
<212> TYPE: RNA
<213> ORGANISM: Artificial Sequence
<220> FEATURE:
<223> OTHER INFORMATION: Short hairpin RNA

<400> SEQUENCE: 55
aaagagaaug aaccugagcg uc 22

<210> SEQ ID NO 56
<211> LENGTH: 22
<212> TYPE: RNA
<213> ORGANISM: Artificial Sequence
<220> FEATURE:
<223> OTHER INFORMATION: Short hairpin RNA

<400> SEQUENCE: 56
aaacaggugc cuuucuccga cg 22

<210> SEQ ID NO 57
<211> LENGTH: 22
<212> TYPE: RNA
<213> ORGANISM: Artificial Sequence
<220> FEATURE:
<223> OTHER INFORMATION: Short hairpin RNA

<400> SEQUENCE: 57
uuucggccag ucccuaauug gc 22

<210> SEQ ID NO 58
<211> LENGTH: 22
<212> TYPE: RNA
<213> ORGANISM: Artificial Sequence
<220> FEATURE:
<223> OTHER INFORMATION: Short hairpin RNA

<400> SEQUENCE: 58
uuucuccccg acgaagccgc uc 22

<210> SEQ ID NO 59
<211> LENGTH: 22
<212> TYPE: DNA
<213> ORGANISM: Artificial Sequence
<220> FEATURE:
<223> OTHER INFORMATION: mP1 (DNA)

<400> SEQUENCE: 59
tattccacat cgcacaatcc tg 22

<210> SEQ ID NO 60
<211> LENGTH: 22
<212> TYPE: RNA
<213> ORGANISM: Artificial Sequence
<220> FEATURE:
<223> OTHER INFORMATION: mP1 (RNA)

<400> SEQUENCE: 60
uauuccacau cgcacaaucc ug 22

<210> SEQ ID NO 61
<211> LENGTH: 22
<212> TYPE: DNA
<213> ORGANISM: Artificial Sequence
<220> FEATURE:
<223> OTHER INFORMATION: mP2 (DNA)

<400> SEQUENCE: 61
aatcctgtgg cctccatcct ga 22

<210> SEQ ID NO 62
<211> LENGTH: 22
<212> TYPE: RNA
<213> ORGANISM: Artificial Sequence
<220> FEATURE:
<223> OTHER INFORMATION: mP2 (RNA)

<400> SEQUENCE: 62
aauccugugg ccuccauccu ga 22

<210> SEQ ID NO 63
<211> LENGTH: 22
<212> TYPE: DNA
<213> ORGANISM: Artificial Sequence
<220> FEATURE:
<223> OTHER INFORMATION: mP3 (DNA)

<400> SEQUENCE: 63
tcagggagca gactattcca ca 22

<210> SEQ ID NO 64
<211> LENGTH: 22
<212> TYPE: RNA
<213> ORGANISM: Artificial Sequence
<220> FEATURE:
<223> OTHER INFORMATION: mP3 (RNA)

<400> SEQUENCE: 64
ucagggagca gacuauucca ca 22

<210> SEQ ID NO 65
<211> LENGTH: 22
<212> TYPE: DNA
<213> ORGANISM: Artificial Sequence
<220> FEATURE:
<223> OTHER INFORMATION: mP4 (DNA)

<400> SEQUENCE: 65
atgtccccgc gtcgcccact cc 22

<210> SEQ ID NO 66
<211> LENGTH: 22
<212> TYPE: RNA
<213> ORGANISM: Artificial Sequence
<220> FEATURE:
<223> OTHER INFORMATION: mP4 (RNA)

<400> SEQUENCE: 66
auguccccgc gucgcccacu cc 22

<210> SEQ ID NO 67
<211> LENGTH: 22
<212> TYPE: DNA
<213> ORGANISM: Artificial Sequence
<220> FEATURE:
<223> OTHER INFORMATION: mP5 (DNA)

<400> SEQUENCE: 67
aatgattatc cagagcaggc gc 22

<210> SEQ ID NO 68
<211> LENGTH: 22
<212> TYPE: RNA

<213> ORGANISM: Artificial Sequence
<220> FEATURE:
<223> OTHER INFORMATION: mP5 (RNA)

<400> SEQUENCE: 68
aaugauuauc cagagcaggc gc 22

<210> SEQ ID NO 69
<211> LENGTH: 22
<212> TYPE: DNA
<213> ORGANISM: Artificial Sequence
<220> FEATURE:
<223> OTHER INFORMATION: mP6 (DNA)

<400> SEQUENCE: 69
atagggacgt cggagaacaa gc 22

<210> SEQ ID NO 70
<211> LENGTH: 22
<212> TYPE: RNA
<213> ORGANISM: Artificial Sequence
<220> FEATURE:
<223> OTHER INFORMATION: mP6 (RNA)

<400> SEQUENCE: 70
auagggacgu cggagaacaa gc 22

<210> SEQ ID NO 71
<211> LENGTH: 22
<212> TYPE: DNA
<213> ORGANISM: Artificial Sequence
<220> FEATURE:
<223> OTHER INFORMATION: mP7 (DNA)

<400> SEQUENCE: 71
tatgcccgcg ccccgccgcc ct 22

<210> SEQ ID NO 72
<211> LENGTH: 22
<212> TYPE: RNA
<213> ORGANISM: Artificial Sequence
<220> FEATURE:
<223> OTHER INFORMATION: mP7 (RNA)

<400> SEQUENCE: 72
uaugcccgcg ccccgccgcc cu 22

<210> SEQ ID NO 73
<211> LENGTH: 22
<212> TYPE: DNA
<213> ORGANISM: Artificial Sequence
<220> FEATURE:
<223> OTHER INFORMATION: mP8 (DNA)

<400> SEQUENCE: 73
tacgcggtgc ccaccccgc tc 22

<210> SEQ ID NO 74
<211> LENGTH: 22
<212> TYPE: RNA
<213> ORGANISM: Artificial Sequence
<220> FEATURE:
<223> OTHER INFORMATION: mP8 (RNA)

<400> SEQUENCE: 74
uacgcggugc ccaccccgc uc 22

<210> SEQ ID NO 75
<211> LENGTH: 22
<212> TYPE: DNA
<213> ORGANISM: Artificial Sequence
<220> FEATURE:
<223> OTHER INFORMATION: mP9 (DNA)

<400> SEQUENCE: 75
ttatccagag caggcgccgc cc 22

<210> SEQ ID NO 76
<211> LENGTH: 22
<212> TYPE: RNA
<213> ORGANISM: Artificial Sequence
<220> FEATURE:
<223> OTHER INFORMATION: mP9 (RNA)

<400> SEQUENCE: 76
uuauccagag caggcgccgc cc 22

<210> SEQ ID NO 77
<211> LENGTH: 22
<212> TYPE: DNA
<213> ORGANISM: Artificial Sequence
<220> FEATURE:
<223> OTHER INFORMATION: mP10 (DNA)

<400> SEQUENCE: 77
actccggcct ggcacggggg cg 22

<210> SEQ ID NO 78
<211> LENGTH: 22
<212> TYPE: RNA
<213> ORGANISM: Artificial Sequence
<220> FEATURE:
<223> OTHER INFORMATION: mP10 (RNA)

<400> SEQUENCE: 78
acuccggccu ggcacggggg cg 22

<210> SEQ ID NO 79
<211> LENGTH: 22
<212> TYPE: DNA
<213> ORGANISM: Artificial Sequence
<220> FEATURE:
<223> OTHER INFORMATION: mSense1 (DNA)

<400> SEQUENCE: 79
tatgacccct gctgtgctct ct 22

<210> SEQ ID NO 80
<211> LENGTH: 22
<212> TYPE: RNA
<213> ORGANISM: Artificial Sequence
<220> FEATURE:
<223> OTHER INFORMATION: mSense1 (RNA)

<400> SEQUENCE: 80
uaugaccccu gcugugcucu cu 22

<210> SEQ ID NO 81
<211> LENGTH: 22
<212> TYPE: DNA
<213> ORGANISM: Artificial Sequence
<220> FEATURE:

<223> OTHER INFORMATION: mSense2 (DNA)

<400> SEQUENCE: 81
ataatcattg ctcgtggggc gg 22

<210> SEQ ID NO 82
<211> LENGTH: 22
<212> TYPE: RNA
<213> ORGANISM: Artificial Sequence
<220> FEATURE:
<223> OTHER INFORMATION: mSense2 (RNA)

<400> SEQUENCE: 82
auaaucauug cucguggggc gg 22

<210> SEQ ID NO 83
<211> LENGTH: 22
<212> TYPE: DNA
<213> ORGANISM: Artificial Sequence
<220> FEATURE:
<223> OTHER INFORMATION: mSense3 (DNA)

<400> SEQUENCE: 83
tataggggcg cggcgcggtg cc 22

<210> SEQ ID NO 84
<211> LENGTH: 22
<212> TYPE: RNA
<213> ORGANISM: Artificial Sequence
<220> FEATURE:
<223> OTHER INFORMATION: mSense3 (RNA)

<400> SEQUENCE: 84
uauaggggcg cggcgcggug cc 22

<210> SEQ ID NO 85
<211> LENGTH: 22
<212> TYPE: DNA
<213> ORGANISM: Artificial Sequence
<220> FEATURE:
<223> OTHER INFORMATION: mSense4 (DNA)

<400> SEQUENCE: 85
aaagggagtg gacgcgggga gt 22

<210> SEQ ID NO 86
<211> LENGTH: 22
<212> TYPE: RNA
<213> ORGANISM: Artificial Sequence
<220> FEATURE:
<223> OTHER INFORMATION: mSense4 (RNA)

<400> SEQUENCE: 86
aaagggagug gacgcgggga gu 22

<210> SEQ ID NO 87
<211> LENGTH: 22
<212> TYPE: DNA
<213> ORGANISM: Artificial Sequence
<220> FEATURE:
<223> OTHER INFORMATION: mSense5 (DNA)

<400> SEQUENCE: 87
aatagtctgc tccctgagct gg 22

<210> SEQ ID NO 88
<211> LENGTH: 22
<212> TYPE: RNA
<213> ORGANISM: Artificial Sequence
<220> FEATURE:
<223> OTHER INFORMATION: mSense5 (RNA)

<400> SEQUENCE: 88
aauagucugc ucccugagcu gg 22

<210> SEQ ID NO 89
<211> LENGTH: 22
<212> TYPE: DNA
<213> ORGANISM: Artificial Sequence
<220> FEATURE:
<223> OTHER INFORMATION: mSense6 (DNA)

<400> SEQUENCE: 89
ttgttctccg acgtccctat ga 22

<210> SEQ ID NO 90
<211> LENGTH: 22
<212> TYPE: RNA
<213> ORGANISM: Artificial Sequence
<220> FEATURE:
<223> OTHER INFORMATION: mSense6 (RNA)

<400> SEQUENCE: 90
uuguucuccg acgucccuau ga 22

<210> SEQ ID NO 91
<211> LENGTH: 22
<212> TYPE: DNA
<213> ORGANISM: Artificial Sequence
<220> FEATURE:
<223> OTHER INFORMATION: mSense7 (DNA)

<400> SEQUENCE: 91
attgctcgtg gggcggcggg ag 22

<210> SEQ ID NO 92
<211> LENGTH: 22
<212> TYPE: RNA
<213> ORGANISM: Artificial Sequence
<220> FEATURE:
<223> OTHER INFORMATION: mSense7 (RNA)

<400> SEQUENCE: 92
auugcucgug gggcggcggg ag 22

<210> SEQ ID NO 93
<211> LENGTH: 350
<212> TYPE: DNA
<213> ORGANISM: homo sapiens

<400> SEQUENCE: 93
ctgctctcag aggacgcgcg gcaggcaaag agaatgaacc tgagcgtcca cgaaacgtcc 60
tgcacggctc ccgggagctg ggaggaacag gtgcctttct ccgacgtccg cgggcgacgc 120
ctgccgcacc ttgcccgctg ccgcgcccct cccgggcacc cctcgccctc ggcgcccctg 180
cccccacccc cagtgccagg gcggaggcag tcccggctcg caggtaatta ttgccagcgg 240
agcccgccgg ggagcggggg tgggcgcgcc ggcggtgggc gggcgggcgc ggcggggcgc 300
gggcataaag gggcgcggcg cggggccccg gagcctggct cccgcgcagc 350

<210> SEQ ID NO 94
<211> LENGTH: 350
<212> TYPE: DNA
<213> ORGANISM: homo sapiens

<400> SEQUENCE: 94
gacgagagtc tcctgcgcgc cgtccgtttc tcttacttgg actcgcaggt gctttgcagg 60
acgtgccgag ggccctcgac cctccttgtc cacggaaaga ggctgcaggc gcccgctgcg 120
gacggcgtgg aacgggcgac ggcgcgggga gggcccgtgg ggagcgggag ccgcggggac 180
gggggtgggg gtcacggtcc cgcctccgtc agggccgagc gtccattaat aacggtcgcc 240
tcgggcggcc cctcgccccc acccgcgcgg ccgccacccg cccgcccgcg ccgccccgcg 300
cccgtatttc cccgcgccgc gccccggggc ctcggaccga gggcgcgtcg 350

<210> SEQ ID NO 95
<211> LENGTH: 457
<212> TYPE: DNA
<213> ORGANISM: homo sapiens

<400> SEQUENCE: 95
ggcgaggggt gcccgggagg ggcgcggcag cgggcaaggt gcggcaggcg tcgcccgcgg 60
acgtcggaga aaggcacctg tttctcccag ctcccgggag ccgtgcagga cgtttcgtgg 120
acgctcaggt tcattctctt tgcctgccgc gcgtcctctg agagcagccc tggagcggct 180
tcgtcgggga gaaaaggcgc cgaccaactt tccccgactt gggggcggga tcctgccggg 240
ccctagcgga gcgcgccgct ggggaagcac ctgctctcac ttttctccca ctcggaggcc 300
caaagaagct ccggctggac attgctggag ccaattaggg actggccgaa atcctagagg 360
gactgccagg tgggacagcc gagggggaac ttcgccgtgc gctgaaaggg attcccccctt 420 aggaaggtga agttattgat gcattgaaga aaaggac 457

<210> SEQ ID NO 96
<211> LENGTH: 457
<212> TYPE: DNA
<213> ORGANISM: homo sapiens

<400> SEQUENCE: 96
ccgctcccca cgggccctcc ccgcgccgtc gcccgttcca cgccgtccgc agcgggcgcc 60
tgcagcctct ttccgtggac aaagagggtc gagggccctc ggcacgtcct gcaaagcacc 120
tgcgagtcca agtaagagaa acggacggcg cgcaggagac tctcgtcggg acctcgccga 180
agcagcccct cttttccgcg gctggttgaa aggggctgaa cccccgccct aggacggccc 240
gggatcgcct cgcgcggcga ccccttcgtg gacgagagtg aaaagagggt gagcctccgg 300
gtttcttcga ggccgacctg taacgacctc ggttaatccc tgaccggctt taggatctcc 360
ctgacggtcc accctgtcgg ctcccccttg aagcggcacg cgactttccc taagggggaa 420
tccttccact tcaataacta cgtaacttct tttcctg 457

<210> SEQ ID NO 97
<211> LENGTH: 350
<212> TYPE: DNA
<213> ORGANISM: homo sapiens

<400> SEQUENCE: 97
aacaccagtc ccaggaaggc aaagggagtg gacgcgggga gtgggcgacg cggggacatc 60
tcaggatgga ggccacagga ttgtgcgatg tggaatagtc tgctccctga gctggctgca 120

-continued

```
gcaggtgctt gttctccgac gtccctatga cccctgctgt gctctctctg ggcaccctgg    180

ctggctgagc ccctgtcccg cccccgtgcc aggccggagt gggggcggc gcctgctctg    240

gataatcatt gctcgtgggg cggcgggagc gggggtgggc accgcgtagg gagggcggcg    300

gggcgcgggc atataggggc gcggcgcggt gccctcccgg ctcccgcagc               350


<210> SEQ ID NO 98
<211> LENGTH: 350
<212> TYPE: DNA
<213> ORGANISM: homo sapiens

<400> SEQUENCE: 98

ttgtggtcag ggtccttccg tttccctcac ctgcgcccct cacccgctgc gcccctgtag     60

agtcctacct ccggtgtcct aacacgctac accttatcag acgagggact cgaccgacgt    120

cgtccacgaa caagaggctg cagggatact ggggacgaca cgagagagac ccgtgggacc    180

gaccgactcg ggacagggc gggggcacgg tccggcctca ccccccgccg cggacgagac    240

ctattagtaa cgagcacccc gccgccctcg cccccacccg tggcgcatcc ctcccgccgc    300

cccgcgcccg tatatccccg cgccgcgcca cgggagggcc gagggcgtcg               350
```